US008778874B2

(12) United States Patent
Arimoto et al.

(10) Patent No.: US 8,778,874 B2
(45) Date of Patent: Jul. 15, 2014

(54) GLYCOPEPTIDE ANTIBIOTIC MONOMER DERIVATIVES

(75) Inventors: Hirokazu Arimoto, Sendai (JP); Jun Lu, Chicago, IL (US); Yoshinori Yamano, Toyonaka (JP); Tatsuro Yasukata, Osaka (JP); Osamu Yoshida, Osaka (JP); Tsutomu Iwaki, Osaka (JP); Yutaka Yoshida, Osaka (JP); Issei Kato, Osaka (JP); Kenji Morimoto, Osaka (JP); Kayo Yasoshima, Osaka (JP)

(73) Assignees: National University Corporation Nagoya University, Aichi (JP); Shionogi & Co., Ltd., Osaka (JP)

( * ) Notice: Subject to any disclaimer, the term of this patent is extended or adjusted under 35 U.S.C. 154(b) by 1319 days.

(21) Appl. No.: 11/791,446

(22) PCT Filed: Nov. 24, 2005

(86) PCT No.: PCT/JP2005/021587
§ 371 (c)(1),
(2), (4) Date: May 24, 2007

(87) PCT Pub. No.: WO2006/057303
PCT Pub. Date: Jun. 1, 2006

(65) Prior Publication Data
US 2008/0097078 A1   Apr. 24, 2008

(30) Foreign Application Priority Data

Nov. 29, 2004  (JP) ................................. 2004-344231
Jul. 22, 2005  (JP) ................................. 2005-212471

(51) Int. Cl.
*A61K 38/00* (2006.01)
*A61P 31/04* (2006.01)
*A61K 38/14* (2006.01)
*C07K 9/00* (2006.01)
*A61K 38/04* (2006.01)

(52) U.S. Cl.
CPC ............... *C07K 9/008* (2013.01); *A61K 38/04* (2013.01); *A61K 38/00* (2013.01)
USPC ........................................ 514/3.2; 530/322

(58) Field of Classification Search
CPC .......... A61K 38/04; A61K 38/00; C07K 9/008
USPC ........................................ 514/3.2; 530/322
See application file for complete search history.

(56) References Cited

U.S. PATENT DOCUMENTS

| 4,497,802 | A | 2/1985 | Debono |
| 4,639,433 | A | 1/1987 | Hunt et al. |
| 4,643,987 | A | 2/1987 | Nagarajan et al. |
| 4,698,327 | A | 10/1987 | Nagarajan et al. |
| 5,591,714 | A | 1/1997 | Nagarajan et al. |
| 5,840,684 | A | 11/1998 | Cooper et al. |
| 5,843,889 | A | 12/1998 | Cooper et al. |
| 6,455,669 | B1 * | 9/2002 | Judice et al. ................... 530/317 |
| 6,498,238 | B1 * | 12/2002 | Kim et al. ..................... 536/16.8 |
| 6,699,836 | B2 | 3/2004 | Kahne et al. |
| 2003/0068669 | A1 | 4/2003 | Thorson |
| 2004/0259228 | A1 | 12/2004 | Thorson |
| 2005/0239689 | A1 | 10/2005 | Thorson |
| 2005/0266523 | A1 | 12/2005 | Thorson |

FOREIGN PATENT DOCUMENTS

| EP | 0 201 251 | 12/1986 |
| EP | 0 435 503 | 7/1991 |
| EP | 0 667 353 | 8/1995 |
| EP | 0 801 075 | 7/1999 |
| EP | 0 802 199 | 12/1999 |
| EP | 1 031 576 | 8/2000 |
| EP | 0 667 353 | 10/2003 |
| JP | 0 273 727 | 7/1988 |
| JP | 0 301 785 | 2/1989 |
| JP | 01-240196 | 9/1989 |
| JP | 04-108800 | 4/1992 |
| JP | 7-258289 | 10/1995 |
| JP | 2000-302687 | 10/2000 |
| JP | 2001-163898 | 6/2001 |
| JP | 2003-026725 | 1/2003 |
| JP | 2006-503015 | 1/2006 |
| WO | 93/03060 | 2/1993 |
| WO | 96/30401 | 10/1996 |

(Continued)

OTHER PUBLICATIONS

Vippagunta, S.R., Brittain, H.G., Grant, D.J.W. (2001) Crystalline solids. Advanced Drug Delivery Reviews, vol. 48, pp. 3-26.*
Morissette, S.L., Almarsson, Ö., Peterson, M.L., Remenar, J.F., Read, M.J., Lemmo, A.V., Ellis, S., Cima, M.J., Gardner, C.R. (2004) High-throughput crystallization: polymorphs, salts, co-crystals and solvates of pharmaceutical solids. Advanced Drug Delivery Reviews, vol. 56, pp. 275-300.*
J. K. Judice et al., "Semi-Synthetic Glycopeptide Antibacterials", Bioorganic & Medicinal Chemistry Letters, vol. 13, pp. 4165-4168, 2003.

(Continued)

*Primary Examiner* — Scarlett Goon
(74) *Attorney, Agent, or Firm* — Wenderoth, Lind & Ponack, L.L.P.

(57) ABSTRACT

Novel glycopeptide antibiotic derivatives. These derivatives are represented by the formula (aglycon part of glycopeptide antibiotic derivative)-(Sac-NH)—$R^A$ [wherein (aglycon part of glycopeptide antibiotic derivative) is the part formed by removing the sugar part from a known glycopeptide antibiotic derivative; (Sac-NH) part is an amino sugar part or a sugar chain part containing an amino sugar; and $R^A$ represents, e.g., the formula —$X^1$—$Ar^1$—$X^2$—Y—$X^3$—$Ar^2$ (wherein $X^1$, $X^2$, and $X^3$ each represents 1) a single bond or 2) a heteroatom or heteroatom-containing group selected from the group consisting of —N=, =N—, —$NR^1$—, —O—, etc.; Y represents —$NR^2$CO— or —$CONR^2$— (wherein $R^2$ represents hydrogen or lower alkyl), etc.)]. These derivatives have antibacterial activity against vancomycin-resistant bacteria.

22 Claims, No Drawings

(56) References Cited

FOREIGN PATENT DOCUMENTS

| | | |
|---|---|---|
| WO | 97/28812 | 8/1997 |
| WO | 97/38702 | 10/1997 |
| WO | 98/52589 | 11/1998 |
| WO | 98/52592 | 11/1998 |
| WO | 00/04044 | 1/2000 |
| WO | 00/39156 | 7/2000 |
| WO | 00/42067 | 7/2000 |
| WO | 00/59528 | 10/2000 |
| WO | 00/69893 | 11/2000 |
| WO | 01/81372 | 11/2001 |
| WO | 01/81373 | 11/2001 |
| WO | 03/018608 | 3/2003 |
| WO | 2004/019970 | 3/2004 |
| WO | 2004/044222 | 5/2004 |
| WO | 2005/018743 | 3/2005 |
| WO | 2006/003456 | 1/2006 |
| WO | 2006/057288 | 6/2006 |
| WO | 2006/093933 | 9/2006 |
| WO | 2006/094082 | 9/2006 |

OTHER PUBLICATIONS

O. Yoshida et al., "Novel Semi-Synthetic Glycopeptide Antibiotics Active Against Methicillin-Resistant *Staphylococcus aureus* (MRSA) and Vancomycin-Resistant *Enterococci* (VRE): Doubly-Modified Water-Soluble Derivatives of Chloroorienticin B", Bioorganic & Medicinal Chemistry Letters, vol. 12, pp. 3027-3031, 2002.
Griffith BR, Langenhan JM, Thorson JS. 'Sweetening' natural products via glycorandomization. Curr Opin Biotechnol. Dec. 2005;16(6):622-30. Epub Oct. 13, 2005.
Salas JA, Méndez C. Engineering the glycosylation of natural products in actinomycetes. Trends Microbiol. May 2007;15(5):219-32. Epub Apr. 6, 2007.
Lu W, Oberthür M, Leimkuhler C, Tao J, Kahne D, Walsh CT. Characterization of a regiospecific epivancosaminyl transferase GtfA and enzymatic reconstitution of the antibiotic chloroeremomycin. Proc Natl Acad Sci U S A. Mar. 30, 2004;101(13):4390-5. Epub Mar. 18, 2004.
Oberthür M, Leimkuhler C, Kruger RG, Lu W, Walsh CT, Kahne D. A systematic investigation of the synthetic utility of glycopeptide glycosyltransferases. J Am Chem Soc. Aug. 3, 2005;127(30):10747-52.
Mulichak AM, Losey HC, Walsh CT, Garavito RM. Structure of the UDP-glucosyltransferase GtfB that modifies the heptapeptide aglycone in the biosynthesis of vancomycin group antibiotics. Structure. Jul. 3, 2001;9(7):547-57.
Cooper RD, Snyder NJ, Zweifel MJ, Staszak MA, Wilkie SC, Nicas TI, Mullen DL, Butler TF, Rodriguez MJ, Huff BE, Thompson RC. Reductive alkylation of glycopeptide antibiotics: synthesis and antibacterial activity. J Antibiot (Tokyo). Jun. 1996;49(6):575-81.
Shi Z, Griffin JH. Catalysis of Carbamate Hydrolysis by Vancomycin and Semisynthetic Derivatives. J. Am. Chem. Soc. 1993; 115: 6482-6486.
Sundram UN, Griffin, JH. General and Efficient Method for the Solution- and Solid-Phase Synthesis of Vancomycin Carboxamide Derivatives. J. Org. Chem. 1995; 60: 1102-1103.
Pavlov AY, Lazhko EI, Preobrazhenskaya MN. A new type of chemical modification of glycopeptides antibiotics: aminomethylated derivatives of eremomycin and their antibacterial activity. J Antibiot (Tokyo). Jun. 1997;50(6):509-13.
Malabarba A, Nicas TI, Thompson RC. Structural modifications of glycopeptide antibiotics. Med Res Rev. Jan. 1997;17(1):69-137.
Allen NE, LeTourneau DL, Hobbs JN Jr. The role of hydrophobic side chains as determinants of antibacterial activity of semisynthetic glycopeptide antibiotics. J Antibiot (Tokyo). Aug. 1997;50(8):677-84.
Rodriguez MJ, Snyder NJ, Zweifel MJ, Wilkie SC, Stack DR, Cooper RD, Nicas TI, Mullen DL, Butler TF, Thompson RC. Novel glycopeptide antibiotics: N-alkylated derivatives active against vancomycin-resistant *enterococci*. J Antibiot (Tokyo). Jun. 1998;51(6):560-9.
Thayer DA, Wong CH. Vancomycin analogues containing monosaccharides exhibit improved antibiotic activity: a combined one-pot enzymatic glycosylation and chemical diversification strategy. Chem Asian J. Sep. 18, 2006;1(3):445-52.
Fu X, Albermann C, Jiang J, Liao J, Zhang C, Thorson JS. Antibiotic optimization via in vitro glycorandomization. Nat Biotechnol. Dec. 2003;21(12):1467-9.
Melançon CE 3rd, Thibodeaux CJ, Liu HW. Glyco-stripping and glyco-swapping. ACS Chem Biol. Sep. 19, 2006;1(8):499-504.
Balzarini J, Keyaerts E, Vijgen L, Egberink H, De Clercq E, Van Ranst M, Printsevskaya SS, Olsufyeva EN, Solovieva SE, Preobrazhenskaya MN. Inhibition of feline (FIPV) and human (SARS) coronavirus by semisynthetic derivatives of glycopeptide antibiotics. Antiviral Res. Oct. 2006;72(1):20-33.
Maffioli SI, Ciabatti R, Romanò G, Marzorati E, Preobrazhenskaya M, Pavlov A. Synthesis and antibacterial activity of alkyl derivatives of the glycopeptides antibiotic A40926 and their amides. Bioorg Med Chem Lett. Aug. 15, 2005;15(16):3801-5.
Fu X, Albermann C, Zhang C, Thorson JS. Diversifying vancomycin via chemoenzymatic strategies. Org Lett. Apr. 14, 2005;7(8):1513-5.
Kruger RG, Lu W, Oberthür M, Tao J, Kahne D, Walsh CT. Tailoring of glycopeptide scaffolds by the acyltransferases from the teicoplanin and A-40,926 biosynthetic operons. Chem Biol. Jan. 2005;12(1):131-40.
Ritter TK, Mong KK, Liu H, Nakatani T, Wong CH. A programmable one-pot oligosaccharide synthesis for diversifying the sugar domains of natural products: a case study of vancomycin. Angew Chem Int Ed Engl. Oct. 6, 2003;42(38):4657-60.
Balzarini J, Pannecouque C, De Clercq E, Pavlov AY, Printsevskaya SS, Miroshnikova OV, Reznikova MI, Preobrazhenskaya MN. Antiretroviral activity of semisynthetic derivatives of glycopeptide antibiotics. J Med Chem. Jun. 19, 2003;46(13):2755-64.
Chen Z, Eggert US, Dong SD, Shaw SJ, Sun B, LaTour JV, Kahne D. Structural Requirements for VanA activity of vancomycin analogues. Tetrahedron. 2002; 58: 6585-6594.
Blizzard TA, Kim RM, Morgan JD 2nd, Chang J, Kohler J, Kilburn R, Chapman K, Hammond ML. Antibacterial activity of G6-quaternary ammonium derivatives of a lipophilic vancomycin analogue. Bioorg Med Chem Lett. Mar. 25, 2002;12(6):849-52.
Nicolaou KC, Cho SY, Hughes R, Winssinger N, Smethurst C, Labischinski H, Endermann R. Solid- and solution-phase synthesis of vancomycin and vancomycin analogues with activity against vancomycin-resistant bacteria. Chemistry. Sep. 3, 2001;7(17):3798-823.
Kerns R, Dong SD, Fukuzawa S, Carbeck J, Kohler J, Silver L, Kahne D. The Role of Hydrophobic Substituents in the Biological Activity of Glycopeptide Antibiotics. J. Am. Chem. Soc. 2000; 122: 12608-12609.
Pavlov AY, Preobrazhenskaya MN, Malabarba A, Ciabatti R. Synthesis and antibacterial activity of derivatives of the glycopeptide antibiotic A-40926 N-alkylated at the aminoglucuronyl moiety. J Antibiot (Tokyo). May 1998;51(5):525-7.
Nagarajan R. Structure-activity relationships of vancomycin-type glycopeptide antibiotics. J Antibiot (Tokyo). Aug. 1993;46(8):1181-95.
Hubbard BK, Walsh CT. Vancomycin assembly: nature's way. Angew Chem Int Ed Engl. Feb. 17, 2003;42(7):730-65.
Parenti F, Cavalleri B. Proposal to name the vancomycin-ristocetin like glycopeptides as dalbaheptides. J Antibiot (Tokyo). Dec. 1989;42(12):1882-3.
Rao AVR, Gurjar MK, Reddy KL, Rao AS. Studies Directed toward the Synthesis of Vancomycin and Related Cyclic Peptides. Chem. Rev. 1995; 95: 2135-2167.
Nicolaou KC, Boddy CN, Brase S, Winssinger N. Chemistry, Biology, and Medicine of the Glycopeptide Antibiotics. Angew Chem Int Ed Engl. Aug. 1999;38(15):2096-2152.
Van Bambeke F, Van Laethem Y, Courvalin P, Tulkens PM. Glycopeptide antibiotics: from conventional molecules to new derivatives. Drugs. 2004;64(9):913-36.

(56) References Cited

OTHER PUBLICATIONS

Kahne D, Leimkuhler C, Lu W, Walsh C. Glycopeptide and lipoglycopeptide antibiotics. Chem Rev. Feb. 2005;105(2):425-48.
Gerhard U, Mackay JP, Maplestone RA, Williams DH. The Role of the Sugar and Chlorine Substituents in the Dimerization of Vancomycin Antibiotics. J. Am. Chem. Soc. 1993; 115: 232-237.
Pace JL, Yang G. Glycopeptides: Update on an old successful antibiotic class. Biochem Pharmacol. Mar. 30, 2006;71(7):968-80.
Ward KE, Mersfelder TL, LaPlante KL. Oritavancin—an investigational glycopeptide antibiotic. Expert Opin Investig Drugs. Apr. 2006;15(4):417-29.
Williams DH and Bardsley B. The Vancomycin Group of Antibiotics and the Fight against Resistant Bacteria. Angew. Chem. Int. Ed. 1999; 38: 1172-1193.
Malabarba A, Nicas TI, Ciabatti R. Glycopeptide resistance in multiple antibiotic-resistant Gram-positive bacteria: a current challenge for novel semi-synthetic glycopeptides derivatives. Eur. J. Med. Chem. 1997; 32: 459-478.
Yoshida O, Yasukata T, Sumino Y, Munekage T, Narukawa Y, Nishitani Y. Novel semi-synthetic glycopeptide antibiotics active against methicillin-resistant *Staphylococcus aureus* (MRSA) and vancomycin-resistant *Enterococci* (VRE): doubly-modified water-soluble derivatives of chloroorienticin B. Bioorg Med Chem Lett. Nov. 4, 2002;12(21):3027-31.
Judice JK, Pace JL. Semi-synthetic glycopeptide antibacterials. Bioorg Med Chem Lett. Dec. 1, 2003;13(23):4165-8.
Nagarajan R, Berry DM, Schabel AA. The structural relationships of A82846B and its hydrolysis products with chloroorienticins A, B and C. J Antibiot (Tokyo). Sep. 1989;42(9):1438-40.

J. P. Mackay et al., "Glycopeptide Antibiotic Activity and the Possible Role of Dimerization: A Model for Biological Signaling", J. Am. Chem. Soc., vol. 116, No. 11, pp. 4581-4590, 1994.
J. P. Mackay et al., "Dissection of the Contributions toward Dimerization of Glycopeptide Antibiotics", J. Am. Chem. Soc., vol. 116, No. 11, pp. 4573-4580, 1994.
G. J. Sharman et al., "The Roles of Dimerization and Membrane Anchoring in Activity of Glycopeptide Antibiotics Against Vancomycin-Resistant Bacteria", J. Am. Chem. Soc., vol. 119, No. 50, pp. 12041-12047, 1997.
U. N. Sundram et al., "Novel Vancomycin Dimers with Activity Against Vancomycin-Resistant *Enterococci*", J. Am. Chem. Soc., vol. 118, No. 51, pp. 13107-13108, 1996.
M. N. Preobrazhenskaya et al., Patents on Glycopeptides of the Vancomycin Family and their Derivatives as Antimicrobials, Expert Opinion Ther. Patents, vol. 14, No. 2, pp. 141-173, 2004.
J. F. Barrett, "Recent developments in glycopeptide antibacterials", Current Opinion in Investigational Drugs, vol. 6, No. 8, pp. 781-790, 2005.
N. Reyes et al., "Efficacy of Telavancin (TD-6424), a Rapidly Bactericidal Lipoglycopeptide with Multiple Mechanisms of Action, in a Murine Model of Pneumonia Induced by Methicillin-Resistant *Staphylococcus aureus*", Antimicrobial Agents and Chemotherapy, vol. 49, No. 10, pp. 4344-4346, Oct. 2005.
US Office Action issued Jul. 6, 2011 in co-pending U.S. Appl. No. 12/224,443.
F. Parenti et al., "Novel Glycopeptide Antibiotics of the Dalbaheptide Group", Drugs of the Future, vol. 15, No. 1, 1990, pp. 57-72.
Aldo Trani et al., "Carboxyhydrazides of the Aglycone of Teicoplanin Synthesis and Antibacterial Activity", The Journal of Antibiotics, vol. XLIII, No. 11, 1990, pp. 1471-1481.

* cited by examiner

GLYCOPEPTIDE ANTIBIOTIC MONOMER DERIVATIVES

This application is a U.S. national stage of International Application No. PCT/JP2005/021587 filed Nov. 24, 2005.

TECHNICAL FIELD

The invention relates to a glycopeptide antibiotic derivative and a pharmaceutical formulation comprising such derivative.

BACKGROUND OF THE INVENTION

Glycopeptide antibiotics, which have a complex polycyclic peptide structure, are produced in various microorganism and effective to most gram-positive bacteria as an antimicrobial. In recent years, there are emergences of drug-resistant strains such as penicillin-resistant, cephalosporin-resistant, and serious problems of infections with multidrug resistant and methicillin-resistant *Staphylococcus aureus* (MRSA) has been raised in clinical practice. Glycopeptide antibiotics, such as vancomycin, are effective typically to these resistant strains, and vancomycin has been a drug as an ultimate tool for infections with MRSA and other resistant strains.

In certain strains, however, there is growing concern of emergence of resistance to vancomycin, such as vancomycin-resistant enterococci (VRE). VRE has a different mechanism and degree of resistance, depending on the gene type of a resistance-related gene such as Van A, B, C, D, E, G. For example, teicoplanin, which is a glycopeptide antibiotic as with vancomycin, is effective to Van B type VRE. On the other hand, effective glycopeptide antibiotic has not been released for Van A type VRE, while clinical measures to fight such resistant strain is especially needed. Furthermore, *Staphylococcus aureus* that has acquired the resistance of VRE (VRSA) has been discovered recently. Therefore, need for development of glycopeptide derivative having improved activity and/or selectivity exists. Many vancomycins and other glycopeptide derivatives have been known in the art. See, e.g., references as follows.
(1) Japanese Patent Publication 61-251699
(2) Japanese Patent Publication 7-258289
(3) WO96/30401
(4) WO00/39156
(5) Japanese Patent Publication 2000-302687
(6) WO2004/44222
(7) WO2001/81372

SUMMARY OF THE INVENTION

The invention relates to a novel glycopeptide antibiotic derivative that has an increased and improved property compared with that of conventional glycopeptide antibiotics. Certain glycopeptide derivatives of the invention, particularly vancomycin derivatives, show an increased antimicrobial activity compared with vancomycin itself.

The invention provides:
(1) A compound of the formula:
(aglycon part of glycopeptide antibiotic derivative)-(Sac-NH)—$R^4$ or a pharmaceutically acceptable salt or solvate thereof, wherein,
"(aglycon part of glycopeptide antibiotic derivative)" is a part of known glycopeptide antibiotic derivative from which a sugar moiety has been removed:
"(Sac-NH)" is an amino sugar or an amino sugar-containing sugar chain;

$R^4$ is presented by the formula:

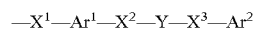

wherein $X^1$, $X^2$ and $X^3$ are independently
1) single bond;
2) a heteroatom-containing group selected from the group consisting of —N=, =N—, —$NR^1$— wherein $R^1$ is hydrogen or lower alkyl, —O—, —S—, —SO— and —$SO_2$—, or a linkage thereof; or
3) optionally substituted alkylene or alkenylene optionally interrupted by one or more same or different heteroatomic group;

Y is —$NR^2CO$—, —$CONR^2$— wherein $R^2$ is hydrogen or lower alkyl, or a group of the formula:

[Formula 1]

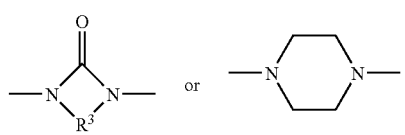

wherein $R^3$ is alkylene; and $Ar^1$ and $Ar^2$ are independently a carbocycle or heterocycle which is optionally substituted and may have an unsaturated bond.

Preferably, the formula:

[Formula 2]

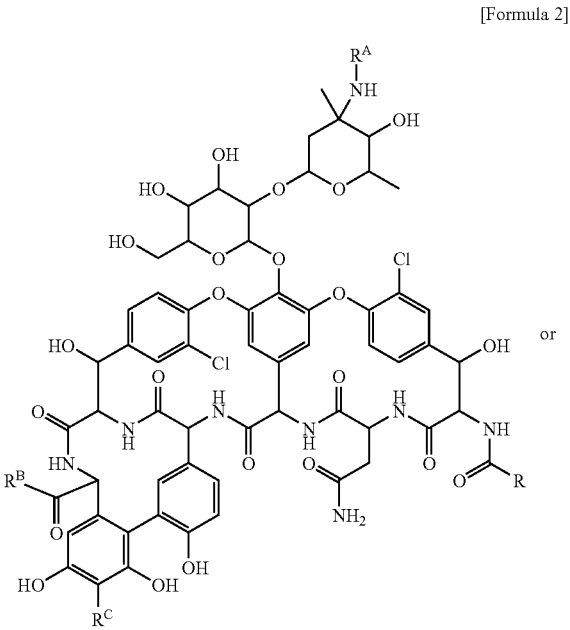

or

-continued

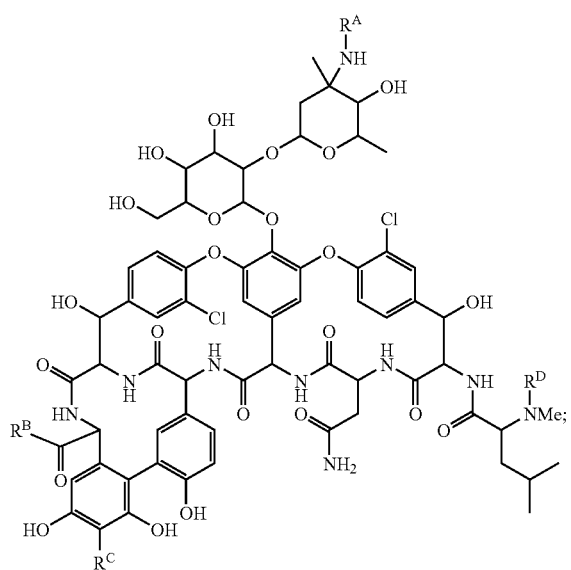

[Formula 3]

more preferably, the formula:

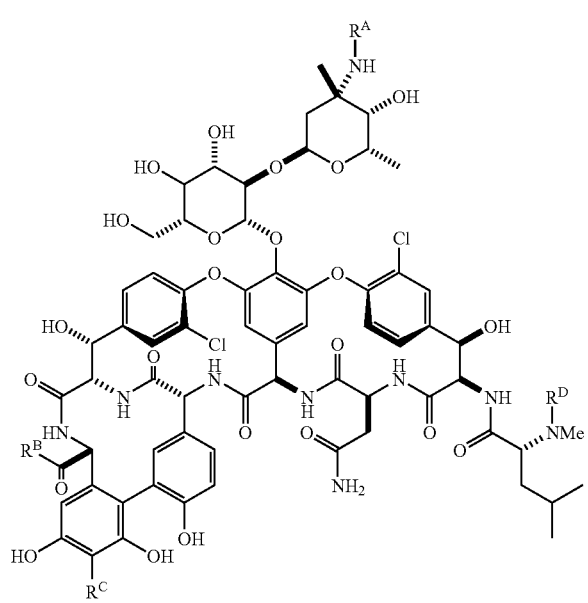

[Formula 4]

wherein,

R$^A$ is as defined above;

R$^B$ is —OH, —NR$^5$R$^{5'}$ wherein R$^5$ and R$^{5'}$ are independently hydrogen, optionally substituted alkyl, —NH—R, —NH—COR, —NH—CONHR, —O—R wherein each R is independently hydrogen or optionally substituted alkyl or amino sugar residue, or —OR$^6$ wherein R$^6$ is optionally substituted alkyl that may comprise a heteroatomic group;

R$^C$ is hydrogen or optionally substituted alkyl that may comprise a heteroatomic group, preferably —NH—; and R$^D$ is hydrogen or lower alkyl, R is optionally substituted alkyl, with the proviso that (aglycon part of glycopeptide antibiotic derivative)-(Sac-NH) moiety is not represented by the formula:

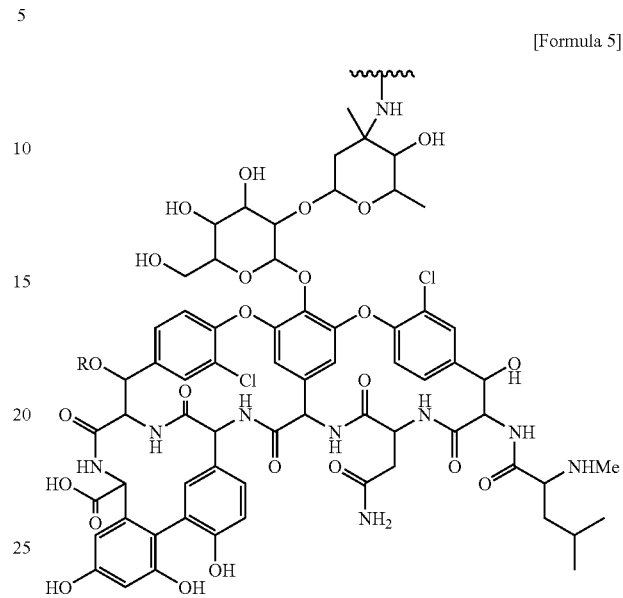

[Formula 5]

wherein R is sugar residue.

(2) A pharmaceutical formulation, preferably an antimicrobial formulation, comprising the compound, pharmaceutically acceptable salt or solvate thereof of the present invention as described above.

The invention is also relates to a compound, a pharmaceutically acceptable salt or solvate thereof as described above in (1) and a pharmaceutical composition as described above in (2), excluding that R$^A$ is 4-(monofluorobenzoylamino)benzyl.

The invention is also relates to a compound, a pharmaceutically acceptable salt or solvate thereof as described above in (1) and a pharmaceutical composition as described above in (2), excluding that Ar$^1$ is phenylene, Y is —NR$^2$CO—, and Ar$^2$ is monofluorophenyl.

The invention is also relates to a compound, a pharmaceutically acceptable salt or solvate thereof as described above in (1) and a pharmaceutical composition as described above in (2), excluding that Ar$^2$ is monofluorophenyl.

The invention is also relates to a compound, a pharmaceutically acceptable salt or solvate thereof, and a pharmaceutical formulation, preferably antimicrobial formulation comprising the same, as described in the following (3) to (18).

(3) The compound according to (1) wherein Y is —NR$^2$CO— or —CONR$^2$— wherein R$^2$ is hydrogen or lower alkyl;

(4) The compound according to (1) wherein Ar$^1$ and Ar$^2$ are optionally substituted aryl, or optionally substituted heteroaryl, optionally substituted heterocycle, or optionally substituted cycloalkyl;

(5) The compound according to (1) wherein Ar$^1$ and Ar$^2$ are optionally substituted aryl, optionally substituted heteroaryl, optionally substituted heterocycle, or optionally substituted cycloalkyl, and Y is —NHCO— or —CONH—;

(6) The compound according to (1) wherein X$^1$ is lower alkylene;

(7) The compound according to (1) wherein X$^2$ is a single bond, lower alkylene or a heteroatomic group as described above;

(8) The compound according to (1) wherein $X^3$ is a single bond, lower alkylene or a heteroatomic group as described above (9) The compound according to (1) wherein $X^1$ is lower alkylene; $X^2$ is a single bond, lower alkylene or a heteroatomic group as described above; $X^3$ is a single bond, lower alkylene or a heteroatomic group as described above; Y is —NHCO— or —CONH—; $Ar^1$ is optionally substituted phenyl, optionally substituted heteroaryl, optionally substituted heterocycle, or optionally substituted cycloalkyl; and $Ar^2$ is optionally substituted phenyl, optionally substituted heterocycle or optionally substituted cycloalkyl.

(10) The compound according to (1) wherein $X^1$ is lower alkylene; $X^2$ and $X^3$ are independently a single bond, lower alkylene or a heteroatomic group as described above; Y is a group of the formula:

[Formula 6]

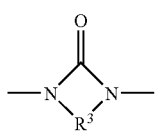

wherein $R^3$ is alkylene;

$Ar^1$ is optionally substituted phenyl, optionally substituted heteroaryl, optionally substituted heterocycle, or optionally substituted cycloalkyl; and $Ar^2$ is optionally substituted aryl, optionally substituted heterocycle or optionally substituted cycloalkyl;

(11) The compound of any one of (1) to (10) wherein $Ar^2$ is any one of aryl, heterocycle or fused rings of the formula:

[Formula 7]

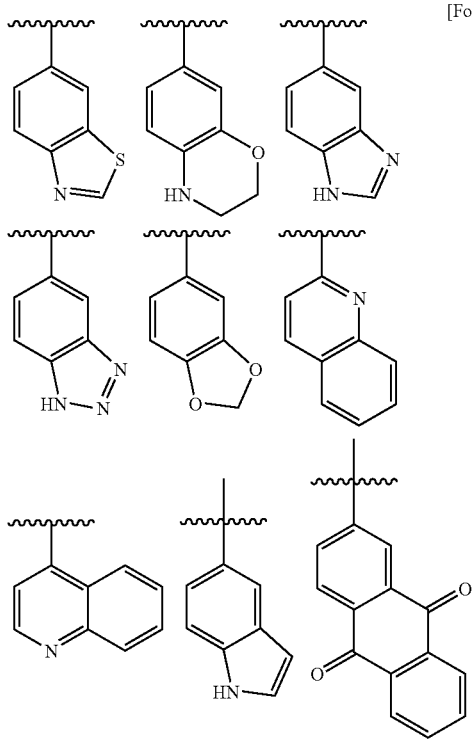

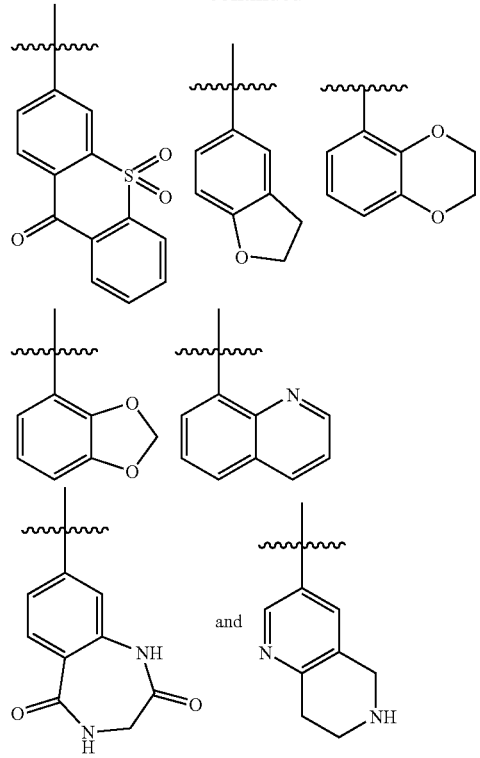

that is optionally substituted with one or more of the substituent selected from the group consisting of lower alkyl, lower alkoxy, cycloalkyl, aryloxy, aralkyloxy, optionally substituted aryloxy lower alkyl, optionally substituted aryloxycarbonyl, lower alkoxycarbonyl, nitro, hydroxy, carboxy, cyano, oxo, $SO_2NH_2$, $SO_2Me$, $SO_2$-cyclic amino, optionally substituted amino, optionally substituted carbamoyl, optionally substituted carbamoyloxy, halo, lower alkyl halide, lower alkoxy halide, lower alkylthio halide, lower alkylcarbonyl halide, heterocyclo lower alkyl, heterocyclo lower alkoxy, cycloalkyl lower alkoxy, aralkyloxy, optionally substituted heteroaryl, optionally substituted heteroaryl-lower alkyl, optionally substituted heteroaryl-lower alkyloxy, heterocycle, heterocycle lower alkyloxy, optionally substituted aryl, and optionally substituted heteroaryl;

(12) The compound of any one of (1) to (10) wherein $Ar^2$ is aryl that is optionally substituted with one or more of the substituent selected from the group consisting of halo, mono-, di- or tri-halogenated lower alkyl, mono-, di- or tri-halogenated lower alkoxy, mono-, di- or tri-halogenated lower alkylthio, mono- or di-lower alkylamino, cycloalkylmethyloxy, benzyloxy, lower alkoxycarbonylamino, nitro;

(13) The compound of any one of (1) to (12) wherein $Ar^1$ is phenyl optionally substituted with an optionally substituted amino;

(14) The compound of any one of (1) to (12) wherein $Ar^1$ is optionally substituted heteroaryl;

(15) The compound of any one of (1) to (12) wherein $X^1$ is lower alkylene; $X^2$ is a single bond, lower alkylene or a heteroatomic group as described above; $X^3$ is a single bond, lower alkylene or heteroatomic group; Y is —NHCO— or —CONH—; $Ar^1$ is optionally substituted heteroaryl; and $Ar^2$ is optionally substituted phenyl, optionally substituted heterocycle or optionally substituted cycloalkyl;

(16) The compound as described preferably in (1) or of any one of (3) to (15) wherein $R^B$ is —OH; $R^C$ is hydrogen; and $R^D$ is hydrogen;

(17) The compound as described preferably in (1) or of any one of (3) to (15) wherein $R^B$ is —$NR^5R^{5'}$ wherein $R^5$ and $R^{5'}$ are independently hydrogen, optionally substituted alkyl, —NH—R, —NH—COR, —NH—CONHR, —O—R wherein each R is independently hydrogen or optionally substituted alkyl, or amino sugar residue, $R^C$ is hydrogen; and $R^D$ is hydrogen;

(18) The compound as described preferably in (1) or any one of (3) to (15) wherein $R^B$ is —$NR^5R^{5'}$ wherein $R^5$ is hydrogen, $R^{5'}$ is alkyl-NH—R, —NH—COR, —NH—CONHR, —O—R wherein each R is independently hydrogen or optionally substituted alkyl, or amino sugar residue, which are substituted with a hydrophilic substituent, $R^C$ is hydrogen; and $R^D$ is hydrogen.

The invention is also related to a compound as described above in (1) of the formula:

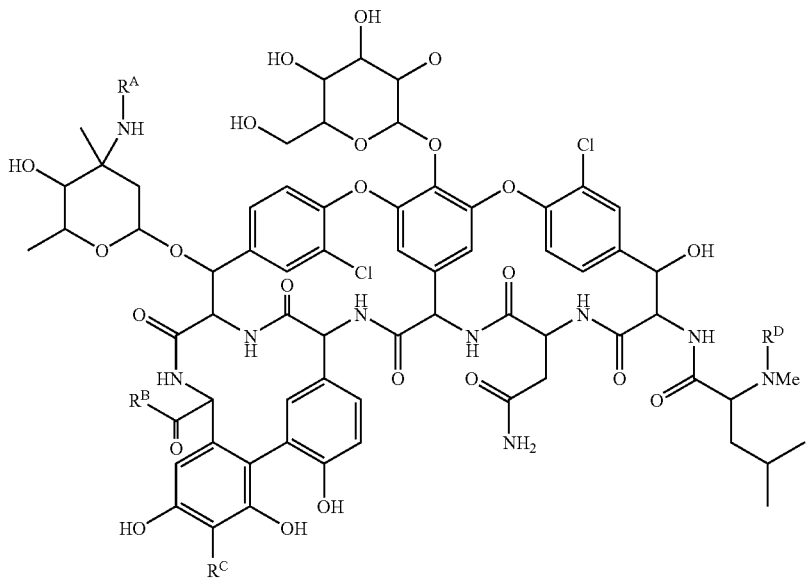

and a pharmaceutically acceptable salt or solvate thereof, wherein, $R^A$ is the formula —$X^1$—$Ar^1$—$X^2$—Y—$X^3$—$Ar^2$
wherein, $X^1$, $X^2$ and $X^3$ are independently
1) single bond;
2) heteroatom or heteroatomic group, selected from the group consisting of —N=, =N—, —$NR^1$—, —O—, —S—, —SO— and —$SO_2$— wherein $R^1$ is hydrogen or lower alkyl; or
3) optionally substituted alkylene or alkenylene optionally interrupted by one or more same or different heteroatomic group;
Y is —$NR^2CO$—, —$CONR^2$— wherein $R^2$ is hydrogen or lower alkyl, or a group represented by the formula:

[Formula 9]

wherein $R^3$ is alkylene;
$Ar^1$ and $Ar^2$ are independently a carbocycle or heterocycle which is optionally substituted and may have an unsaturated bond;
$R^B$ is —OH or —$NR^5R^{5'}$ wherein $R^5$ and $R^{5'}$ are independently hydrogen or optionally substituted alkyl;
$R^C$ is hydrogen or optionally substituted alkyl that may comprise a heteroatomic group; and
$R^D$ is hydrogen or lower alkyl.

The invention is also related to the compound represented by the formula of [formula 7] and a pharmaceutically acceptable salt or solvate thereof, wherein $X^1$ is lower alkylene; $X^2$ is a single bond or lower alkylene that may comprise a heteroatomic group; $X^3$ is a single bond; Y is —NHCO— or —CONH—; $Ar^1$ is optionally substituted phenyl; and $Ar^2$ is optionally substituted phenyl and $R^B$ is OH, $R^C$ and $R^D$ are hydrogen.

Effect of the Invention

The glycopeptide antibiotic derivative of the invention, a pharmaceutically acceptable salt, or solvate thereof shows an antimicrobial activity against various microorganisms such as *staphylococcus* including MRSA, *streptococcus*, pneumococcus and *enterococcus*. The compound is also effective against vancomycin-resistant strains thereof, particularly vancomycin-resistant *enterococcus* (VRE) and vancomycin-resistant *staphylococcus aureus* (VRSA). Thus, the compound is useful in the treatment or prevention of various bacterial infectious diseases such as meningitis, sepsis, pneumonia, arthritis, peritonitis, bronchitis, empyema and the like. The more preferred compound of the invention is highly water-soluble and shows good pharmacokinetics and/or is safe with respect to toxicity.

DETAILED DESCRIPTION OF THE PREFERRED EMBODIMENTS (1) Compound

In order to describe the compound of the invention, the terms as used herein have the following meaning solely or in combination with other terms as used herein.

The term "Glycopeptide antibiotic derivative aglycone part" refers to a moiety remaining after removal of a sugar moiety as described bellow, from a known glycopeptide antibiotic derivative characterized by polycyclic peptide core optionally substituted with a sugar group. One or more, preferably one "sugar moiety" may be removed. For example, in case that glycopeptide antibiotic derivative is vancomycin, the aglycone part is that remaining after the sugar chain (disaccharide) moiety containing an amino sugar (i.e. α-L-vancosaminyl-β-D-glucopyranose). Also, vancomycin derivatives having a modification at the N-terminal of the peptide chain, such as that having removal of the N-methyl-D-leucine and its acylated form, was known (Expert Opin. Ther. Patents (2004) 14, 141-173). Thus, the aglycone part includes such part of these vancomycin derivatives, from which "sugar moiety" has been removed as described above. Known glycopeptide antibiotic derivatives can be found in: Japanese Patent Publication 61-251699, Japanese Patent Publication 7-258289; WO96/30401; WO00/39156; Japanese Patent Publication 2000-302687; WO2004/44222; U.S. Pat. Nos. 4,639,433; 4,643,987; 4,497,802; 4,698,327; 5,591,714; 5,840,684; and 5,843,889; EP0802199; EP0801075; EP0667353; WO97/28812; WO97/38702; WO98/52589; WO98/52592; and J. Am. Chem. Soc., 1996, 118, 13107-13108; J. Am. Chem. Soc., 1997, 119, 12041-12047; and J. Am. Chem. Soc., 1994, 116, 4573-4590.

Specifically, the compound of the invention can be selected from the group consisting of the following compounds.

The compound of the formula:

or a pharmaceutically acceptable salt or solvate thereof, wherein, $R$ and $R_1$ is independently hydrogen or methyl;

$R_2$ and $R_3$ is independently hydrogen or, a group of the formula $R_6R_7CH—$, wherein $R_6$ and $R_7$ is independently $R_5$, $R_5—(C_1-C_5)$-alkyl or $R_5—(C_2-C_5$-alkenyl), wherein $R_5$ is hydrogen, $C_1-C_{10}$-alkyl, $C_2-C_{10}$-alkenyl, $C_1-C_4$-alkoxy, $C_3-C_{10}$-cycloalkyl, $C_5-C_{12}$-cycloalkenyl, phenyl, naphthyl, indenyl, tetralinyl, decalinyl, adamantyl, a monocyclic heteroring containing 3-8 heteroatoms or bicyclic heteroring containing 6-11 heteroatoms, with the proviso that at least one of these atoms is carbon, at least one of these heteroatoms is selected form O, N and S, and $R_5$ is optionally substituted with one or more selected from hydroxy, nitro, $C_1-C_{10}$-alkoxy, $C_1-C_{10}$-alkyl, phenyl, $C_1-C_6$-alkylthio, nitrile, halo, $C_2-C_4$-acylamino, amino, $C_1-C_4$-dialkylamino;

$R_4$ is hydrogen, or $R_1$ and $R_2$, and/or $R_3$ and $R_4$ together represent a group of the formula:

[Formula 11]

wherein $R_6$ and $R_7$ are $R_5$, $R_5—(C_1-C_5$-alkyl) or $R_5—(C_2-C_5$-alkenyl);

N is 1 or 2, with the proviso that: (i) at least one of $R_2$ and $R_3$ is not hydrogen, (ii) when n is 2, then R is hydrogen, (iii) when R is methyl and $R_3$ is hydrogen, then $R_2$ is not methyl, (iv) when R and $R_1$ are both hydrogen, then $R_2$ is hydrogen or methyl and n is 1

(Japanese Patent Publication 61-251699).

[Formula 10]

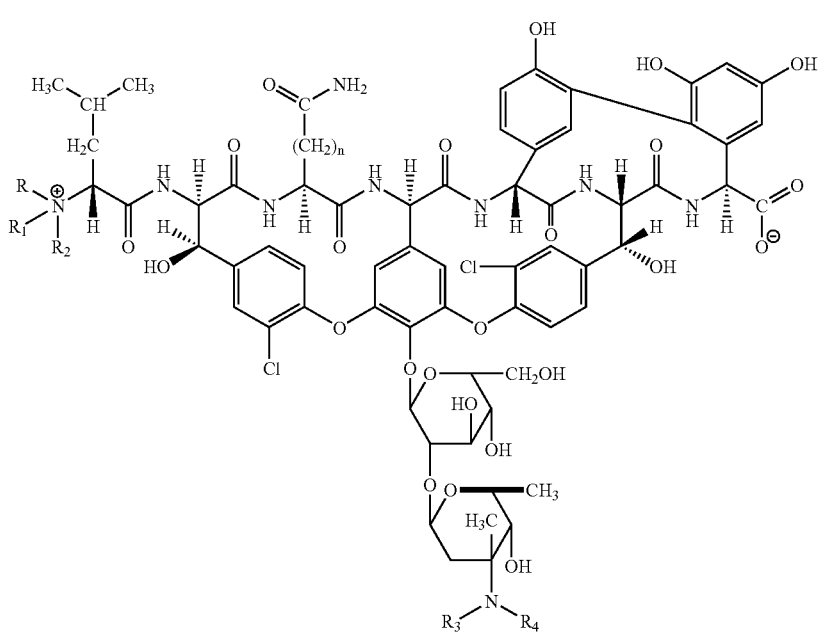

The compound of the formula:

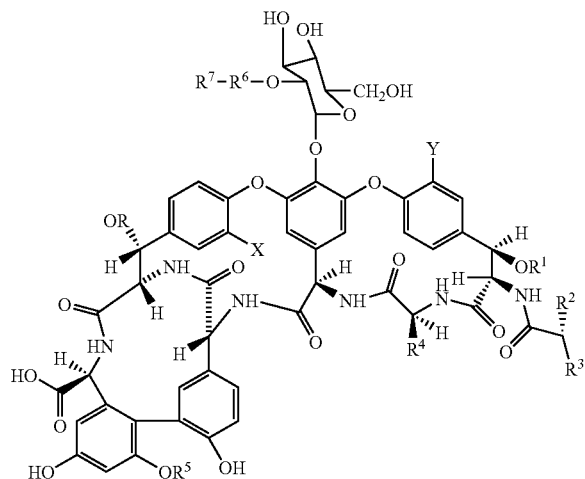

or a pharmaceutically acceptable salt or solvate thereof, wherein,

X and Y is independently hydrogen or chloro;

R is hydrogen, 4-epi-vancosaminyl, actinosaminyl or ristosaminyl;

$R^1$ is hydrogen or mannose;

$R^2$ is —$NH_2$, —$NHCH_3$ or —$N(CH_3)_2$;

$R^3$ is —$CH_2CH(CH_3)_2$, [p-OH, m-Cl]phenyl, p-rhamnosephenyl, [p-rhamnose-galactose]phenyl, [p-galactose-galactose]phenyl or [p-$CH_3$O-rhamnose]phenyl;

$R^4$ is —$CH_2$ $(CO)NH_2$, benzyl, [p-OH]phenyl or [p-OH, m-Cl]phenyl;

$R^5$ is hydrogen or mannose;

$R^6$ is 4-epi-vancosaminyl, L-acosaminyl, L-ristosaminyl or L-actinosaminyl;

$R^7$ is $(C_2-C_{16})$alkenyl, $(C_2-C_{12})$alkynyl, $(C_1-C_{12})$alkyl-$R^8$, $(C_1-C_{12}$-alkyl)-halo, $(C_2-C_6$-alkenyl)-$R^8$, $(C_2-C_6$-alkynyl)-$R^8$, $(C_1-C_{12}$-alkyl)-O—$R^8$ and $R^7$ connects to the amino group of $R^6$;

$R^8$ is
a) polycyclic aryl unsubstituted or substituted with one or more independently selected from the group consisting of (i) hydroxy, (ii) halo, (iii) nitro, (iv) $(C_1-C_6)$-alkyl, (v) $(C_1-C_6)$-alkenyl, (vi) $(C_1-C_6)$-alkynyl, (vii) $(C_1-C_6)$-alkyl, $(C_1-C_6)$-alkoxy, (viii) halo-$(C_1-C_6)$-alkyl, (ix) halo-$(C_1-C_6)$-alkoxy, (x) carbo-$(C_1-C_6)$-alkoxy, (xi) carbobenzyloxy, (xii) $(C_1-C_6)$-alkyl, $(C_1-C_6)$-carbobenzyloxy substituted with alkoxy, halo or nitro, (xiii) a group of the formula: —$S(O)n'R^9$ wherein n' is 0-2, $R^9$ is $(C_1-C_6)$-alkyl, phenyl or phenyl substituted with $(C_1-C_6)$-alkyl, $(C_1-C_6)$-alkoxy, halo or nitro, and (xiv) a group of the formula: —$C(O)N(R^{10})_2$ wherein $R^{10}$ are independently hydrogen, $(C_1-C_6)$-alkyl, $(C_1-C_6)$-alkoxy, phenyl, or phenyl substituted with $(C_1-C_6)$-alkyl, $(C_1-C_6)$-alkoxy, halo or nitro;
b) heteroaryl unsubstituted or substituted with one or more selected independently from the group consisting of (i) halo, (ii) $(C_1-C_6)$-alkyl, (iii) $(C_1-C_6)$-alkoxy, (iv) halo-$(C_1-C_6)$-alkyl, (v) halo-$(C_1-C_6)$-alkoxy, (vi) phenyl, (vii) thiophenyl, (viii) phenyl substituted with halo, $(C_1-C_6)$-alkyl, $(C_1-C_6)$-alkenyl, $(C_1-C_6)$-alkynyl, $(C_1-C_6)$-alkoxy or nitro, (ix) carbo-$(C_1-C_6)$alkoxy, (x) carbobenzyloxy, (xi) carbobenzyloxy substituted with $(C_1-C_6)$-alkyl, $(C_1-C_6)$-alkoxy halo or nitro, (xii) a group of the formula: —$S(O)n'R^9$ as defined above, (xiii) a group of the formula: —$C(O)N(R^{10})_2$ as defined above and (xiv) thienyl;

c) a group of the formula:

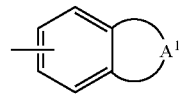

wherein, $A^1$ is —$OC(A^2)_2$-$C(A^2)_2$—$O$—, —$O$—$C(A^2)_2$-$O$—, —$C(A^2)_2$-$O$— or —$C(A^2)_2$-$C(A^2)_2$-$C(A^2)_2$-$C(A^2)_2$-, wherein each $A^2$ is independently selected from hydrogen, $(C_1-C_6)$-alkyl, $(C_1-C_6)$alkoxy and $(C_4-C_{10})$-cycloalkyl;

d) a group of the formula:

wherein, p is 1 to 5, $R^{11}$ is selected independently form the group consisting of (i) hydrogen, (ii) nitro, (iii) hydroxy, (iv) halo, (v) $(C_1-C_8)$-alkyl, (vi) $(C_1-C_6)$-alkoxy, (vii) $(C_9-C_{12})$-alkyl, (viii) $(C_2-C_9)$-alkynyl, (ix) $(C_9-C_{12})$-alkoxy, (x) $(C_1-C_3)$-alkoxy, substituted with $(C_1-C_3)$-alkoxy, hydroxy, halo-$(C_1-C_3)$-alkoxy or $(C_1-C_4)$alkylthio, (xi) $(C_2-C_5)$-alkenyloxy, (xii) $(C_1-C_{13})$-alkynyloxy, (xiii) halo-$(C_1-C_6)$-alkyl, (xiv) halo-$(C_1-C_6)$-alkoxy, (xv) $(C_2-C_6)$-alkylthio, (xvi) $(C_2-C_{10})$-alkanoyloxy, (xvii) carboxy-$(C_2-C_4)$-alkenyl, (xviii) $(C_1-C_3)$-alkylsulfonyloxy, (xix) carboxy-$(C_1-C_3)$-alkyl, (xx) N-[di$(C_1-C_3)$alkyl]amino-$(C_1-C_3)$alkoxy, (xxi) cyano-$(C_1-C_6)$-alkoxy and (xxii) diphenyl-$(C_1-C_6)$-alkyl, with the proviso that: when $R^{11}$ is $(C_1-C_8)$-alkyl, $(C_1-C_8)$-alkoxy or halo, then P is 2 or more, and when $R^7$ is $(C_1-C_3$-alkyl)-$R^8$, then $R^{11}$ is not hydrogen, $(C_1-C_8)$-alkyl, $(C_1-C_8)$-alkoxy or halo;

e) a group of the formula:

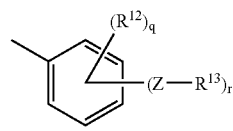

wherein, q is 0 to 4, $R^{12}$ is selected independently from the group consisting of (i) halo, (ii) nitro, (iii) $(C_1-C_6)$-alkyl, (iv) $(C_1-C_6)$-alkoxy, (v)

halo-(C₁-C₆)-alkyl, (vi) halo-(C₁-C₆)-alkoxy and (vii) hydroxy and (vii) (C₁-C₆)-thioalkyl, r is 1 to 5, with the proviso that q+r is not more than 5, Z is selected independently from the group consisting of (i) single bond, (ii) divalent ($C_1$-$C_6$)-alkyl, unsubstituted or substituted with hydroxy, ($C_1$-$C_6$)-alkyl or ($C_1$-$C_6$)-alkoxy, (iii) divalent ($C_2$-$C_6$)-alkenyl, (iv) divalent ($C_2$-$C_6$)-alkynyl, or (v) a group of the formula: —(C($R^{14}$)₂)s-$R^{15}$— or —$R^{15}$—(C($R^{14}$)₂)s- wherein, S is 0-6, $R^{14}$ are independently selected from hydrogen, ($C_1$-$C_6$)-alkyl or ($C_4$-$C_{10}$)-cycloalkyl, $R^{15}$ is a group selected from —O—, —S—, —SO—, —SO₂—, —SO₂—O—, —C(O)—, —OC(O)—, —C(O)O—, —NH—, —N($C_1$-$C_6$-alkyl)- and —C(O)NH—, —NHC(O)—, —N═N—, $R^{13}$ is selected independently from the group consisting of (i) ($C_4$-$C_{10}$)-heterocyclyl, (ii) heteroaryl, (iii) ($C_4$-$C_{10}$)-cycloalkyl unsubstituted or substituted with ($C_1$-$C_6$)-alkyl or (iv) phenyl unsubstituted or substituted with 1-5 substituents selected independently from the group consisting of halo, hydroxy, nitro, ($C_1$-$C_{10}$)-alkyl, ($C_1$-$C_{10}$)-alkoxy, halo-($C_1$-$C_3$)-alkoxy, halo-($C_1$-$C_3$)-alkyl, ($C_1$-$C_3$)-alkoxyphenyl, phenyl, phenyl-($C_1$-$C_3$)-alkyl, ($C_1$-$C_6$)-alkoxyphenyl, phenyl-($C_1$-$C_3$)-alkynyl and ($C_1$-$C_6$)-alkylphenyl;

f) ($C_4$-$C_{10}$)-cycloalkyl unsubstituted or substituted with one or more selected independently from the group consisting of (i) ($C_1$-$C_6$)-alkyl, (ii) ($C_1$-$C_6$)-alkoxy, (iii) ($C_1$-$C_6$)-alkenyl, (iv) ($C_1$-$C_6$)-alkynyl, (v) ($C_4$-$C_{10}$)-cycloalkyl, (vi) phenyl, (vii) phenylthio, (viii) phenyl substituted with nitro, halo, ($C_1$-$C_6$)-alkanoyloxy or carbocycloalkoxy, and (ix) a group of the formula: —Z—$R^{13}$ wherein Z and $R^{13}$ is as defined above;

g) a group of the formula:

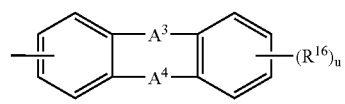

[Formula 16]

wherein, $A^3$ and $A^4$ are (i) a bond, (ii) —O—, (iii) —S(O)t- wherein t is 0 to 2, (iv) —C($R^{17}$)₂— wherein $R^{17}$ is independently selected from hydrogen, ($C_1$-$C_6$)-alkyl, hydroxy, ($C_1$-$C_6$)-alkyl, ($C_1$-$C_6$)-alkoxy, or both $R^{17}$s together represent O, (v) —N($R^{18}$)₂— wherein $R^{18}$ is independently selected from hydrogen, ($C_1$-$C_6$)-alkyl, ($C_1$-$C_6$)-alkenyl, ($C_1$-$C_6$)-alkynyl, ($C_4$-$C_{10}$)-cycloalkyl, phenyl, or phenyl substituted with nitro, halo or ($C_1$-$C_6$)-alkanoyloxy, or both $R^{18}$s together represent ($C_4$-$C_{10}$)-cycloalkyl, $R^{16}$ is $R^{12}$ or $R^{13}$ as defined above, and u is 0-4.

The compound of the formulae (1) and (2):

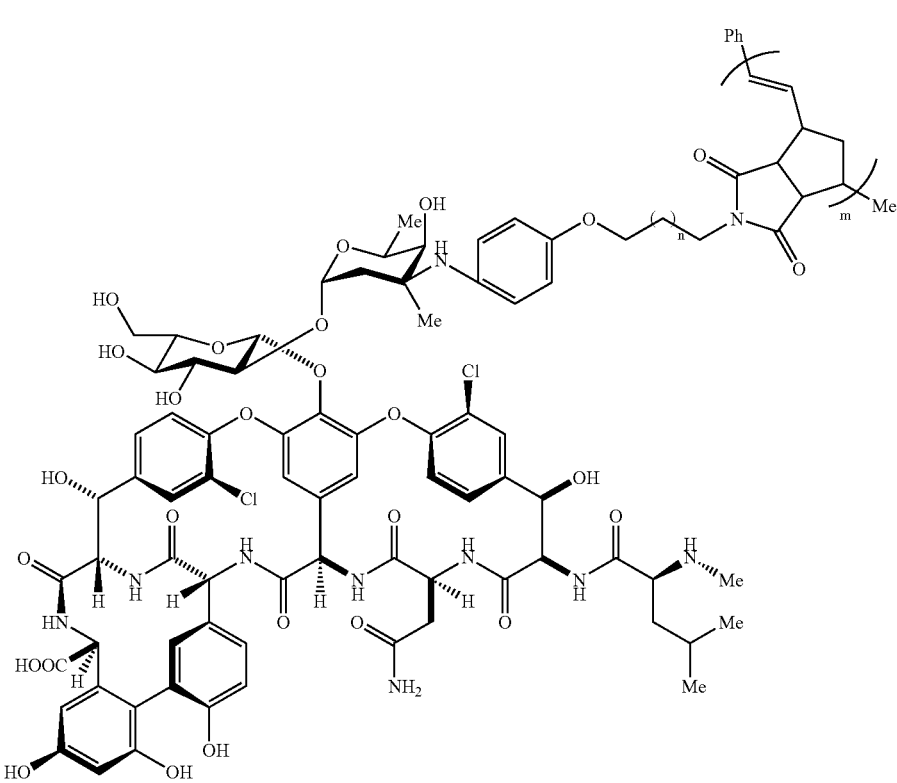

[Formula 17]

(1)

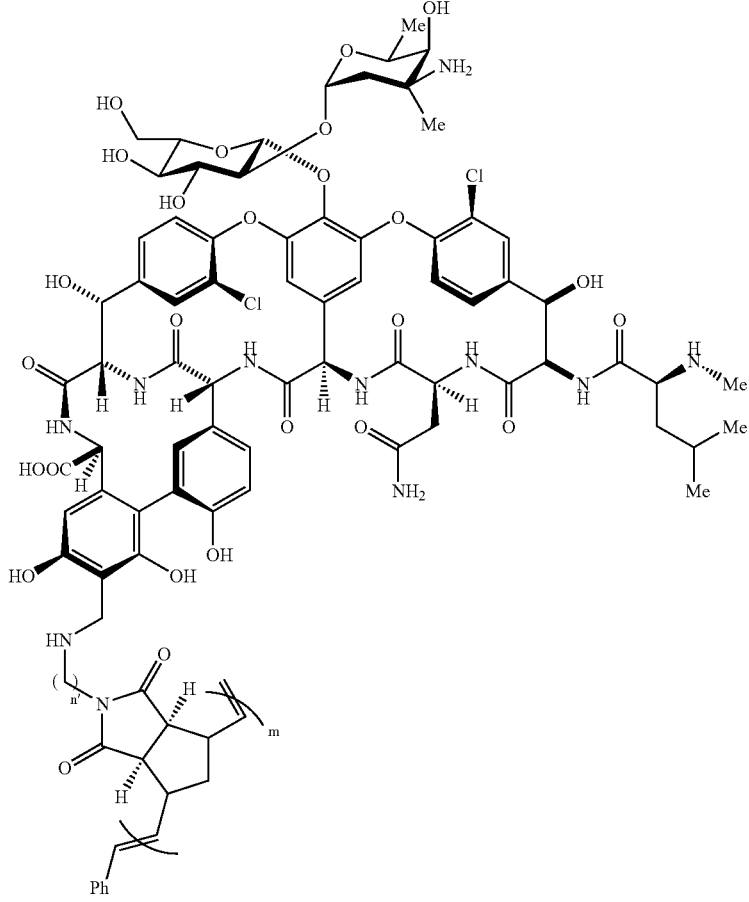

(2)

wherein,
   n is an integer from 0 to 10,
   n' is an integer from 1 to 12, and
   m is an integer from 2 to 60
(Japanese Patent Publication 2000-302687); or
   The compound of the formula I:

and a pharmaceutically acceptable salt, stereoisomer and prodrug thereof,
wherein,
   $R^1$ is selected from the group consisting of hydrogen, alkyl, substituted alkyl, alkenyl, substituted alkenyl, alkynyl, substituted alkynyl, cycloalkyl, substituted cycloalkyl, cycloalk-

[Formula 18]

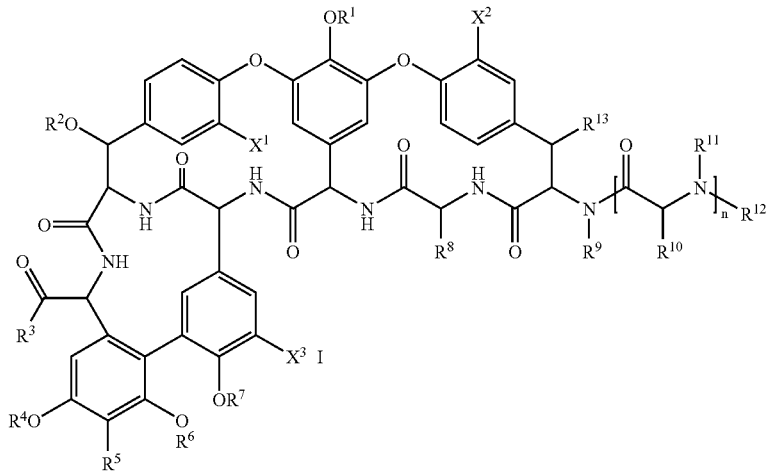

enyl, substituted cycloalkenyl, aryl, heteroaryl, heterocyclic ring and —$R^a$—Y—$R^b$—$(Z)_x$; or a saccharide group optionally substituted with —$R^a$—Y—$R^b$—$(Z)_x$;

$R^2$ is hydrogen, or a saccharide group optionally substituted with —$R^a$—Y—$R^b$—$(Z)_x$;

$R^3$ is —$OR^c$ or —$NR^cR^c$;

$R^4$ is selected from the group consisting of hydrogen, alkyl, substituted alkyl, alkenyl, substituted alkenyl, alkynyl, substituted alkynyl, —$R^a$—Y—$R^b$—$(Z)_x$, —$C(O)R^d$ and a saccharide group optionally substituted with —$R^a$—Y—$R^b$—$(Z)_x$;

$R^5$ is selected from the group consisting of hydrogen, halo, —$CH(R^c)$—$NR^cR^c$, —$CH(R^c)$—$NR^cR^e$ and —$CH(R^c)$—$NR^c$—$R^a$—Y—$R^b$—$(Z)_x$;

$R^6$ is selected from the group consisting of hydrogen, alkyl, substituted alkyl, alkenyl, substituted alkenyl, alkynyl, substituted alkynyl, —$R^a$—Y—$R^b$—$(Z)_x$, —$C(O)R^d$ and a saccharide group optionally substituted with —$NR^c$—$R^a$—Y—$R^b$—$(Z)_x$, or $R^5$ and $R^6$ together with the atom to which they are attached to form a heterocyclic ring optionally substituted with —$NR^c$—$R^a$—Y—$R^b$—$(Z)_x$;

$R^7$ is selected from the group consisting of hydrogen, alkyl, substituted alkyl, alkenyl, substituted alkenyl, alkynyl, substituted alkynyl, —$R^a$—Y—$R^b(Z)_x$, and —$C(O)R^d$;

$R^8$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic ring;

$R^9$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic ring;

$R^{10}$ is selected from the group consisting of alkyl and substituted alkyl;

$R^{11}$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic ring, or $R^{10}$ and $R^{11}$ together with the carbon and nitrogen atoms to which they are attached to form a heterocyclic ring;

$R^{12}$ is selected from the group consisting of hydrogen, alkyl, substituted alkyl and —$C(O)OR^d$;

$R^{13}$ is selected from the group consisting of hydrogen or —$OR^{14}$;

$R^{14}$ is selected from the group consisting of hydrogen, —$C(O)R^d$ and a saccharide group;

$R^a$ is independently selected from the group consisting of alkylene, substituted alkylene, alkenylene, substituted alkenylene, alkynylene and substituted alkynylene;

$R^b$ is independently selected from the group consisting of alkylene, substituted alkylene, alkenylene, substituted alkenylene, alkynylene and substituted alkynylene;

$R^c$ is independently selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic ring and —$C(O)R^d$ $R^d$ is independently selected from the group consisting of alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic ring;

$R^e$ is a saccharide group;

$X^1$, $X^2$ and $X^3$ are selected from the group consisting of hydrogen or chloro;

Y is selected independently from the group consisting of oxygen, sulphur, —S—S—, —$NR^c$—, —S(O)—, —$SO_2$—, —$NR^cC(O)$—, —$OSO_2$—, —OC(O)—, —$NR^cSO_2$—, —$C(O)NR^c$—, —C(O)O—, —$SO_2NR^c$—, —$SO_2O$—, —P(O) ($OR^c$) O—, —P(O) ($OR^c$) $NR^c$—, —$OP(O)(OR^c)$ O—, —$OP(O)(OR^c)NR^c$—, —OC(O)O—, —$NR^cC(O)$ O—, —$NR^cC(O)NR^c$—, —$OC(O)NR^c$— and —$NR^cSO_2NR^c$—;

Z is selected independently from the group consisting of hydrogen, aryl, cycloalkyl, cycloalkenyl, heteroaryl and heterocyclic ring;

n is, 0, 1 or 2; and

X is 1 or 2, with the proviso that at least one of $R^1$, $R^2$, $R^4R^5$, $R^6$ or $R^7$ is a group of the formula —$R^a$—Y—$R^b$—$(Z)_x$; and further that (i) when Y is —$NR^C$—, $R^C$ is 1 to 4 carbon alkyl, Z is hydrogen, and $R^b$ is alkylene, then $R^b$ contains at least five carbon atoms;

(ii) when Y is —$C(O)NR^c$—, Z is hydrogen, and $R^b$ is alkylene, then $R^b$ is at least five carbon atoms;

(iii) when Y is sulphur, Z is hydrogen, and $R^b$ is alkylene, then $R^b$ is at least seven carbon atoms; and (iv) when Y is oxygen, Z is hydrogen, and $R^b$ is alkylene, then $R^b$ is at least eleven carbon atoms (Japanese Patent Publication 2002-533472).

The compound of the formula I:

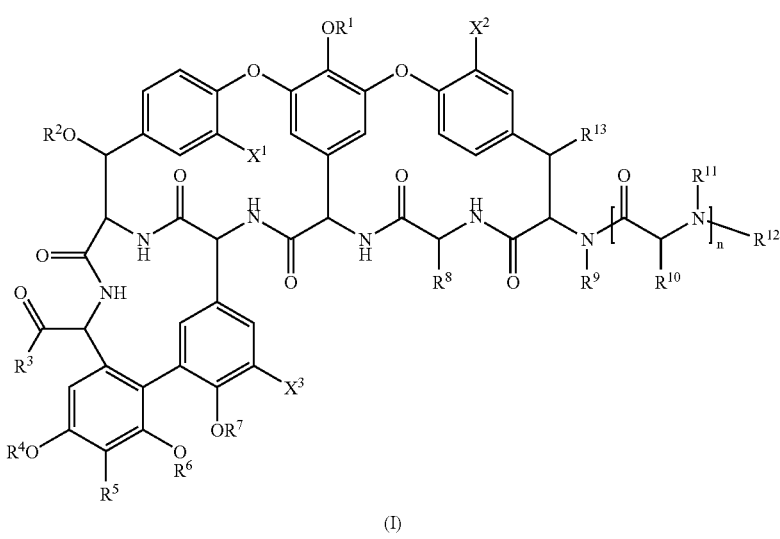

(I)

and a pharmaceutically acceptable salt, stereoisomer and prodrug thereof,
wherein, $R^1$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic ring and —$R^a$—Y—$R^b$—$(Z)_x$, or $R^1$ is a saccharide group optionally substituted with —$R^a$—Y—$R^b$—$(Z)_x$, $R^f$, —C(O)$R^f$ or —C(O)—$R^a$—Y—$R^b$—$(Z)_x$;

$R^2$ is hydrogen, or a saccharide group optionally substituted with —$R^a$—Y—$R^b$—$(Z)_x$, $R^f$, —C(O)$R^f$ or —C(O)—$R^a$—Y—$R^b$—$(Z)_x$;

$R^3$ is —$OR^c$, —$NR^cR^c$, —O—$R^a$—Y—$R^b$—$(Z)_x$, —$NR^c$—$R^a$—Y—$R^b$—$(Z)_x$, —$NR^CR^e$, or —O—$R^e$, or $R^3$ is a N-, O- or S-linked group containing one or more phosphono moiety;

$R^4$ is selected from the group consisting of hydrogen, alkyl, substituted alkyl, alkenyl, substituted alkenyl, alkynyl, substituted alkynyl, —$R^a$—Y—$R^b$—$(Z)_x$, —C(O)$R^d$ and —$R^a$—Y—$R^b$—$(Z)_x$, $R^f$, —C(O)$R^f$ or a saccharide group optionally substituted with —C(O)—$R^a$—Y—$R^b$—$(Z)_x$;

$R^5$ is selected from the group consisting of hydrogen, halo, —CH($R^c$)—$NR^cR^c$, —CH($R^c$)—$NR^CR^e$, —CH($R^C$)—$NR^c$—$R^a$—Y—$R^b$—$(Z)_x$, —CH($R^C$)—Rx, —CH($R^c$)—$NR^c$—$R^a$—C(=O)—$R_x$ and a group containing one or more phosphono moiety;

$R^6$ is selected from the group consisting of hydrogen, alkyl, substituted alkyl, alkenyl, substituted alkenyl, alkynyl, substituted alkynyl, —$R^a$—Y—$R^b$—$(Z)_x$, —C(O)$R^d$ and a saccharide group optionally substituted with —$NR^c$—$R^a$—Y—$R^b$—$(Z)_x$, or $R^5$ and $R^6$ together with the atom to which they are attached to form a heterocyclic ring optionally substituted with —$NR^C$—$R^a$—Y—$R^b$—$(Z)_x$;

$R^7$ is selected from the group consisting of hydrogen, alkyl, substituted alkyl, alkenyl, substituted alkenyl, alkynyl, substituted alkynyl, —$R^a$—Y—$R^b$—$(Z)_x$ and —C(O)$R^d$;

$R^8$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic ring;

$R^9$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic ring;

$R^{10}$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic ring; or $R^B$ and $R^{10}$ together form —$Ar^1$—O—O—$Ar^2$— wherein, $Ar^1$ and $Ar^2$ are independently arylene or heteroarylene;

$R^{11}$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic ring, or $R^{10}$ and $R^{11}$ together with the carbon atom and nitrogen atom to which they are attached to form a heterocyclic ring;

$R^{12}$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic ring, —C(O)$R^d$, —C(NH)$R^d$, —C(O)$NR^CR^c$, —C(O)$OR^d$, C(NH)$NR^CR^c$ and —$R^a$—Y—$R^b$—$(Z)_x$, or $R^{11}$ and $R^{12}$ together with the nitrogen atom to which they are attached to form a heterocyclic ring;

$R^{13}$ is selected from the group consisting of hydrogen or —$OR^{14}$;

$R^{14}$ is selected from the group consisting of hydrogen, —C(O)$R^d$ and a saccharide group;

$R^a$ is selected independently from the group consisting of alkylene, substituted alkylene, alkenylene, substituted alkenylene, alkynylene and substituted alkynylene;

$R^b$ is selected independently from the group consisting of a covalent bond, alkylene, substituted alkylene, alkenylene, substituted alkenylene, alkynylene and substituted alkynylene, with the proviso that: $R^b$ is not covalent bond when Z is hydrogen;

$R^c$ is selected independently from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic ring and —C(O)R$^d$;

R$^d$ is selected independently from the group consisting of alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic ring;

R$^e$ is a saccharide group;

R$^f$ is independently alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl or heterocyclic ring;

R$^X$ is N-linked aminosaccharide or N-linked heterocyclic ring, and X$^1$, X$^2$ and X$^3$ are selected independently from hydrogen or chlorine;

Y is selected independently from the group consisting of oxygen, sulphur, —S—S—, —NR$^C$—, —S(O)—, —SO$_2$—, —NR$^C$C(O)—, —OSO$_2$—, —OC(O)—, —NR$^c$SO$_2$—, —C(O)NR$^c$—, —C(O)O—, —SO$_2$NR$^c$—, —SO$_2$O—, —P(O)(OR$^c$)O—, —P(O)(OR$^c$)NR$^c$—, —OP(O)(OR$^c$)O—, —OP(O)(OR$^c$)NR$^c$—, —OC(O)O—, —NR$^C$C(O)O—, NR$^C$C(O)NR$^c$—, —OC(O)NR$^c$—, —C(=O)— and —NR$^c$SO$_2$NR$^c$—;

Z is selected independently from hydrogen, aryl; cycloalkyl, cycloalkenyl, heteroaryl and heterocyclic ring;

n is 0, 1 or 2; and x is 1 or 2

(Japanese Patent Publication 200 3-531869).

The glycopeptide of the formula:

A$_1$–A$_2$–A$_3$–A$_4$–A$_5$–A$_6$–A$_7$ each of the groups A$_2$ to A$_7$ comprises a modified or unmodified alpha-amino acid residue, whereby (i) the group A$_1$ is linked to an amino group on the group A$_2$, (ii) each of the groups A$_2$, A$_4$ and A$_6$ bears an aromatic side chain, which aromatic side chains are cross-linked together by two or more covalent bonds, and (iii) the group A$_7$ bears a terminal carboxyl, ester, amide, or N-substituted amide group; and one or more of the groups A$_1$ to A$_7$ is linked via a glycosidic bond to one or more glycosidic groups each having one or more sugar residues; wherein at least one of said sugar residues is a disaccharide modified to bear one or more substituents of the formula: YXR, N$^+$ (R$_1$)=CR$_2$R$_3$, N=PR$_1$R$_2$R$_3$, N$^+$R$_1$R$_2$R$_3$ or P$^+$R$_1$R$_2$R$_3$ in which the group Y is a single bond, O, NR$_1$, or S; the group X is O, NR$_1$, S, SO$_2$, C(O)O, C(O)S, C(S)O, C(S)S, C(NR$_1$)O, C(O)NR$_1$, or halo (in which case Y and R are absent); and R, R$_1$, R$_2$, and R$_3$ are independently hydrogen, alkyl, aryl, aralkyl, alkanoyl, aroyl, aralkanoyl, heterocyclic, heterocyclic-carbonyl, heterocyclic-alkyl, heterocyclic-alkyl-carbonyl, alkylsulfonyl or arylsulfonyl;

with the proviso that at least one of the substituents of the formula YXR is not hydroxyl; X and Y are not both O; X and Y are not S and O, or O and S, respectively; and if two or more of said substituents are present, they can be the same or different; and with the proviso that when A$_4$ is linked to a disaccharide having a glucose residue that bears an N-substituted aminohexose residue, then said glucose residue is modified to bear at least one of said substituents YXR, N$^+$ (R$_1$) =CR$_2$R$_3$, N=PR$_1$R$_2$R$_3$, N$^+$R$_1$R$_2$R$_3$ or P$^+$R$_1$R$_2$R$_3$ (Japanese Patent Publication 2002-520422).

The compound of the formula:

[Formula 20]

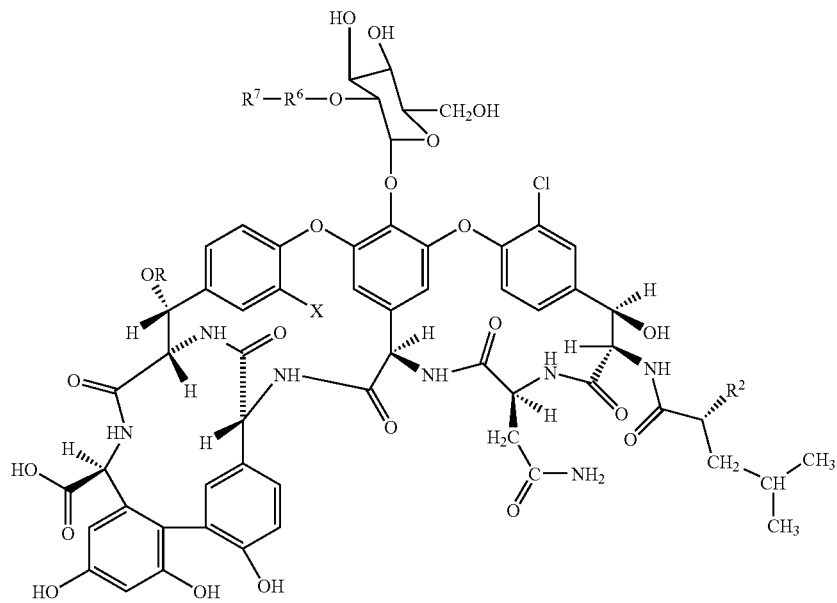

and a pharmaceutically acceptable salts thereof, wherein, each dash represents a covalent bond;

the group A$_1$ comprises a modified or unmodified alpha-amino acid residue, alkyl, aryl, aralkyl, alkanoyl, aroyl, aralkanoyl, heterocycle, heterocyclic-carbonyl, heterocyclic-alkyl, heterocyclic-alkyl-carbonyl, alkylsulfonyl, arylsulfonyl, guanidinyl, carbamoyl, or xanthyl;

or salt thereof, wherein:

X is hydrogen or chloro;

R is 4-epi-vancosaminyl or a group of the formula —R$^a$-R$^{7a}$, wherein R$^a$ is 4-epi-vancosaminyl and R$^{7a}$, defined below, is attached to the amino group of R$^a$;

R$^2$ is —NHCH$_3$ or —N(CH$_3$)R$^{7b}$, wherein R$^{7b}$ is defined below;

R$^6$ is 4-epi-vancosaminyl;

$R^7$ is as defined below, is attached to the amino group of $R^6$; and $R^7$, $R^{7a}$ and $R^{7b}$ are each independently selected from the group consisting of hydrogen, $C_{2-16}$alkenyl, $C_{2-12}$alkynyl, $(C_{1-12}$alkyl$)$-$R^8$, $(C_{1-12}$alkyl$)$-halo, $(C_{2-6}$alkenyl$)$-$R^8$, $(C_{2-6}$alkynyl$)$-$R^8$ and $(C_{1-12}$alkyl$)$-O—$R^8$, with the proviso that $R^7$, $R^{7a}$ and $R^{7b}$ are not all hydrogen, and $R^8$ is selected from the group consisting of a) multicyclic aryl unsubstituted or substituted with one or more substituents independently selected from the group consisting of:
  (i) hydroxy,
  (ii) halo,
  (iii) nitro,
  (iv) $C_{1-6}$alkyl,
  (v) $C_{1-6}$alkenyl,
  (vi) $C_{1-6}$alkynyl,
  (vii) $C_{1-6}$alkoxy,
  (viii) halo-$(C_{1-6}$alkyl$)$,
  (ix) halo-$(C_{1-6}$alkoxy$)$,
  (x) carbo-$(C_{1-6}$alkoxy$)$,
  (xi) carbobenzyloxy,
  (xii) carbobenzyloxy substituted with $C_{1-6}$alkyl, $C_{1-6}$alkoxy, halo or nitro,
  (xiii) a group of the formula —S(O)n'—$R^9$ wherein n' is 0-2 and $R^9$ is $C_{1-6}$alkyl, phenyl or phenyl substituted with $C_{1-6}$alkyl, $C_{1-6}$alkoxy, halo, or nitro and
  (xiv) a group of the formula —C(O)N$(R^{10})_2$ wherein each $R^{10}$ substituent is independently hydrogen, $C_{1-6}$alkyl, $C_{1-6}$alkoxy, phenyl, or phenyl substituted with $C_{1-6}$ alkyl, $C_{1-6}$alkoxy, halo, or nitro;

b) heteroaryl unsubstituted or substituted with one or more substituents independently selected from the group consisting of:
  (i) halo,
  (ii) $C_{1-6}$alkyl,
  (iii) $C_{1-6}$alkoxy,
  (iv) halo-$(C_{1-6}$alkyl$)$,
  (v) halo-$(C_{1-6}$alkoxy$)$,
  (vi) phenyl,
  (vii) thiophenyl,
  (viii) phenyl substituted with halo, $C_{1-6}$alkyl, $C_{1-6}$alkenyl, $C_{1-6}$alkynyl, $C_{1-6}$alkoxy, or nitro,
  (ix) carbo-$(C_{1-6}$alkoxy$)$,
  (x) carbobenzyloxy,
  (xi) carbobenzyloxy substituted with $C_{1-6}$alkyl, $C_{1-6}$alkoxy, halo or nitro,
  (xii) a group of the formula —S(O)n'—$R^9$ as defined above,
  (xiii) a group of the formula —C(O)N$(R^{10})_2$ as defined above, and
  (xiv) thienyl;

c) a group of the formula:

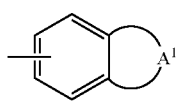

[Formula 21]

wherein $A^1$ is —OC$(A^2)_2$C$(A^2)_2$O—, —OC$(A^2)_2$O—, —C$(A^2)_2$O— or —C$(A^2)_2$C$(A^2)_2$C$(A^2)_2$C$(A^2)_2$-, and each $A^2$ substituent is independently selected from hydrogen, $C_{1-6}$alkyl, $C_{1-6}$alkoxy and $C_{4-10}$cycloalkyl;

d) a group of the formula:

[Formula 22]

wherein
  p is from 1 to 5; and
  $R^{11}$ is independently selected from the group consisting of:
  (i) hydrogen,
  (ii) nitro,
  (iii) hydroxy,
  (iv) halo
  (v) $C_{1-8}$alkyl,
  (vi) $C_{1-8}$alkoxy,
  (vii) $C_{9-12}$alkyl,
  (viii) $C_{2-9}$alkynyl,
  (ix) $C_{9-12}$alkoxy,
  (x) $C_{1-3}$alkoxy substituted with $C_{1-3}$alkoxy, hydroxy, halo-$C_{1-3}$alkoxy or $C_{1-4}$alkylthio,
  (xi) $C_{2-5}$alkenyloxy,
  (xii) $C_{1-13}$alkynyloxy,
  (xiii) halo-$C_{1-6}$alkyl,
  (xiv) halo-$C_{1-6}$alkoxy,
  (xv) $C_{2-6}$alkylthio,
  (xvi) $C_{2-10}$alkanoyloxy,
  (xvii) carboxy-$(C_{2-4}$alkenyl$)$,
  (xviii) $C_{1-3}$alkylsulfonyloxy,
  (xix) carboxy-$(C_{1-3}$alkyl$)$,
  (xx) N-[di$(C_{1-3}$alkyl]amino-$(C_{1-3}$alkoxy),
  (xxi) cyano-$(C_{1-6}$alkoxy) and
  (xxii) diphenyl-$(C_{1-6}$alkyl),
  with the proviso that when $R^{11}$ is $C_{1-9}$alkyl, $C_{1-8}$alkoxy or halo, p must be greater or equal to 2, or when $R^7$ is $C_{1-3}$alkyl-$R^8$ then $R^{11}$ is not hydrogen, $C_{1-9}$alkyl, $C_{1-8}$alkoxy or halo;

e) a group of the formula:

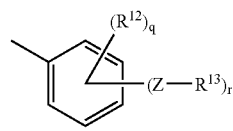

[Formula 23]

wherein
  q is 0 to 4;
  $R^{12}$ is independently selected from the group consisting of:
  (i) halo,
  (ii) nitro,
  (iii) $C_{1-6}$alkyl,
  (iv) $C_{1-6}$alkoxy,
  (v) halo-$(C_{1-6}$alkyl),
  (vi) halo-$(C_{1-6}$alkoxy),
  (vii) hydroxy and
  (viii) $C_{1-6}$thioalkyl,
  r is 1 to 5; with the proviso that the sum of q and r is no greater than 5;
  Z is selected from the group consisting of:
  (i) single bond,
  (ii) divalent $C_{1-6}$alkyl unsubstituted or substituted with hydroxy, $C_{1-6}$alkyl, or $C_{1-6}$alkoxy,
  (iii) divalent $C_{2-6}$alkenyl,
  (iv) divalent $C_{2-6}$alkynyl, or
  (v) a group of the formula —(C$(R^{14})_2$)s$R^{15}$— or —$R^{15}$(C$(R^{14})_2$)s-, wherein s is 0-6, wherein each $R^{14}$ substituent is independently selected from hydrogen, $C_{1-6}$alkyl or $C_{4-10}$cycloalkyl, and $R^{15}$ is selected from —O—, —S—, —SO—, —SO$_2$—, —SO$_2$O—, —C(O)—, —OC(O)—, —C(O)O—, —NH—, —N($C_{1-6}$alkyl)-, —C(O)NH—, —NHC(O)— and —N=N—;

$R^{13}$ is independently selected from the group consisting of:
(i) $C_{4-10}$heterocycle,
(ii) heteroaryl,
(iii) $C_{4-10}$cycloalkyl unsubstituted or substituted with $C_{1-6}$alkyl or
(iv) phenyl unsubstituted or substituted with 1 to 5 substituents independently selected from: halo, hydroxy, nitro, $C_{1-10}$alkyl, $C_{1-10}$alkoxy, halo-$C_{1-3}$alkoxy, halo-$C_{1-3}$alkyl, $C_{1-3}$alkoxyphenyl, phenyl, phenyl-($C_{1-3}$alkyl), $C_{1-6}$alkoxyphenyl, phenyl-($C_{1-3}$alkynyl) and $C_{1-6}$alkylphenyl;

f) $C_{4-10}$cycloalkyl unsubstituted or substituted with one or more substituents independently selected from the group consisting of:
(i) $C_{1-6}$alkyl,
(ii) $C_{1-6}$alkoxy,
(iii) $C_{1-6}$alkenyl,
(iv) $C_{1-6}$alkynyl,
(v) $C_{4-10}$cycloalkyl,
(vi) phenyl,
(vii) phenylthio,
(viii) phenyl substituted with nitro, halo, $C_{1-6}$alkanoyloxy or carbocycloalkoxy and
(ix) a group represented by the formula —$ZR^{13}$ wherein Z and $R^{13}$ is as defined above; and
g) a group of the formula:

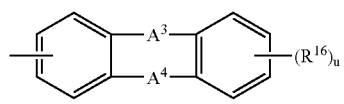

[Formula 24]

wherein
$A^3$ and $A^4$ are each independently selected from
(i) a bond,
(ii) —O—,
(iii) —S(O)t-, wherein t is 0 to 2,
(iv) —C($R^{17}$)$_2$—, wherein each $R^{17}$ substituent is independently selected from hydrogen, $C_{1-6}$alkyl, hydroxy and $C_{1-6}$alkoxy, or both $R^{17}$ substituents taken together are O,
(v) —N($R^{18}$)$_2$—, wherein each $R^{18}$ substituent is independently selected from hydrogen, $C_{1-6}$alkyl, $C_{1-6}$alkenyl, $C_{1-6}$alkynyl, $C_{4-10}$cycloalkyl, phenyl, phenyl substituted with nitro, halo, $C_{1-6}$alkanoyloxy or both $R^{18}$ substituents taken together are $C_{4-10}$cycloalkyl;
$R^{16}$ is $R^{12}$ or $R^{13}$ as defined above: and
u is 0-4,
excluding compounds wherein R is 4-epi-vancosaminyl and $R^2$ is —NH(CH$_3$)
(Japanese Patent Publication 11-502534).

Examples of the glycopeptide antibiotic derivatives are for example, vancomycin, teicoplanin, ristomycin, ristocetin, actaplanin, actinoidin, ardacin, avoparcin, azureomycin, balhimycin, chloroorienticin A, chloroorienticin B, chloropolysporin, decaplanin, N-demethylvancomycin, eremomycin, galacardin, helvecardin, izupeptin, kibdelin, mannopeptin, orienticin, parvodicin, synmonicin, oritavancin, telavancin, dalbavancin, A-40926, etc.

The term "sugar moiety" refers to a monosaccharide or a polysaccharide (e.g., disaccharide) moiety, and includes amino sugar, a sugar chain moiety containing amino sugar, or other sugar or sugar chain moieties. Amino sugar moiety or sugar chain (preferably disaccharide) containing amino sugar moiety is preferred, for example, in case of vancomycin, disaccharide attached to the phenol moiety, i.e., α-L-vancosaminyl-β-D-glucopyranose moiety. The sugar moiety typically includes, for example, D-glucose, D-mannose, D-xylose, D-galactose, vancosamin, 3-desmethyl-vancosamin, 3-epi-vancosamin, 4-epi-vancosamin, acosamin, actinosamin, daunosamin, 3-epi-daunosamin, ristosamin, N-methyl-D-glucamin, D-glucuronic acid, N-Acetyl-D-glucosamin, N-Acetyl-D-galactosamine, sialic acid, 2-O—(α-L-vancosaminyl)-p-β-glucopyranose, 2-O-(3-desmethyl-α-L-vancosaminyl)-β-D-glucopyranose, sucrose, lactose, or maltose.

The term "sugar residue" refers to a residual moiety of the above "sugar moiety" from which one OH has been removed.

The term "amino sugar residue" refers to a residual moiety of the "amino sugar" or "a sugar chain moiety containing amino sugar" from which one amino group has been removed.

The term "Sac-NH" moiety refers to an amino sugar moiety or a sugar chain moiety containing amino sugar as known in glycopeptide antibiotic derivatives. The term "amino sugar moiety" refers to a monosaccharide group having an amino group or a substituted amino group. Typical amino sugar moiety includes L-vancosaminyl, 3-desmethyl-vancosaminyl, 3-epi-vancosaminyl, 4-epi-vancosaminyl, 4-keto-vancosaminyl, acosaminyl, actinosaminyl, daunosaminyl, 3-epi-daunosaminyl, ristosaminyl, N-methyl-D-glucaminyl, N-Acetyl-D-glucosamyl, or N-acyl-D-glucosamyl, etc. Actinosaminyl, acosaminyl, 4-epi-vancosaminyl, 4-keto-vancosaminyl, ristosaminyl, or vancosaminyl is preferred. Particularly, L-vancosaminyl is preferred. Also, α-L-vancosaminyl-β-D-glucopyranose, 3-desmethyl-α-L-vancosaminyl-β-D-glucopyranose can be exemplified for a sugar chain moiety containing amino sugar.

As described above, "(aglycon part of glycopeptide antibiotic derivative)-(Sac-NH)" is a glycopeptide antibiotic derivative having a terminal amino sugar moiety.

Thus, glycopeptide antibiotic derivatives of the invention is a compound having $R^4$ group attached to the amino group of the terminal amino sugar.

$R^4$ is represented by the formula: —$X^1$—$Ar^1$—$X^1$—Y—$X^3$—$Ar^2$. $R^4$ group is characterized in that Y moiety comprises an amide bond.

The term "lower alkyl" refers to a saturated straight or branched hydrocarbon mono radical having 1 to 6 carbons, and includes methyl, ethyl, n-propyl, isopropyl, n-butyl, isobutyl, sec-butyl, tert-butyl, n-pentyl, isopentyl, neopentyl, tert-pentyl, N-hexyl, isohexyl.

The term "linking group" in the definition for $X^1$, $X^2$ and $X^3$ refers to a linking group that comprises a hetero atom selected from the group consisting of —N=, =N—, —NR$^1$— (wherein $R^1$ is hydrogen or lower alkyl), —O—, —S—, —SO— and —SO$_2$— selected from the group, and includes for example —S—S—, —NR$^1$CO—, —NR$^1$O—, —NR$^1$S—, —OSO$_2$—, —OCO—, —SO$_2$NR$^1$—, etc.

The term "alkylene" refers to a saturated straight or branched hydrocarbon diradical having 1 to 6 carbons, and includes for example methylene, ethylene, trimethylene, propylene, tetramethylene, ethylethylene, pentamethylene or hexamethylene, etc. A saturated straight or branched alkylene having one to four carbon atoms, such as methylene, ethylene, trimethylene or tetramethylene is preferred. Preferred is methylene.

The term "alkenylene" refers to an unsaturated straight or branched hydrocarbon diradical of 2 to 6 carbons, having one or more double bond in the above "alkylene", and includes for example vinylene, propenylene or butenylene. A straight chain alkenylene of 2 or 3 carbons, such as vinylene or propenylene, is preferred.

The term "optionally substituted alkylene or alkenylene" refers to alkylene or alkenylene having 1 to 5 substituents, preferably 1 to 3 substituents, wherein said substituent is selected from the group consisting of: optionally substituted alkyl (e.g., methyl, ethyl, isopropyl, benzyl, carbamoylalkyl (e.g., carbamoylmethyl), mono- or di-alkylcarbamoylalkyl (e.g., dimethylcarbamoylethyl), hydroxyalkyl, heterocyclealkyl (e.g., morpholinoethyl, tetrahydropyranylethyl), alkoxycarbonylalkyl (e.g., ethoxycarbonylmethyl, ethoxycarbonylethyl), mono- or di-alkylaminoalkyl (e.g., dimethylamminioethyl) etc), alkoxyalkyl (e.g., methoxyethyl, ethoxymethyl, ethoxyethyl, i-propoxyethyl etc), acyl (e.g., formyl, optionally substituted alkylcarbonyl (e.g., acetyl, Propionyl, butyryl, isobutyryl, valeryl, isovaleryl, pivaloyl, hexanoyl, octanoyl, methoxyethylcarbonyl, 2,2,2-trifluoroethylcarbonyl, ethoxycarbonylmethylcarbonyl, alkoxyalkylcarbonyl (e.g., methoxyethylcarbonyl), alkylcarbamoylalkylcarbonyl (e.g., methylcarbamoylethylcarbonyl), alkoxycarbonylacetyl etc), optionally substituted arylcarbonyl (e.g., benzoyl, toluoyl etc)), optionally substituted aralkyl (e.g., benzyl, 4-F-benzyl etc), hydroxy, optionally substituted alkylsulfonyl (e.g., methanesulfonyl, ethanesulphonyl, isopropylsulphonyl, 2,2,2-trifluoroethanesulphonyl, benzylsulphonyl, methoxyethylsulphonyl etc), arylsulfonyl optionally substituted with alkyl or halo (e.g., benzenesulfonyl, toluenesulfonyl, 4-fluorobenzenesulfonyl), cycloalkyl (e.g., cyclopropyl etc), aryl optionally substituted with alkyl (e.g., 4-methylphenyl etc), alkylaminosulphonyl (e.g., methylaminosulphonyl, dimethylamminiosulphonyl etc), alkylaminocarbonyl (e.g., dimethylaminocarbonyl etc), alkoxycarbonyl (e.g., ethoxycarbonyl etc), cycloalkylcarbonyl (e.g., cyclopropylcarbonyl, cyclohexylcarbonyl etc), optionally substituted sulfamoyl (e.g., sulfamoyl, methylsulfamoyl, dimethylsulfamoyl etc), alkylcarbonylamino (e.g., methylcarbonylamino), heterocycle (e.g., morpholino, tetrahydropyranyl), optionally substituted amino (e.g., mono- or di-alkylamino (such as dimethylamminio), formylamino).

Thus, "optionally substituted alkylene or alkenylene optionally interrupted by one or more same or different heteroatomic group" refers to alkylene or alkenylene optionally substituted and optionally interrupted by one or more same or different of a heteroatomic group selected from the group consisting of —N═, ═N—, —NR$^1$— wherein R$^1$ is hydrogen or lower alkyl, —O—, —S—, —SO— and —SO$_2$—. In this regard, "interrupted" means the presence of a heteroatomic group between carbon atoms composing such alkylene or alkenylene or between said carbon atom and Ar$^1$, Y or Ar$^2$. For example, —O—CH$_2$—, —CH$_2$—O—, —CH$_2$—O—CH$_2$—, CH$_2$—NH—CH$_2$—, —O—CH$_2$—O—, —CH$_2$—O—CH$_2$—NH—CH$_2$—, CH$_2$—N═CH—, —CH$_2$—O—CH═N—CH$_2$—, and —O—CH═CH—, —CH═CH—O—, —CH═CH—O—CH$_2$—, CH$_2$—NH—CH═CH—, —O—CH═CH—O—, or —(CH$_2$—O)—Ar$^1$—(O—CH$_2$—O)—Y—(O—CH$_2$)—Ar$^2$, etc. are exemplified. Also, in the case that alkylene is substituted with oxo, —CO— is preferably exemplified.

X$^1$ is preferably C$_1$-C$_3$ alkylene.

X$^2$ is preferably a single bond, C$_1$-C$_3$ alkylene, O or NH, more preferably, single bond or NH.

Y is preferably, —NHCO—, —CONH—, —NMeCO—, —CONMe— or a radical as follows:

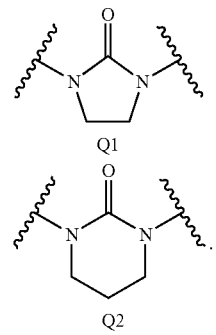

Also, Y is may be a piperazine ring group, and more preferably, —NHCO— or —CONH—.

X$^3$ is preferably a single bond, C$_1$-C$_3$ alkylene, O or NH, more preferably a single bond.

Also, —Y—X$^3$— and —X$^2$—Y— may form a structure of the formula:

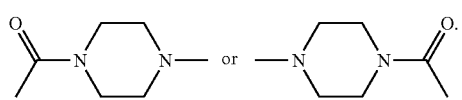

Ar$^1$ and Ar$^2$ are each a carbocycle or a heterocycle that may be substituted or unsaturated.

The term "optionally unsaturated carbocycle" in the definition for Ar$^1$ and Ar$^2$ refers to a cycloalkyl of 3-10 carbon or a cycloalkenyl or aryl of 3-10 carbon.

The term "cycloalkyl" includes, for example, cyclopropyl, cyclobutyl, cyclopentyl, cyclohexylyl, cycloheptyl, cyclooctyl, etc. Cycloalkyl of 3-6 carbon atoms, such as cyclopentyl, cyclohexylyl, is preferred.

The term "cycloalkenyl" includes, for example, cyclopropenyl (e.g., 1-cyclopropenyl), cyclobutenyl (e.g., 1-cyclobutenyl), cyclopentenyl (e.g., 1-cyclopentene-1-yl, 2-cyclopentene-1-yl, 3-cyclopentene-1-yl), cyclohexenyl (e.g., 1-cyclohexene-1-yl, 2-cyclohexene-1-yl, 3-cyclohexene-1-yl), cycloheptenyl (e.g., 1-cycloheptenyl), cyclooctenyl (e.g., 1-cyclooctenyl). Particularly, 1-cyclohexene-1-yl, 2-cyclohexene-1-yl, 3-cyclohexene-1-yl are preferred.

The term "aryl" refers to a monocyclic aromatic hydrocarbon group (phenyl) and a polycyclic aromatic hydrocarbon group (e.g., 1-naphthyl, 2-naphythyl, 1-anthryl, 2-anthryl, 9-anthryl, 1-phenanthryl, 2-phenanthryl, 3-phenanthryl, 4-phenanthryl, 9-phenanthryl etc). Phenyl or naphythyl (e.g., 1-naphythyl, 2-naphythyl) is preferred.

The term "optionally unsaturated heterocycle" in the definition for Ar$^1$ and Ar$^2$ means a heterocycle or a heteroaryl.

The term "heterocycle" refers to a nonaromatic heterocyclic group having at least one N, O or S atom within the ring, the ring being optionally substituted at a substitutable position. Examples are 1-pyrrolinyl, 2-pyrrolinyl, 3-pyrrolinyl, 1-pyrrolindinyl, 2-pyrrolindinyl, 3-pyrrolindinyl, 1-imidazolinyl, 2-imidazolinyl, 4-imidazolinyl, 1-imidazolidinyl, 2-imidazolidinyl, 4-imidazolidinyl, 1-pyrazolynyl, 3-pyrazolynyl, 4-pyrazolynyl, 1-pyrazolidinyl, 3-pyrazolidinyl, 4-pyrazolidinyl, piperidino, 2-piperidyl, 3-piperidyl, 4-piperidyl, 1-piperazinyl, 2-piperazinyl, 2-morpholinyl, 3-morpholinyl, morpholino, tetrahydropyranyl etc. The "a nonaromatic heterocyclic group" may be saturated or unsaturated so long as it is not aromatic.

The term "heteroaryl" refers to a monocyclic aromatic heterocyclic group and a condensed aromatic heterocyclic group. The monocyclic aromatic heterocyclic group is that optionally substituted at a substitutable position and derived from a 5-8 membered aromatic ring that may contain one to four O, S, and/or N atom within the ring. The condensed aromatic heterocyclic group is that optionally substituted at a substitutable position and wherein a 5-8 membered aromatic ring containing one to four O, S, and/or N atom within the ring is condensed with one to four 5-8 membered aromatic carbocycles or another 5-8 membered aromatic hetero ring.

The "heteroaryl" includes, for example, furyl (e.g., 2-furyl, 3-furyl), thienyl (e.g., 2-thienyl, 3-thienyl), pyrrolyl (e.g., 1-pyrrolyl, 2-pyrrolyl, 3-pyrrolyl), imidazolyl (e.g., 1-imidazolyl, 2-imidazolyl, 4-imidazolyl), pyrazolyl (e.g., 1-pyrazolyl, 3-pyrazolyl, 4-pyrazolyl), triazolyl (e.g., 1,2,4-triazol-1-yl, 1,2,4-triazol-3-yl, 1,2,4-triazol-4-yl), tetrazolyl (e.g., 1-tetrazolyl, 2-tetrazolyl, 5-tetrazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), thiazolyl (e.g., 2-thiazolyl, 4-thiazolyl, 5-thiazolyl), thiadiazolyl, isothiazolyl (e.g., 3-isothiazolyl, 4-isothiazolyl, 5-isothiazolyl), pyridyl (e.g., 2-pyridyl, 3-pyridyl, 4-pyridyl), pyridazinyl (e.g., 3-pyridazinyl, 4-pyridazinyl), pyrimidinyl (e.g., 2-pyrimidinyl, 4-pyrimidinyl, 5-pyrimidinyl), furazanyl (e.g., 3-furazanyl), pyrazinyl (e.g., 2-pyrazinyl), oxadiazolyl (e.g., 1,3,4-oxadiazole-2-yl), benzofuryl (e.g., 2-benzo[b]furyl, 3-benzo[b]furyl, 4-benzo[b]furyl, 5-benzo[b]furyl, 6-benzo[b]furyl, 7-benzo[b]furyl), benzthienyl (e.g., 2-benzo[b]thienyl, 3-benzo[b]thienyl, 4-benzo[b]thienyl, 5-benzo[b]thienyl, 6-benzo[b]thienyl, 7-benzo[b]thienyl), benzimidazolyl (e.g., 1-benzoimidazolyl, 2-benzoimidazolyl, 4-benzoimidazolyl, 5-benzoimidazolyl), dibenzofuryl, benzoxazolyl, quinoxalyl (e.g., 2-quinoxalinyl, 5-quinoxalinyl, 6-quinoxalinyl), cinnolinyl (e.g., 3-cinnolinyl, 4-cinnolinyl, 5-cinnolinyl, 6-cinnolinyl, 7-cinnolinyl, 8-cinnolinyl), quinazolyl (e.g., 2-quinazolinyl, 4-quinazolinyl, 5-quinazolinyl, 6-quinazolinyl, 7-quinazolinyl, 8-quinazolinyl), quinolyl (e.g., 2-quinolyl, 3-quinolyl, 4-quinolyl, 5-quinolyl, 6-quinolyl, 7-quinolyl, 8-quinolyl), phthalazinyl (e.g., 1-phthalazinyl, 5-phthalazinyl, 6-phthalazinyl), isoquinolyl (e.g., 1-isoquinolyl, 3-isoquinolyl, 4-isoquinolyl, 5-isoquinolyl, 6-isoquinolyl, 7-isoquinolyl, 8-isoquinolyl), puryl, pteridinyl (e.g., 2-pteridinyl, 4-pteridinyl, 6-pteridinyl, 7-pteridinyl), carbazolyl, phenanthridinyl, acridinyl (e.g., 1-acridinyl, 2-acridinyl, 3-acridinyl, 4-acridinyl, 9-acridinyl), indolyl (e.g., 1-indolyl, 2-indolyl, 3-indolyl, 4-indolyl, 5-indolyl, 6-indolyl, 7-indolyl), isoindolyl, phenazinyl (e.g., 1-phenazinyl, 2-phenazinyl) or phenanthridinyl (e.g., 1-phenanthridinyl, 2-phenanthridinyl, 3-phenanthridinyl, 4-phenanthridinyl), etc.

The carbocycle and/or heterocycle in $Ar_1$ and $Ar_2$ also include those wherein an aromatic ring is condensed with a nonaromatic ring.

As obvious from the definition of $R^A$, which is a divalent group, a carbon atom or a hetero atom within the carbocycle or heterocycle, described above as a monovalent group in $R^A$, should involve in a linkage to another group.

Preferred $R^A$ is a divalent ring group as follows:

[Formula 27]

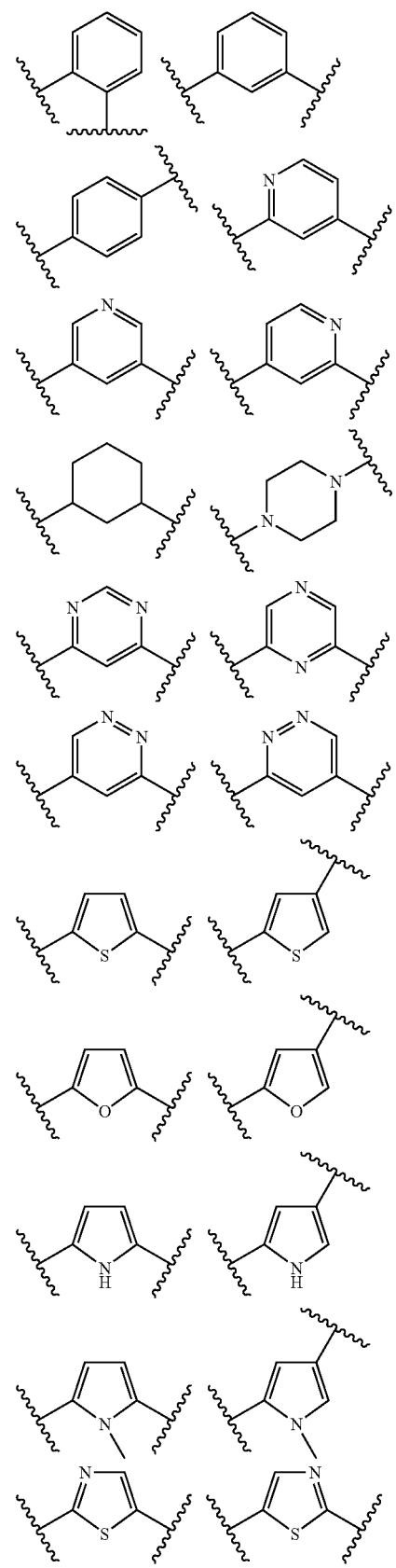

-continued

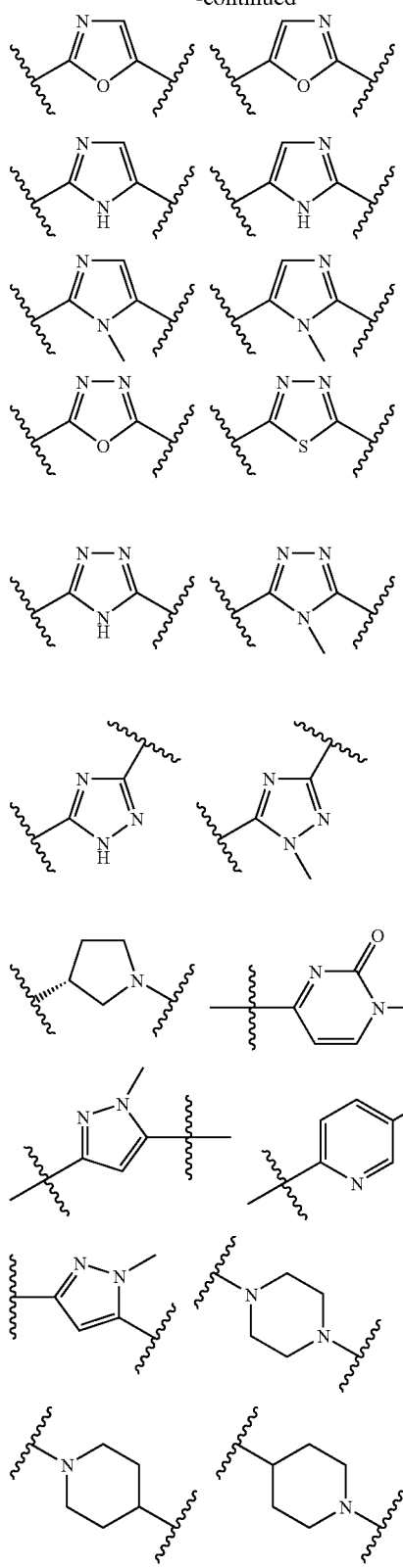

[Formula 28]

Ar² may be selected form the following groups:

[Formula 29]

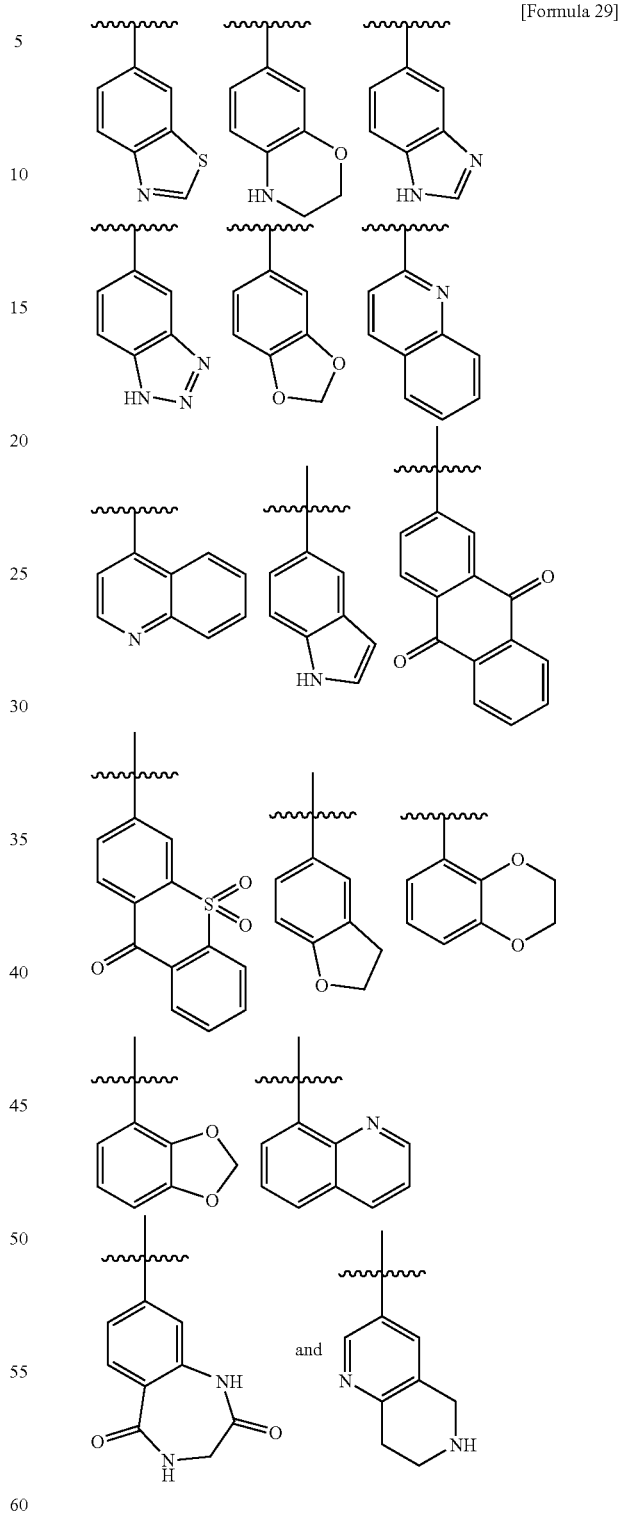

Particularly, phenylenes, such as 1,2-, 1,3-, and 1,4-phenylene, are preferred. Also, preferred embodiment of the heterocycle group includes a five or six membered ring containing one to two N atom.

Ar² is preferably an optionally substituted aryl, particularly preferably an optionally substituted phenyl.

Substituent for "a carbocycle or heterocycle which is optionally substituted and may have an unsaturated bond" in the definition for Ar¹ and Ar² include lower alkyl, hydroxy lower alkyl, optionally substituted lower alkoxy (for example: hydroxy, phenyloxy, optionally substituted heterocycle (preferably 5-6 membered ring), lower alkoxy, optionally substituted amino (for example, lower alkyl, lower alkenyl, cyano, phenyl), optionally substituted lower alkoxy lower alkyl (for example: hydroxy, lower alkoxy, optionally substituted heterocycle (preferably 5-6 membered ring)), cycloalkyl, optionally substituted aryloxy, optionally substituted aralkyloxy, optionally substituted aryloxy lower alkyl, optionally substituted aryloxycarbonyl, lower alkoxycarbonyl, nitro, hydroxy, carboxy, lower alkoxycarbonyl, cyano, oxo, carboxy lower alkenyl, $SO_2$-cyclic amino (preferably 5-6 membered ring), lower alkylsulfonylamino, optionally substituted amino (for example: lower alkyl, lower alkoxy, acyl (e.g., lower alkylcarbonyl, amino lower alkylcarbonyl, lower alkylamino lower alkylcarbonyl), heterocycle (preferably 5-6 membered ring)), optionally substituted amino lower alkyl, optionally substituted carbamoyl (for example: lower alkyl, CN, OH), optionally substituted carbamoyloxy, halo, lower alkyl halide, lower alkoxy halide, lower alkylthio halide, lower alkylcarbonyl halide, heterocyclo lower alkyl, heterocyclo lower alkoxy, cycloalkyl lower alkoxy, optionally substituted aralkyloxy, optionally substituted heteroaryl (preferably 5-6 membered ring), optionally substituted heteroaryl-lower alkyl, optionally substituted heteroaryl-lower alkyloxy, optionally substituted heterocycle, optionally substituted heterocycle lower alkyl, optionally substituted heterocycle lower alkyloxy, optionally substituted heterocyclecarbonyl lower alkenyl, optionally substituted heterocycleamino, optionally substituted aryl, and optionally substituted heterocyclecarbonyl lower alkenyl, $SCO_2R$, $OC(=S)OR$, $OC(=O)SR$, $C(=S)OR$, $SC(=O)SR$, $SC(=S)SR$, $OC(=S)NH_2$, $SC(=O)NH_2$, $SC(=S)NH_2$, $OC(=S)NHR$, $SC(=O)NHR$, $SC(=S)NHR$, $OSO_2NHR$, $OSO_2NHPh$, $OC(=S)NR_2$, $SC(=O)NR_2$, $SC(=S)NR_2$, $C(=S)NH_2$, $C(=S)NHR$, $C(=S)NR_2$ (R is lower alkyl), CONHCN, CONHOH, etc.

The optionally substituted amino as described above is for example amino, mono- or di-lower alkylamino, phenylamino, N-alkyl-n-phenylamino, mono- or di-lower alkoxy lower alkylamino, mono- or di-hydroxy lower alkylamino lower alkoxycarbonylamino, lower alkylcarbamoylamino, lower alkylcarbonylamino, $NHC(=O)SR$, $NHC(=S)OR$, $NHC(=S)SR$, $NHC(=S)R$, $NH(CH_2)_2OH$, $N[(CH_2)_2OH]_2$ (R is lower alkyl), optionally substituted heterocycleamino (substituent: lower alkyl), optionally substituted acetylamino (for example: optionally substituted heterocycle(substituent: e.g., lower alkyl), amino, alkylamino), etc. The substituent of the above optionally substituted aryl, aralkyl, heteroaryl, heterocycle includes, lower alkyl, lower alkoxy, lower alkoxy lower alkyl, heterocycle (preferably 5-6 membered ring), cyano, etc.

The substituent for "carbocycle or heterocycle which may have an unsaturated bond" in the definition for $Ar^1$ and $Ar^2$ is, more specifically, methyl, ethyl, n-propyl, isopropyl, n-butyl, isobutyl, t-butyl, vinyl, allyl, propargyl, OH, methoxy, ethoxy, n-propyloxy, isopropyloxy, n-butyloxy, isobutyloxy, t-butyloxy, vinyloxy, allyloxy, propargyloxy, benzyloxy, 2,3,4-picolyloxy, furfuryloxy, thiophenemethyloxy, imidazolylmethyloxy, pyrazolylmethyloxy, triazolylmethyloxy, thiazolylmethyloxy, oxazolylmethyloxy, isoxazolylmethyloxy, phenylethyloxy, 2,3,4-pyridylethyloxy, furylethyloxy, thiopheneethyloxy, imidazolylethyloxy, pyrazolylethyloxy, triazolylethyloxy, thiazolylethyloxy, oxazolylethyloxy, isoxazolylethyloxy, cyclopropylmethyloxy, cyclopentylmethyloxy, cyclohexylmethyloxy, tetrahydropyran-4-ylmethyloxy, [1,3]dioxolan-2-ylmethyloxy, $OCO_2Me$, $NHCO_2Me$, $OCONHMe$, NHCONHMe, NHCOMe, $CONH_2$, CONHMe, $CONMe_2$, OCONHPh, $SCO_2Me$, $OC(=S)OMe$, $OC(=O)SMe$, $C(=S)OMe$, $SC(=O)SMe$, $SC(=S)SMe$, $NHC(=O)SMe$, $NHC(=S)OMe$, $NHC(=S)SMe$, $OC(=S)NH_2$, $SO_2NH_2$, $SO_2Me$, $SC(=O)NH_2$, $SC(=S)NH_2$, $OC(=S)NHMe$, $SC(=O)NHMe$, $SC(=S)NHMe$, $OSO_2NHMe$, $OSO_2NHPh$, $OC(=S)NMe_2$, $SC(=O)NMe_2$, $SC(=S)NMe_2$, $NHC(=S)Me$, $C(=S)NH_2$, $C(=S)NHMe$, $C(=S)NMe_2$, $NO_2$, $NH_2$, NHMe, $NMe_2$, NHEt, $NEt_2$, $NH(CH_2)_2OH$), $N[(CH_2)_2OH]_2$, piperazinyl, 4-alkylpiperidino (e.g., 4-methylpiperidino), piperidinyl, morpholino, F, Cl, Br, $CF_3$, $OCF_3$, $OCH_2CF_3$, CN, oxo, etc. $Ar^1$ or $Ar^2$ may contain preferably 1 to 3 of these substituents.

For example, more preferred combinations of the substituents include 1) lower alkyl, aralkyloxy and nitro, 2) lower alkyl, aralkyloxy and amino, 3) lower alkyl, hydroxy and nitro, and 4) lower alkyl, hydroxy and amino, etc.

One preferred embodiment of $Ar^1$ is optionally substituted phenylene. Preferred substituent on phenylene include halo, hydroxy, hydroxy lower alkyl, optionally substituted lower alkoxy, optionally substituted amino (substituent: e.g., lower alkyl, heterocycle, heterocycle lower alkyl, lower alkoxy lower alkyl, hydroxy lower alkyl, lower alkylsulfonyl), optionally substituted amino lower alkyl, optionally substituted heterocycle, optionally substituted heterocycle lower alkyl, phenylene optionally substituted with heterocycle lower alkyl optionally substituted, optionally substituted carbamoyl (substituent: e.g., lower alkyl), optionally substituted carbamoyl lower alkenyl. Preferred heterocycle is a heterocycle optionally each substituted with lower alkyl such as morpholino, piperidino, piperidino), pyridyl etc.

One preferred embodiment of $Ar^1$ is optionally substituted 5 to 7-membered heterocycle. Preferred substituent on the heterocycle includes lower alkyl, oxo, halo, amino lower alkyl, mono- or di-lower alkylamino lower alkyl, lower alkoxy lower alkyl.

For $Ar^2$, aryl or heterocycle, optionally substituted with one or more substituent selected from the group consisting of halo, mono-, di- or tri-halogenated lower alkyl, mono-, di-, tri- or tetra-halogenated lower alkoxy, mono-, di-, tri- or tetra-halogenated lower alkylthio, mono- or di-lower alkylamino, cycloalkylmethyloxy, optionally substituted benzyloxy, lower alkoxycarbonylamino, nitro, heterocycle (e.g., morpholino, piperidino, piperidino, pyrrolidino optionally substituted independently with lower alkyl etc.), optionally substituted acetylamino, optionally substituted lower alkoxy, acyl (e.g., optionally substituted lower alkylcarbonyl), and optionally substituted lower alkyloxycarbonyl, is preferred.

The term "aralkyloxy" refers to a group wherein O atom is substituted the above "alkyl" substituted with the above "aryl" and, for example, benzyloxy, diphenylmethyloxy, triphenylmethyloxy, phenetyloxy, 1-naphythylmethyloxy, 2-naphythylmethyloxy, etc.

The term "lower alkoxy" refers to a group wherein O atom is substituted with the above "lower alkyl", and for example, methoxy, ethoxy, n-propoxy, isopropoxy, n-butoxy, isobutoxy, tert-butoxy, etc. Particularly, methoxy, ethoxy are preferred.

The term "aryloxy" refers to a group wherein O atom is substituted with the above "aryl".

The term "optionally substituted amino" is an amino substituted or unsubstituted.

The term "optionally substituted carbamoyl" is a carbamoyl substituted or unsubstituted.

For substituents of "optionally substituted amino" and "optionally substituted carbamoyl" include, optionally substituted alkyl (e.g., methyl, ethyl, isopropyl, benzyl, carbamoylalkyl (e.g., carbamoylmethyl), mono- or di-alkylcarbamoylalkyl (e.g., dimethylcarbamoylethyl), hydroxyalkyl, heterocyclealkyl (e.g., morpholinoethyl, tetrahydropyranylethyl), alkoxycarbonylalkyl (e.g., ethoxycarbonylmethyl, ethoxycarbonylethyl), mono- or di-alkylaminoalkyl (e.g., dimethylamminioethyl) etc), alkoxyalkyl (e.g., methoxyethyl, ethoxymethyl, ethoxyethyl, i-propoxyethyl etc), acyl (e.g., formyl, optionally substituted alkylcarbonyl (e.g., acetyl, Propionyl, butyryl, isobutyryl, valeryl, isovaleryl, pivaloyl, hexanoyl, octanoyl, methoxyethylcarbonyl, 2,2,2-trifluoroethylcarbonyl, ethoxycarbonylmethylcarbonyl, alkoxyalkylcarbonyl (e.g., methoxyethylcarbonyl), alkylcarbamoylalkylcarbonyl (e.g., methylcarbamoylethylcarbonyl), alkoxycarbonylacetyl etc), optionally substituted arylcarbonyl (e.g., benzoyl, toluoyl etc)), optionally substituted aralkyl (e.g., benzyl, 4-F-benzyl etc), hydroxy, optionally substituted alkylsulfonyl (e.g., methanesulfonyl, ethanesulphonyl, isopropylsulphonyl, 2,2,2-trifluoroethanesulphonyl, benzylsulphonyl, methoxyethylsulphonyl etc), arylsulfonyl optionally substituted with alkyl or halo (e.g., benzenesulfonyl, toluenesulfonyl, 4-fluorobenzenesulfonyl), cycloalkyl (e.g., cyclopropyl etc), aryl optionally substituted with alkyl (e.g., 4-methylphenyl etc), alkylaminosulphonyl (e.g., methylaminosulphonyl, dimethylamminiosulphonyl etc), alkylaminocarbonyl (e.g., dimethylaminocarbonyl etc), alkoxycarbonyl (e.g., ethoxycarbonyl etc), cycloalkylcarbonyl (e.g., cyclopropylcarbonyl, cyclohexylcarbonyl etc), optionally substituted sulfamoyl (e.g., sulfamoyl, methylsulfamoyl, dimethylsulfamoyl etc), alkylcarbonylamino (e.g., methylcarbonylamino), heterocycle (e.g., morpholino, tetrahydropyranyl), optionally substituted amino (e.g., mono- or di-alkylamino (e.g., dimethylamminio), formylamino), etc. It may be mono- or di-substituted with the above substituent.

The amino group of "optionally substituted amino" and "optionally substituted carbamoyl" may be substituted with alkylene such as trimethylene, tetramethylene, pentamethylene, or the N atom of the amino group together to form a ring that may contain O, S atom.

For the amino group of "optionally substituted amino" and "optionally substituted carbamoyl", the two substituents of the amino group taken together with a nitrogen atom to which they are attached form a nitrogen containing heterocycle that may contain S and/or O atom within the ring, preferably 5 to 7 membered and preferably saturated, and said ring may be substituted with oxo, lower alkyl or hydroxy etc. The ring may be substituted at S atom with oxo.

For example, 5 or 6-membered ring such as piperidino, piperidino, morpholino, pyrrolidino, thiazin-2-yl, 2-oxopiperidino, 2-oxopyrrolidino, 1,1-dioxido-1,2-thiazin-2-yl, 4-hydroxymorpholino are preferred.

Substituent of "optionally substituted aryl" and "optionally substituted heteroaryl" is that as described above for "optionally substituted amino group".

Preferred embodiments of the group of the formula: —$X^1$—$Ar^1$—$X^2$—Y—$X^3$—$Ar^2$ for $R^A$ are as follows:

(1) —$CH_2$— (Substituted) Ph-CONR—(Substituted Ph)
(2) —$CH_2$— (Substituted) Ph-NRCO—(Substituted Ph)
(3) —$CH_2$— (Substituted) Ph-$CH_2$—CONR—(Substituted Ph)
(4) —$CH_2$— (Substituted) Ph-$CH_2$—NRCO—(Substituted Ph)
(5) —$CH_2$— (Substituted) Ph-X—CONR—(Substituted Ph)
(6) —$CH_2$— (Substituted) Ph-X—NRCO—(Substituted Ph)
(7) —$CH_2$— (Substituted) Ph-Q-(Substituted Ph)
(8) —$CH_2$— (Substituted) Het-CONR—(Substituted Ph)
(9) —$CH_2$— (Substituted) Het-NRCO—(Substituted Ph)
(10) —$CH_2$— (Substituted) Ph-CONR—$CH_2$—(Substituted Ph)
(11) —$CH_2$— (Substituted) Ph-NRCO—$CH_2$—(Substituted Ph)
(12) —$CH_2$— (Substituted) Ph-$CH_2$—CONR—$CH_2$—(Substituted Ph)
(13) —$CH_2$-(Substituted) Ph-$CH_2$—NRCO—$CH_2$—(Substituted Ph)
(14) —$CH_2$— (Substituted) Ph-X—CONR—$CH_2$—(Substituted Ph)
(15) —$CH_2$— (Substituted) Ph-X—NRCO—$CH_2$—(Substituted Ph)
(16) —$CH_2$— (Substituted) Ph-Q-$CH_2$—(Substituted Ph)
(17) —$CH_2$— (Substituted) Het-CONR—$CH_2$—(Substituted Ph)
(18) —$CH_2$— (Substituted) Het-NRCO—$CH_2$—(Substituted Ph)
(19) —$(CH_2)_m$—(Substituted) Ph-CONR—(Substituted Ph)
(20) —$(CH_2)_m$—(Substituted) Ph-NRCO—(Substituted Ph)
(21) —$(CH_2)_m$—(Substituted) Ph-$CH_2$—CONR—(Substituted Ph)
(22) —$(CH_2)_m$—(Substituted) Ph-$CH_2$—NRCO—(Substituted Ph)
(23) —$(CH_2)_m$—(Substituted) Ph-X—CONR—(Substituted Ph)
(24) —$(CH_2)_m$—(Substituted) Ph-X—NRCO—(Substituted Ph)
(25) —$(CH_2)_m$—(Substituted) Ph-Q-(Substituted Ph)
(26) —$(CH_2)_m$—(Substituted) Het-CONR—(Substituted Ph)
(27) —$(CH_2)_m$—(Substituted) Het-NRCO—(Substituted Ph)

wherein, Ph=phenyl; R=hydrogen or lower alkyl; X=O or NH; Q is Q1 or Q2 as defined above; Het is heteroaryl or heterocycle (preferably 5 or 6-membered); M is 2 or 3; "Substitutied" means "optionally substituted".

Chemically modified groups $R^B$, $R^C$, $R^D$ include substituents as disclosed in Japanese Patent Publication 2001-163898. Examples of those substituents are specifically as bellows.

$R^B$ can be selected from the groups as listed in (2-1)-(2-7):
(2-1) hydroxy:
(2-2) optionally substituted mono- or di-alkylamino (with the exception of the groups as described in (2-4)), wherein two alkyl moieties together form a ring, and wherein said substituent is amino, monoalkylamino, dialkylamino, trialkylammonium, hydroxy, guanidino, carboxy, alkyloxycarbonyl, carbamoyl optionally substituted with cyano, mono- or di-alkylcarbamoyl, mono- or di-arylcarbamoyl, aryl, alkylamido or arylamido, alkylurea or arylurea, —(C=O)$N^-$—$N^+$ $(R^X)_3$, —$N^+$ $(R^X)_2$ $(CH_2)_m COOR^Y$, —$N^+$ $(R^X)_2(CH_2)_m$ $N^+$ $(R^X)_3$, —$SO_2$—$OR^Y$ or —P=O$(OR^Y)_2$ in which m is 1 to 3, $R^X$ is $C_1$-$C_3$ alkyl, and $R^Y$ is hydrogen or $C_1$-$C_3$ alkyl, or combination of these substituents, and wherein alkyl in said substituent may further be substituted with alkyloxycarbonyl or aryloxycarbonyl and aryl ring in said substituent may further be substituted with alkyl optionally substituted with halo, nitro, amino, hydroxy, carboxy, alkyloxycarbonyl, or amino, hydroxyalkyl or thioalkyl optionally acylated, or combination thereof;
(2-3) cycloalkylamino optionally substituted with amino or hydroxy;
(2-4) di-substituted methylamino —NHCHR$^6$R$^7$, wherein R$^6$ is selected from carboxy, optionally substituted alkyloxycarbonyl, carbamoyl, or optionally substituted monoalkylcarbamoyl, or optionally substituted cycloalkylcarbamoyl, wherein said substituent is amino, monoalkylamino, dialkylamino, trialkylammonium, carboxy, hydroxy, —(C=O)N⁻—N⁺ ($R^X$)$_3$, aryl optionally substituted with —(CH$_2$)$_m$ COOR$^X$ in which m is 1 to 3 and R$^X$ is C$_1$-C$_3$ alkyl, —N⁺ ($R^X$)$_2$ (CH$_2$)$_m$COOR$^Y$, in which R$^Y$ is hydrogen or C$_1$-C$_3$ alkyl, or —N⁺ ($R^X$)$_2$ (CH$_2$)$_m$N⁺ ($R^X$)$_3$, or combination thereof, and wherein R$^7$ is indole, thioindole or imidazolyl wherein the nitrogen atom is optionally substituted with C$_1$-C$_3$ alkyl;

(2-5) tripeptide R-A$_1$-A$_2$-A$_3$-: wherein A$^1$, A$^2$ and A$^3$ are independently any amino acid unit, R is hydroxy, amino or optionally substituted mono- or di-alkylamino at the carboxy terminal of said tripeptide, and wherein said substituent is amino, monoalkylamino, dialkylamino, trialkylammonium, guanidino or aryl;

(2-6) hydrazino or hydroxamic acid which may be substituted with alkyl or arylalkyl optionally substituted further with alkyl; and (2-7) alkoxy which may be substituted with arylcarbonyl optionally substituted with nitro, hydroxamic acid or alkyl; with the proviso that any aryl ring present in the groups in (2-2)-(2-7) may contain a heteroatom, and any carbon-carbon single bond may be interrupted with a heteroatom or a heterogroup selected from —O(P=O)(OR$^F$)O— (R$^F$ is hydrogen, alkyloxycarbonyl or aryloxycarbonyl), and imino. R$^B$ is preferably —OH, —NHR$^5$, or —NHR$^5$R$^{5'}$ wherein R$^5$ and R$^{5'}$ is hydrogen, optionally substituted alkyl, —NH—R, —NH—COR, —NH—CONHR, —O—R (each R is independently hydrogen or optionally substituted alkyl), or amino sugar residue. Preferably, either of R$^5$ and R$^{5'}$ is hydrogen.

Preferred substituents for optionally substituted alkyl are hydrophilic substituents such as, for example, same or different 1 to 10, preferably 1 to 6, substituents selected from amino, mono- or di-lower alkylamino, trialkylamine, amino lower alkylamino, hydroxy lower alkylamino, hydroxy, carboxy, lower alkoxycarbonyl, SO$_3$H, PO$_3$H$_2$, optionally substituted carbamoyl, quaternary ammonium group (e.g., tri-alkylamino (e.g., —N⁺ (CH$_3$)$_3$)), optionally substituted heterocyclic group (heterocycle or heteroaryl), optionally substituted heterocyclic ring thio, guanidino, NHSO$_2$NH$_2$, hydroxy lower alkoxy. A nitrogen atom in the heterocyclic ring may be quaternized to form a salt. Substituents for the optionally substituted heterocyclic include hydroxy, amino, carboxy, amino lower alkyl, quaternary ammonium lower alkyl. The lower alkyl group on the quaternary ammonium group may further be substituted with substituted alkyl (substituent: carboxy, hydroxy, quaternary ammonium group).

R$^C$ is selected from the group consisting of the following (3-1)-(3-4):

(3-1) hydrogen;

(3-2) aminomethyl optionally substituted with alkyl, cycloalkyl or alkylene, wherein said alkyl, cycloalkyl and alkylene may by substituted with amino optionally substituted with alkyloxycarbonyl or aryloxycarbonyl, monoalkylamino, dialkylamino, trialkylammonium, aryl optionally substituted with cycloalkyl, hydroxy, guanidino, —O—(P=O)(OH)$_2$, carboxy, —N⁺ ($R^X$)$_2$ (CH$_2$)$_m$N⁺ ($R^X$)$_3$, or —(C=O)—N⁻—N⁺ ($R^X$)$_3$, in which m is 1 to 3, R$^X$ is C$_1$-C$_3$ alkyl, or combination thereof, and wherein alkyl of said monoalkylamino or dialkylamino is further optionally substituted with amino;

(3-3) alkynyl that may have a substituent wherein said substituent is amino optionally substituted with alkyloxycarbonyl or aryloxycarbonyl, or aryl;

(3-4) halo;
with the proviso that any aryl ring present in the groups in (3-2) and (3-3) may contain a heteroatom, and any carbon-carbon single bond may be interrupted with a heteroatom or a heterogroup selected from —O(P=O)(OR$^F$)O— (R$^F$ is hydrogen, alkyloxycarbonyl or aryloxycarbonyl), amido or imino.

R$^C$ is preferably hydrogen or optionally substituted alkyl. Substituent for such optionally substituted alkyl is preferably —NHR$^5$ described above or those described above for optionally substituted alkyl in R$^5$.

Preferred combination of R$^B$ and R$^C$ includes instance such as R$^B$ is hydrogen, —NHR$^5$ (R$^5$ is mono- or di-lower alkylamino lower alkyl, tri-lower alkylammonium lower alkyl, or amino sugar residue), —NR$^5$R$^{5'}$ (R$^5$ and R$^{5'}$ is together hydroxy lower alkyl), or —NHCH$_2$CON—N⁺ (Me)$_3$; and R$^C$ is hydrogen, mono- or di-substituted amino lower alkyl (Example for substituent: lower alkyl, mono- or di-lower alkylamino lower alkyl, tri-lower alkylammonium lower alkyl, hydroxy lower alkyl, hydroxy lower alkoxy lower alkyl, —CH$_2$CON—N⁺ (Me)$_3$, lower alkyl substituted with 1 to 6 hydroxy, and carboxy, hydroxy, oxo, optionally substituted carbamoyl, guanidido, sulfonate group, phosphate group, lower alkyl substituted with NHSO$_2$NH$_2$ and/or amino, optionally substituted heterocycle lower alkyl (substituent: amino lower alkyl), optionally substituted quaternary ammonium lower alkyl (substituent: carboxy, hydroxy, quaternary ammonium group)). Specific combinations are provided in the following Tables 1-6 to 1-8. Also, other preferred embodiments are presented in the following Tables 47 to 53, 99 to 108.

R$^D$ is selected from the group consisting of the following (4-1)-(4-6):

(4-1) hydrogen;

(4-2) alkyl that may have a substituent, wherein said substituent is alkyloxycarbonyl, amino, optionally alkylated aryl, arylcarbonyl, carbamoyl, mono- or di-alkylcarbamoyl or mono- or di-arylalkylcarbamoyl, or combination thereof, and wherein alkyl or aryl in said substituent further may be substituted with amino or hydroxy optionally substituted with alkyloxycarbonyl or aryloxycarbonyl;

(4-3) alkyloxycarbonyl that may be substituted with optionally alkylated aryl;

(4-4) arylamido or arylthioamido;

(4-5) amino or amidino optionally alkylated; and (4-6) nitroso; with the proviso that any aryl ring present in the groups in (4-2) to (4-5) may contain a heteroatom, and any carbon-carbon single bond may be interrupted with a heteroatom. R$^D$ is preferably hydrogen or optionally substituted alkyl. Also, the N-terminal moiety may be converted to —NH$_2$ by removing the leucine residue, and further optionally acylated, according to a procedure as described in literatures such as Expert Opin. Ther. Patents (2004) 14, 141-173 (e.g., Table 110).

Preferred compounds of the invention are categorized as follows:

1) A compound or pharmaceutically acceptable salt or solvate thereof wherein R$^A$ is represented by the formula: —

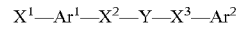

in which each variable is as defined above;

2) A compound, a pharmaceutically acceptable salt, or solvate thereof wherein Ar$^1$ and Ar$^2$ are optionally substituted aryl or optionally substituted heteroaryl or optionally substituted cycloalkyl;

3) A compound, a pharmaceutically acceptable salt, or solvate thereof wherein Ar$^1$ and Ar$^2$ are optionally substituted benzene ring, and Y is —NHCO— or —CONH—;

4) A compound, a pharmaceutically acceptable salt, or solvate thereof wherein X$^1$ is lower alkylene;

5) A compound, a pharmaceutically acceptable salt, or solvate thereof wherein X$^2$ is a single bond, lower alkylene or a heteroatomic group as described above;

6) A compound, a pharmaceutically acceptable salt, or solvate thereof wherein X$^3$ is a single bond, lower alkylene or a heteroatomic group as described above;

7) A compound, a pharmaceutically acceptable salt, or solvate thereof wherein R$^A$ is represented by the formula:

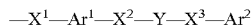

—X$^1$—Ar$^1$—X$^2$—Y—X$^3$—Ar$^2$ in which X$^1$ is lower alkylene; X$^2$ is a single bond, lower alkylene or a heteroatomic group as described above; X$^3$ is a single bond, lower alkylene or a heteroatomic group as described above; Y is —NHCO— or —CONH—; Ar$^1$ is optionally substituted benzene ring; and Ar$^2$ is optionally substituted benzene ring, optionally substituted heterocycle or optionally substituted cycloalkyl;

8) A compound, a pharmaceutically acceptable salt, or solvate thereof wherein R$^A$ is represented by the formula:

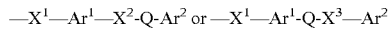

—X$^1$—Ar$^1$—X$^2$-Q-Ar$^2$ or —X$^1$—Ar$^1$-Q-X$^3$—Ar$^2$ in which X$^1$ is lower alkylene; X$^2$ and X$^3$ are a single bond, lower alkylene or a heteroatomic group as described above; Ar$^1$ is optionally substituted benzene ring; and Ar$^2$ is optionally substituted benzene ring, optionally substituted heterocycle or optionally substituted cycloalkyl;

9) A compound, a pharmaceutically acceptable salt, or solvate thereof wherein R$^A$ is a benzene ring or a heterocycle optionally substituted with one or more substituent selected from the group consisting of lower alkyl, nitro, aralkyloxy, optionally substituted amino, hydroxy, halo, oxo, lower alkoxy, aryloxy, carbamoyl, optionally substituted carbamoyloxy, and heterocycle group; another preferred embodiment of Ar$^2$ is aryl optionally substituted with one or more substituent selected from the group consisting of halo, mono-, di- or tri-halogenated lower alkyl, mono-, di- or tri-halogenated lower alkoxy, mono-, di- or tri-halogenated lower alkylthio, mono- or di-lower alkylamino, cycloalkylmethyloxy, benzyloxy, lower alkoxycarbonylamino, and nitro; and 10) A compound, a pharmaceutically acceptable salt, or solvate thereof wherein amino sugar moiety is L-vancosaminyl, 3-desmethyl-vancosaminyl, 3-epi-vancosaminyl, 4-epi-vancosaminyl, 4-keto-vancosaminyl, acosaminyl, actinosaminyl, daunosaminyl, 3-epi-daunosaminyl, ristosaminyl, N-methyl-D-glucaminyl, N-Acetyl-D-glucosamyl, or N-acyl-D-glucosamyl, more preferably L-vancosaminyl.

The compound may be constituted with any combination of two or more of the above categories 1) to 10).

11) More preferred compound of the invention is that wherein R$^A$ is a group represented by the formula:

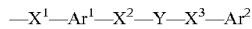

—X$^1$—Ar$^1$—X$^2$—Y—X$^3$—Ar$^2$ in which X$^1$ is lower alkylene; X$^2$ is a single bond; X$^3$ is a single bond; Y is —NHCO— or —CONH—; Ar$^1$ is optionally substituted benzene ring; and Ar$^2$ is optionally substituted benzene ring, optionally substituted heterocycle or optionally substituted cycloalkyl, preferably optionally substituted benzene ring. Substituent for Ar$^1$ includes optionally substituted amino and/or substituent for Ar$^2$ is preferably one or more selected from the group consisting of halo, mono-, di- or tri-halogenated lower alkyl, mono-, di- or tri-halogenated lower alkoxy, mono-, di- or tri-halogenated lower alkylthio, mono- or di-lower alkylamino, cycloalkylmethyloxy, benzyloxy, lower alkoxycarbonylamino, and nitro; R$^B$ is —NR$^5$R$^{5'}$; R$^C$ is a group other than hydrogen (preferably optionally substituted alkyl); and/or R$^D$ is a group other than hydrogen (e.g., optionally substituted alkyl).

Preferred chemical modifications for R$^B$ and R$^C$ are as described above.

Another preferred embodiment of the compound is as follows.

12) Ar$^1$ is optionally substituted heteroaryl;

13) X$^1$ is lower alkylene; X$^2$ is a single bond, lower alkylene or a heteroatomic group as described above; X$^3$ is a single bond, lower alkylene or heteroatomic group; Y is —NHCO— or —CONH—; Ar$^1$ is optionally substituted heteroaryl; and Ar$^2$ is optionally substituted phenyl, optionally substituted heterocycle or optionally substituted cycloalkyl;

14) R$^B$ is —OH; R$^C$ is hydrogen; and R$^D$ is hydrogen;

15) R$^B$ is —NR$^5$R$^5$, wherein R$^5$ and R$^{5'}$ are independently hydrogen, optionally substituted alkyl, or amino sugar residue; R$^C$ is hydrogen; and R$^D$ is hydrogen;

16) R$^B$ is —NR$^5$R$^{5'}$ wherein R$^5$ is hydrogen; R$^{5'}$ is alkyl or, amino sugar residue substituted with a hydrophilic substituent; R$^C$ is hydrogen; and R$^D$ is hydrogen;

17) R$^B$ is —OH; R$^C$ is optionally substituted alkyl in which alkyl moiety may be interrupted with a heteroatomic group; and R$^D$ is hydrogen;

18) R$^B$ is —OH; R$^C$ is alkyl substituted with a hydrophilic substituent in which alkyl moiety may be interrupted with a heteroatomic group; and R$^D$ is hydrogen;

19) X$^1$ is lower alkylene; X$^2$ is a single bond, lower alkylene or a heteroatomic group; X$^3$ is a single bond, lower alkylene or a heteroatomic group; Y is —NHCO— or —CONH—; Ar$^1$ is optionally substituted phenyl or optionally substituted heteroaryl; Ar$^2$ is optionally substituted phenyl, optionally substituted heterocycle or optionally substituted cycloalkyl; and the compound meets at least one of the requirements 1)-3) for R$^B$, R$^C$ and R$^D$:

1) R$^B$ is —NR$^5$R$^{5'}$ wherein R$^5$ and R$^{5'}$ are independently hydrogen, optionally substituted alkyl, or amino sugar residue;

2) R$^C$ is optionally substituted alkyl in which alkyl moiety may be interrupted with a heteroatomic group;

3) R$^D$ is lower alkyl;

(20) X$^1$ is lower alkylene, preferably C$_1$-C$_3$ alkylene; X$^2$ is a single bond, lower alkylene or a heteroatomic group as described above (e.g., NH), preferably a single bond; X$^3$ is a single bond, lower alkylene or heteroatomic group (e.g., NH), preferably a single bond; Y is —NHCO— or —CONH—; Ar$^1$ is optionally substituted heteroaryl or optionally substituted heterocycle (preferably 5-6 membered ring); and Ar$^2$ is optionally substituted phenyl, optionally substituted heterocycle (preferably 5-6 membered ring) or optionally substituted cycloalkyl (preferably 3-7 membered ring). One of such embodiment includes compounds that further meet at least one of the requirements 1)-4) for R$^B$, R$^C$ and R$^D$:

1) R$^B$ is —OH, —NR$^5$R$^{5'}$ wherein R$^5$ and R$^{151}$ are independently hydrogen, optionally substituted alkyl, —NH—R, —NH—COR, —NH—CONHR, —O—R (each R is independently hydrogen or optionally substituted alkyl) or amino sugar residue, or —OR$^6$ (R$^6$ is optionally substituted alkyl in which alkyl moiety may be interrupted with a heteroatomic group such as, preferably one to two NH, O etc.);

2) R$^C$ is optionally substituted alkyl in which alkyl moiety may be interrupted with a heteroatomic group;

3) R$^D$ is lower alkyl;

4) leucine residue has been removed at the N-terminal

More specifically, the compounds of the invention are listed bellow.

TABLE 1
| $R^A$ | $R^B$ | $R^C$ | $R^D$ |
|---|---|---|---|
| 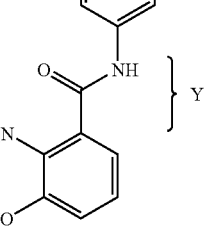 | OH or NH—R | CH$_2$—NH—R | H |
| 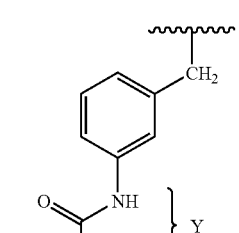 | OH or NH—R | CH$_2$—NH—R | H |
| $R^B$ | $R^C$ | $R^D$ |
|---|---|---|
| —NH(CH$_2$)$_2$NMe$_2$ | H | H |
| —NH(CH$_2$)$_2$N$^+$Me$_3$ | H | H |
| —NH(CH$_2$)$_3$NMe$_2$ | H | H |
| —NH(CH$_2$)$_3$N$^+$Me$_3$ | H | H |
| —NH(CH$_2$)$_2$NH(CH$_2$)$_2$NH$_2$ | H | H |
| —NH(CH$_2$)$_2$NH(CH$_2$)$_2$OH | H | H |
| —N[(CH$_2$)$_2$OH]$_2$ | H | H |
| —NHCH$_2$CO$_2$H | H | H |
| —NH(CH$_2$)$_2$CO$_2$H | H | H |
| —NH(CH$_2$)$_2$SO$_3$H | H | H |
| —NH(CH$_2$)$_2$PO$_3$H$_2$ | H | H |
| 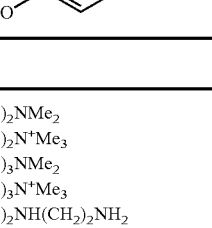 | H | H |
| 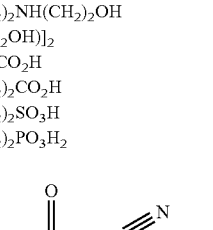 | H | H |
| 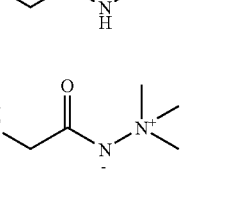 | H | H |
| 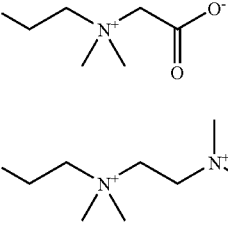 | H | H |

TABLE 1-continued
| Structure | | |
|---|---|---|
| 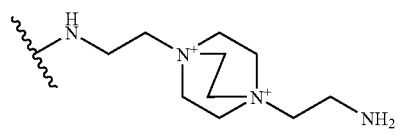 | H | H |
| 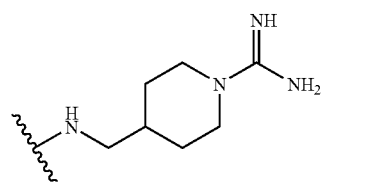 [SMILES: *NCC1CCN(C(=N)N)CC1] | H | H |
| 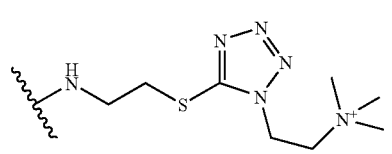 [SMILES: *NCCSc1nnnn1CC[N+](C)(C)C] | H | H |
| 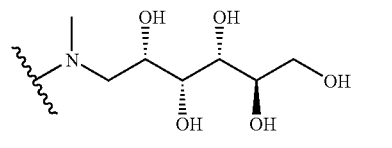 | H | H |
| 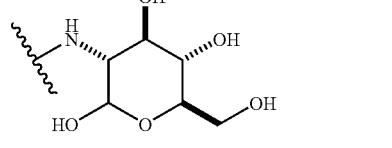 | H | H |
| 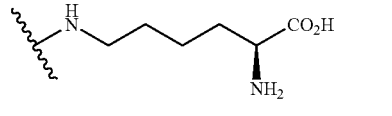 [SMILES: *NCCCC[C@H](N)C(=O)O] | H | H |
| 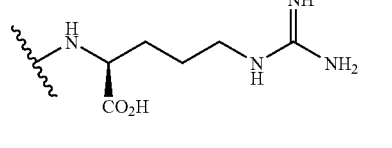 | H | H |
| 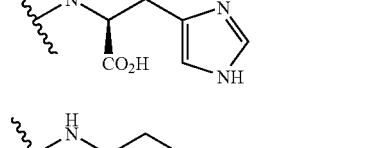 | H | H |
| 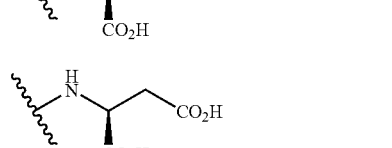 | H | H |
| | H | H |
| H | —CH$_2$NHMe | H |
| H | —CH$_2$NH(CH$_2$)$_2$NH$_2$ | H |
| H | —CH$_2$NH(CH$_2$)$_2$NMe$_2$ | H |
| H | —CH$_2$NH(CH$_2$)$_2$N$^+$Me$_3$ | H |
| H | —CH$_2$N[(CH$_2$)$_2$OH]$_2$ | |
| H | —CH$_2$NHCH$_2$CO$_2$H | H |
| H | —CH$_2$NH(CH$_2$)$_2$CO$_2$H | H |
| H | —CH$_2$NH(CH$_2$)$_2$SO$_3$H | H |
| H | —CH$_2$NHCH$_2$PO$_3$H$_2$ | H |

TABLE 1-continued
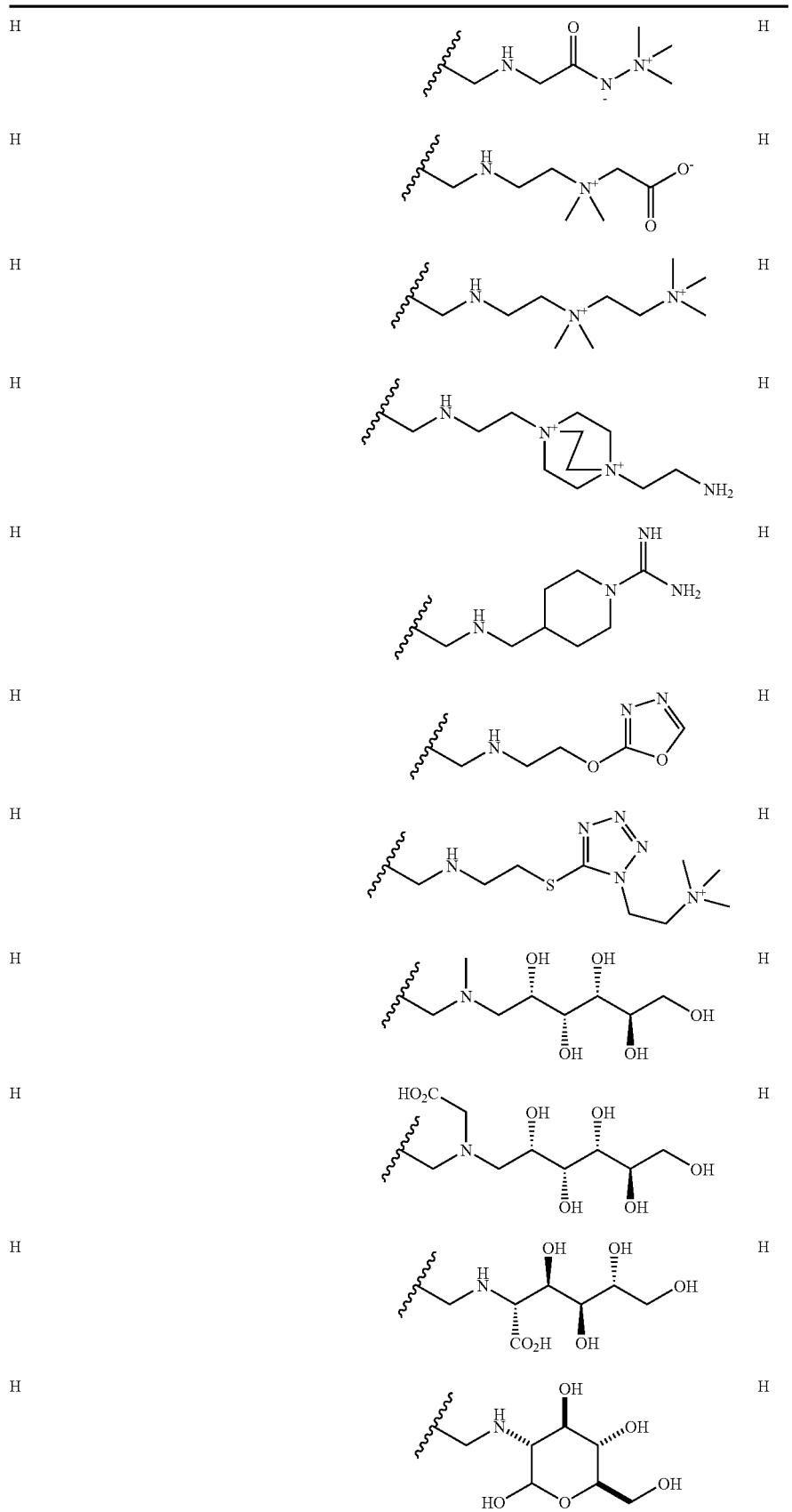

TABLE 1-continued

| | | |
|---|---|---|
| H | [structure: ~NH-CH2CH2CH2CH2-CH(NH2)-CO2H, lysine-like] | H |
| H | [structure: ~NH-CH(CO2H)-CH2CH2CH2-NH-C(=NH)NH2, arginine-like] | H |
| H | [structure: ~NH-CH(CO2H)-CH2-(imidazole), histidine-like] | H |
| H | [structure: ~NH-CH(CO2H)-CH2-CONH2, asparagine-like] | H |
| —NH(CH$_2$)$_3$NMe$_2$ | —CH$_2$NH(CH$_2$)$_2$N$^+$Me$_3$ | H |
| —NH(CH$_2$)$_3$NMe$_2$ | —CH$_2$N[(CH$_2$)$_2$OH]$_2$ | H |
| —NH(CH$_2$)$_3$NMe$_2$ | [structure: ~NH-CH2-C(=O)-N(-)-N+Me3] | H |
| —NH(CH$_2$)$_3$NMe$_2$ | [structure: ~N(Me)-CH2-(CHOH)4-CH2OH, N-methylglucamine] | H |
| —NH(CH$_2$)$_3$NMe$_2$ | [structure: ~NH+-CH2CH2CH2CH2-CH(NH2)-CO2H] | H |
| —NH(CH$_2$)$_2$N$^+$Me$_3$ | —CH$_2$NH(CH$_2$)$_2$N$^+$Me$_3$ | H |
| —NH(CH$_2$)$_2$N$^+$Me$_3$ | —CH$_2$N[(CH$_2$)$_2$OH]$_2$ | H |
| —NH(CH$_2$)$_2$N$^+$Me$_3$ | [structure: ~NH-CH2-C(=O)-N(-)-N+Me3] | H |
| —NH(CH$_2$)$_2$N$^+$Me$_3$ | [structure: ~N(Me)-CH2-(CHOH)4-CH2OH] | H |
| —NH(CH$_2$)$_2$N$^+$Me$_3$ | [structure: ~NH-CH2CH2CH2CH2-CH(NH2)-CO2H] | H |
| —N[(CH$_2$)$_2$OH]$_2$ | —CH$_2$NH(CH$_2$)$_2$N$^+$Me$_3$ | H |
| —N[(CH$_2$)$_2$OH]$_2$ | —CH$_2$N[(CH$_2$)$_2$OH]$_2$ | H |

TABLE 1-continued

| | | |
|---|---|---|
| —N[(CH$_2$)$_2$OH]$_2$ | ~NH-CH$_2$-C(O)-N$^-$-N$^+$Me$_3$ (with methyl on amide N) | H |
| —N[(CH$_2$)$_2$OH]$_2$ | ~N(Me)-CH$_2$-CHOH-CHOH-CHOH-CHOH-CH$_2$OH | H |
| —N[(CH$_2$)$_2$OH]$_2$ | ~NH-(CH$_2$)$_4$-CH(NH$_2$)-CO$_2$H | H |
| —NH(CH$_2$)$_2$CO$_2$H | —CH$_2$NH(CH$_2$)$_2$N$^+$Me$_3$ | H |
| —NH(CH$_2$)$_2$CO$_2$H | —CH$_2$N[(CH$_2$)$_2$OH]$_2$ | H |
| —NH(CH$_2$)$_2$CO$_2$H | ~NH-CH$_2$-C(O)-N$^-$-N$^+$Me$_3$ | H |
| —NH(CH$_2$)$_2$CO$_2$H | ~N(Me)-CH$_2$-CHOH-CHOH-CHOH-CHOH-CH$_2$OH | H |
| —NH(CH$_2$)$_2$CO$_2$H | ~NH-(CH$_2$)$_4$-CH(NH$_2$)-CO$_2$H | H |
| ~NH-CH$_2$-C(O)-N$^-$-N$^+$Me$_3$ | —CH$_2$NH(CH$_2$)$_2$N$^+$Me$_3$ | H |
| ~NH-CH$_2$-C(O)-N$^-$-N$^+$Me$_3$ | —CH$_2$N[(CH$_2$)$_2$OH]$_2$ | H |
| ~NH-CH$_2$-C(O)-N$^-$-N$^+$Me$_3$ | ~NH-CH$_2$-C(O)-N$^-$-N$^+$Me$_3$ | H |
| ~NH-CH$_2$-C(O)-N$^-$-N$^+$Me$_3$ | ~N(Me)-CH$_2$-CHOH-CHOH-CHOH-CHOH-CH$_2$OH | H |
| ~NH-CH$_2$-C(O)-N$^-$-N$^+$Me$_3$ | ~NH-(CH$_2$)$_4$-CH(NH$_2$)-CO$_2$H | H |

TABLE 1-continued
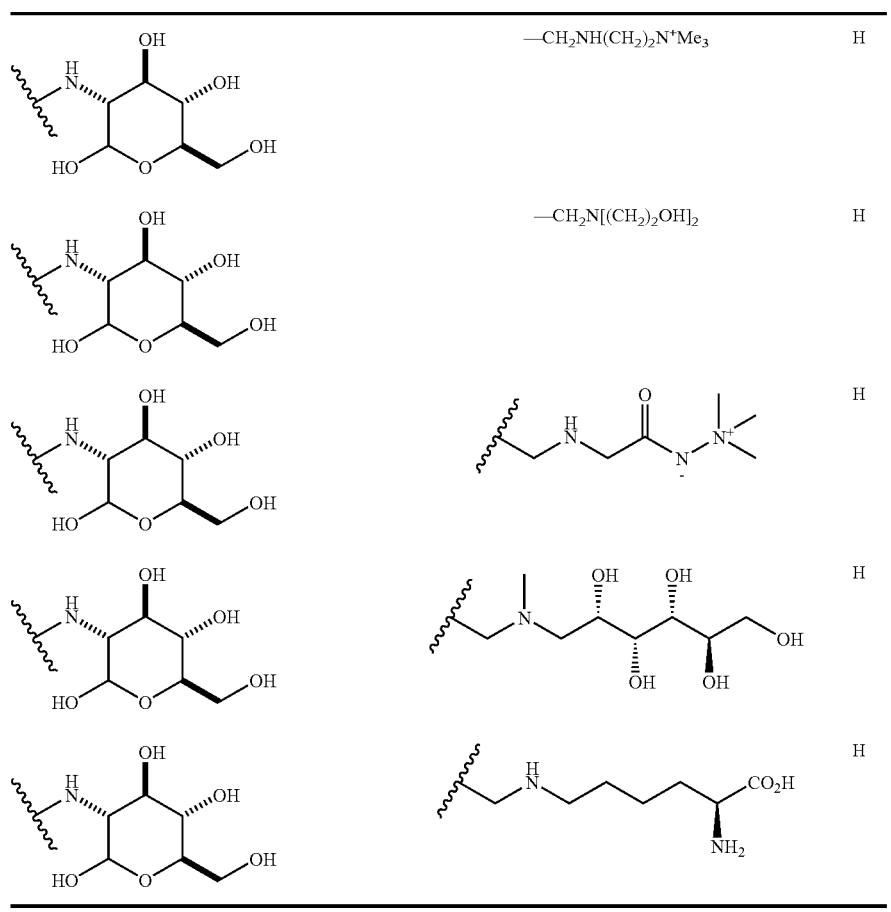
TABLE 2
| $R^A$ | $R^B$ | $R^C$ | $R^D$ |
|---|---|---|---|
| (structure shown below) | OH or NH—R | CH$_2$—NH—R | H or Me |
$R^A$
| Ar2 | | | | | | | | | |
|---|---|---|---|---|---|---|---|---|---|
| R11 | R12 | R13 | R14 | R15 | X3 | Y | X2 | Ar1 | X1 |
| NO2 | OH | Me | H | H | bond | CONH | bond | (m-phenylene) | CH2 |

TABLE 2-continued

| | | | | | | | | |
|---|---|---|---|---|---|---|---|---|
| NO2 | OMe | Me | H | H | bond | CONH | bond | *m-phenylene* | CH2 |
| NO2 | OiPr | Me | H | H | bond | CONH | bond | *m-phenylene* | CH2 |
| NO2 | OnBu | Me | H | H | bond | CONH | bond | *m-phenylene* | CH2 |
| NO2 | OBn | H | H | H | bond | CONH | bond | *m-phenylene* | CH2 |
| NO2 | OBn | Me | H | H | bond | CONH | bond | *m-phenylene* | CH2 |
| NO2 | O-Picolyl | Me | H | H | bond | CONH | bond | *m-phenylene* | CH2 |
| NO2 | O-Furfuryl | Me | H | H | bond | CONH | bond | *m-phenylene* | CH2 |
| NO2 | O-Thiophene methyl | Me | H | H | bond | CONH | bond | *m-phenylene* | CH2 |
| NO2 | O-Cyclohexyl methyl | Me | H | H | bond | CONH | bond | *m-phenylene* | CH2 |
| NO2 | O-Tetrahydro pyran-4-yl | Me | H | H | bond | CONH | bond | *m-phenylene* | CH2 |
| NO2 | O-[1,3]dioxo-lan-2-ylmethyl | Me | H | H | bond | CONH | bond | *m-phenylene* | CH2 |

TABLE 2-continued

| | | | | | | | | |
|---|---|---|---|---|---|---|---|---|
| NH2 | OH | Me | H | H | bond | CONH | bond | *m*-phenylene | CH2 |
| NH2 | OMe | Me | H | H | bond | CONH | bond | *m*-phenylene | CH2 |
| NH2 | OiPr | Me | H | H | bond | CONH | bond | *m*-phenylene | CH2 |
| NH2 | OnBu | Me | H | H | bond | CONH | bond | *m*-phenylene | CH2 |
| NH2 | OBn | H | H | H | bond | CONH | bond | *m*-phenylene | CH2 |
| NH2 | OBn | Me | H | H | bond | CONH | bond | *m*-phenylene | CH2 |
| NMe2 | OH | Me | H | H | bond | CONH | bond | *m*-phenylene | CH2 |
| NMe2 | OMe | Me | H | H | bond | CONH | bond | *m*-phenylene | CH2 |
| NMe2 | OiPr | Me | H | H | bond | CONH | bond | *m*-phenylene | CH2 |
| NMe2 | OnBu | Me | H | H | bond | CONH | bond | *m*-phenylene | CH2 |
| NMe2 | OBn | H | H | H | bond | CONH | bond | *m*-phenylene | CH2 |

TABLE 2-continued

| | | | | | | | | |
|---|---|---|---|---|---|---|---|---|
| NMe2 | OBn | Me | H | H | bond | CONH | bond | *m-phenylene* | CH2 |
| NH(CH2)2OH | OH | H | H | H | bond | CONH | bond | *m-phenylene* | CH2 |
| NH(CH2)2OH | OMe | H | H | H | bond | CONH | bond | *m-phenylene* | CH2 |
| NH(CH2)2OH | OiPr | H | H | H | bond | CONH | bond | *m-phenylene* | CH2 |
| NH(CH2)2OH | OnBu | H | H | H | bond | CONH | bond | *m-phenylene* | CH2 |
| NH(CH2)2OH | OBn | H | H | H | bond | CONH | bond | *m-phenylene* | CH2 |
| NH(CH2)2OH | O-Picolyl | H | H | H | bond | CONH | bond | *m-phenylene* | CH2 |
| Pyperizin-N-yl | OMe | H | H | H | bond | CONH | bond | *m-phenylene* | CH2 |
| Pyperazin-N-yl | OMe | H | H | H | bond | CONH | bond | *m-phenylene* | CH2 |
| NHAc | OH | H | H | H | bond | CONH | bond | *m-phenylene* | CH2 |
| NHAc | OMe | H | H | H | bond | CONH | bond | *m-phenylene* | CH2 |

TABLE 2-continued
| | | | | | | | | |
|---|---|---|---|---|---|---|---|---|
| NHAc | OiPr | H | H | H | bond | CONH | bond | 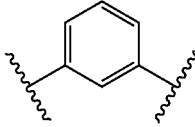 | CH2 |
| NHAc | OnBu | H | H | H | bond | CONH | bond | 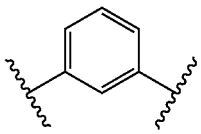 [SMILES: *c1cccc(*)c1] | CH2 |
| NHAc | OBn | H | H | H | bond | CONH | bond | 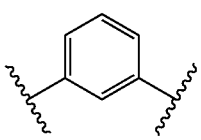 [SMILES: *c1cccc(*)c1] | CH2 |
| NHAc | O-Picolyl | H | H | H | bond | CONH | bond | 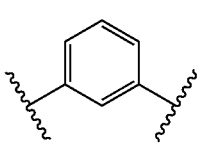 [SMILES: *c1cccc(*)c1] | CH2 |
| NHCO2Me | OBn | H | H | H | bond | CONH | bond | 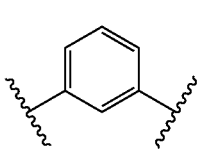 [SMILES: *c1cccc(*)c1] | CH2 |
| NHCONHMe | OBn | H | H | H | bond | CONH | bond | 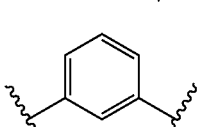 | CH2 |
| NC(=S)NH2 | OBn | H | H | H | bond | CONH | bond | 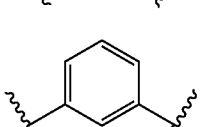 | CH2 |
| OCONH2 | OBn | H | H | H | bond | CONH | bond | 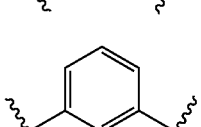 | CH2 |
| CONHMe | OBn | H | H | H | bond | CONH | bond | 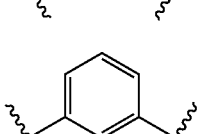 | CH2 |
| CN | OH | H | H | H | bond | CONH | bond |  | CH2 |
| CN | OMe | H | H | H | bond | CONH | bond | 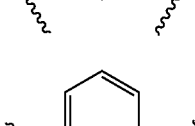 | CH2 |

TABLE 2-continued

| | | | | | | | | |
|---|---|---|---|---|---|---|---|---|
| CN | OiPr | H | H | H | bond | CONH | bond (m-phenylene) | CH2 |
| CN | OnBu | H | H | H | bond | CONH | bond (m-phenylene) | CH2 |
| CN | OBn | H | H | H | bond | CONH | bond (m-phenylene) | CH2 |
| CN | O-Picolyl | H | H | H | bond | CONH | bond (m-phenylene) | CH2 |
| OBn | NO2 | H | H | H | bond | CONH | bond (m-phenylene) | CH2 |
| OMe | NO2 | H | H | H | bond | CONH | bond (m-phenylene) | CH2 |
| OBn | NHMe | H | H | H | bond | CONH | bond (m-phenylene) | CH2 |
| OBn | NHAc | H | H | H | bond | CONH | bond (m-phenylene) | CH2 |
| OBn | H | NO2 | H | H | bond | CONH | bond (m-phenylene) | CH2 |
| OBn | H | H | NO2 | H | bond | CONH | bond (m-phenylene) | CH2 |
| OBn | H | H | H | NO2 | bond | CONH | bond (m-phenylene) | CH2 |

TABLE 2-continued

| | | | | | | | | |
|---|---|---|---|---|---|---|---|---|
| NO2 | H | OBn | H | H | bond | CONH | bond *m*-phenylene | CH2 |
| NO2 | H | H | OBn | H | bond | CONH | bond *m*-phenylene | CH2 |
| NO2 | H | H | H | OBn | bond | CONH | bond *m*-phenylene | CH2 |
| NO2 | H | OMe | H | H | bond | CONH | bond *m*-phenylene | CH2 |
| NO2 | H | H | OMe | H | bond | CONH | bond *m*-phenylene | CH2 |
| NO2 | H | H | H | OMe | bond | CONH | bond *m*-phenylene | CH2 |
| NO2 | Me | OBn | H | H | bond | CONH | bond *m*-phenylene | CH2 |
| NHAc | H | OBn | H | H | bond | CONH | bond *m*-phenylene | CH2 |
| NHAc | H | H | OBn | H | bond | CONH | bond *m*-phenylene | CH2 |
| NHAc | H | H | H | OBn | bond | CONH | bond *m*-phenylene | CH2 |
| NHAc | H | OMe | H | H | bond | CONH | bond *m*-phenylene | CH2 |

TABLE 2-continued
| | | | | | | | | |
|---|---|---|---|---|---|---|---|---|
| NHAc | H | H | OMe | H | bond | CONH | bond | 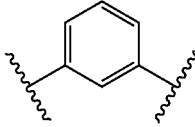 | CH2 |
| NHAc | H | H | H | OMe | bond | CONH | bond | 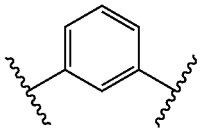 [SMILES: *c1cccc(*)c1] | CH2 |
| F | OH | Me | H | H | bond | CONH | bond | 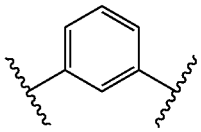 [SMILES: *c1cccc(*)c1] | CH2 |
| F | OMe | Me | H | H | bond | CONH | bond | 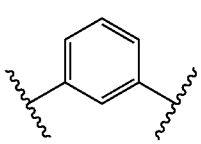 [SMILES: *c1cccc(*)c1] | CH2 |
| F | OiPr | Me | H | H | bond | CONH | bond | 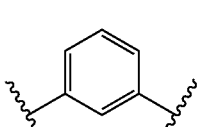 | CH2 |
| F | OnBu | Me | H | H | bond | CONH | bond | 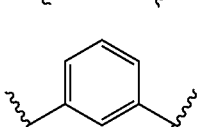 | CH2 |
| F | OBn | H | H | H | bond | CONH | bond | 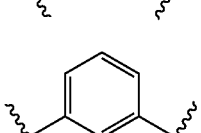 | CH2 |
| F | OBn | Me | H | H | bond | CONH | bond | 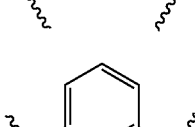 | CH2 |
| F | O-Picolyl | Me | H | H | bond | CONH | bond | 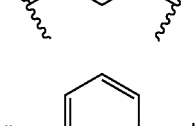 | CH2 |
| Cl | OH | Me | H | H | bond | CONH | bond | 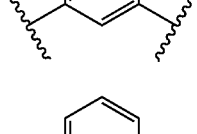 | CH2 |
| Cl | OMe | Me | H | H | bond | CONH | bond | 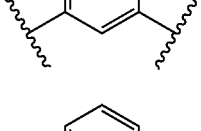 | CH2 |

TABLE 2-continued

| | | | | | | | | |
|---|---|---|---|---|---|---|---|---|
| Cl | OiPr | Me | H | H | bond | CONH | bond | *m*-phenylene | CH2 |
| Cl | OnBu | Me | H | H | bond | CONH | bond | *m*-phenylene | CH2 |
| Cl | OBn | H | H | H | bond | CONH | bond | *m*-phenylene | CH2 |
| Cl | OBn | Me | H | H | bond | CONH | bond | *m*-phenylene | CH2 |
| Cl | O-Picolyl | Me | H | H | bond | CONH | bond | *m*-phenylene | CH2 |
| Br | OBn | Me | H | H | bond | CONH | bond | *m*-phenylene | CH2 |
| OCF3 | OBn | Me | H | H | bond | CONH | bond | *m*-phenylene | CH2 |
| NO2 | F | H | H | H | bond | CONH | bond | *m*-phenylene | CH2 |
| NO2 | Cl | H | H | H | bond | CONH | bond | *m*-phenylene | CH2 |
| NO2 | Br | H | H | H | bond | CONH | bond | *m*-phenylene | CH2 |
| NO2 | OCF3 | H | H | H | bond | CONH | bond | *m*-phenylene | CH2 |

TABLE 2-continued
| | | | | | | | | |
|---|---|---|---|---|---|---|---|---|
| NHAc | F | Me | H | H | bond | CONH | bond | 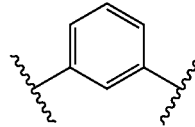 | CH2 |
| NHAc | Cl | Me | H | H | bond | CONH | bond | 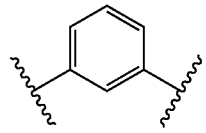 [SMILES: *c1cccc(*)c1] | CH2 |
| NHAc | Br | Me | H | H | bond | CONH | bond | 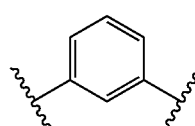 | CH2 |
| NHAc | OCF3 | Me | H | H | bond | CONH | bond | 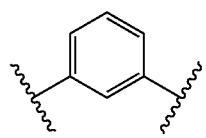 [SMILES: *c1cccc(*)c1] | CH2 |
| NO2 | OCONHPh | H | H | H | bond | CONH | bond | 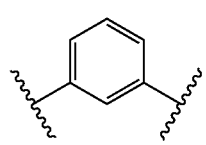 [SMILES: *c1cccc(*)c1] | CH2 |
| NO2 | OCONHMe | H | H | H | bond | CONH | bond | 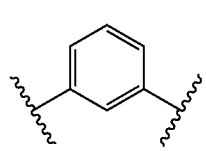 [SMILES: *c1cccc(*)c1] | CH2 |
| CN | OCONHPh | H | H | H | bond | CONH | bond | 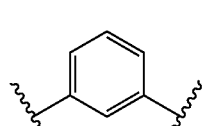 | CH2 |
| CN | OCONHMe | H | H | H | bond | CONH | bond | 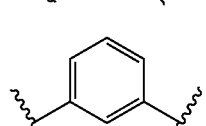 | CH2 |
| H | SO2NHPh | H | H | H | bond | CONH | bond | 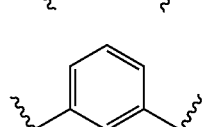 | CH2 |
| NO2 | SO2NHMe | H | H | H | bond | CONH | bond | 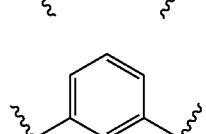 | CH2 |
| NO2 | OH | H | H | H | bond | CONMe | bond | 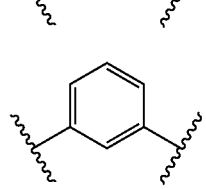 | CH2 |

TABLE 2-continued

| | | | | | | | | |
|---|---|---|---|---|---|---|---|---|
| NO2 | OMe | H | H | H | bond | CONMe | bond | *m*-phenylene | CH2 |
| NO2 | OiPr | H | H | H | bond | CONMe | bond | *m*-phenylene | CH2 |
| NO2 | OnBu | H | H | H | bond | CONMe | bond | *m*-phenylene | CH2 |
| NO2 | OBn | H | H | H | bond | CONMe | bond | *m*-phenylene | CH2 |
| NO2 | OBn | Me | H | H | bond | CONMe | bond | *m*-phenylene | CH2 |
| NO2 | O-Picolyl | H | H | H | bond | CONMe | bond | *m*-phenylene | CH2 |
| NO2 | OBn | H | H | H | CH2 | CONH | bond | *m*-phenylene | CH2 |
| NO2 | OMe | H | H | H | CH2 | CONH | bond | *m*-phenylene | CH2 |
| NHMe | OMe | H | H | H | CH2 | CONH | bond | *m*-phenylene | CH2 |
| NO2 | OBn | H | H | H | O | CONH | bond | *m*-phenylene | CH2 |
| NO2 | OMe | H | H | H | O | CONH | bond | *m*-phenylene | CH2 |

TABLE 2-continued
| | | | | | | | | | |
|---|---|---|---|---|---|---|---|---|---|
| NHMe | OMe | H | H | H | O | CONH | bond | 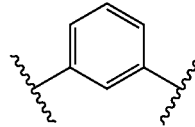 | CH2 |
| NO2 | OBn | H | H | H | NH | CONH | bond | 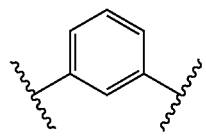 [SMILES: *c1cccc(*)c1] | CH2 |
| NO2 | OMe | H | H | H | NH | CONH | bond | 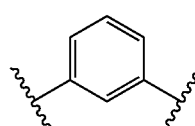 | CH2 |
| NHMe | OMe | H | H | H | NH | CONH | bond | 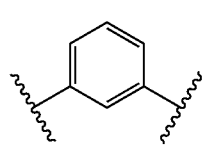 [SMILES: *c1cccc(*)c1] | CH2 |
| NO2 | OBn | H | H | H | bond | CONH | CH2 | 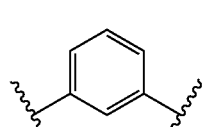 | CH2 |
| NO2 | OMe | H | H | H | bond | CONH | CH2 | 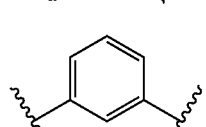 | CH2 |
| NHMe | OMe | H | H | H | bond | CONH | CH2 | 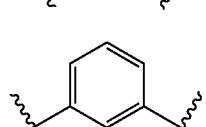 | CH2 |
| NO2 | OBn | H | H | H | bond | NHCO | O | 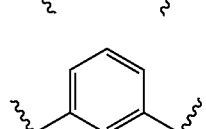 | CH2 |
| NO2 | OMe | H | H | H | bond | NHCO | O | 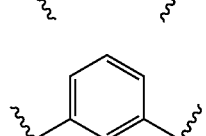 | CH2 |
| NHMe | OMe | H | H | H | bond | NHCO | O | 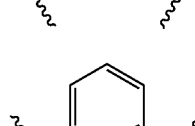 | CH2 |
| NO2 | OBn | H | H | H | bond | NHCO | NH |  | CH2 |

TABLE 2-continued
| | | | | | | | | | |
|---|---|---|---|---|---|---|---|---|---|
| NO2 | OMe | H | H | H | bond | NHCO | NH | 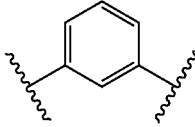 | CH2 |
| NHMe | OMe | H | H | H | bond | NHCO | NH | 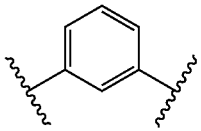 [SMILES: *c1cccc(*)c1] | CH2 |
| NHMe | OBn | H | H | H | bond | NMeCO | O | 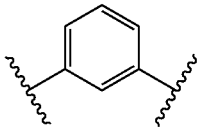 [SMILES: *c1cccc(*)c1] | CH2 |
| NHMe | OBn | H | H | H | bond | NMeCO | NH | 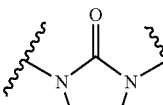 | CH2 |
| NHMe | OBn | H | H | H | 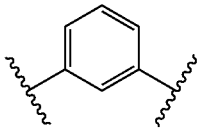 [SMILES: *c1cccc(*)c1] | | | 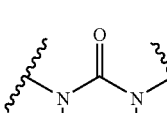 | CH2 |
| NHMe | OBn | H | H | H | 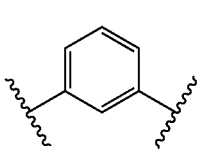 [SMILES: *c1cccc(*)c1] | | | 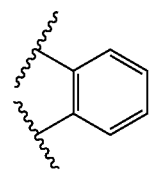 [SMILES: *c1ccccc1*] | CH2 |
| NO2 | OBn | Me | H | H | bond | CONH | bond | 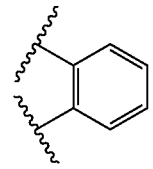 [SMILES: *c1ccccc1*] | CH2 |
| NHMe | OBn | H | H | H | bond | CONH | bond | 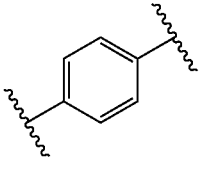 [SMILES: *c1ccc(*)cc1] | CH2 |
| NO2 | OBn | Me | H | H | bond | CONH | bond | 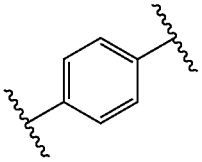 [SMILES: *c1ccc(*)cc1] | CH2 |
| NHMe | OBn | H | H | H | bond | CONH | bond | 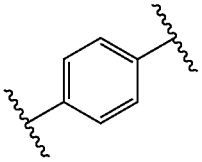 [SMILES: *c1ccc(*)cc1] | CH2 |

TABLE 2-continued
| | | | | | | | | | |
|---|---|---|---|---|---|---|---|---|---|
| NO2 | OBn | Me | H | H | bond | CONH | bond | 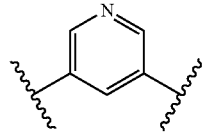 [SMILES: *c1cncc(*)c1] | CH2 |
| NHMe | OBn | H | H | H | bond | CONH | bond | 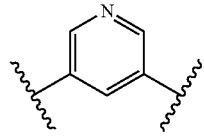 [SMILES: *c1cncc(*)c1] | CH2 |
| NO2 | OBn | Me | H | H | bond | CONH | bond | 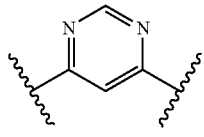 [SMILES: *c1cc(*)ncn1] | CH2 |
| NHMe | OBn | H | H | H | bond | CONH | bond | 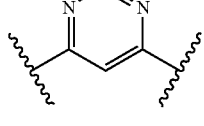 | CH2 |
| NO2 | OBn | Me | H | H | bond | CONH | bond | 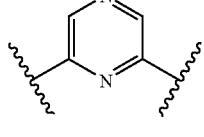 | CH2 |
| NO2 | OBn | Me | H | H | bond | CONH | bond | 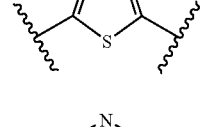 | CH2 |
| NHMe | OBn | H | H | H | bond | CONH | bond | 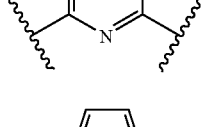 | CH2 |
| NHMe | OBn | H | H | H | bond | CONH | bond | 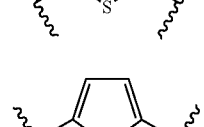 | CH2 |
| NO2 | OBn | Me | H | H | bond | CONH | bond | 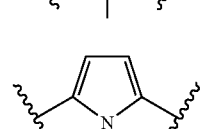 | CH2 |
| NHMe | OBn | H | H | H | bond | CONH | bond | 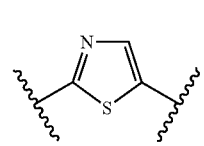 [SMILES: *c1cnc(*)s1] | CH2 |
| NO2 | OBn | Me | H | H | bond | CONH | bond |  | CH2 |

TABLE 2-continued
| | | | | | | | | | |
|---|---|---|---|---|---|---|---|---|---|
| NHMe | OBn | H | H | H | bond | CONH | bond | 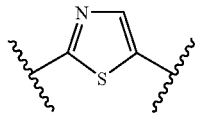 [SMILES: *c1cnc(*)s1] | CH2 |
| NO2 | OBn | Me | H | H | bond | CONH | bond | 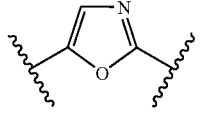 [SMILES: *c1cnc(*)o1] | CH2 |
| NHMe | OBn | H | H | H | bond | CONH | bond | 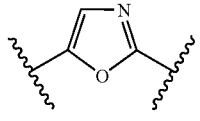 [SMILES: *c1cnc(*)o1] | CH2 |
| NO2 | OBn | Me | H | H | bond | CONH | bond | 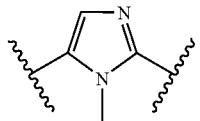 [SMILES: *c1cnc(*)n1C] | CH2 |
| NO2 | OBn | Me | H | H | bond | CONH | bond | 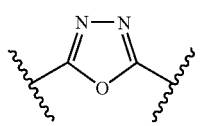 [SMILES: *c1nnc(*)o1] | CH2 |
| NHMe | OBn | H | H | H | bond | CONH | bond | 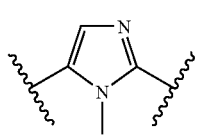 [SMILES: *c1cnc(*)n1C] | CH2 |
| NHMe | OBn | H | H | H | bond | CONH | bond | 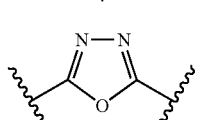 | CH2 |
| NO2 | OBn | Me | H | H | bond | CONH | bond | 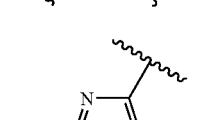 | (CH2)2 |
| NO2 | OBn | Me | H | H | bond | CONH | bond | 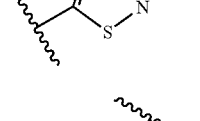 | (CH2)2 |
| NO2 | OBn | Me | H | H | bond | CONH | bond | 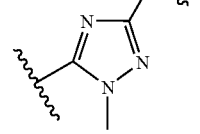 | (CH2)2 |
| NHMe | OBn | H | H | H | bond | CONH | bond | 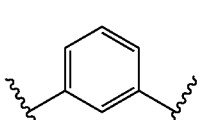 | (CH2)2 |

| | | | | | | | | | |
|---|---|---|---|---|---|---|---|---|---|
| NHMe | OBn | H | H | H | bond | CONH | bond | 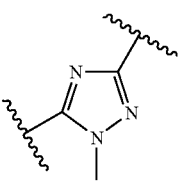 [SMILES: *c1nc(*)n(C)n1] | (CH2)2 |
| NHMe | OBn | H | H | H | bond | CONH | bond | 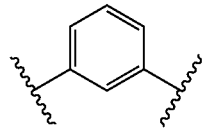 [SMILES: *c1cccc(*)c1] | (CH2)2 |
| NO2 | OBn | Me | H | H | bond | CONH | bond | 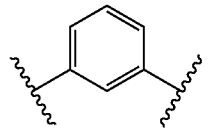 | (CH2)3 |
| NHMe | OBn | H | H | H | bond | CONH | bond | 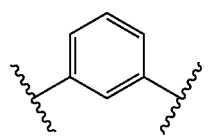 [SMILES: *c1cccc(*)c1] | (CH2)3 |
| 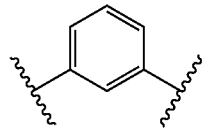 | | | | | bond | CONH | bond | 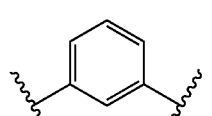 | CH2 |
| 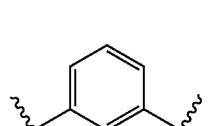 | | | | | bond | CONH | bond | | CH2 |
| 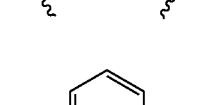 | | | | | bond | CONH | bond | | CH2 |
| 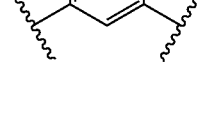 | | | | | bond | CONH | bond | | CH2 |
| 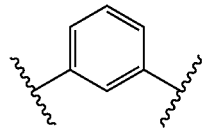 [SMILES: *c1cccc(*)c1] | | | | | bond | CONH | bond | | CH2 |
|  | | | | | bond | CONH | bond |  | CH2 |

TABLE 2-continued

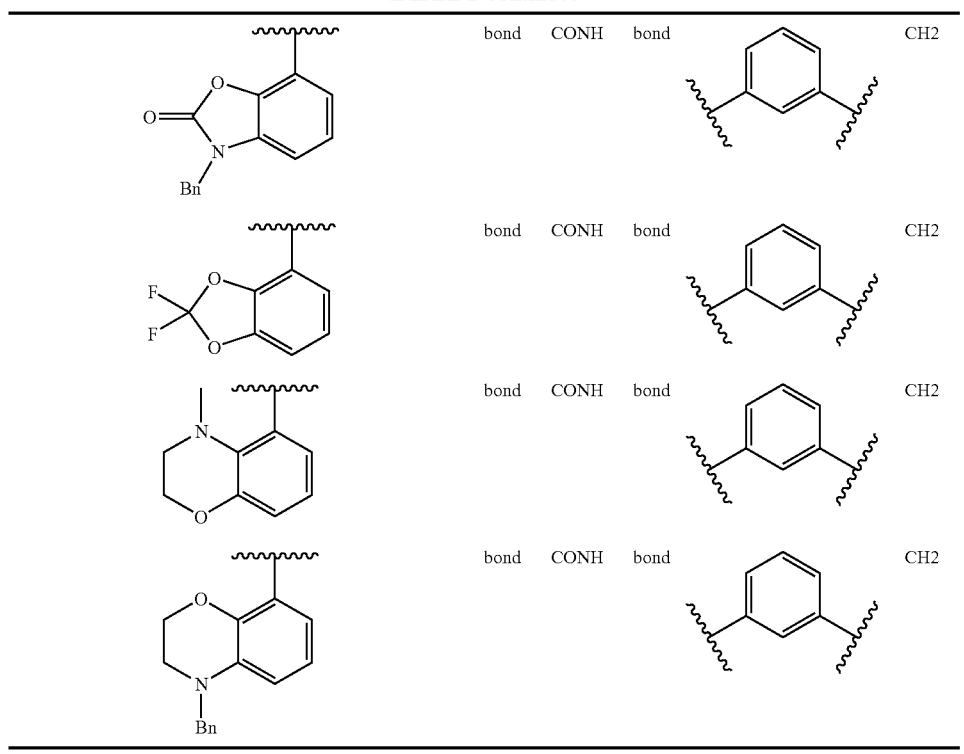

In the above tables, Me: methyl, Et: ethyl, Pr: n-propyl, iPr: isopropyl, iBu: isobutyl, tBu: t-butyl, bond: single bond Table 1 provides an illustrative expansion of $R^B$, $R^C$ and $R^D$ with respect to each of two $R^A$, and Table 2 provides an illustrative expansion of $R^A$ with respect to two of $R^B$, $R^C$ and $R^D$. The compound of the invention includes any combination of the groups listed in Table 1 and Table 2.

The present invention encompasses the compounds as described above, a pharmaceutically acceptable salt and solvate thereof. Any theoretically available tautomer and geometric isomer of such compound are also within the scope of the present invention.

The term "pharmaceutically acceptable" means harmless with respect to the prevention and the treatment. Pharmaceutically acceptable salts of a compound of the present invention include, as basic salts, for example, alkali metal salts such as sodium or potassium salts; alkaline-earth metal salts such as calcium or magnesium salts; ammonium salts; aliphatic amine salts such as trimethylamine, triethylamine, dicyclohexylamine, ethanolamine, diethanolamine, triethanolamine or procaine salts, meglumine salt, diethanolamine salt or ethylenediamine salt; aralkyl amine salts such as N,N-dibenzylethylenediamine salts, benethamine salt; heterocyclic aromatic amine salts such as pyridine salts, picoline salts, quinoline salts or isoquinoline salts; quaternary ammonium salts such as tetramethylammonium salts, tetraethylammonium salts, benzyltrimethylammonium salts, benzyltriethylammonium salts, benzyltributylammonium salts, methyltrioctylammonium salts or tetrabutylammonium salts; and basic amino acid salts such as arginine salts or lysine salts. Acid salts include, for example, mineral acid salts such as hydrochloride, sulfates salts, nitrate salts, phosphates salts, carbonates salts, hydrogencarbonates or perchlorate; organic acid salts such as acetates, propionates, lactates, maleates, fumarates, tararic acid salts, malates, citrates salts, or ascorbates; sulfonates such as methanesulfonates, isethionates, benzenesulfonates, or p-toluenesulfonates; and acidic amino acid salts such as aspartates or glutamates.

Furthermore, various solvates of a compound of the present invention, for example, monosolvate, disolvate, monohydrate or dihydrate are also within the scope of the present invention (2) General Procedure Below is described a representative procedure for the production of a compound of the invention. The preparation of the compound is not intend to limit to such procedure, and of cause, can be conducted by another procedure.

The compound of the invention may be synthesized using vancomycin or its known derivative as a starting material, by chemical modification of the amino moiety ($R^A$) at the amino sugar, or the C terminal ($R^B$), the resorcinol moiety ($R^C$), or the methylamino moiety at the N terminal ($R^D$). Such chemical modification can be conducted according to the procedure, for example, as disclosed in Japanese Patent Publication No. 7-258289, WO00/39156, Japanese Patent Publication No. 2001-163898. Specifically, it may be conducted in the following manner.

1) Modification of $R^A$ Moiety

Typically, vancomycin as a starting material may be reacted, optionally in the presence of a base, with a different aldehyde corresponding to $R^A$ moiety of the formula —$X^1$—$Ar^1$—$X^2$—Y—$X^3$—$Ar^2$ to form an intermediate Schiff base, followed by reduction to N-alkylate to afford a desired secondary amine.

The Schiff base formation is conducted specifically in a polar solvent such as dimethylformamide or methanol or mixture thereof, optionally under inert atmosphere such as nitrogen or argon gas and optionally in the presence of a base, at a temperature between about 25° C. and about 100° C. Preferably, the reaction is conducted at room temperature to 100° C., preferably about 60° C. to about 80° C., for about 30 minute to 2 hours. The base used in the reaction is, for example, alkylamine (e.g., diisopropylethylamine, etc). The intermediate Schiff base, preferably without purification, may be reduced with a hydrogenated metal complex or subjected to a catalytic reduction. A metal borohydride, such as sodium borohydride or sodium cyanoborohydride, may be used as a hydrogenated metal complex. The catalytic reduction may be conducted using hydrogen in the presence of homogeneous or heterogeneous catalysis such as Crabtree catalyst, Wilkinson catalyst, palladium on carbon, platinum on carbon or rhodium on carbon. The reduction reaction is conducted at about 25° C. to about 100° C. for about 1 to 24 hours. Preferably, the reaction is conducted in the above solvent, using an excessive amount (e.g., 3-5 equiv) of sodium cyanoborohydride at about 60° C. to about 80° C.

2) Modification of $R^B$ Moiety

Typically, vancomycin as a starting material may be subjected to amidation of the carboxylic acid moiety at the C terminal to provide a different amido derivative wherein $R^B = -NR^5R^{5'}$, according to a conventional procedure.

3) Modification of $R^C$ Moiety

Typically, vancomycin as a starting material may be subjected to alkylation of the resorcinol moiety, according to a conventional procedure.

4) Modification of $R^D$ Moiety

Typically, vancomycin as a starting material may be subjected to N-alkylation of the methylamine moiety at the N-tarminal, according to a conventional procedure.

(3) Pharmaceutical Composition

The invention also provides a pharmaceutical formulation comprising a novel glycopeptide derivative of the invention. Thus, the glycopeptide compound in a form of pharmaceutically acceptable salt may be formulated preferably for oral or parenteral administration for therapeutic and prophylactic treatment of bacterial infection.

For oral administration, the compounds of the present invention can be used in any form of usual formulations, for example, solid formulations such as tablets, powders, granules, capsules; aqueous formulations; oleaginous suspensions; solutions such as syrup or elixir. For parenteral administration, the compounds of the present invention can be used as an aqueous or oleaginous suspension injection, or nose drops. In the preparation of such formulations, conventional excipients, binding agents, lubricants, aqueous solvents, oleaginous solvents, emulsifying agents, suspending agents, preservatives, stabilizers, and the like can be optionally used. Preferred is an oral agent or an intravenous injection as an antimicrobial agent.

A formulation according to the present invention may be manufactured by combining (for example, admixing) a therapeutically effective amount of a compound of the present invention with a pharmaceutically acceptable carrier or diluent. The formulation of the present invention may be manufactured with well-known and easily available ingredients in accordance with a known method.

In the case of manufacturing a pharmaceutical composition according to the present invention, an active ingredient is admixed or diluted with a carrier, or they are contained in a carrier in the form of capsule, sacheier, paper, or another container. In the case of functioning a carrier as a diluent, the carrier is a solid, semi-solid, or liquid material which functions as a medium. Accordingly, a formulation according to the present invention may be produced in the form of tablet, pill, powder medicine, intraoral medicine, elixir agent, suspending agent, emulsifier, dissolving agent, syrup agent, aerosol agent (solid in liquid medium), and ointment. Such a formulation may contain up to 10% of an active compound. It is preferred to formulate a compound of the present invention prior to administration.

Any suitable carrier well known to those skilled in the art may be used for the formulation. In such formulation, a carrier is in the form of solid, liquid, or a mixture of solid and liquid. For instance, a compound of the present invention is dissolved into 4% dextrose/0.5% sodium citrate aqueous solution for intravenous injection. Solid formulation includes powder, tablet, and capsule. Solid carrier consists of one or more of material(s) for serving also as fragrant, lubricant, dissolving agent, suspension, binder, tablet disintegrator, capsule. A tablet for oral administration contains a suitable excipient such as calcium carbonate, sodium carbonate, lactose, calcium phosphate and the like together with a disintegrator such as corn starch, alginic acid and the like and/or a binder such as gelatin, acacia and the like, and a lubricant such as magnesium stearate, stearic acid, talc and the like.

In a powder medicine, a carrier is a finely pulverized solid which is blended with finely pulverized active ingredients. In a tablet, active ingredients are admixed with a carrier having required binding power in a suitable ratio, and it is solidified in a desired shape and size. Powder medicine and tablet contain about 1 to about 99% by weight of the active ingredients being novel compounds according to the present invention. Example of suitable solid carriers include magnesium carbonate, magnesium stearate, talc, sugar, lactose, pectin, dextrin, starch, gelatin, tragacanth gum, methyl cellulose, sodium carboxymethylcellulose, low-melting wax, and cocoa butter.

A liquid formulation includes suspending agent, emulsifier, syrup agent, and elixir agent. Active ingredients may be dissolved or suspended into a pharmaceutically acceptable carrier such as sterile water, a sterile organic solvent, a mixture thereof and the like. Active ingredients may be dissolved frequently into a suitable organic solvent such as propylene glycol aqueous solution. When finely pulverized active ingredients are dispersed into aqueous starch, sodium carboxylmethylcellulose solution, or suitable oil, the other compositions can be prepared.

Although an appropriate dosage of the compound of the present invention varies depending on the administration route, age, body weight, conditions of the patient, and kind of disease, in the case of oral administration, the daily dosage can be between approximately 0.1-7000 m g, preferably approximately 0.5-2000 m g, for an adult. The daily dosage can be administered in divisions. In the case of parenteral administration, the daily dosage for an adult can be between approximately 0.1-1000 m g, preferably approximately 0.5-500 mg.

EXAMPLES

The present invention is further explained by the following Examples, which are not intended to limit the scope of the present invention in any way.

MS data in the following Preparations and Examples are expressed as a calculated average molar weight (C=12.0107, H=1.0079, O=15.9994, N=14.0067, Cl=35.4527, P=30.9738, Na=22.9898).

Preparation 1

Preparation of carboxylic acid 3

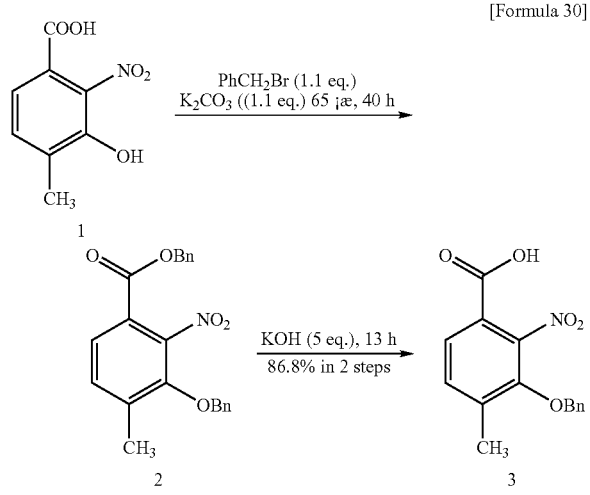

[Formula 30]

Carboxylic acid 3 was prepared as follows.

To a solution of 3.943 g (20.0 mmol) of 4-methyl-3-hydroxy-2-nitrobenzoic acid 1 (Aldrich) in 40 mL of dry DMF was added 4.98 mL (42 mmol) of benzyl bromide and finely powdered $K_2CO_3$ 5.8 g (42 mmol). This mixture was stirred at 65° C. under argon for 40 h. The reaction was worked up by pouring the solution into water and EtOAc. The product was extracted with EtOAc (3×40 mL). The ethyl acetate layers were combined, washed with water and brine, and dried over $MgSO_4$. Filtration and evaporation in vacuo gave a viscous yellow oil 2. $R_f$=0.87 (EtOAc:EtOH=4:1). $^1$H NMR (CDCl$_3$): 7.76 (d, J=8.00, 1H), 7.42 (m, 11H), 5.33 (s, 2H), 4.96 (s, 2H), 2.40 (s, 3H).

Hydrolysis of crude ester 2 was carried out with 5.6 g (100 mmol) KOH, 20 mL of THF, 20 mL of water, and 30 mL $CH_3OH$. The reaction was stirred until TLC analysis showed complete consumption of starting material (about 16 h). The reaction was acidified and extracted with chloroform (3×30 mL). The chloroform layers were combined and washed with water and dried over $MgSO_4$. Filtration and evaporation of the solvent in vacuo left a pale yellow powder. The product was recrystallized from EtOAc/hexane to give 4.984 g (86%) of white crystals. $R_f$=0.60 (EtOAc:EtOH=4:1). $^1$H NMR (CDCl$_3$): 7.82 (d, 1H, J=8.04 Hz), 7.38-7.43 (m, 6H), 4.98 (s, 2H), 2.43 (s, 3H).

Example 1

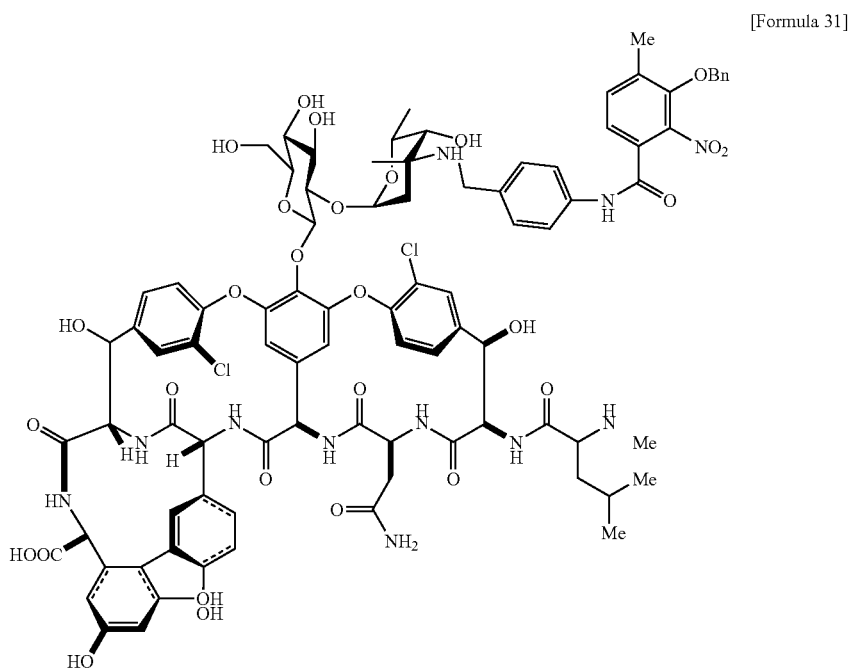

[Formula 31]

Aldehyde 5 was prepared from the carboxylic acid 3, and the aldehyde was then reacted with vancomycin to afford the desired compound.

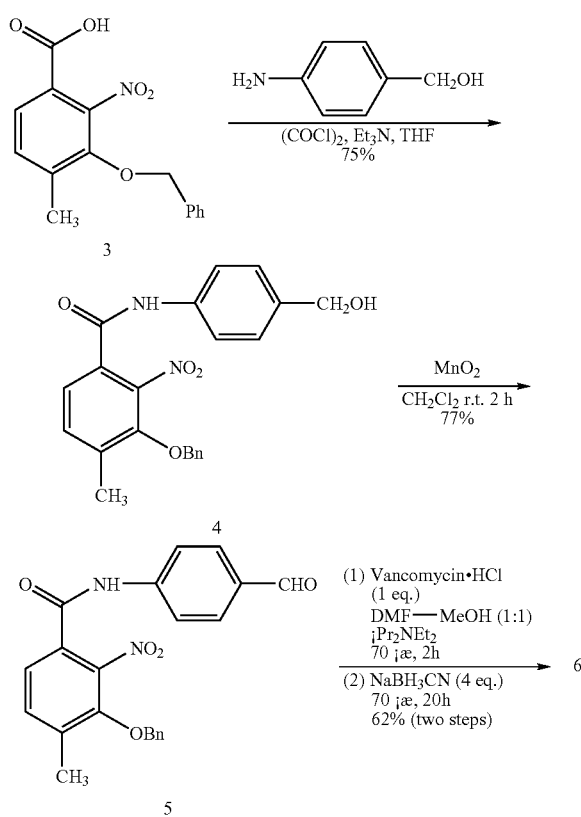

[Formula 32]

Compound 4

A mixture of 0.574 g (2 mmol) of the acid 3, 0.226 mL (2.6 mmol, 1.3 equiv) of oxalyl chloride, 20 mL of dichloromethane, and 2 drops of DMF was heated to reflux for 40 min. The dichloromethane and excess oxalyl chloride was distilled until a viscous, yellow oil was obtained. The residue was dissolved in THF and quickly transferred to a 100 mL round-bottom flask containing 0.246 g (2 mmol) 4-aminobenzyl alcohol (Wako), 0.348 mL (2.5 mmol) of triethylamine, and 10 mL THF all cooled to 0° C. in an ice bath. After addition of the acid chloride, the solution was stirred at 0° C. for 30 min. The reaction was worked up by pouring the solution into a flask containing EtOAc and aqueous $NaHCO_3$. The product was extracted with ethyl acetate (3×30 mL). The ethyl acetate extracts were combined and washed with water and brine and dried over $MgSO_4$. Filtration and evaporation of solvent in vacuo afforded the product as a pale yellow solid. The product was recrystallized from EtOAc/hexane to give 0.588 g (75%) of white crystals. $^1$H NMR ($CDCl_3$): 7.74 (s, 1H,), 7.55 (d, 2H, J=7.60 Hz), 7.34 (d, 2H, J=7.60 Hz), 7.36-7.45 (m, 7H), 5.02 (s, 2H), 4.67 (s, 2H), 2.40 (s, 3H).

Compound 5

A mixture of 0.588 g of compound 4, 3 g of $MnO_2$ and 20 mL of dichloromethane was stirred at room temperature for 3 h until TLC analysis showed complete consumption of starting material. Evaporation of solvent in vacuo give 0.46 g (77%) of pale yellow solid. $^1$H NMR ($CDCl_3$): 9.95 (s, 1H,), 7.89 (d, 2H, J=8.32 Hz), 7.76 (d, 2H, J=8.32 Hz), 7.39-7.45 (m, 7H), 5.03 (s, 2H), 2.43 (s, 3H).

Compound 6

0.114 mL (2 eq.) of diisopropylethylamine (DIEA) was added to a solution of 0.495 g (0.333 mmol, 1 eq.) vancomycin in DMF/MeOH (1:1, 20 mL) and the 0.13 g (0.333 mmol, 1 eq.) aldehyde 5. The solution was heated at 70° C. for 2 h and then allowed to cool to room temperature. After 0.0836 g (1.332 mmol, 4 eq.) $NaBH_3CN$ was added, the reaction mixture was stirred at 70° C. for an additional 24 h, and allowed to cool to ambient temperature overnight. Then poured into 400 mL of $Et_2O$. The white precipitate was isolated by centrifugation. Purification of precipitate by reverse-phase column chromatography yielded 0.376 g (62%) of compound 6 as a white solid: $R_f$=0.45 ($CH_3CN:H_2O:TFA$=1:1:0.01), MS (MALDI-TOF, CHCA) calcd for $C_{88}H_{93}Cl_2N^{11}NaO_{28}$[M+Na]$^+$ 1846.63. found 1846.15.

Example 2

[Formula 33]

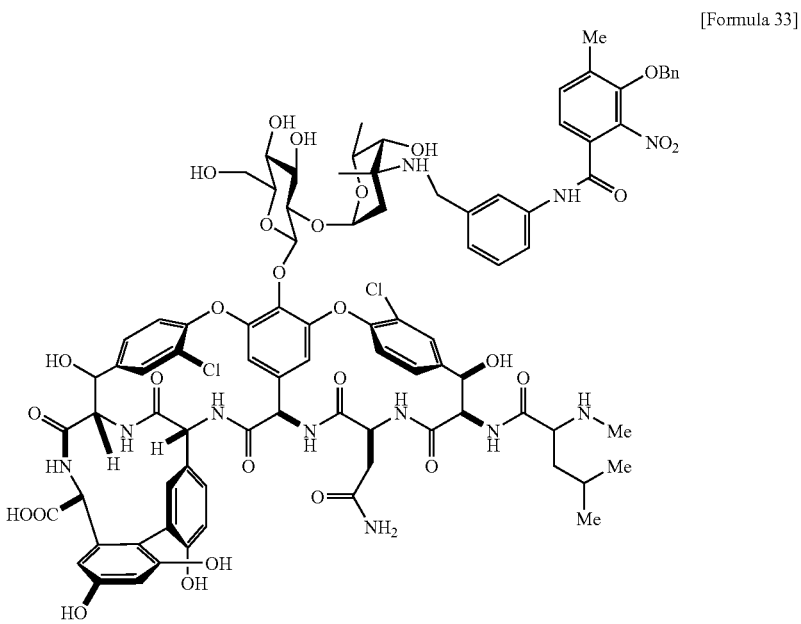

Compound 10 was prepared as described in Example 1.

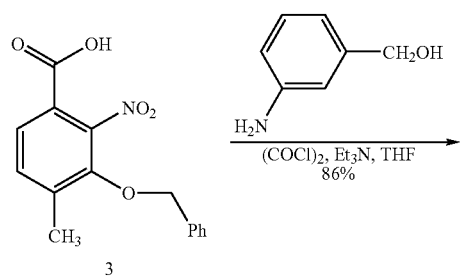

[Formula 34]

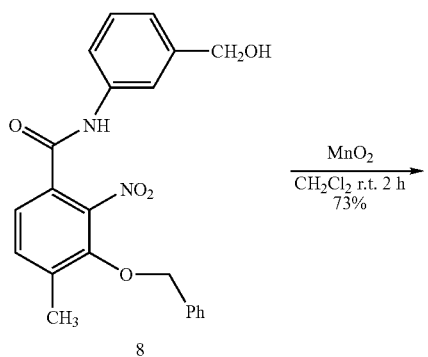

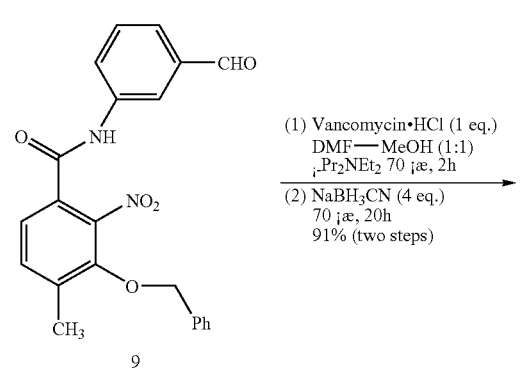

Compound 8

A mixture of 0.574 g (2 mmol) of the acid 3, 0.226 mL (2.6 mmol, 1.3 equiv) of oxalyl chloride, 20 mL of dichloromethane, and 2 drops of DMF was heated to reflux for 40 min. The dichloromethane and excess oxalyl chloride was distilled until a viscous, yellow oil was obtained. The residue was dissolved in THF and quickly transferred to a 100 mL round-bottom flask containing 0.246 g (2 mmol) 3-aminobenzyl alcohol (Wako), 0.348 mL (2.5 mmol) of triethylamine, and 10 mL THF all cooled to 0° C. in an ice bath. After addition of the acid chloride, the solution was stirred at 0. ° C. for 30 min. The reaction was worked up by pouring the solution into a flask containing EtOAc and aqueous $NaHCO_3$. The product was extracted with ethyl acetate (3×30 mL). The ethyl acetate extracts were combined and washed with water and brine and dried over $MgSO_4$. Filtration and evaporation of solvent in vacuo afforded the product as a pale yellow solid. The product was purified by column chromatography (EtOAc) yielded 0.678 g (86%) compound 8. $R_f$=0.62 (EtOAc), $^1$H NMR ($CDCl_3$): 7.78 (s, 1H,), 7.63 (s, 1H), 7.36-7.45 (m, 9H), 7.19 (d, 1H, J=7.60 Hz), 5.03 (s, 2H), 4.72 (s, 2H), 2.42 (s, 3H).

Compound 9

A mixture of 0.678 g of compound 8, 3.07 g of $MnO_2$ and 20 mL of dichloromethane was stirred at room temperature for 2 h until TLC analysis showed complete consumption of starting material. Evaporation of solvent in vacuo give 0.554 g crude product, and purified by column chromatography (EtOAc) yielded 0.491 g (73%) compound 9. $^1$H NMR ($CDCl_3$): 10.01 (s, 1H,), 7.92 (d, 1H, J=7.60 Hz), 7.85 (s, 1H), 7.71 (d, 1H, J=8.00 Hz), 7.54 (t, 1H, J=8.00 Hz), 7.37-7.45 (m, 7H), 5.03 (s, 2H), 2.42 (s, 3H).

Compound 10

0.114 mL (2 eq.) DIEA was added to a solution of 0.495 g (0.333 mmol, 1 eq.) vancomycin in DMF/MeOH (1:1, 20 mL) and the 0.13 g (0.333 mmol, 1 eq.) aldehyde 9. The solution was heated at 70° C. for 2 h and then allowed to cool to room temperature. After 0.0836 g (1.332 mmol, 4 eq.) $NaBH_3CN$ was added, the reaction mixture was stirred at 70° C. for an additional 24 h, and allowed to cool to ambient temperature overnight. Then poured into 400 mL of $Et_2O$. The white precipitate was isolated by centrifugation. Purification of precipitate by reverse-phase column chromatography yielded 0.565 g (93%) of compound 10 as a white solid: $R_f$=0.51 ($CH_3CN:H_2O:TFA$=1:1:0.01), MS (MALDI-TOF, CHCA) calcd for $C_{88}H_{93}Cl_2N_{11}NaO_{28}$ $[M+Na]^+$1846.63. found 1846.37.

Example 3
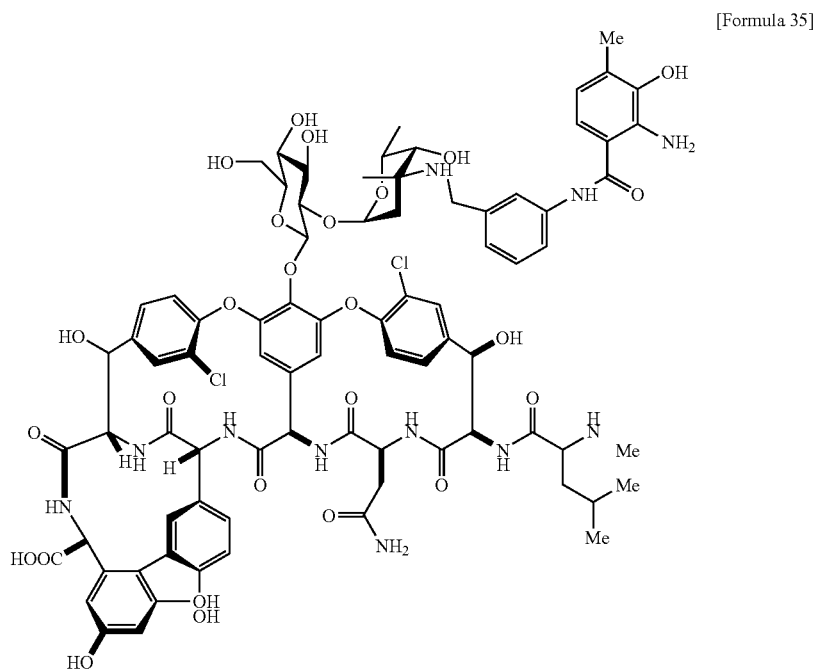
11
Compound 11
A solution of compound 10 obtained in Example 2 (51.8 mg, 0.028 mmol) in methanol (3 mL) was reduced with hydrogen in the presence of 10% Pd—C catalyst (50 mg) (about 3 h) to give the corresponding aminophenol 11. MS (MALDI-TOF, CHCA) calcd for $C_{81}H_{89}Cl_2N_{11}NaO_{26}$ [M+Na]$^+$ 1726.53. found 1726.67.
Example 4
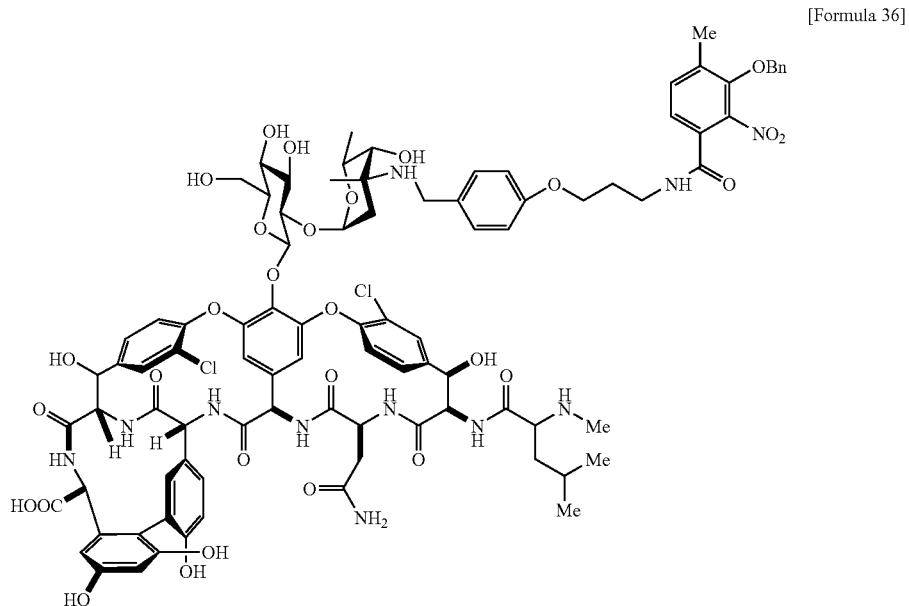
16

Compound 16 was prepared as described in Example 1.

[Formula 37]

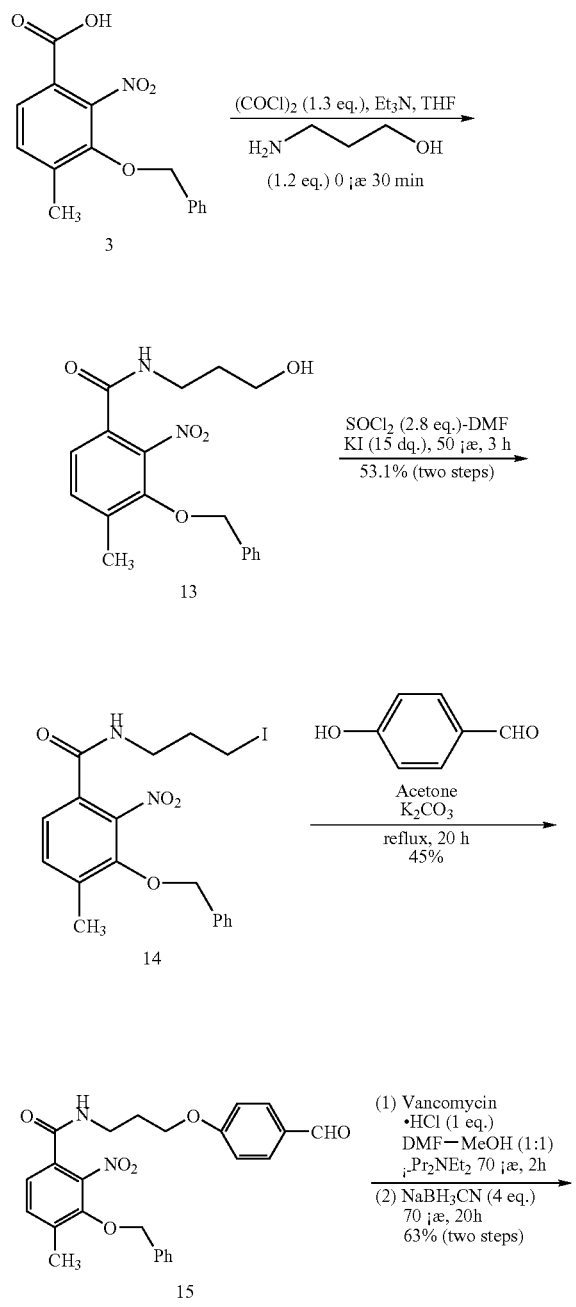

Compound 13

A mixture of 2.87 g (10.0 mmol) of the acid 3 (as prepared in Preparation 1), 1.13 mL (1.3 equiv) of oxalyl chloride, 80 mL of dichloromethane, and 2 drops of DMF was heat to reflux for 40 min. The dichloromethane and excess oxalyl chloride was distilled until a viscous, yellow oil was obtained. The residue was dissolved in THF and quickly transferred to a 250 mL round-bottom flask containing 0.92 mL (12 mmol, 1.2 equiv) of 3-amino-1-propanol, 3.48 mL (25 mmol, 2.5 equiv) of triethylamine, and 80 mL of THF all cooled to 0° C. in an ice bath. After addition of the acid chloride, the solution was stirred at 0° C. for 30 min. The reaction was worked up by pouring the solution into a flask containing EtOAc and aqueous NaHCO$_3$. The product was extracted with ethyl acetate (3×40 mL). The ethyl acetate extracted were combined and washed with water and brine and dried over MgSO$_4$. Filtration and evaporation of solvent in vacuo afforded the product as a viscous pale yellow oil. This crude material was subjected to the next reaction without further purification. R$_f$=0.65 (EtOAC:EtOH=4:1), $^1$H NMR 7.28-7.42 (m, 7H,), 4.98 (s, 2H), 3.73 (t, 2H, J=5.60 Hz), 3.55 (q, 2H, J=5.60 Hz), 2.36 (s, 3H), 1.77 (m, 2H).

Compound 14

To a stirred solution of thionyl chloride (2.04 mL, 28 mmol) in DMF (10 mL) at 0° C. under argon were added KI (24.5 g, 0.15 mol in 70 mL of DMF) and the alcohol 13 (10 mmol in 30 mL of DMF) through syringe. The reaction mixture was stirred at 50° C. for the 3 h and then quenched with water and extracted with ether (3×100 mL). The combined ether extracts were washed successively with aqueous sodium thiosulfate solution and water. The organic solution was dried over anhydrous MgSO$_4$. Filtration and evaporation of solvent in vacuo afforded the product as a pale yellow solid. The product was recrystallized from EtOAc/hexane to give 2.41 g (53.1%, two steps) of pale yellow crystals. $^1$H NMR 7.36-7.43 (m, 6H,), 7.28 (d, 1H, J=8.40 Hz), 4.99 (s, 2H), 3.51 (q, 2H, J=6.40 Hz), 3.24 (t, 2H, J=6.40 Hz), 2.38 (s, 3H), 2.12 (m, 2H).

Compound 15

To a solution of 4-hydroxybenzaldehyde (0.336 g, 2.75 mmol) in 10 mL of acetone were added anhydrous potassium carbonate (0.345 g, 2.5 mmol) and compound 14 (1.135 g, 2.5 mmol). The reaction was heat to reflux for 20 h. The mixture was cooled to room temperature, and then poured into 200 mL of water. Filtration afforded the product as a white solid, and purified by column chromatography (5% MeOH/CHCl$_3$) yielded 0.504 g (45%) of compound 15. R$_f$=0.50 (CHCl$_3$:MeOH=95:5), $^1$H NMR (CDCl$_3$): 9.89 (s, 1H,), 7.84 (d, 2H, J=8.40 Hz), 7.27-7.41 (m, 7H), 7.27 (s, 1H), 7.01 (d, 2H, J=8.40 Hz), 4.99 (s, 2H), 4.17 (t, 2H, J=6.00 Hz), 3.64 (t, 2H, J=6.00 Hz), 2.38 (s, 3H), 2.15 (m, 3H).

Compound 16

0.114 mL (2 eq.) DIEA was added to a solution of 0.495 g (0.333 mmol, 1 eq.) vancomycin in DMF/MeOH (1:1, 20 mL) and the 0.149 g (0.333 mmol, 1 eq.) aldehyde 15. The solution was heated at 70° C. for 2 h and then allowed to cool to room temperature. After 0.0836 g (1.332 mmol, 4 eq.) NaBH$_3$CN was added, the reaction mixture was stirred at 70° C. for an additional 24 h, and allowed to cool to ambient temperature overnight. Then poured into 400 mL of Et$_2$O. The white precipitate was isolated by centrifugation. Purification of precipitate by reverse-phase column chromatography yielded 0.396 g (63%) of compound 16 as a white solid: R$_f$=0.34 (CH$_3$CN:H$_2$O:TFA=1:1:0.01), MS (MALDI, CHCA) calcd for C$_{91}$H$_{99}$Cl$_2$N$_{11}$NaO$_{29}$ [M+Na]$^+$1904.71. found 1905.04.

Example 5

[Formula 38]

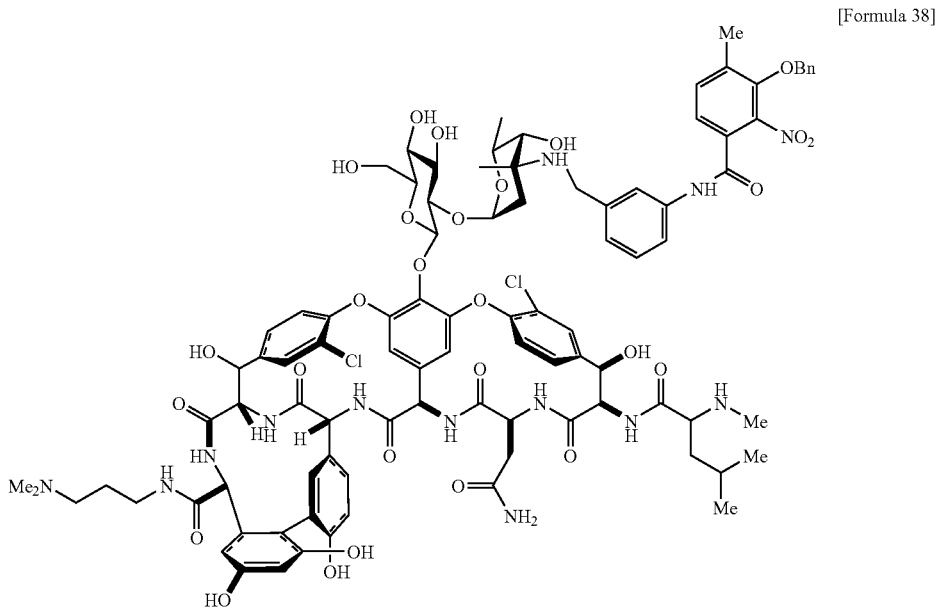

24

Compound 24

Compound 10 (as prepared in Example 2, 364.2 m g, 0.2 mmol) was dissolved in 4 mL of dry dimethyl sulfoxide (DMSO). To this was added 4 mL of dry dimethylformamide (DMF) and 50.4 µL (0.4 mmol, 2 equiv) of 3-(dimethylamino)propylamine (Nacalai). The mixture was cooled to 0° C., and 113.6 mg (0.3 mmol, 1.5 equiv) of HBTU (TCI) and 40.5 mg (0.3 mmol, 1.5 equiv) of HOBT (Wako) in 0.5 mL of DMF was added, followed by 17 µL (1 mmol, 5.0 equiv) of diisopropylethylamine (DIEA). The reaction was then allowed to warm to room temperature and was stirred overnight (about 12 h). The reaction mixture was poured into 200 mL of $CH_2Cl_2$. The resulting precipitate was filtered, washed with $CH_2Cl_2$, and dried under vacuum. Purification of precipitate by reverse-phase HPLC(Develosil ODS-HG-5, D 20 mm×250 mm, $CH_3CN:H_2O:TFA=1:2:0.1\%$, flow rate 2 mL/min, UV: 215 nm, $t_R=18.63$ min) yielded 45.5 mg (45%) of compound 24 as a pale solid: MS (MALDI-TOF, CHCA) calcd for $C_{93}H_{105}Cl_2N_{13}NaO_{27}$ $[M+Na]^+$1930.80. found 1931.59.

Example 6

[Formula 39]

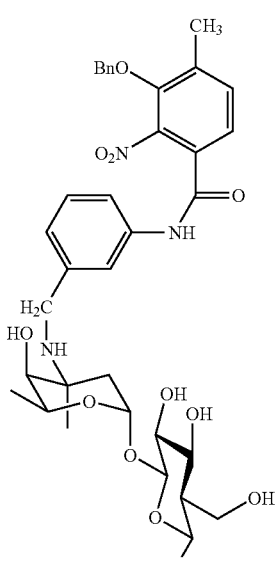

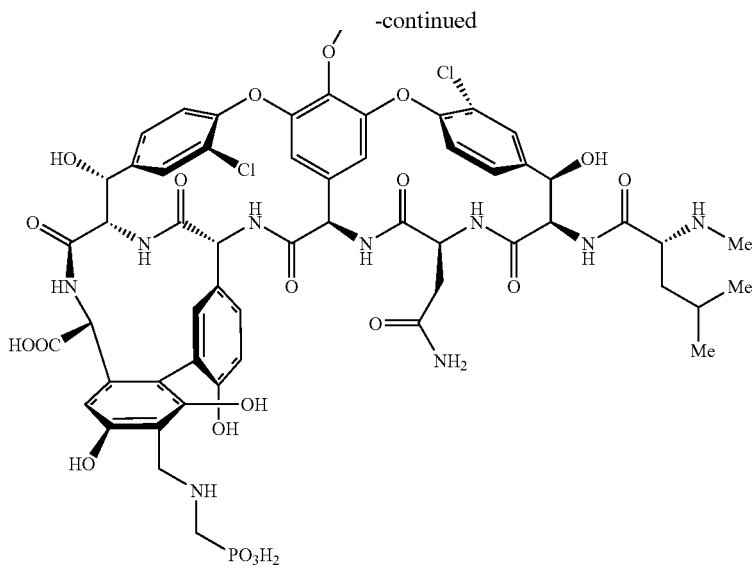

26

Compound 26

(Aminomethyl)phosphonic acid (Aldrich) (155.4 m g, 1.4 mmol) and DIEA (0.24 mL, 1.4 mmol) were combined in water (1.5 mL) and stirred until homogenous. Acetonitrile (5 mL) and formaldehyde (37% solution in water, 16.5 μL, 0.22 mmol) were then added, followed by compound 10 (364.2 m g, 0.2 mmol) and DIEA (0.24 mL, 1.4 mmol). The mixture was stirred at room temperature for 20 h, then the solution was neutralized with 20% aqueous TFA. The acetonitrile was removed under reduced pressure, and the resulting suspension was lyophilized. The recovered solid was purified by reverse-phase HPLC(Develosil ODS-HG-5, D 20 mm×250 mm, $CH_3CN:H_2O:TFA=1:1:0.1\%$, flow rate 3 mL/min, UV: 215 nm, $t_R$=13.58 min) yielded 66.1 mg (17%) of compound 26: MS (MALDI-TOF, CHCA) calcd for $C_{90}H_{99}Cl_2N_{12}NaO_{31}p$ $[M+Na]^+$1969.68. found 1967.77.

Example 7

Compound 27

[Formula 40]

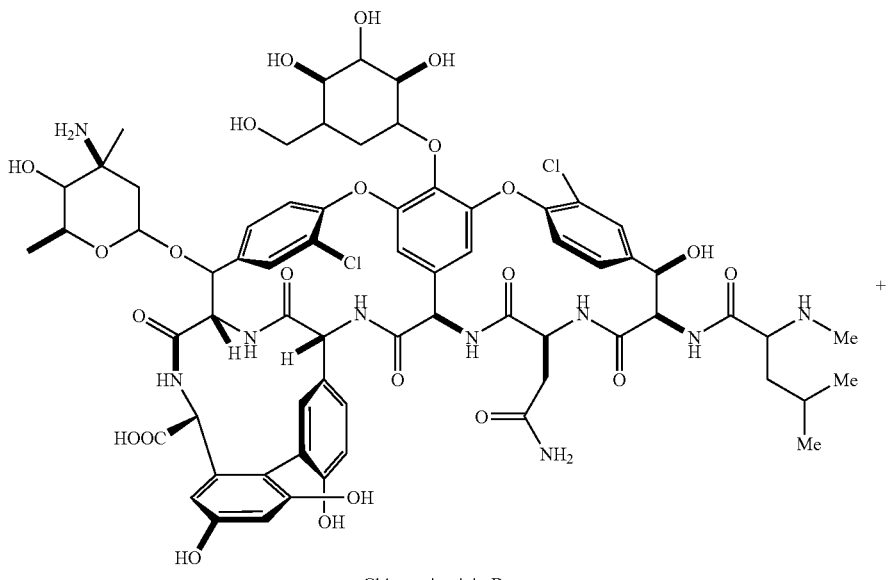

Chloroorienticin B

-continued

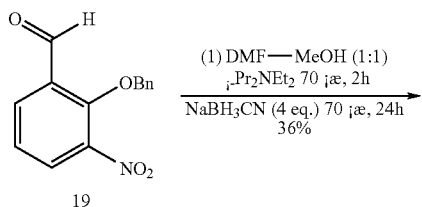

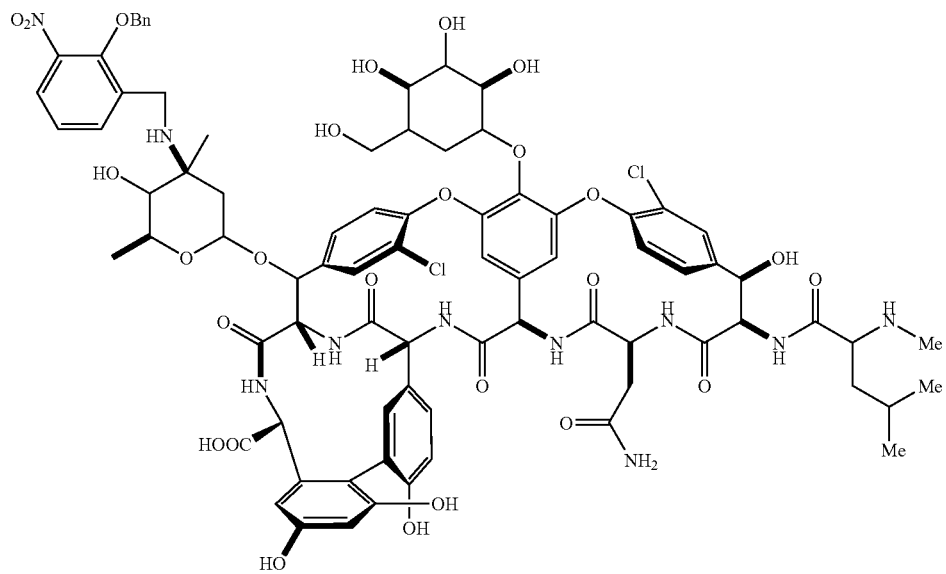

0.114 mL (2 equiv) of diisopropylethylamine (DIEA) was added to chloroorienticin B (0.495 g, 0.333 mmol, 1 equiv) and aldehyde 19 (0.0857 g, 0.333 mmol, 1 equiv) in 1:1 dimethylformamide (DMF)/methanol (MeOH) (20 mL). The solution was heated at 70° C. for 3 hours and then cooled to room temperature. 0.084 g of sodium cyano borohydride (NaBH$_3$CN) (1.332 mmol, 4 equiv) was added, and the reaction mixture was stirred at 70° C. for additional 24 hours, and allowed to cool to ambient temperature overnight. Then poured into 300 mL of diethylether (Et$_2$O). The precipitate was isolated by centrifugation. Purification of precipitate by HPLC (Develosil ODS-HG-5, (20 mm×250 mm, acetonitrile:water:trifluoroacetate (TFA)=1:2:0.1%, flow rate 3 mL/minute, UV:215 nm) yielded compound 27 (110.2 m g, 36%) as a pale yellow solid.

MS (MALDI-TOF, CHCA) Calculated for C$_{80}$H$_{86}$Cl$_2$N$_{10}$NaO$_{27}$ [M+Na]$^+$1713.49. Found 1713.94.

Example 8

Compound 29

[Formula 41]

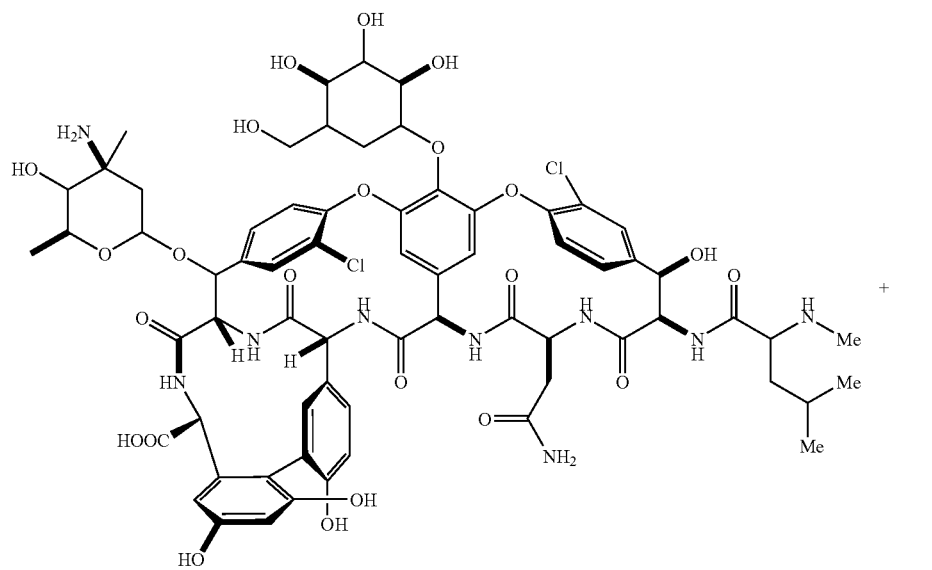

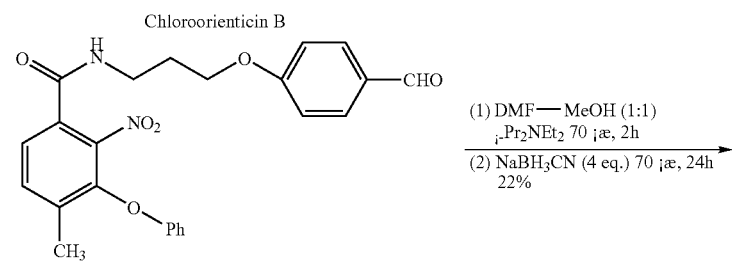

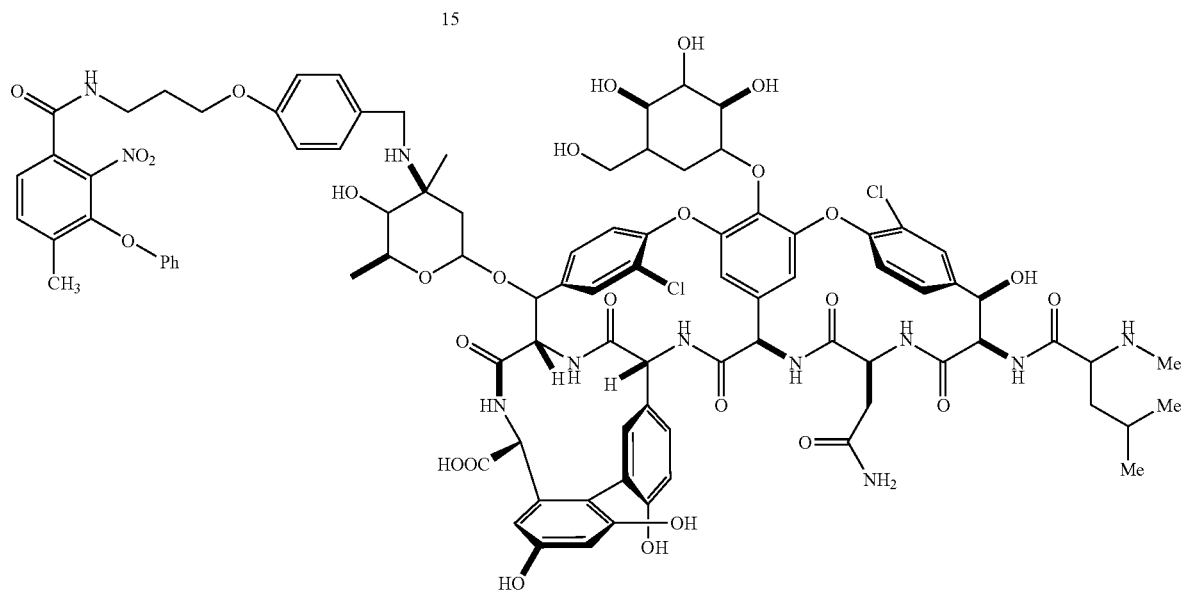

DIEA (0.114 mL, 2 equiv) was added to chloroorienticin B (0.495 g, 0.333 mmol, 1 equiv) and aldehyde 15 (0.149 g, 0.333 mmol, 1 equiv) in DMF/MeOH (1:1, 20 mL). The solution was heated at 70° C. for 2 h and then allowed to cool to room temperature. After 0.0836 g (1.332 mmol, 4 eq.) NaBH$_3$CN was added, the reaction mixture was stirred at 70° C. for an additional 24 h, and allowed to cool to ambient temperature overnight. Then poured into 400 mL of Et$_2$O.

The white precipitate was isolated by centrifugation. Purification of precipitate by reverse-phase column chromatography yielded compound 29 (0.135 g, 22%) as a white solid.
MS (MALDI, CHCA) Calculated for $C_{91}H_{99}Cl_2N_{11}NaO_{29}$
[M+Na]$^+$:1904.71. Found 1904.95.
Example 9
Compound 31
[Formula 42]
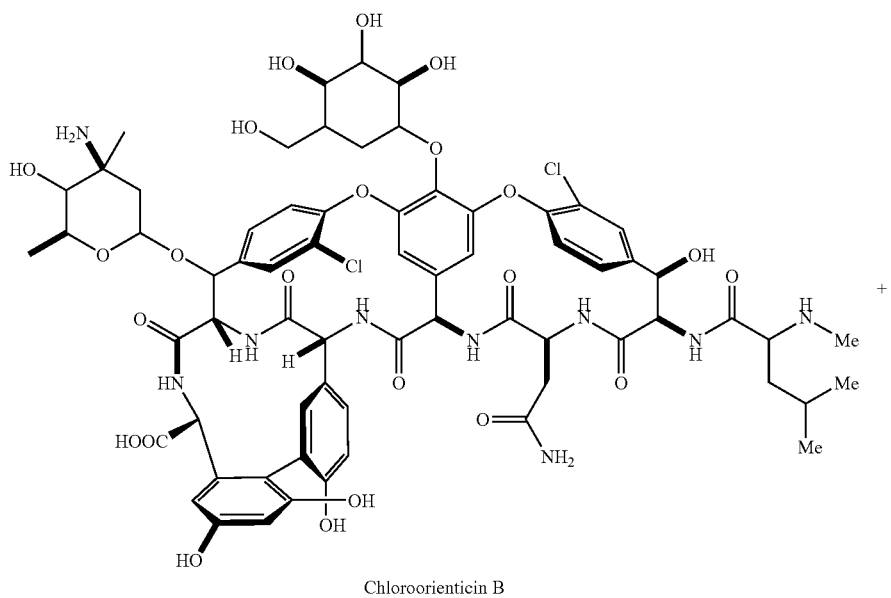
Chloroorienticin B
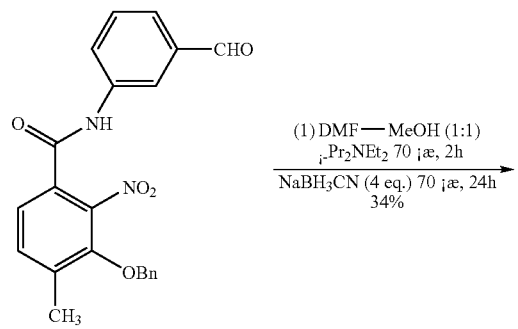
9

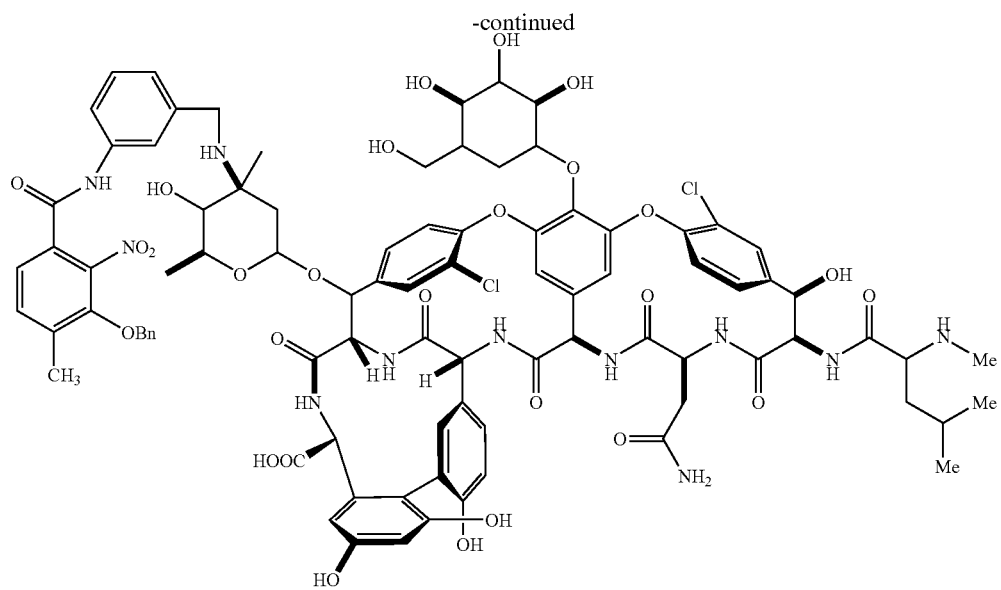

31

DIEA (0.114 mL, 2 equiv) was added to chloroorienticin B (0.495 g, 0.333 mmol, 1 equiv) and aldehyde 9 (0.13 g, 0.333 mmol, 1 equiv) in DMF/MeOH (1:1, 20 mL). The solution was heated at 70° C. for 2 h and then allowed to cool to room temperature. After 0.0836 g (1.332 mmol, 4 eq.) NaBH$_3$CN was added, the reaction mixture was stirred at 70° C. for additional 24 h, and allowed to cool to ambient temperature overnight. Then poured into 400 mL of Et$_2$O. The white precipitate was isolated by centrifugation. Purification of precipitate by reverse-phase column chromatography yielded compound 31 (0.205 g, 34%) as a white solid. MS (MALDI-TOF, CHCA) Calculated for $C_{88}H_{93}Cl_2N_{11}NaO_{28}$ [M+Na]$^+$: 1846.63. Found: 1846.64.

Example 10

Compound 37 was prepared from carboxylic acid 32 according to the following scheme.

[Formula 43]

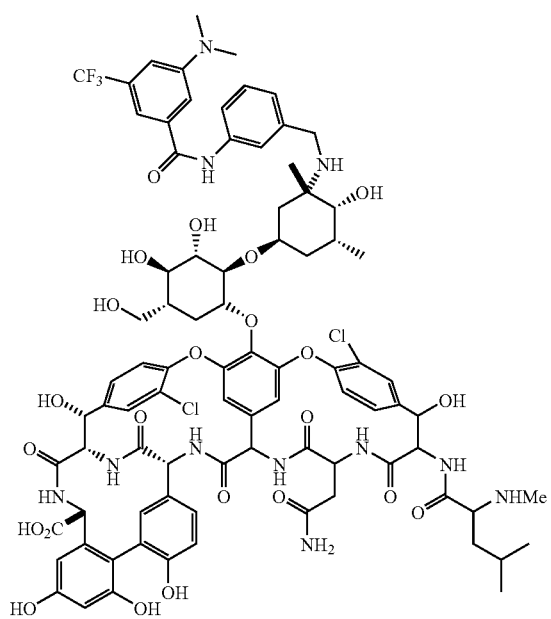

37

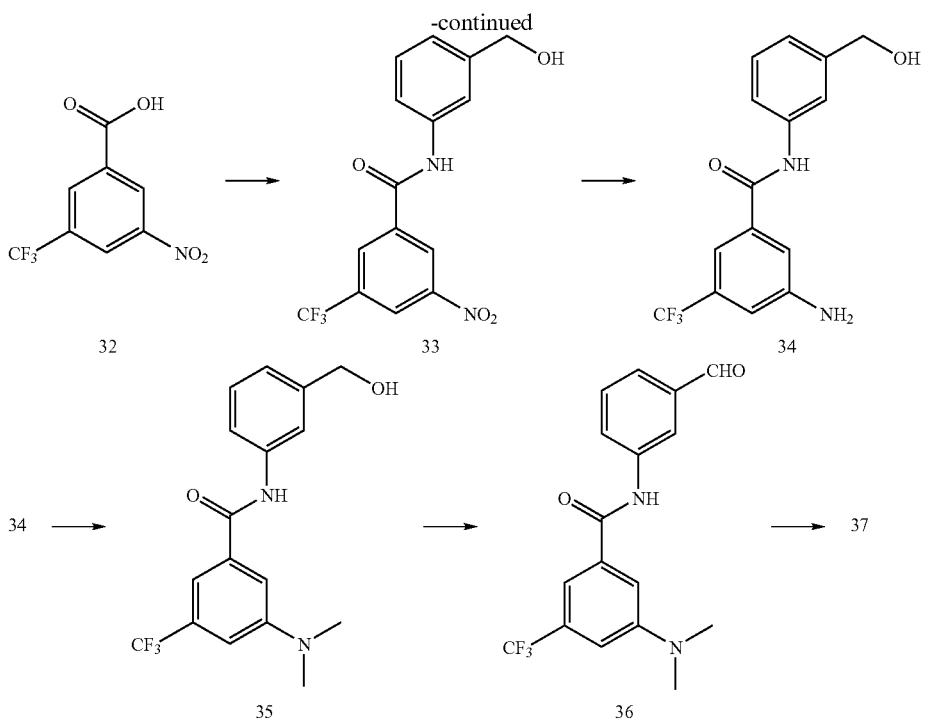

Compound 33

5-nitro-3-trifluoromethyl benzoic acid 32 (34.2 g, 145.5 mmol) was added to oxalyl chloride (16.5 mL, 189 mmol) suspended in dichloromethane (500 mL). Obtained suspension is added with dimethylformamide (0.5 mL) and stirred at 45° C. for 1 hour. The reaction mixture was concentrated in vacuo and dissolved in THF (300 mL). The solution was added dropwise under nitrogen stream and ice cooling to 3-aminobenzyl alcohol (18.5 g, 150 mmol) and triethylamine (20.3 mL, 182 mmol).

The mixture was stirred at room temperature for 2 h, and the solution was concentrated in vacuo after filtration to isolate precipitated insoluble material. The obtained residue was added with water and diisopropylether, followed by filtrated to isolate the precipitated crystal to afford compound 33 as a pale yellow powder. Yield: 49.9 g (100%). 1H-NMR (DMSO-d6) δ: 10.72 (1H, s), 9.06 (1H, s), 8.76 (1H, s), 8.69 (1H, s), 7.75 (1H, s), 7.70 (1H, d, J=8.1 Hz), 7.34 (1H, t, J=7.8 Hz), 7.11 (1H, d, J=7.6 Hz), 5.27 (1H, t, J=5.8 Hz), 4.54 (2H, d, J=6.1 Hz).

Compound 34

An aqueous solution of ammonium chloride (15M, 30 mL) was added to a suspension of compound 33 (49.9 g, 145.5 mmol) in ethanol (600 mL) and stirred at 90° C. to dissolve. The reaction mixture was added with iron (73 g, 1310 mmol) over 1 hour, stirred at 90° C. for 20 h. The reaction mixture was filtered though celite, and the solution was concentrated in vacuo. The residue was added with water, precipitated crystal was filtrated to isolate, and washed with diisopropylether to yield compound 34 as a pale yellow powder. Yield: 39.9 g (88%).

1H-NMR (DMSO-d6) δ: 10.26 (1H, s), 7.75 (1H, s), 7.66 (1H, d, J=8.1 Hz), 7.38 (2H, d, J=5.6 Hz), 7.30 (1H, t, J=7.8 Hz), 7.06 (2H, d, J=9.1 Hz), 5.84 (2H, s), 5.22 (1H, t, J=5.6 Hz), 4.52 (2H, d, J=5.6 Hz).

Compound 35

Compound 34 (39.9 g, 128.6 mmol) in acetonitrile (280 mL) was added with 37% formalin (46.2 mL, 643 mmol) with stirring under ice-cooling, and then sodium cyanoborohydride (40.3 g, 643 mmol) was added. After acetic acid (40 mL) was dropped to the obtained mixture under ice-cooling, the mixture was stirred under ice-cooling for 30 min. 37% formalin (28 mL, 386 mmol) was added and stirred under ice-cooling for 60 min, and the obtained solution was concentrated in vacuo. The residue was added with 2N sodium hydroxide, pH was adjusted to 8-9 to cause precipitation. The precipitate was filtered to isolate, washed with water and diisopropylether to yield compound 35 as a pale yellow powder. Yield: 42.7 g (98%). 1H-NMR (DMSO-d6) δ: 10.32 (1H, s), 7.73 (1H, s), 7.68 (1H, d, J=8.1 Hz), 7.50 (2H, d, J=12.6 Hz), 7.31 (1H, t, J=7.7 Hz), 7.08-7.06 (2H, m), 5.24 (1H, br s), 4.53 (2H, d, J=11.4 Hz), 3.05 (6H, s).

Compound 36

Oxalyl chloride (16.5 mL, 189 mmol) in dichloro methane (100 mL) was dropped to dimethylsulphoxide (26 mL, 267 mmol) in dichloromethane (100 mL) at −78° C. After the mixture was stirred at −78° C. for 15 minutes, a mixture of compound 35 (37.6 g, 111.2 mmol) in dichloromethane (300 mL) and dimethylsulphoxide (30 mL) was dropped at −78° C., and stirred at −30° C. for 1 hour. Triethylamine (47 mL, 334 mmol) in dichloro methane (50 mL) was added dropwise to the reaction mixture, and stirred at −20° C. for 30 minutes. The solution was concentrated in vacuo. The residue was added with water, filtered to isolate preciptated crystal, and washed with diisopropylether to yield compound 36 as pale yellow powder. Yield: 36 g (96%).

1H-NMR (DMSO-d6) δ: 10.60 (1H, s), 10.03 (1H, s), 8.36 (1H, s), 8.10 (1H, d, J=10.6 Hz), 7.70 (1H, t, J=6.2 Hz), 7.62 (1H, t, J=9.1 Hz), 7.53 (2H, d, J=13.6 Hz), 7.10 (1H, s), 3.06 (6H, s).

Compound 37

A mixture of vancomycin hydrochloride (44.6 g, 30 mmol) and compound 36 (10.6 g, 31.5 mmol) in methanol (300 mL) and dimethylformamide (300 mL) was added with diisopropylethylamine (10.5 mL, 60 mmol) and stirred at 70° C. for 2 h. The reaction mixture was added with sodium cyanoborohydride (7.5 g, 120 mmol) and stirred at 70° C. for 12 h. The reaction mixture was poured into ether (1500 mL), and the precipitate was filtered to isolate and purified by reverse-phase column chromatography, and lyophilized to yield compound 37 as white powder.

Yield: 17.1 g (28%).

Elemental analysis: $C_{83}H_{90}Cl_2F_3N_{11}O_{25} \cdot 2.5HCl \cdot 10H_2O$ calcd. C: 56.34%, H: 5.13%. N: 8.71%, Cl: 4.01%, F: 3.22%

Found: C: 48.75%, H: 5.36%. N: 7.77%, Cl: 7.68%, F: 2.73%

MS (ESI): 1770[M+3]+, 1768[M+1]−

Example 11

The following compounds were prepared in a similar manner as described above.

TABLE 3

| $R^A$ | $R^B$ | $R^C$ | $R^D$ |
|---|---|---|---|
| (structure with X1, Ar1, X2, Y, X3, Ar2) | OH | H | H |

| $R^A$ | | | | | | | |
|---|---|---|---|---|---|---|---|
| Ar2 | X3 | Y | X2 | Ar1 | X1 | Mass | Elemental Analysis |
| (phenyl with NO₂, OBn) | bond | NHCO | bond | (m-phenylene) | CH2 | [M + 1]⁻ = 1822 | Calcd. for C88H93Cl2N11O28•3.8HCl•14.7H2O<br>C: 47.46%, H: 5.71%, N: 6.92%, Cl: 9.23%<br>Found: C: 47.40%, H: 5.57%, N: 7.14%, Cl: 9.15% |
| (phenyl with NO₂, OBn) | bond | CONMe | bond | (m-phenylene) | CH2 | [M + 1]⁻ = 1837 | Calcd. for C89H95Cl2N11O28•2.0HCl•12.0H2O<br>C: 50.26%, H: 5.73%, N: 7.24%, Cl: 6.67%<br>Found: C: 50.21%, H: 5.16%, N: 7.13%, Cl: 6.59% |
| (phenyl with NO₂, OMe) | bond | CONMe | bond | (m-phenylene) | CH2 | [M + 1]⁻ = 1746 | Calcd. for C82H89Cl2N11O28•1.8HCl•10.0H2O<br>C: 49.41%, H: 5.60%, N: 7.73%, Cl: 6.76%<br>Found: C: 49.40%, H: 5.38%, N: 7.66%, Cl: 6.70% |
| (phenyl with Cl) | bond | CONH | bond | (m-phenylene) | CH2 | [M + 1]⁻ = 1692 | Calcd. for C80H85Cl3N10O25•1.9HCl•11.3H2O<br>C: 48.88%, H: 5.61%, N: 7.13%, Cl: 8.84%<br>Found: C: 48.88%, H: 5.48%, N: 7.29%, Cl: 8.81% |
| (phenyl with F) | bond | CONH | bond | (m-phenylene) | CH2 | [M + 3]⁺ = 1678<br>[M + 1]⁻ = 1675 | Calcd. for C80H85Cl2FN10O25•1.1HCl•8.7H2O<br>C: 51.29%, H: 5.57%, N: 8.48%, Cl: 5.87%, F: 1.01%<br>Found: C: 51.14%, H: 5.86%, N: 8.73%, Cl: 5.83%, F: 0.63% |

TABLE 4

| Structure 1 | | | | Structure 2 | | MS | Analysis |
|---|---|---|---|---|---|---|---|
| 3-CF3-phenyl | bond | CONH | bond | 1,3-phenylene | CH2 | [M + 1]+ = 1727<br>[M + 1]- = 1725 | Calcd. for C81H85Cl2F3N10O25•1.6HCl•8.5H2O<br>C: 50.20%, H: 5.39%, N: 1.23%,<br>Cl: 6.59%, F: 2.94%<br>Found: C: 50.18%, H: 5.37%,<br>N: 7.32%, Cl: 6.60%, F: 2.87% |
| 3-F-phenyl | bond | CONH | bond | 1,3-phenylene | CH2 | [M + 1]- = 1675 | Calcd. for C80H85Cl2FN10O25•1.6HCl•9.1H2O<br>C: 50.60%, H: 5.56%, N: 7.38%,<br>Cl: 6.72%, F: 1.00%<br>Found: C: 50.56%, H: 5.47%, N: 7.66%,<br>Cl: 6.81%, F: 1.03% |
| 4-F-phenyl | bond | CONH | bond | 1,3-phenylene | CH2 | [M + 1]- = 1675 | Calcd. for C80H85Cl2FN10O25•1.1HCl•10.4H2O<br>C: 50.47%, H: 5.66%, N: 8.36%,<br>Cl: 5.77%, F: 1.00%<br>Found: C: 50.30%, H: 5.81%, N: 8.55%,<br>Cl: 5.85%, F: 0.66% |
| 2-naphthyl | bond | CONH | bond | 1,3-phenylene | CH2 | [M + 1]- = 1707 | Calcd. for C84H88Cl2N10O25•1.7HCl•10.3H2O<br>C: 51.58%, H: 5.68%, N: 7.16%, Cl: 6.71%<br>Found: C: 51.52%, H: 5.57%, N: 7.35%, Cl: 6.76% |
| 2-OMe-phenyl | bond | CONH | bond | 1,3-phenylene | CH2 | [M + 1]- = 1687 | Calcd. for C81H88Cl2N10O26•1.8HCl•10.2H2O<br>C: 50.20%, H: 5.73%, N: 7.23%, Cl: 6.95%<br>Found: C: 50.21%, H: 5.56%, N: 7.47%, Cl: 6.90% |
| 2-OEt-phenyl | bond | CONH | bond | 1,3-phenylene | CH2 | [M + 3]+ = 1703<br>[M + 1]- = 1701 | Calcd. for C82H90Cl2N10O26•2.1HCl•9.6H2O<br>C: 50.45%, H: 5.75%, N: 7.18%, Cl: 7.45%<br>Found: C: 50.39%, H: 5.53%, N: 7.48%, Cl: 7.44% |
| 4-pyridyl | bond | CONH | bond | 1,3-phenylene | CH2 | [M + 1]- = 1658 | Calcd. for C79H85Cl2N11O25•3.0HCl•10.4H2O<br>C: 48.50%, H: 5.61%, N: 7.88%, Cl: 9.06%<br>Found: C: 48.41%, H: 5.46%, N: 8.10%, Cl: 9.12% |
| 4-CN-phenyl | bond | CONH | bond | 1,3-phenylene | CH2 | [M + 1]- = 1682 | Calcd. for C81H85Cl2N11O25•1.5HCl•10.4H2O<br>C: 50.52%, H: 5.62%, N: 8.00%, Cl: 6.44%<br>Found: C: 50.49%, H: 5.54%, N: 8.13%, Cl: 6.39% |
| fluorenon-4-yl | bond | CONH | bond | 1,3-phenylene | CH2 | [M + 1]- = 1759 | Calcd. for C87H88Cl2N11O26•1.9HCl•10.2H2O<br>C: 51.89%, H: 5.52%, N: 6.96%, Cl: 6.87%<br>Found: C: 51.81%, H: 5.39%, N: 7.10%, Cl: 6.87% |

TABLE 5

| | | | | | | | |
|---|---|---|---|---|---|---|---|
| 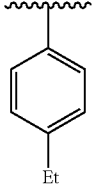 | bond | CONH | bond | 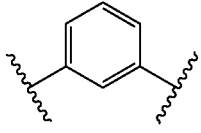 [SMILES: *c1cccc(*)c1] | CH2 | [M + 1]⁻ = 1685 | Calcd. for C82H90Cl2N10O25•1.3HCl•9.7H2O C: 51.60%, H: 5.85%, N: 7.34%, Cl: 6.13% Found: C: 51.57%, H: 5.79%, N: 7.39%, Cl: 6.16% |
| 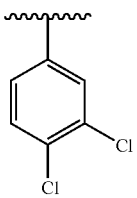 | bond | CONH | bond | 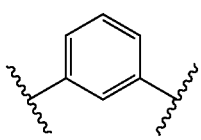 [SMILES: *c1cccc(*)c1] | CH2 | [M + 1]⁻ = 1726 | Calcd. for C80H84Cl4N10O25•1.9HCl•10.4H2O C: 48.43%, H: 5.42%, N: 7.06%, Cl: 10.54% Found: C: 48.43%, H: 5.03%, N: 7.18%, Cl: 10.47% |
| 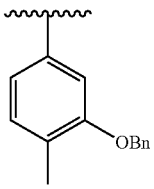 | bond | NHCO | NH | 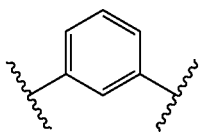 [SMILES: *c1cccc(*)c1] | CH2 | [M + 1]⁻ = 1792 | Calcd. for C88H95Cl2N11O26•1.9HCl•8.4H2O C: 52.47%, H: 5.69%, N: 7.65%, Cl: 6.86% Found: C: 52.48%, H: 5.71%, N: 7.70%, Cl: 6.80% |
| 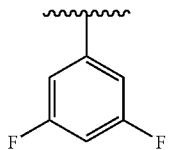 [SMILES: *c1cc(F)cc(F)c1] | bond | CONH | bond | 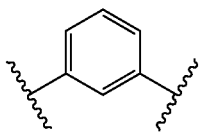 [SMILES: *c1cccc(*)c1] | CH2 | [M + 1]⁻ = 1693 | Calcd. for C80H84Cl2F2N10O25•1.5HCl•8.2H2O C: 50.65%, H: 5.41%, N: 7.38%, Cl: 6.54%, F: 2.00% Found: C: 50.56%, H: 5.09%, N: 7.57%, Cl: 6.56%, F: 1.93% |
| 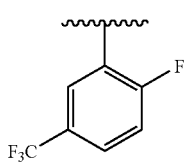 [SMILES: *c1cc(C(F)(F)F)ccc1F] | bond | CONH | bond | 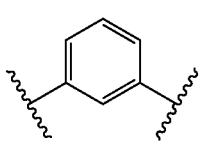 [SMILES: *c1cccc(*)c1] | CH2 | [M + 3]⁺ = 1745 [M + 1]⁻ = 1743 | Calcd. for C81H84Cl2F4N10O25•1.9HCl•8.9H2O C: 49.28%, H: 5.29%, N: 7.10%, Cl: 7.00%, F: 3.85% Found: C: 49.21%, H: 5.03%, N: 7.20%, Cl: 6.94%, F: 3.76% |
| 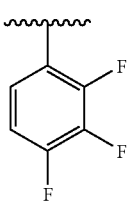 [SMILES: *c1ccc(F)c(F)c1F] | bond | CONH | bond | 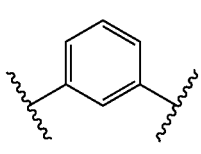 [SMILES: *c1cccc(*)c1] | CH2 | [M + 3]⁺ = 1713 [M + 1]⁻ = 1711 | Calcd. for C80H83Cl2F3N10O25•1.9HCl•9.3H2O C: 49.29%, H: 5.35%, N: 7.19%, Cl: 7.09%, F: 2.92% Found: C: 49.29%, H: 5.11%, N: 7.27%, Cl: 7.14%, F: 2.77% |
| 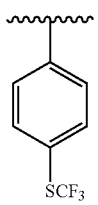 | bond | CONH | bond | 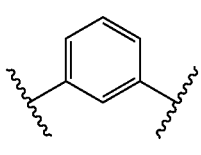 [SMILES: *c1cccc(*)c1] | CH2 | [M + 1]⁻ = 1757 | Calcd. for C81H85Cl2F3N10O25S•2.2HCl•8.9H2O C: 48.66%, H: 5.29%, N: 7.01%, Cl: 7.45%, F: 2.85%, S: 1.60% Found: C: 48.64%, H: 5.24%, N: 7.01%, Cl: 7.42%, F: 2.75%, S: 1.61% |
| 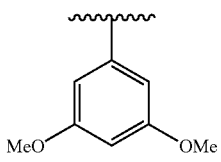 | bond | CONH | bond | 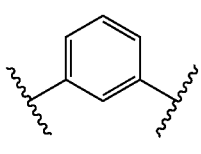 [SMILES: *c1cccc(*)c1] | CH2 | [M + 3]⁺ = 1719 [M + 1]⁻ = 1717 | Calcd. for C82H90Cl2N10O27•1.4HCl•10.7H2O C: 50.19%, H: 5.79%, N: 7.14%, Cl: 6.14% Found: C: 50.15%, H: 5.70%, N: 7.29%, Cl: 6.08% |

TABLE 5-continued

| Structure | | | | | | |
|---|---|---|---|---|---|---|
| 3-bromopyridin-5-yl | bond | CONH | bond | 1,3-phenylene | CH2 | [M + 1]⁻ = 1737 | Calcd. for C79H84BrCl2N11O25•1.6HCl•10.4H2O<br>C: 47.82%, H: 5.41%, N: 7.77%,<br>Cl: 6.43%, Br: 4.03%<br>Found: C: 47.80%, H: 5.33%, N: 7.81%,<br>Cl: 6.39%, Br: 4.12% |

TABLE 6

| Structure | | | | | | | |
|---|---|---|---|---|---|---|---|
| 3-(SCHF2)phenyl | bond | CONH | bond | 1,3-phenylene | CH2 | [M + 3]⁺ = 1741<br>[M + 1]⁻ = 1739 | Calcd. for C81H86Cl2F2N10O25S•2.1HCl•9.0H2O<br>C: 49.15%, H: 5.40%, N: 7.08%, Cl: 7.34%,<br>F: 1.92%, S: 1.62%<br>Found: C: 49.18%, H: 5.26%, N: 7.12%, Cl: 7.26%,<br>F: 1.81%, S: 1.63% |
| 2-chloropyridin-4-yl | bond | CONH | bond | 1,3-phenylene | CH2 | [M + 1]⁻ = 1693 | Calcd. for C79H84Cl3N11O25•1.8HCl•11.2H2O<br>C: 48.38%, H: 5.56%, N: 7.86%, Cl: 8.68%<br>Found: C: 48.34%, H: 5.45%, N: 7.78%, Cl: 8.72% |
| 2-bromo-5-methoxyphenyl | bond | CONH | bond | 1,3-phenylene | CH2 | [M + 1]⁺ = 1768<br>[M + 1]⁻ = 1766 | Calcd. for C81H87BrCl2N10O26•1.4HCl•10.6H2O<br>C: 48.42%, H: 5.50%, N: 6.97%,<br>Cl: 6.00%, Br: 3.98%<br>Found: C: 48.34%, H: 5.42%, N: 7.09%,<br>Cl: 5.96%, Br: 4.36% |
| 3,5-dimethoxy-4-methylphenyl | bond | CONH | bond | 1,3-phenylene | CH2 | [M + 1]⁻ = 1731 | Calcd. for C83H92Cl2N10O27•1.8HCl•9.7H2O<br>C: 50.53%, H: 5.78%, N: 7.10%, Cl: 6.83%<br>Found: C: 50.53%, H: 5.56%, N: 7.11%, Cl: 6.78% |
| 4-benzyloxy-3,5-dimethylphenyl | bond | CONH | bond | 1,3-phenylene | CH2 | [M + 1]⁻ = 1791 | Calcd. for C89H96Cl2N10O26•1.5HCl•10.0H2O<br>C: 52.72%, H: 5.84%, N: 6.91%, Cl: 6.12%<br>Found: C: 52.73%, H: 5.81%, N: 6.91%, Cl: 6.12% |
| 4-cyano-2-fluorophenyl | bond | CONH | bond | 1,3-phenylene | CH2 | [M + 1]⁻ = 1700 | Calcd. for C81H84Cl2FN11O25•1.9HCl•9.4H2O<br>C: 50.14%, H: 5.44%, N: 7.94%,<br>Cl: 7.13%, F: 0.98%<br>Found: C: 49.88%, H: 5.37%, N: 8.24%,<br>Cl: 7.09%, F: 0.93% |
| 2,4-dichlorophenyl | bond | CONH | bond | 1,3-phenylene | CH2 | [M + 3]⁺ = 1728<br>[M + 1]⁻ = 1726 | Calcd. for C80H84Cl4N10O25•1.3HCl•9.8H2O<br>C: 49.24%, H: 5.42%, N: 7.18%, Cl: 9.63%<br>Found: C: 49.21%, H: 5.25%, N: 7.38%, Cl: 9.64% |

TABLE 6-continued

| Structure 1 | L1 | L2 | L3 | Structure 2 | L4 | MS | Analysis |
|---|---|---|---|---|---|---|---|
| 2-Cl, 4-NO2 phenyl | bond | CONH | bond | 1,3-phenylene | CH2 | [M + 1]⁻ = 1736 | Calcd. for C80H84Cl3N11O27•1.2HCl•10.1H2O<br>C: 48.93%, H: 5.41%, N: 7.85%, Cl: 7.58%<br>Found: C: 48.92%, H: 5.32%, N: 7.93%, Cl: 7.60% |
| 2-Cl, 4-SO2NH2, 5-Cl phenyl | bond | CONH | bond | 1,3-phenylene | CH2 | [M + 1]⁻ = 1805 | Calcd. for C80H85Cl4N11O27S•1.7HCl•10.6H2O<br>C: 46.66%, H: 5.28%, N: 7.48%,<br>Cl: 9.81%, S: 1.56%<br>Found: C: 46.56%, H: 5.09%, N: 7.75%, Cl: 9.87%<br>F: 1.64% |

TABLE 7

| Structure 1 | L1 | L2 | L3 | Structure 2 | L4 | MS | Analysis |
|---|---|---|---|---|---|---|---|
| 2-Cl, 4-(pyrazol-1-yl) phenyl | bond | CONH | bond | 1,3-phenylene | CH2 | [M + 1]⁻ = 1758 | Calcd. for<br>C83H87Cl3N12O25•1.1HCl•11.1H2O<br>C: 49.87%, H: 5.56%, N: 8.41%, Cl: 7.27%<br>Found: C: 49.86%, H: 5.45%, N: 8.43%,<br>Cl: 7.25% |
| 2-Me, 4-F phenyl | bond | CONH | bond | 1,3-phenylene | CH2 | [M + 3]⁺ = 1691<br>[M + 1]⁻ = 1689 | Calcd. for<br>C81H87Cl2FN10O25•1.8HCl•9.4H2O<br>C: 50.53%, H: 5.63%, N: 7.27%,<br>Cl: 7.00%, F: 0.99%<br>Found: C: 50.52%,<br>H: 5.47%, N: 7.34%, Cl: 7.03%, F: 0.95% |
| 2-(4-fluorophenylamino) phenyl | bond | CONH | bond | 1,3-phenylene | CH2 | [M + 3]⁺ = 1769<br>[M + 1]⁻ = 1767 | Calcd. for<br>C86H90Cl2FN11O25•1.6HCl•8.8H2O<br>C: 52.05%, H: 5.55%, N: 7.76%,<br>Cl: 6.43%, F: 0.96%<br>Found: C: 52.03%,<br>H: 5.57%, N: 7.73%, Cl: 6.44%, F: 0.90% |
| 3-CO2Me phenyl | bond | CONH | bond | 1,3-phenylene | CH2 | [M + 1]⁻ = 1715 | Calcd. for<br>C82H88Cl2N10O27•1.4HCl•9.6H2O<br>C: 50.75%, H: 5.64%, N: 7.22%, Cl: 6.21%<br>Found: C: 50.71%,<br>H: 5.50%, N: 7.29%, Cl: 6.13% |
| 4-OCHF2 phenyl | bond | CONH | bond | 1,3-phenylene | CH2 | [M + 3]⁺ = 1727<br>[M + 1]⁻ = 1725 | Calcd. for<br>C81H86Cl2F2N10O26•1.9HCl•8.4H2O<br>C: 49.96%, H: 5.52%, N: 7.19%,<br>Cl: 7.10%, F: 1.95%<br>Found: C: 49.90%,<br>H: 5.25%, N: 7.49%, Cl: 7.10%, F: 1.88% |
| 2,3-dihydrobenzo[1,4]dioxin-5-yl | bond | CONH | bond | 1,3-phenylene | CH2 | [M + 1]⁻ = 1716 | Calcd. for<br>C82H88Cl2N10O27•1.3HCl•11.3H2O<br>C: 50.06%, H: 5.73%, N: 7.12%, Cl: 5.95%<br>Found: C: 50.05%,<br>H: 5.58%, N: 7.20%, Cl: 5.99% |

TABLE 7-continued

| | | | | | | | |
|---|---|---|---|---|---|---|---|
| 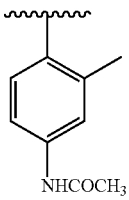 | bond | CONH | bond | 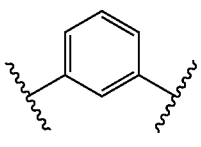 [SMILES: *c1cccc(*)c1] | CH2 | [M + 3]⁺ = 1729<br>[M + 1]⁻ = 1727 | Calcd. for<br>C83H91Cl2N11O26·2HCl·11.6H2O<br>C: 49.38%, H: 5.81%, N: 7.63%, Cl: 7.38%<br>Found: C: 49.40%,<br>H: 5.57%, N: 7.65%, Cl: 7.33% |
| 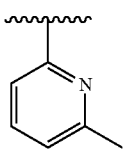 | bond | CONH | bond | 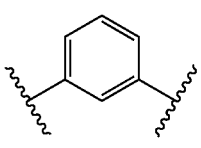 [SMILES: *c1cccc(*)c1] | CH2 | [M + 3]⁺ = 1674<br>[M + 1]⁻ = 1672 | Calcd. for<br>C80H87Cl2N11O25·1.8HCl·10.8H2O<br>C: 49.69%, H: 5.75%, N: 7.97%, Cl: 6.97%<br>Found: C: 49.67%,<br>H: 5.59%, N: 8.15%, Cl: 6.89% |
| 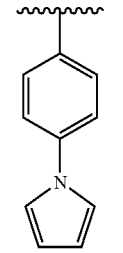 | bond | CONH | bond | 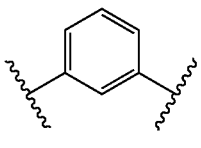 [SMILES: *c1cccc(*)c1] | CH2 | [M + 3]⁺ = 1724<br>[M + 1]⁻ = 1722 | Calcd. for<br>C84H89Cl2N11O25·2.0HCl·10.4H2O<br>C: 50.86%, H: 5.68%. N: 7.77%, Cl: 7.15%<br>Found: C: 50.82%,<br>H: 5.50%, N: 7.96%, Cl: 7.09% |

TABLE 8

| | | | | | | | |
|---|---|---|---|---|---|---|---|
| 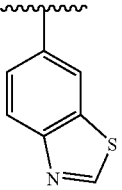 | bond | CONH | bond | 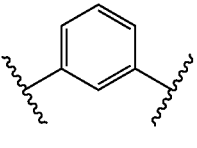 [SMILES: *c1cccc(*)c1] | CH2 | [M + 3]⁺ = 1716<br>[M + 1]⁻ = 1714 | Calcd. for<br>C81H85Cl2N11O25S·2.2HCl·10.8H2O<br>C: 48.88%, H: 5.51%,<br>N: 7.74%, Cl: 7.48%, S: 1.61%<br>Found: C: 48.85%,<br>H: 5.50%, N: 7.92%, Cl: 7.40%, S: 1.50% |
| 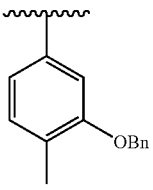 [SMILES: *c1ccc(C)c(OCc2ccccc2)c1] | bond | NHCO | bond | 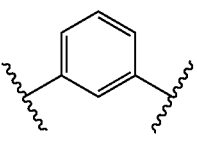 | CH2 | [M + 1]⁻ = 1775 | Calcd. for C88H94Cl2N10O26·1.7HCl·8.9H2O<br>C: 52.82%, H: 5.72%, N: 7.00%, Cl: 6.56%<br>Found: C: 52.79%, H: 5.70%, N: 1.10%, Cl: 6.49% |
| 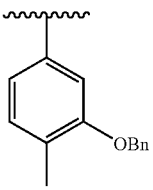 [SMILES: *c1ccc(C)c(OCc2ccccc2)c1] | CH2 | NHCO | bond | 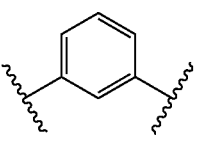 [SMILES: *c1cccc(*)c1] | CH2 | [M + 3]⁺ = 1793<br>[M + 1]⁻ = 1791 | Calcd. for C89H96Cl2N10O26·1.8HCl·8.4H2O<br>C: 53.19%, H: 5.75%, N: 6.97%, Cl: 6.70%<br>Found: C: 53.12%, H: 5.72%, N: 7.23%, Cl: 6.77% |
| 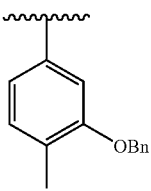 [SMILES: *c1ccc(C)c(OCc2ccccc2)c1] | bond | NHCO | CH2 | 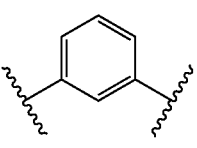 | CH2 | [M + 3]⁺ = 1793<br>[M + 1]⁻ = 1791 | Calcd. for C89H96Cl2N10O26·1.8HCl·9.1H2O<br>C: 52.86%, H: 5.78%, N: 6.93%, Cl: 6.66%<br>Found: C: 52.87%, H: 5.66%, N: 6.83%, Cl: 6.63% |

TABLE 9

| | R^A | R^B | R^C | R^D |
|---|---|---|---|---|
| | (structure: X³—Y—X² with Ar¹ and Ar² branches, X¹ terminal) | OH | H | H |

| R^A | | | | | | | |
|---|---|---|---|---|---|---|---|
| Ar2 | X3 | Y | X2 | Ar1 | X1 | Mass | Elemetal Analysis |
| phenyl | bond | CONH | bond | 1,3-phenylene | CH2 | [M + 3]⁺ = 1659<br>[M + 1]⁻ = 1657 | Calcd. for C80H86Cl2N10O25•2HCl•13H2O<br>C: 48.88%, H: 5.85%, N: 7.13%, Cl: 7.21%<br>Found: C: 49.00%, H: 5.73%, N: 7.35%, Cl: 6.83% |
| 4-methylphenyl | bond | CONH | bond | 1,3-phenylene | CH2 | [M + 1]⁻ = 1673 | Calcd. for C81H88Cl2N10O25•2HCl•15H2O<br>C: 48.27%, H: 6.00%, N: 6.95%, Cl: 7.04%<br>Found: C: 48.14%, H: 6.05%, N: 7.25%, Cl: 6.86% |
| 2-nitrophenyl | bond | CONH | bond | 1,3-phenylene | CH2 | [M + 1]⁻ = 1704 | Calcd. for C80H85Cl2N11O27•2HCl•11H2O<br>C: 48.66%, H: 5.56%, N: 7.80%, Cl: 7.18%<br>Found: C: 48.80%, H: 5.97%, N: 7.90%, Cl: 6.79% |
| 3-methoxyphenyl | bond | CONH | bond | 1,3-phenylene | CH2 | [M + 1]⁻ = 1687 | Calcd. for C81H88Cl2N10O26•2HCl•12H2O<br>C: 49.19%, H: 5.81%, N: 7.08%, Cl: 7.17%<br>Found: C: 49.10%, H: 5.98%, N: 7.57%, Cl: 6.20% |
| 3-methoxy-4-methylphenyl | bond | CONH | bond | 1,3-phenylene | CH2 | [M + 1]⁻ = 1703 | Calcd. for C82H90Cl2N10O26•2HCl•14H2O<br>C: 48.57%, H: 5.97%, N: 6.91%, Cl: 6.99%<br>Found: C: 48.77%, H: 5.88%, N: 7.10%, Cl: 6.60% |
| 3-benzyloxyphenyl | bond | CONH | bond | 1,3-phenylene | CH2 | [M + 1]⁻ = 1763 | Calcd. for C87H92Cl2N10O26•2HCl•9H2O<br>C: 52.25%, H: 5.65%, N: 7.00%, Cl: 7.09%<br>Found: C: 51.97%, H: 5.56%, N: 7.08%, Cl: 7.31% |

TABLE 9-continued

| | | | | | | |
|---|---|---|---|---|---|---|
| 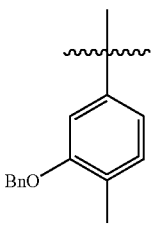 | bond | CONH | bond | 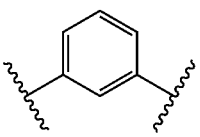 [SMILES: *c1cccc(*)c1] | CH2 | [M + 1]⁻ = 1777 | Calcd. for C88H94Cl2N10O26•3HCl•10H2O<br>C: 51.10%, H: 5.70%, N: 6.77%, Cl: 8.57%<br>Found: C: 51.30%, H: 5.68%, N: 6.94%, Cl: 7.97% |

TABLE 10

| | | | | | | |
|---|---|---|---|---|---|---|
| 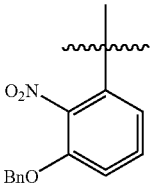 [SMILES: *C1=C([N+](=O)[O-])C(OCc2ccccc2)=C=C=C1] | bond | CONH | bond | 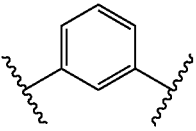 | CH2 | [M + 1]⁻ = 1810 | Calcd for C87H91Cl2N11O28•1HCl•12H2O<br>C: 50.61%, H: 5.67%, N: 7.47%, Cl: 5.16%<br>Found: C: 50.54%, H: 5.50%, N: 7.47%, Cl: 5.55% |
| 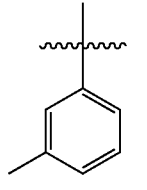 | bond | CONH | bond | 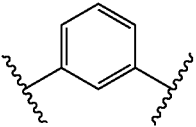 | CH2 | [M + 1]⁻ = 1671 | Calcd. for C81H88Cl2N10O25•2HCl•9H2O<br>C: 51.00%, H: 5.71%, N: 7.34%, Cl: 7.43%<br>Found: C: 51.04%, H: 5.72%, N: 7.63%, Cl: 6.81% |
| 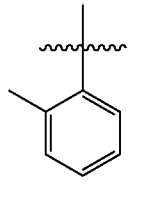 | bond | CONH | bond | 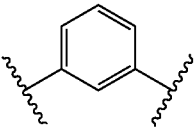 [SMILES: *c1cccc(*)c1] | CH2 | [M + 3]⁺ = 1683<br>[M + 1]⁺ = 1661 | Calcd. for C81H88Cl2N10O25•2HCl•13H2O<br>C: 49.14%, H: 5.91%, N: 7.08%, Cl: 7.16%<br>Found: C: 48.78%, H: 5.72%, N: 7.24%, Cl: 8.05% |
| 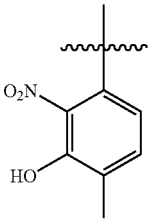 [SMILES: *c1ccc(C)c(O)c1[N+](=O)[O-]] | bond | CONH | bond | 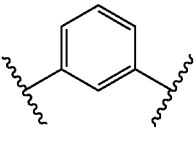 [SMILES: *c1cccc(*)c1] | CH2 | [M + 1]⁻ = 1732 | Calcd. for C81H87Cl2N11O28•2HCl•12H2O<br>C: 48.10%, H: 5.63%, N: 7.62%, Cl: 7.01%<br>Found: C: 48.25%, H: 5.66%, N: 7.86%, Cl: 6.75% |
| 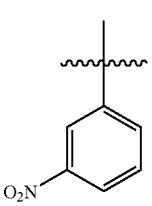 [SMILES: *c1cccc([N+](=O)[O-])c1] | bond | CONH | bond | 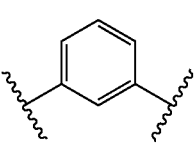 [SMILES: *c1cccc(*)c1] | CH2 | [M + 1]⁻ = 1702 | Calcd. for C80H85Cl2N11O27•2HCl•12H2O<br>C: 48.22%, H: 5.61%, N: 7.73%, Cl: 7.12%<br>Found: C: 48.17%, H: 5.61%, N: 7.83%, Cl: 6.66% |
| 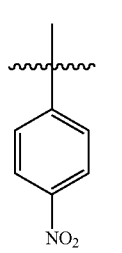 | bond | CONH | bond | 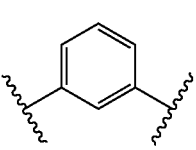 | CH2 | [M + 1]⁻ = 1702 | Calcd. for C80H85Cl2N11O27•2HCl•12H2O<br>C: 48.22%, H: 5.61%, N: 7.73%, Cl: 7.12%<br>Found: C: 48.30%, H: 5.54%, N: 8.05%, Cl: 6.66% |

TABLE 10-continued

| R1 | | | R2 | | MS | Analysis |
|---|---|---|---|---|---|---|
| 2-BnO-phenyl | bond | CONH | bond | 1,3-phenylene | CH2 [M + 1]⁻ = 1763 | Calcd. for C87H92Cl2N10O26•1HCl•13H2O<br>C: 51.34%, H: 5.89%, N: 6.88%, Cl: 5.23%<br>Found: C: 51.04%, H: 5.94%, N: 7.09%, Cl: 5.94% |
| 4-BnO-phenyl | bond | CONH | bond | 1,3-phenylene | CH2 [M + 1]⁻ = 1763 | Calcd. for C87H92Cl2N10O26•2HCl•14H2O<br>C: 50.00%, H: 5.88%, N: 6.70%, Cl: 6.79%<br>Found: C: 49.98%, H: 5.86%, N: 6.98%, Cl: 6.44% |
| 4-tBu-phenyl | bond | CONH | bond | 1,3-phenylene | CH2 [M + 1]⁻ = 1713 | Calcd. for C84H94Cl2N10O25•1.5HCl•9H2O<br>C: 51.28%, H: 6.02%, N: 7.12%, Cl: 6.31%<br>Found: C: 51.21%, H: 5.96%, N: 7.36%, Cl: 6.20% |
| 4-Cl-phenyl | bond | CONH | bond | 1,3-phenylene | CH2 [M + 1]⁻ = 1691 | Calcd. for C80H85Cl3N10O25•0.2HCl•11H2O<br>C: 50.61%, H: 5.69%, N: 7.38%, Cl: 5.98%<br>Found: C: 50.88%, H: 6.08%, N: 7.40%, Cl: 6.15% |

TABLE 11

| R1 | | | R2 | | MS | Analysis |
|---|---|---|---|---|---|---|
| pyrazin-2-yl | bond | CONH | bond | 1,3-phenylene | CH2 [M + 1]⁻ = 1659 | Calcd. for C18H84Cl2N12O25•1.2HCl•9H2O<br>C: 50.20%, H: 5.57%, N: 9.01%, Cl 6.08%<br>Found: C: 50.39%, H: 5.73%, N: 9.02%, Cl: 6.27% |
| 4-CF3-phenyl | bond | CONH | bond | 1,3-phenylene | CH2 [M + 3]⁺ = 1727<br>[M + 1]⁻ = 1725 | Calcd. for C81H85Cl2F3N10O25•1.3HCl•10H2O<br>C: 49.79%, H: 5.48%, N: 7.17%, Cl: 5.99%, F: 2.92%<br>Found: C: 49.86%, H: 5.44%, N: 7.36%, Cl: 6.13%, F: 2.81% |

TABLE 11-continued

| R1 | L1 | L2 | L3 | Ar | L4 | MS | Analysis |
|---|---|---|---|---|---|---|---|
| 4-COOH-phenyl | bond | CONH | bond | 1,3-phenylene | CH2 | [M + 3]+ = 1703<br>[M + 1]− = 1701 | Calcd. for C81H86Cl2N10O27•2HCl•9H2O<br>C: 50.21%, H: 5.51%, N: 7.23%, Cl: 7.32%<br>Found: C: 50.03%, H: 5.52%, N: 7.31%, Cl: 7.38% |
| 3-(2-morpholinoethoxy)-4-methylphenyl | bond | CONH | bond | 1,3-phenylene | CH2 | [M + 1]− = 1800 | Calcd. for C87H99Cl2N11O27•2HCl•7H2O<br>C: 52.23%, H: 5.79%, N: 7.70%, Cl: 7.09%<br>Found: C: 52.28%, H: 6.24%, N: 7.96%, Cl: 7.04% |
| 2-thienyl | bond | CONH | bond | 1,3-phenylene | CH2 | [M + 3]+ = 1665<br>[M + 1]− = 1663 | Calcd. for C78H84Cl2N10O25S1•2HCl•10H2O<br>C: 48.85%, H: 5.57%, N: 7.30%, Cl: 7.40%<br>Found: C: 49.00%, H: 5.12%, N: 7.37%, Cl: 6.98% |
| 3-(N-benzyl-N-methylamino)-4-methylphenyl | bond | CONH | bond | 1,3-phenylene | CH2 | [M + 1]− = 1790 | Calcd. for C89H97Cl2N11O25•1.6 HCl•10.3H2O<br>C: 52.51%, H: 5.90%, N: 7.57%, Cl: 6.27%<br>Found: C: 52.45%, H: 5.56%, N: 7.88%, Cl: 6.16% |
| 5-(benzyloxy)pyridin-3-yl | bond | CONH | bond | 1,3-phenylene | CH2 | [M + 1]− = 1764 | Calcd. for C86H91Cl2N11O26•1.2HCl•9.1H2O<br>C: 52.34%, H: 5.64%, N: 7.81%, Cl: 5.75%<br>Found: C: 52.34%, H: 5.54%, N: 7.84%, Cl: 5.72% |
| pyridin-3-yl | bond | CONH | bond | 1,3-phenylene | CH2 | [M + 3]+ = 1660<br>[M + 1]− = 1658 | Calcd. for C79H85Cl2N11O25•2.5HCl•10.5H2O<br>C: 48.91%, H: 5.64%, N: 7.94%, Cl: 8.22%<br>Found: C: 48.89%, H: 5.49%, N: 8.05%. Cl: 8.17% |
| 4-COOMe-phenyl | bond | CONH | bond | 1,3-phenylene | CH2 | [M + 3]+ = 1717<br>[M + 1]− = 1715 | Calcd. for C82H88Cl2N10O27•2.5 HCl•12.4H2O<br>C: 48.49%, H: 5.72%, N: 6.90%, Cl: 7.85%<br>Found: C: 48.39%, H: 5.50%, N: 7.02%, Cl: 7.91% |

TABLE 11-continued

| | | | | | | | |
|---|---|---|---|---|---|---|---|
| 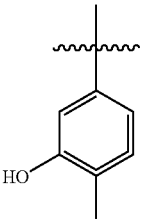 | bond | CONH | bond | 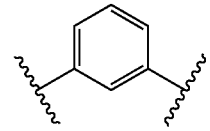 [SMILES: *c1cccc(*)c1] | CH2 | [M + 3]⁺ = 1689 [M + 1]⁻ = 1687 | Calcd. for C81H88Cl2N10O26•2.5HCl•10.2H2O C: 49.55%, H: 5.69%, N: 7.13%, Cl: 8.13% Found: C: 49.47%, H: 5.32%, N: 7.44%, Cl: 8.09% |

TABLE 12

| | | | | | | | |
|---|---|---|---|---|---|---|---|
| 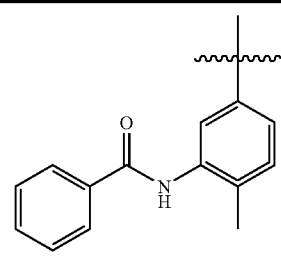 | bond | CONH | bond | 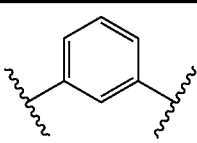 | CH2 | [M + 3]⁺ = 1792 [M + 1]⁻ = 1790 | Calcd. for C88H93Cl2N11O26•1.3HCl•8.7H2O C: 52.96%, H: 5.64%, N: 7.72%, Cl: 5.86% Found: C: 52.95%, H: 5.56%, N: 7.90%, Cl: 5.80% |
| 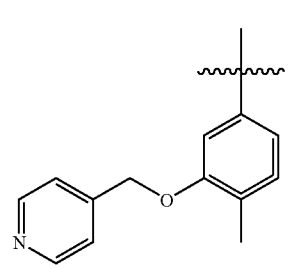 | bond | CONH | bond | 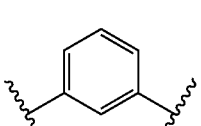 | CH2 | [M + 3]⁺ = 1780 [M + 1]⁻ = 1778 | Calcd. for C86H91Cl2N11O26•2.1HCl•9.4H2O C: 51.35%, H: 5.61%, N: 7.66%, Cl: 7.23% Found: C: 51.37%, H: 5.57%, N: 7.58%, Cl: 7.31% |
| 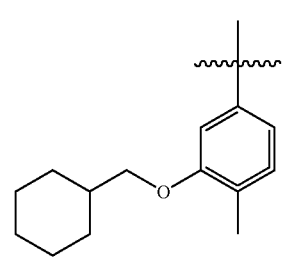 | bond | CONH | bond | 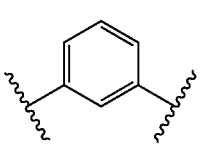 [SMILES: *c1cccc(*)c1] | CH2 | [M + 1]⁻ = 1783 | Calcd. for C88H100Cl2N10O26•1.7 HCl•8.9H2O C: 52.66%, H: 6.00%, N: 6.98%, Cl: 6.54% Found: C: 52.61%, H: 5.84%, N: 7.04%, Cl: 6.44% |
| 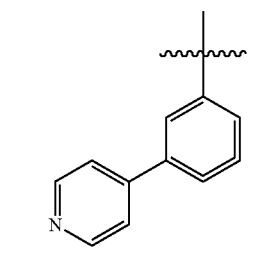 [SMILES: *C1=CC(c2ccncc2)=C=C=C1] | bond | CONH | bond | 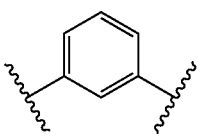 [SMILES: *c1cccc(*)c1] | CH2 | [M + 1]⁻ = 1734 | Calcd. for C85H89Cl2N11O25•2.4 HCl•10.4H2O C: 50.78%, H: 5.63%, N: 7.66%, Cl: 7.76% Found: C: 50.76%, H: 5.62%, N: 7.76%, Cl: 7.80% |
| 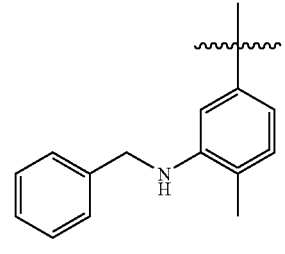 | bond | CONH | bond | 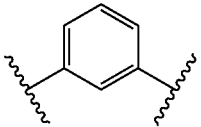 [SMILES: *c1cccc(*)c1] | CH2 | [M + 3]⁺ = 1778 [M + 1]⁻ = 1776 | Calcd. for C88H95Cl2N11O25•1.3HCl•8.8H2O C: 53.28%, H: 5.79%, N: 7.77%, Cl: 5.90% Found: C: 53.23%, H: 5.59%, N: 7.96%, Cl: 5.85% |

TABLE 12-continued

| Structure | | | | | | |
|---|---|---|---|---|---|---|
| (3,5-bis(BnO)-4-methylphenyl) | bond | CONH | bond | (1,3-phenylene) | CH2 | [M + 1]⁻ = 1869  Calcd. for C94H98Cl2N10O27•1.7HCl•9.7H2O  C: 00%, H: 00%, N: 00%, Cl: 00%  Found: C: 00%, H: 00%, N: 00%, Cl: 00% |
| (3-BnO-5-OH-4-methylphenyl) | bond | CONH | bond | (1,3-phenylene) | CH2 | [M + 3]⁺ = 1781  [M + 1]⁻ = 1779  Calcd. for C87H92Cl2N10O27•2HCl•9H2O  C: 51.84%, H: 5.60%, N: 6.95%, Cl: 7.04%  Found: C: 51.89%, H: 5.64%, N: 6.93%, Cl: 6.55% |
| (3-BnO-5-(2-morpholinoethoxy)-4-methylphenyl) | bond | CONH | bond | (1,3-phenylene) | CH2 | [M + 1]⁻ = 1892  Calcd. for C93H103Cl2N11O28•11.6 HCl•2.3H2O  C: 51.08%, H: 5.92%, N: 7.05%, Cl: 6.97%  Found: C: 51.00%, H: 5.71%, N: 7.21%, Cl: 6.87% |
| (3-(phenylamino)phenyl) | bond | CONH | bond | (1,3-phenylene) | CH2 | [M + 1]⁻ = 1748  Calcd. for C86H91Cl2N11O25•1.9 HCl•10.6H2O  C: 51.39%, H: 5.72%, N: 7.67%, Cl: 6.88%  Found: C: 51.36%, H: 5.48%, N: 7.72%, Cl: 6.80% |
| (3-BnO-isoxazol-5-yl) | bond | CONH | bond | (1,3-phenylene) | CH2 | [M + 1]⁻ = 1754  Calcd. for C84H89Cl2N11O27•1.4 HCl•11.4H2O  C: 50.14%, H: 5.67%, N: 7.66%, Cl: 5.99%  Found: C: 50.14%, H: 5.53%, N: 7.79%, Cl: 6.04% |

TABLE 13

| Structure | | | | | | |
|---|---|---|---|---|---|---|
| (1-Bu-piperidin-4-yl) | bond | CONH | bond | (1,3-phenylene) | CH2 | [M + 1]⁻ = 1754  Calcd. for C86H97Cl1N11O25•2.2HCl•12.2H2O  C: 50.25%, H: 6.06%, N: 7.50%, Cl: 7.24%  Found: C: 50.24%, H: 5.88%, N: 7.59%, Cl: 7.29% |

TABLE 13-continued

| | | | | | | |
|---|---|---|---|---|---|---|
| (N-benzylpyrazole) | bond | CONH | bond | (m-phenylene) | CH2 | [M + 1]⁻ = 1737 | Calcd. for C84H90Cl2N12O25•1.6HCl•11.3H2O<br>C: 50.43%, H: 5.75%,<br>N: 8.40%, Cl: 6.38%<br>Found: C: 50.40%, H: 5.66%,<br>N: 8.60%, Cl: 6.37% |
| (BnO-methylphenyl) | bond | CONH | bond | (Br-phenylene) | CH2 | [M + 1]⁻ = 1858 | Calcd. for C88H93Br1Cl2N10O26•1.5HCl•10.8H2O<br>C: 50.17%, H: 5.55%,<br>N: 6.65%, Cl: 5.89%, Br: 3.79%<br>Found: C: 50.18%, H: 5.40%,<br>N: 6.73%, Cl: 5.82%, Br: 3.84% |
| (BnO-methylphenyl) | bond | CONH | bond | (piperidinyl-phenylene) | CH2 | [M + 3]⁺ = 1862<br>[M + 1]⁻ = 1860 | Calcd. for C93H103Cl2N11O26•1.7HCl•10.1H2O<br>C: 53.05%, H: 5.98%,<br>N: 7.32%, Cl: 6.23%<br>Found: C: 53.02%, H: 5.82%,<br>N: 7.55%, Cl: 6.26% |
| (pyrazinylmethoxy-methylphenyl) | bond | CONH | bond | (m-phenylene) | CH2 | [M + 3]⁺ = 1781<br>[M + 1]⁻ = 1779 | Calcd. for C86H92Cl2N12O26•2HCl•11.1H2O<br>C: 50.30%, H: 5.70%,<br>N: 8.19%, Cl: 6.91%<br>Found: C: 50.21%, H: 5.60%,<br>N: 8.44%, Cl: 6.88% |
| (BnO-methylphenyl) | bond | CONH | bond | (COOH-phenylene) | CH2 | [M + 1]⁻ = 1821 | Calcd. for C89H94Cl2N10O28•1.8HCl•10.8H2O<br>C: 51.32%, H: 5.68%,<br>N: 6.72%, Cl: 6.47%<br>Found: C: 51.34%, H: 5.45%,<br>N: 6.38%, Cl: 6.36% |
| (N-benzylimidazole) | bond | CONH | bond | (m-phenylene) | CH2 | [M + 3]⁺ = 1739<br>[M + 1]⁻ = 1737 | Calcd. for C84H90Cl2N12O25•1.9HCl•10.6H2O<br>C: 50.47%, H: 5.70%,<br>N: 8.41%, Cl: 6.92%<br>Found: C: 50.38%,<br>H: 5.34%, N: 8.44%, Cl: 6.93% |

TABLE 13-continued

| R1 | | | | R2 | | Data |
|---|---|---|---|---|---|---|
| 4-F-phenyl | bond | CONH | bond | 1,4-phenyl | CH2 | [M + 1]⁻ = 1675; Calcd. for C80H85Cl2F1N10O25•1.8HCl•10H2O C: 49.99%, H: 5.60%, N: 7.29%, Cl: 7.01%, F: 0.99% Found: C: 49.96%, H: 5.43%, N: 7.48%, Cl: 7.03%, F: 0.95% |
| 3-CF3-5-NH2-phenyl | bond | CONH | bond | 1,4-phenyl | CH2 | [M + 3]⁺ = 1742; [M + 1]⁻ = 1740; Calcd. for C81H86Cl2F3N11O25•2.7HCl•13.4H2O C: 46.74%, H: 5.59%, N: 7.40%, Cl: 8.01%, F: 2.74% Found: C: 46.72%, H: 5.31%, N: 7.54%, Cl: 7.91%. F: 2.51% |
| 3-CF3-5-N(CH3)2-phenyl | bond | CONH | bond | 1,4-phenyl | CH2 | [M + 1]⁻ = 1768; Calcd. for C83H90Cl2F3N11O25•2.8HCl•10.5H2O C: 48.37%, H: 5.57%, N: 7.48%, Cl: 8.26%, F: 2.77% Found: C: 48.20%, H: 5.47%, N: 7.78%, Cl: 8.22%, F: 2.59% |

TABLE 14

| R1 | | | | R2 | | Data |
|---|---|---|---|---|---|---|
| 4-Cl-phenyl | bond | CONH | bond | 1,4-phenyl | CH2 | [M + 1]⁻ = 1691; Calcd. for C80H85Cl3N10O25•1.6HCl•11.9H2O C: 48.88%, H: 5.66%, N: 7.13%, Cl: 8.30% Found: C: 48.82%, H: 5.39%, N: 7.22%, Cl: 8.22% |
| 3-OCF3-phenyl | bond | CONH | bond | 1,4-phenyl | CH2 | [M + 3]⁺ = 1743; [M + 1]⁻ = 1741; Calcd. for C81H85Cl2F3N10O26•2.6HCl•8.5H2O C: 48.88%, H: 5.30%, N: 7.04%, Cl: 8.19%, F: 2.86% Found: C: 49.89%, H: 5.28%, N: 7.44%, Cl: 6.78%, F: 2.73% |
| 4-OCF3-phenyl | bond | CONH | bond | 1,4-phenyl | CH2 | [M + 1]⁻ = 1741; Calcd. for C81H85Cl2F3N10O26•2HCl•10H2O C: 48.66%, H: 5.40%, N: 7.01%, Cl: 7.27%, F: 2.85% Found: C: 48.66%, H: 5.27%, N: 7.27%, Cl: 7.20%, F: 2.72% |

TABLE 14-continued

| Group 1 | | | | Group 2 | | Mass | Analysis |
|---|---|---|---|---|---|---|---|
| 3-Cl-phenyl | bond | CONH | bond | 1,4-phenyl | CH2 | [M+3]⁺ = 1693 [M+1]⁻ = 1691 | Calcd. for C80H85Cl3N10O25•1.2HCl•11.3H2O<br>C: 49.52%, H: 5.65%, N: 7.22%, Cl: 7.67%<br>Found: C: 49.49%, H: 5.53%, N: 7.41%, Cl: 7.72% |
| 4-Br-phenyl | bond | CONH | bond | 1,4-phenyl | CH2 | [M+1]⁻ = 1736 | Calcd. for C80H85Cl2Br1N10O25•1.6HCl•11.6H2O<br>C: 47.93%, H: 5.52%,<br>N: 6.99%, Cl: 6.37%, Br: 3.99%<br>Found: C: 47.93%, H: 5.37%,<br>N: 7.22%, Cl: 6.38%, Br: 3.89% |
| 4-Cl-3-NO2-phenyl | bond | CONH | bond | 1,4-phenyl | CH2 | [M+3]⁺ = 1738 [M+1]⁻ = 1736 | Calcd. for C80H84Cl3N11O27•2.7HCl•8.7H2O<br>C: 48.21%, H: 5.26%, N: 7.73%, Cl: 10.14%<br>Found: C: 48.15%, H: 5.21%, N: 7.97%, Cl: 10.14% |
| 3,5-diCl-phenyl | bond | CONH | bond | 1,4-phenyl | CH2 | [M+1]⁻ = 1725 | Calcd. for C80H84Cl4N10O25•1.9HCl•9H2O<br>C: 49.05%, H: 5.35%, N: 7.15%, Cl: 10.68%<br>Found: C: 49.02%, H: 5.26%, N: 7.30%, Cl: 10.68% |
| 3-CF3-5-F-phenyl | bond | CONH | bond | 1,4-phenyl | CH2 | [M+3]⁺ = 1745 [M+1]⁻ = 1743 | Calcd. for C81H84Cl2F4N10O25•2.1HCl•10.2H2O<br>C: 48.53%, H: 5.35%,<br>N: 6.99%, Cl: 7.25%, F: 3.79%<br>Found: C: 48.54%, H: 5.38%,<br>N: 7.12%, Cl: 7.18%, F: 3.57% |
| 4-SCF3-phenyl | bond | CONH | bond | 1,4-phenyl | CH2 | [M+1]⁻ = 1757 | Calcd. for C81H85Cl2F3N10O25S1•1.9HCl•11.9H2O<br>C: 47.64%, H: 5.46%, N: 6.86%,<br>Cl: 6.77%, F: 2.79%, S: 1.57%<br>Found: C: 47.62%, H: 5.41%, N: 6.96%,<br>Cl: 6.73%, F: 2.62%, S: 1.41% |
| 3-CF3-4-OMe-phenyl | bond | CONH | bond | 1,4-phenyl | CH2 | [M+3]⁺ = 1757 [M+1]⁻ = 1755 | Calcd. for C82H87Cl2F3N10O26•1.9HCl•11.1H2O<br>C: 48.62%, H: 5.53%,<br>N: 6.91%, Cl: 6.83%, F: 2.81%<br>Found: C: 48.63%, H: 5.40%,<br>N: 6.96%, Cl: 6.88%, F: 2.67% |

TABLE 15

| R^A | R^B | R^C | R^D |
|---|---|---|---|
| 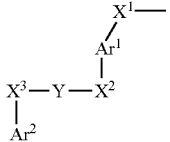 | OH | H | H |

| R^A | | | | | | | |
|---|---|---|---|---|---|---|---|
| Ar2 | X3 | Y | X2 | Ar1 | X1 | Mass | Elemetal Analysis |
| 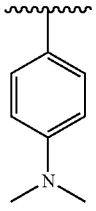 | bond | CONH | bond | 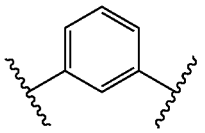 [SMILES: *c1cccc(*)c1] | CH2 | [M + 1]− = 1700 | Calcd. for C82H91Cl2N11O25•3HCl•15H2O C: 57.88%, H: 5.39%, N: 7.06%, Cl: 4.17% Found: C: 47.31%, H: 5.71%, N: 7.47%, Cl: 8.80% |
| 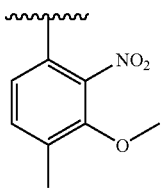 [SMILES: *c1ccc(C)c(OC)c1[N+](=O)[O-]] | bond | CONH | bond | 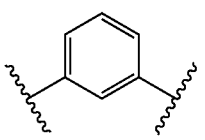 [SMILES: *c1cccc(*)c1] | CH2 | [M + 1]− = 1746 | Calcd. for C82H91Cl2N11O25•3HCl•12H2O C: 56.36%, H: 5.13%, N: 8.82%, Cl: 4.06% Found: C: 45.39%, H: 5.77%, N: 7.16%, Cl: 7.89% |
| 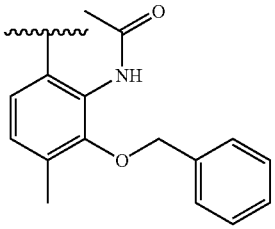 [SMILES: *c1ccc(C)c(OCc2ccccc2)c1NC(C)=O] | bond | CONH | bond | 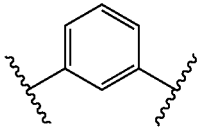 [SMILES: *c1cccc(*)c1] | CH2 | [M + 1]− = 1834 | Calcd. for C90H97Cl2N11O27•2HCl•14H2O C: 58.89%, H: 5.33%, N: 8.39%, Cl: 3.86% Found: C: 49.9%, H: 5.69%, N: 6.63%, Cl: 6.75% |
| 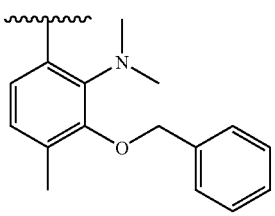 [SMILES: *c1ccc(C)c(OCc2ccccc2)c1N(C)C] | bond | CONH | bond | 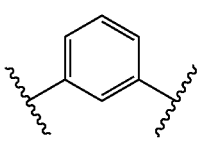 [SMILES: *c1cccc(*)c1] | CH2 | [M + 3]+ = 1822 | Calcd. for C90H99Cl2N11O26•3HCl•12H2O C: 59.34%, H: 5.48%, N: 8.46%, Cl: 3.89% Found: C: 50.64%, H: 5.67%, N: 7.23%, Cl: 7.91% |

TABLE 16

| | | | | | | | |
|---|---|---|---|---|---|---|---|
| 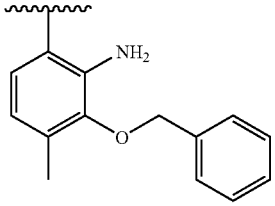 [SMILES: *c1ccc(C)c(OCc2ccccc2)c1N] | bond | CONH | bond | 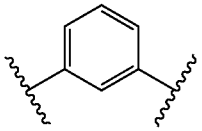 | CH2 | [M + 1]− = 1792 | Calcd. for C88H95Cl2N11O26•3HCl•11H2O C: 58.93%, H: 5.34%, N: 8.59%, Cl: 3.95% Found: C: 50.51%, H: 5.54%, N: 1.34%, Cl: 8.07% |
| 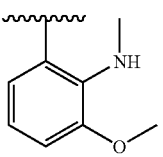 [SMILES: *c1cccc(OC)c1NC] | bond | CONH | bond | 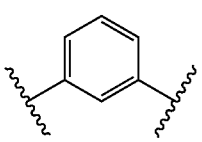 | CH2 | [M + 1]− = 1716 | Calcd. for C82H91Cl2N11O26•3HCl•11H2O C: 57.34%, H: 5.34%, N: 8.97%, Cl: 4.13% Found: C: 48.66%, H: 5.77%, N: 7.70%, Cl: 8.35% |

TABLE 16-continued

| | | | | | | |
|---|---|---|---|---|---|---|
| 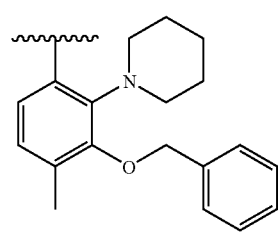 [SMILES: *c1ccc(C)c(OCc2ccccc2)c1N1CCCCC1] | bond | CONH | bond | 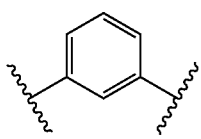 | CH2 | [M + 1]− = 1860 | Calcd. for C93H10Cl2N11O26•2.5HCl•10H2O C: 60.00%, H: 5.58%, N: 8.28%, Cl: 3.81% Found: 0: 52.46%, H: 5.75%, N: 7.44%, Cl: 7.19% |
| 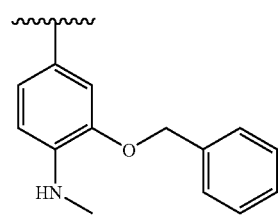 [SMILES: *c1ccc(NC)c(OCc2ccccc2)c1] | bond | CONH | bond | 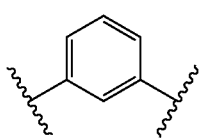 [SMILES: *c1cccc(*)c1] | CH2 | [M + 1]− = 1794 | Calcd. for C88H95Cl2N11O26•2.5HCl•9.5H2O C: 58.93%, H: 5.34%, N: 8.59%, Cl: 3.95% Found: C: 51.24%, H: 5.57%, N: 7.65%, Cl: 8.10% |
| 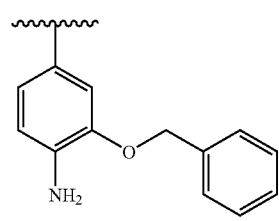 [SMILES: *c1ccc(N)c(OCc2ccccc2)c1] | bond | CONH | bond | 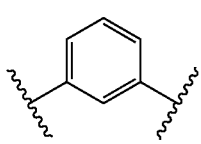 | CH2 | [M + 3]+ = 1780 [M + 1]− = 1778 | Calcd. for C87H93Cl2N11O26•1.5HCl•9H2O C: 58.72%, H: 5.27%, N: 8.66%, Cl: 3.98% Found: C: 52.14%, H: 5.48%, N: 7.9%, Cl: 6.55% |
| 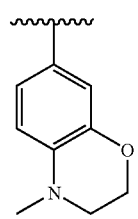 | bond | CONH | bond | 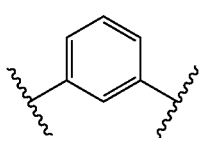 | CH2 | [M + 1]− = 1728 | Calcd. for C83H91Cl2N11O26•1.5HCl•10H2O C: 57.64%, H: 5.30%, N: 8.91%, Cl: 4.10% Found: C: 50.71%, H: 5.65%, N: 8.00%, Cl: 6.62% |
| 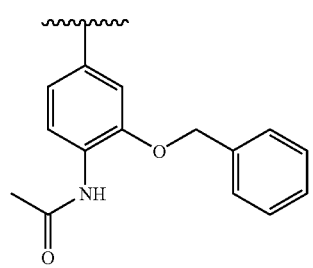 [SMILES: *c1ccc(NC(C)=O)c(OCc2ccccc2)c1] | bond | CONH | bond | 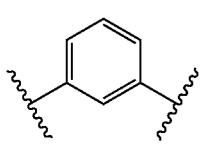 | CH2 | [M + 1]− = 1820 | Calcd. for C89H95Cl2N11O26•2HCl•10H2O C: 58.68%, H: 5.26%, N: 8.46%, Cl: 3.89% Found: C: 51.56%, H: 5.53%, N: 7.64%, Cl: 6.76% |

TABLE 17

| | | | | | | |
|---|---|---|---|---|---|---|
| 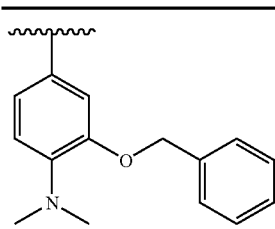 | bond | CONH | bond | 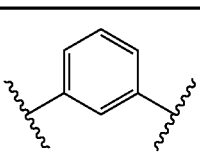 | CH2 | [M + 3]+ = 1808 [M + 1]− = 1806 | Calcd. for C89H97Cl2N11O26•2HCl•10H2O C: 59.13%, H: 5.41%, N: 8.52%, Cl: 3.92% Found: C: 51.96%, H: 5.64%, N: 7.56%, Cl: 7.00% |

TABLE 17-continued
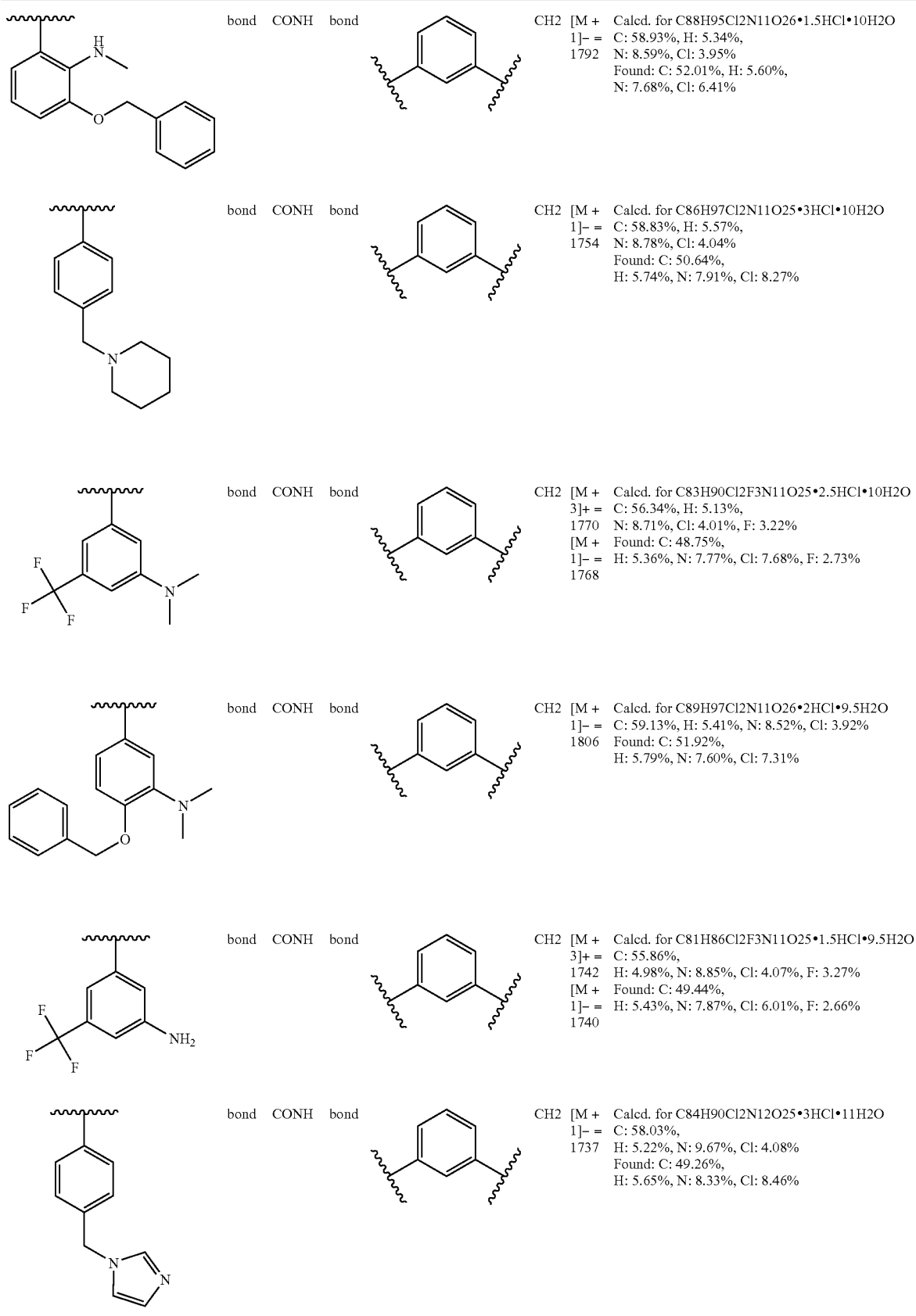

TABLE 18

| R^A | | | | Ar1 | X1 | Mass | Elemental Analysis |
|---|---|---|---|---|---|---|---|
| 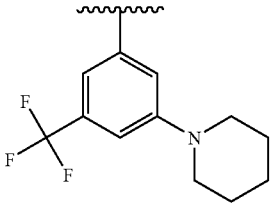 [SMILES: *c1cc(N2CCCCC2)cc(C(F)(F)F)c1] | bond | CONH | bond | 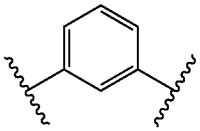 [SMILES: *c1cccc(*)c1] | CH2 | [M + 1]− = 1808 | Calcd. for C86H94Cl2F3N11O25•2.5HCl•11.5H2O<br>C: 57.08%, H: 5.24%,<br>N: 8.51%, Cl: 3.92%, F: 3.15%<br>Found: C: 48.83%, H: 5.54%,<br>N: 7.33%, Cl: 7.86%, F: 2.73% |
| 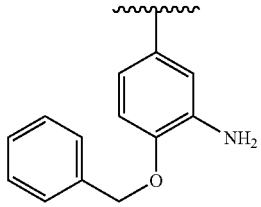 [SMILES: *c1ccc(OCc2ccccc2)c(N)c1] | bond | CONH | bond | 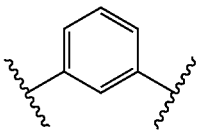 | CH2 | [M + 3]− = 1780 | Calcd. for C87H93Cl2N11O26•1.5HCl•10H2O<br>C: 58.72%,<br>H: 5.27%, N: 8.66%, Cl: 3.98%<br>Found: C: 51.85%,<br>H: 5.60%, N: 8.07%, Cl: 5.80% |

TABLE 19

| $R^A$ | $R^B$ | $R^C$ | $R^D$ |
|---|---|---|---|
| 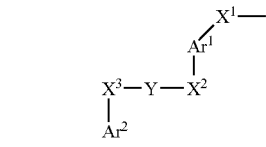 | OH | H | H |

| $R^A$ | | | | | | | |
|---|---|---|---|---|---|---|---|
| Ar2 | X3 | Y | X2 | Ar1 | X1 | Mass | Elemetal Analysis |
| 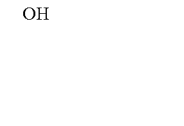 | bond | CONH | bond | 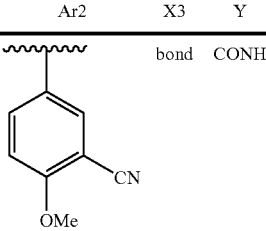 | CH2 | [M + 1]− = 1712 | Calcd. for C82H87Cl2N11O26•1.3HCl•8.7H2O<br>C: 51.36%, H: 5.56%, N: 8.03%, Cl: 6.10%<br>Found: C: 51.34%, H: 5.62%, N: 8.19%, Cl: 6.03% |
| 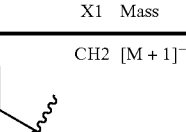 | bond | CONH | bond | 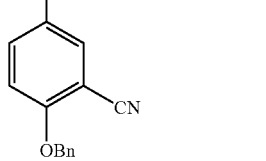 | CH2 | [M + 1]− = 1728 | Calcd. for C88H91Cl2N11O26•1.8HCl•8.9H2O<br>C: 52.44%, H: 5.53%, N: 7.64%, Cl: 6.68%<br>Found: C: 52.41%, H: 5.49%, N: 7.66%, Cl: 6.75% |
| 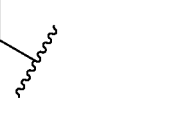 | bond | CONH | bond | 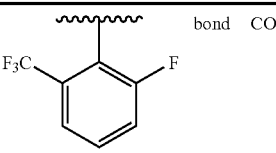 | CH2 | [M + 1]− = 1789 | Calcd. for C88H91Cl2N11O26•2.0HCl•9.5H2O<br>C: 51.97%, H: 5.55%, N: 7.58%, Cl: 6.97%<br>Found: C: 51.97%, H: 5.44%, N: 7.65%, Cl: 7.07% |

TABLE 20

| 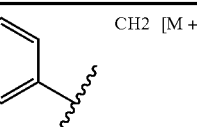 | bond | CONH | bond | 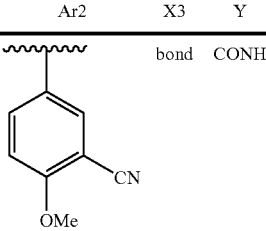 | CH2 | [M + 3]+ = 1745 | Calcd. for C81H84Cl2N10O25•1.5HCl•9.2H2O<br>C: 49.51%, H: 5.33%, N: 7.13%, Cl: 6.32%,<br>F: 3.87%<br>Found: C: 49.50%, H: 5.28%, N: 7.39%,<br>Cl: 6.37%, F: 3.93% |

TABLE 20-continued

| Structure | | | | Structure | | MS | Analysis |
|---|---|---|---|---|---|---|---|
| 2-HO, 6-F phenyl | bond | CONH | bond | 1,3-phenylene | CH2 | [M + 3]⁺ = 1694<br>[M + 1]⁻ = 1692 | Calcd. for C80H85Cl2N10O26•1.3HCl•11.2H2O<br>C: 49.49%, H: 5.64%, N: 7.21%, Cl: 6.03%,<br>F: 0.98%<br>Found: C: 49.48%, H: 5.43%, N: 7.27%,<br>Cl: 5.90%, F: 0.91% |
| 2-CF3 pyridin-5-yl | bond | CONH | bond | 1,3-phenylene | CH2 | [M + 1]⁻ = 1727 | Calcd. for<br>C80H84Cl2F3N11O25•1.5HCl•10.2H2O<br>C: 48.88%, H: 5.43%, N: 7.84%,<br>Cl: 6.31%, F: 2.90<br>Found: C: 48.90%, H: 5.42%, N: 7.94%,<br>Cl: 6.18%, F: 2.76 |
| 2-Br, 6-F phenyl | bond | CONH | bond | 1,3-phenylene | CH2 | [M + 1]⁻ = 1754 | Calcd. for<br>C80H84BrCl2FN10O25•1.8HCl•9.4H2O<br>C: 48.28%, H: 5.30%, N: 7.04%,<br>Br: 4.01, Cl: 6.77%, F: 0.95<br>Found: C: 48.26%, H: 5.29%, N: 7.07%,<br>Br: 3.63, Cl: 6.75%, F: 0.90 |
| 5-butyl pyridin-2-yl | bond | CONH | bond | 1,3-phenylene | CH2 | [M + 3]⁺ = 1716<br>[M + 1]⁻ = 1714 | Calcd. for C83H93Cl2N11O25•2.0HCl•9.5H2O<br>C: 50.87%, H: 5.86%, N: 7.86%, Cl: 7.24%<br>Found: C: 50.86%, H: 5.73%,<br>N: 8.02%, Cl: 7.28% |

TABLE 21

| Structure | | | | Structure | | MS | Analysis |
|---|---|---|---|---|---|---|---|
| 2-F, 4-NO2 phenyl | bond | CONH | bond | 1,3-phenylene | CH2 | [M + 1]⁻ = 1720 | Calcd. for<br>C80H84Cl2FN11O27•1.6HCl•10.2H2O<br>C: 48.93%, H: 5.44%, N: 7.85%,<br>Cl: 6.50%, F: 0.97<br>Found: C: 48.90%, H: 5.28%,<br>N: 8.11%, Cl: 6.46%,<br>F: 0.86 |
| 2-(OCH2CF3), 4-MeO phenyl | bond | CONH | bond | 1,3-phenylene | CH2 | [M + 1]⁻ = 1786 | Calcd. for<br>C83H89Cl2F3N10O27•2.0HCl•9.0H2O<br>C: 49.31%, H: 5.43%, N: 6.93%,<br>Cl: 7.01%, F: 2.82<br>Found: C: 49.30%, H: 5.31%,<br>N: 7.05%, Cl: 7.04%, F: 2.73 |
| 4-Cl, 3-(2,5-dimethylpyrrol-1-yl) phenyl | bond | CONH | bond | 1,3-phenylene | CH2 | [M + 1]⁻ = 1785 | Calcd. for<br>C88H92Cl3N11O25•1.9HCl•10.0H2O<br>C: 50.75%, H: 5.64%, N: 7.57%,<br>Cl: 8.53%<br>Found: C: 50.70%, H: 5.43%,<br>N: 7.82%, Cl: 8.50% |
| 3-propoxy pyridin-2-yl | bond | CONH | bond | 1,3-phenylene | CH2 | [M + 3]⁺ = 1718 | Calcd. for<br>C82H91Cl2N11O26•1.4HCl•10.6H2O<br>C: 50.26%, H: 5.84%, N: 7.86%,<br>Cl: 6.15%<br>Found: C: 50.27%, H: 5.61%,<br>N: 7.89%, Cl: 6.20% |

TABLE 21-continued

| | | | | | | | |
|---|---|---|---|---|---|---|---|
| 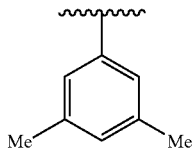 [SMILES: *c1cc(C)cc(C)c1] | bond | CONH | bond | 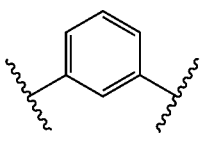 [SMILES: *c1cccc(*)c1] | CH2 | [M + 3]⁺ = 1687<br>[M + 1]⁻ = 1685 | Calcd. for<br>C82H90Cl2N10O25•1.5HCl•10.9H2O<br>C: 50.83%, H: 5.89%, N: 7.23%,<br>Cl: 6.40%<br>Found: C: 50.77%, H: 5.69%,<br>N: 7.46%, Cl: 6.33% |

TABLE 22

| | | | | | | | |
|---|---|---|---|---|---|---|---|
| 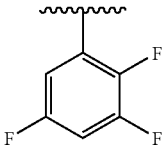 [SMILES: *c1cc(F)cc(F)c1F] | bond | CONH | bond | 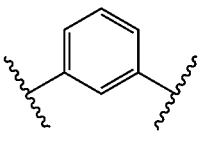 | CH2 | [M + 1]⁻ = 1711 | Calcd. for<br>C80H83Cl2F3N10O25•1.6HCl•10.2H2O<br>C: 49.16%, H: 5.41%, N: 7.17%, Cl: 6.53%,<br>F: 2.92<br>Found: C: 49.18%, H: 5.36%, N: 7.27%,<br>Cl: 6.48%, F: 2.82 |
| 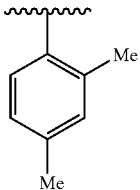 [SMILES: *c1ccc(C)cc1C] | bond | CONH | bond | 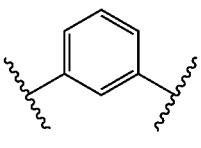 [SMILES: *c1cccc(*)c1] | CH2 | [M + 3]⁺ = 1687<br>[M + 1]⁻ = 1685 | Calcd. for<br>C82H90Cl2N10O25•1.5HCl•10.2H2O<br>C: 51.16%, H: 5.86%, N: 7.28%, Cl: 6.45%<br>Found: C: 51.17%, H: 5.80%, N: 7.71%,<br>Cl: 6.37% |
| 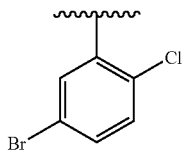 [SMILES: *c1cc(Br)ccc1Cl] | bond | CONH | bond | 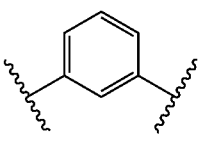 | CH2 | [M + 3]⁺ = 1772<br>[M + 1]⁻ = 1770 | Calcd. for<br>C80H84BrCl3N10O25•1.6HCl•10.3H2O<br>C: 47.67%, H: 5.31%, N: 6.95%, Cl: 8.09%, Br:<br>3.96%<br>Found: C: 47.59%, H: 5.24%, N: 7.20%,<br>Cl: 8.15%, Br 3.84% |
| 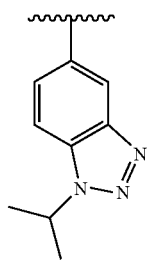 | bond | CONH | bond | 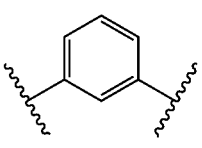 | CH2 | [M + 3]⁺ = 1742<br>[M + 1]⁻ = 1740 | Calcd. for<br>C83H91Cl2N13O25•1.2HCl•11.3H2O<br>C: 50.12%, H: 5.82%, N: 9.16%, Cl: 5.70%<br>Found: C: 50.07%, H: 5.67%, N: 9.29%,<br>Cl: 5.70% |
| 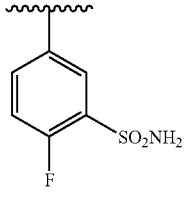 [SMILES: *c1ccc(F)c(S(N)(=O)=O)c1] | bond | CONH | bond | 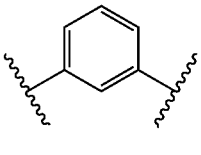 [SMILES: *c1cccc(*)c1] | CH2 | [M + 1]⁻ = 1754 | Calcd. for<br>C80H86Cl2FN11O27S•2.0HCl•10.6H2O<br>C: 47.58%, H: 5.45%, N: 7.63%, Cl: 7.02%, F:<br>0.94%, S: 1.59%<br>Found: C: 47.53%, H: 5.30%, N: 7.73%,<br>Cl: 6.99%, F: 0.91%, S: 1.62% |

TABLE 23

| | | | | | | | |
|---|---|---|---|---|---|---|---|
| 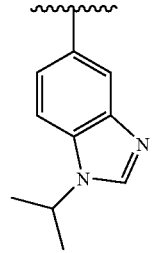 [SMILES: *c1ccc2c(c1)ncn2C(C)C] | bond | CONH | bond | 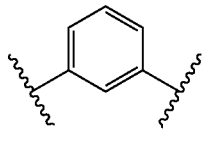 [SMILES: *c1cccc(*)c1] | CH2 | [M + 3]⁺ = 1742<br>[M + 1]⁻ = 1740 | Calcd. for<br>C84H92Cl2N12O25•1.7HCl•10.9H2O<br>C: 50.47%, H: 5.82%, N: 8.41%, Cl: 6.56%<br>Found: C: 50.30%, H: 5.63%, N: 9.22%,<br>Cl: 6.61% |

TABLE 23-continued

| Ar2 | X3 | Y | X2 | Ar1 | X1 | Mass | Elemental Analysis |
|---|---|---|---|---|---|---|---|
| 3,4-difluorophenyl | bond | CONH | bond | 1,3-phenylene | CH2 | [M + 3]$^+$ = 1695<br>[M + 1]$^-$ = 1693 | Calcd. for<br>C80H84Cl2F2N10O25•1.7HCl•10.7H2O<br>C: 49.29%, H: 5.54%, N: 7.19%,<br>Cl: 6.73%, F: 1.95%<br>Found: C: 49.30%, H: 5.42%, N: 7.33%,<br>Cl: 6.67%, F: 1.92% |
| 2,3-difluoro-4-methylphenyl | bond | CONH | bond | 1,3-phenylene | CH2 | [M + 3]$^+$ = 1709<br>[M + 1]$^-$ = 1707 | Calcd. for<br>C81H86Cl2F2N10O25•2.0HCl•8.9H2O<br>C: 50.10%, H: 5.49%, N: 7.21%,<br>Cl: 7.30%, F: 1.96%<br>Found: C: 50.10%, H: 5.53%, N: 7.29%,<br>Cl: 7.21%, F: 1.86% |
| pyridin-2-yl | bond | CONH | bond | 1,3-phenylene | CH2 | [M + 1]$^-$ = 1784 | Calcd. for<br>C84H89Cl2N13O27•2.2HCl•8.3H2O<br>C: 50.11%, H: 5.40%, N: 9.04%, Cl: 7.40%<br>Found: C: 50.09%, H: 5.36%, N: 9.22%,<br>Cl: 7.43% |
| 4-((4-nitro-1H-pyrazol-1-yl)methyl)phenyl | bond | CONH | bond | 1,3-phenylene | CH2 | [M + 3]$^+$ = 1660 | Calcd. for<br>C79H85Cl2N11O25•2.1HCl•10.0H2O<br>C: 49.52%, H: 5.63%, N: 8.04%, Cl: 7.59%<br>Found: C: 49.48%, H: 5.43%, N: 8.10%,<br>Cl: 7.58% |

TABLE 24

| $R^A$ | $R^B$ | $R^C$ | $R^D$ |
|---|---|---|---|
| $\begin{array}{c} X^3-Y-X^2 \\ | \\ Ar^2 \end{array} \begin{array}{c} Ar^1-X^1- \\ \end{array}$ | OH | H | H |

$R^A$

| Ar2 | X3 | Y | X2 | Ar1 | X1 | Mass | Elemental Analysis |
|---|---|---|---|---|---|---|---|
| 3-(benzyloxy)-4-methylphenyl | bond | CONH | bond | 1,3-phenylene | CH2CH2 | [M + 3]+ = 1794<br>[M + 1]− = 1792 | Calcd. for<br>C89H96Cl2N10O26•2.5HCl•<br>10.0H2O<br>C: 51.79%, H: 5.79%, N: 6.79%,<br>Cl: 7.73%<br>Found: C: 51.74%, H: 5.73%,<br>N: 6.91%, Cl: 7.76% |

TABLE 24-continued

| | | | | | | | |
|---|---|---|---|---|---|---|---|
| 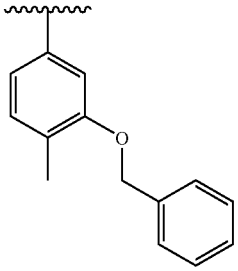 [SMILES: *c1ccc(C)c(OCc2ccccc2)c1] | bond | CONH | bond | 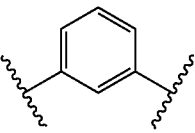 [SMILES: *c1cccc(*)c1] | CH2CH2 CH2 | [M + 3]+ = 1808 [M + 1]− = 1806 | Calcd. for C90H98Cl2N10O26•2.3HCl•9.3H2O C: 52.52%, H: 5.82%, N: 6.81%, Cl: 7.41% Found: C: 52.49%, H: 5.64%, N: 6.84%, Cl: 7.34% |
| 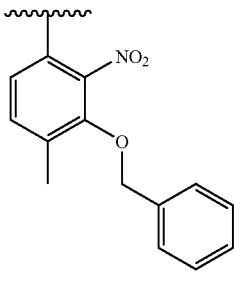 [SMILES: *c1ccc(C)c(OCc2ccccc2)c1[N+](=O)[O-]] | bond | CONH | bond | 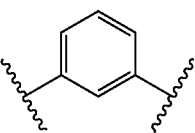 [SMILES: *c1cccc(*)c1] | CH2CH2 CH2 | [M + 3]+ = 1853 [M + 1]− = 1851 | Calcd. for C90H97Cl2N11O28•1.9HCl•9.6H2O C: 51.62%, H: 5.68%, N: 7.36%, Cl: 6.60% Found: C: 51.59%, H: 5.47%, N: 7.43%, Cl: 6.52% |
| 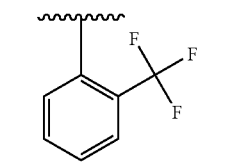 [SMILES: *c1ccccc1C(F)(F)F] | bond | CONH | bond | 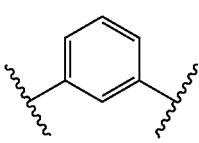 [SMILES: *c1cccc(*)c1] | CH2 | [M + 3]+ = 1727 [M + 1]− = 1725 | Calcd. for C81H85Cl2F3N10O25•1.7HCl• 10.4H2O C: 49.24%, H: 5.48%, N: 7.09%, Cl: 6.64%, F: 2.88% Found: C: 49.21%, H: 5.34%, N: 7.22%, Cl: 6.55%, F: 2.88% |

TABLE 25

| | | | | | | | |
|---|---|---|---|---|---|---|---|
| 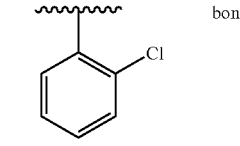 | bond | CONH | bond | 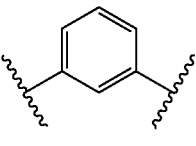 [SMILES: *c1cccc(*)c1] | CH2 | [M + 3]+ = 1693 [M + 1]− = 1691 | Calcd. for C80H85Cl3N10O25•1.9HCl•9.3H2O C: 49.79%, H: 5.51%, N: 7.26%, Cl: 9.00% Found: C: 49.77%, H: 5.35%, N: 7.21%, Cl: 9.00% |
| 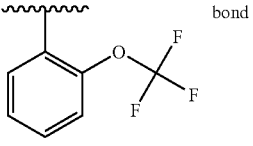 | bond | CONH | bond | 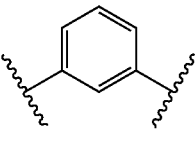 [SMILES: *c1cccc(*)c1] | CH2 | [M + 3]+ = 1743 [M + 1]− = 1741 | Calcd. for C81H85Cl2F3N10O26•1.8HCl•9.8H2O C: 49.02%, H: 5.40%, N: 7.06%, Cl: 6.79%, F: 2.87% Found: C: 49.03%, H: 5.33%, N: 7.24%, Cl: 6.87%, F: 2.79% |
| 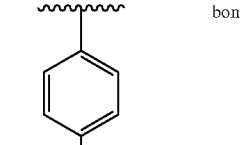 | bond | CONH | bond | 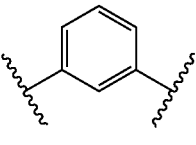 [SMILES: *c1cccc(*)c1] | CH2 | [M + 3]+ = 1743 [M + 1]− = 1741 | Calcd. for C81H85Cl2F3N10O26•1.7HCl•10.0H2O C: 49.02%, H: 5.42%, N: 7.06%, Cl: 6.61%, F: 2.87% Found: C: 48.98%, H: 5.18%, N: 7.21%, Cl: 6.61%, F: 2.78% |
| 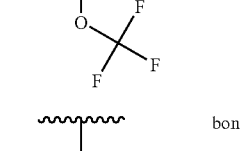 | bond | CONH | bond | 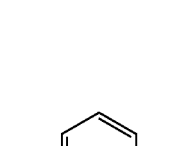 | CH2 | [M + 3]+ = 1761 [M + 1]− = 1759 | Calcd. for C81H84Cl3F3N10O25•1.3HCl•9.7H2O C: 49.06%, H: 5.32%, N: 7.06%, Cl: 7.69%, F: 2.87% Found: C: 48.99%, H: 5.13%, N: 7.32%, Cl: 7.72%, F: 2.77% |

TABLE 25-continued

| Structure | | | | Structure | | MS | Analysis |
|---|---|---|---|---|---|---|---|
| 2-bromophenyl | bond | CONH | bond | m-phenylene | CH2 | [M + 1]− = 1735 | Calcd. for C80H85BrCl2N10O25•1.8HCl•10.4H2O<br>C: 48.27%, H: 5.45%, N: 7.04%, Br: 4.01%, Cl: 6.77%<br>Found: C: 48.56%, H: 5.22%, N: 7.16%, Br: 3.71%, Cl: 6.83% |
| 3,5-dichlorophenyl | bond | CONH | bond | m-phenylene | CH2 | [M + 1]− = 1725 | Calcd. for C80H84Cl4N10O25•1.7HCl•9.7H2O<br>C: 48.92%, H: 5.39%, N: 7.13%, Cl: 10.29%<br>Found: C: 48.92%, H: 5.23%, N: 7.18%, Cl: 10.30% |
| 4-bromophenyl | bond | CONH | bond | m-phenylene | CH2 | [M + 1]− = 1736 | Calcd for C80H85BrCl2N10O25•1.9HCl•9.4H2O<br>C: 48.63%, H: 5.39%, N: 7.09%, Br: 4.04%, Cl: 7.00%<br>Found: C: 48.58%, H: 5.24%, N: 7.18%, Br: 3.91%, Cl: 7.01% |
| benzo[1,3]dioxol-5-yl | bond | CONH | bond | m-phenylene | CH2 | [M + 1]− = 1702 | Calcd. for C81H86Cl2N10O27•1.2HCl•9.9H2O<br>C: 50.55%, H: 5.60%, N: 7.28%, Cl: 5.89%<br>Found: C: 50.55%, H: 5.49%, N: 7.42%, Cl: 5.94% |

TABLE 26

| Structure | | | | Structure | | MS | Analysis |
|---|---|---|---|---|---|---|---|
| 4-methoxyphenyl | bond | CONH | bond | m-phenylene | CH2 | [M + 3]+ = 1689<br>[M + 1]− = 1687 | Calcd for C81H88Cl2N10O26•1.2HCl•10.4H2O<br>C: 50.68%, H: 5.78%, N: 7.30%, Cl: 5.91%<br>Found: C: 50.67%, H: 5.63%, N: 7.32% Cl: 5.84% |
| 4-ethoxyphenyl | bond | CONH | bond | m-phenylene | CH2 | [M + 3]+ = 1703<br>[M + 1]− = 1701 | Calcd. for C82H90Cl2N10O26•1.7HCl•8.1H2O<br>C: 51.55%, H: 5.69%, N: 7.33%, Cl: 6.87%<br>Found: C: 51.55%, H: 5.71%, N: 7.42%, Cl: 6.92% |
| 3-(trifluoromethoxy)phenyl | bond | CONH | bond | m-phenylene | CH2 | [M + 1]− = 1742 | Calcd. for C81H85Cl2F3N10O26•2.0HCl•10.8H2O<br>C: 48.40%, H: 5.45%, N: 6.97%, Cl: 7.06%, F: 2.84%<br>Found: C: 48.38%, H: 5.28%, N: 7.17%, Cl: 7.05%, F: 2.70% |

TABLE 26-continued

| Ar1 | L1 | L2 | L3 | Ar2 | L4 | MS | Analysis |
|---|---|---|---|---|---|---|---|
| 4-F-3-Me-phenyl | bond | CONH | bond | 1,3-phenylene | CH2 | [M + 3]+ = 1691<br>[M + 1]− = 1689 | Calcd. for C81H87Cl2FN10O25•1.2HCl•10.5H2O<br>C: 50.58%, H: 5.72%, N: 7.28%, Cl: 5.90%,<br>F: 0.99%<br>Found: C: 50.54%, H: 5.58%, N: 7.37%, Cl: 5.89%,<br>F: 0.95% |
| 3-Br-phenyl | bond | CONH | bond | 1,3-phenylene | CH2 | [M + 1]− = 1736 | Calcd. for C80H85BrCl2N10O25•1.9HCl•10.2H2O<br>C: 48.27%, H: 5.43%, N: 7.04%, Br: 4.01%,<br>Cl: 6.95%<br>Found: C: 48.27%, H: 5.25%, N: 7.07%, Br: 3.85%,<br>Cl: 6.98% |
| 2,4-diF-phenyl | bond | CONH | bond | 1,3-phenylene | CH2 | [M + 1]− = 1694 | Calcd. for C80H84Cl2F2N10O25•1.6HCl•10.1H2O<br>C: 49.66%, H: 5.51%, N: 7.24%, Cl: 6.60%,<br>F: 1.96%<br>Found: C: 49.59%, H: 5.50%, N: 7.37%, Cl: 6.65%,<br>F: 1.88% |
| 3,4-diMe-phenyl | bond | CONH | bond | 1,3-phenylene | CH2 | [M + 3]+ = 1687<br>[M + 1]− = 1685 | Calcd. for C82H90Cl2N10O25•1.2HCl•11.1H2O<br>C: 51.02%, H: 5.92%, N: 7.26%, Cl: 5.88%<br>Found: C: 50.99%, H: 5.74%, N: 7.53%, Cl: 5.95% |
| 2-Cl-6-Me-pyridin-4-yl | bond | CONH | bond | 1,3-phenylene | CH2 | [M + 1]− = 1707 | Calcd. for C80H86Cl3N11O25•1.8HCl•10.6H2O<br>C: 48.91%, H: 5.59%, N: 7.84%, Cl: 8.66%<br>Found: C: 48.87%, H: 5.40%, N: 7.95%, Cl: 8.62% |

TABLE 27

| Ar1 | L1 | L2 | L3 | Ar2 | L4 | MS | Analysis |
|---|---|---|---|---|---|---|---|
| 4-F-3-CF3-phenyl | bond | CONH | bond | 1,3-phenylene | CH2 | [M + 3]+ = 1745<br>[M + 1]− = 1743 | Calcd. for<br>C81H84Cl2F4N10O25•1.7HCl•9.3H2O<br>C: 49.28%, H: 5.33%, N: 7.10%,<br>Cl: 6.65%, F: 3.85%<br>Found: C: 49.24%, H: 5.24%, N: 7.31%,<br>Cl: 6.66%, F: 3.63% |
| 2-Cl-6-F-phenyl | bond | CONH | bond | 1,3-phenylene | CH2 | [M + 1]− = 1709 | Calcd. for<br>C80H84Cl3FN10O25•1.9HCl•8.3H2O<br>C: 49.79%, H: 5.35%, N: 7.26%,<br>Cl: 9.00%, F: 0.98%<br>Found: C: 49.78%, H: 5.27%, N: 7.22%,<br>Cl: 8.93%, F: 0.89% |
| 3-Cl-4-F-phenyl | bond | CONH | bond | 1,3-phenylene | CH2 | [M + 1]− = 1709 | Calcd. for<br>C80H84Cl3FN10O25•1.2HCl•8.9H2O<br>C: 50.17%, H: 5.42%, N: 7.31%,<br>Cl: 7.78%, F: 0.99%<br>Found: C: 50.14%, H: 5.31%, N: 7.49%,<br>Cl: 7.81%, F: 0.87% |

TABLE 27-continued

| Structure | | | | | | |
|---|---|---|---|---|---|---|
| 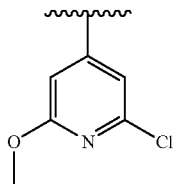 [SMILES: *c1cc(Cl)nc(OC)c1] | bond CONH bond | 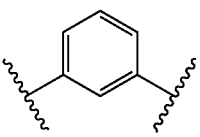 [SMILES: *c1cccc(*)c1] | CH2 | [M + 3]+ = 1724<br>[M + 1]– = 1722 | Calcd. for<br>C80H86Cl3N11O26•1.2HCl•9.1H2O<br>C: 49.74%, H: 5.50%, N: 7.98%,<br>Cl: 7.71%<br>Found: C: 49.72%, H: 5.49%,<br>N: 8.04%, Cl: 7.69% |
| 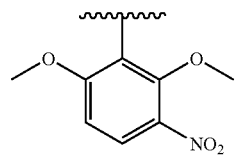 | bond CONH bond | 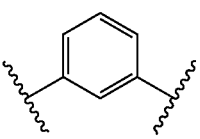 [SMILES: *c1cccc(*)c1] | CH2 | [M + 1]– = 1763 | Calcd. for<br>C82H89Cl2N11O29•1.8HCl•3.3H2O<br>C: 52.15%, H: 5.20%, N: 8.16%,<br>Cl: 7.13%<br>Found: C: 52.14%, H: 5.84%, N: 8.29%,<br>Cl: 7.12% |
| 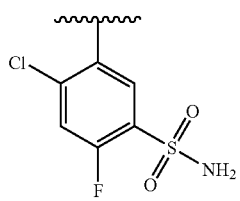 [SMILES: *c1cc(S(N)(=O)=O)c(F)cc1Cl] | bond CONH bond | 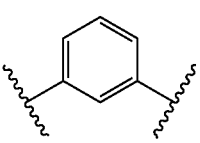 [SMILES: *c1cccc(*)c1] | CH2 | [M + 1]– = 1788 | Calcd. for<br>C80H85Cl3FN11O27S•1.6HCl•10.9H2O<br>C: 46.99%, H: 5.34%, N: 7.54%,<br>Cl: 7.98%, F: 0.93%, S: 1.57%<br>Found: C: 46.99%, H: 5.22%, N: 7.64%,<br>Cl: 8.00%, F: 0.81%, S: 1.41% |
| 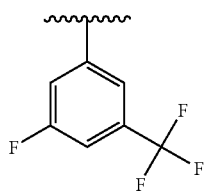 [SMILES: *c1cc(F)cc(C(F)(F)F)c1] | bond CONH bond | 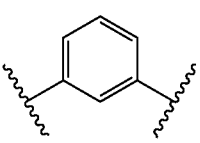 [SMILES: *c1cccc(*)c1] | CH2 | [M + 1]– = 1743 | Calcd. for<br>C81H84Cl2F4N10O25•1.6HCl•7.7H2O<br>C: 50.11%, H: 5.24%, N: 7.21%,<br>Cl: 6.57%, F: 3.91%<br>Found: C: 50.11%, H: 5.27%, N: 7.30%,<br>Cl: 6.62%, F: 3.79% |
| 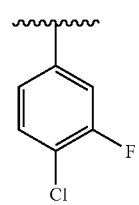 [SMILES: *c1ccc(Cl)c(F)c1] | bond CONH bond | 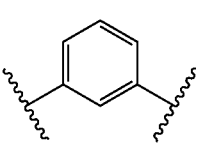 [SMILES: *c1cccc(*)c1] | CH2 | [M + 3]+ = 1711<br>[M + 1]– = 1709 | Calcd. for<br>C80H84Cl3FN10O25•1.3HCl•9.4H2O<br>C: 49.85%, H: 5.44%, N: 7.27%,<br>Cl: 7.91%, F: 0.99%<br>Found: C: 49.74%, H: 5.15%, N: 7.50%,<br>Cl: 7.79%, F: 1.03% |

TABLE 28

| Structure | | | | | | |
|---|---|---|---|---|---|---|
| 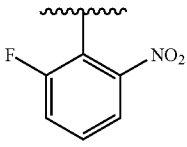 | bond CONH bond | 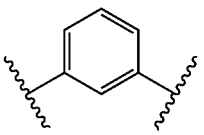 | CH2 | [M + 3]+ = 1722<br>[M + 1]– = 1720 | Calcd. for<br>C80H84Cl2FN11O27•1.4HCl•11.0H2O<br>C: 48.76%, H: 5.49%, N: 7.82%, Cl: 6.12%,<br>F: 0.96%<br>Found: C: 48.63%, H: 4.82%, N: 7.99%,<br>Cl: 6.14%, F: 0.90% |
| 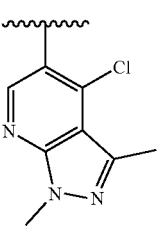 [SMILES: *c1cnc2c(c(C)nn2C)c1Cl] | bond CONH bond | 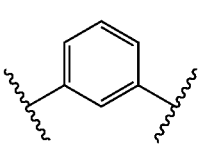 [SMILES: *c1cccc(*)c1] | CH2 | [M + 1]– = 1761 | Calcd. for<br>C82H88Cl3N13O25•1.2HCl•9.0H2O<br>C: 50.05%, H: 5.49%, N: 9.25%,<br>Cl: 7.57%<br>Found: C: 50.14%, H: 5.52%, N: 8.72%,<br>Cl: 7.60% |

TABLE 28-continued

| Structure | | | | | | |
|---|---|---|---|---|---|---|
| 2-Cl, 4-Br phenyl | bond | CONH | bond | 1,3-phenylene | CH2 | [M + 1]− = 1769 — Calcd. for C80H84BrCl3N10O25•1.3HCl•10.3H2O C: 47.93%, H: 5.32%, N: 6.99%, Br: 3.99%, Cl: 7.60% Found: C: 47.84%, H: 5.13%, N: 7.10%, Br: 4.06%, Cl: 7.50% |
| 3-Cl, 4-OCF3 phenyl | bond | CONH | bond | 1,3-phenylene | CH2 | [M + 1]− = 1775 — Calcd. for C81H84Cl3F3N10O26•2.0HCl•8.7H2O C: 48.48%, H: 5.19%, N: 6.98%, Cl: 8.83%, F: 2.84% Found: C: 48.49%, H: 5.03%, N: 6.94%, Cl: 8.74%, F: 2.69% |
| 2-Cl, 4-SO2Me phenyl | bond | CONH | bond | 1,3-phenylene | CH2 | [M + 1]− = 1770 — Calcd. for C81H87Cl3N10O27S•2.1HCl•11.8H2O C: 47.22%, H: 5.51%, N: 6.80%, Cl: 8.78%, S: 1.56% Found: C: 47.23%, H: 5.29%, N: 6.89%, Cl: 8.75%, S: 1.49% |
| 3-OH, 4-F phenyl | bond | CONH | bond | 1,3-phenylene | CH2 | [M + 3]+ = 1694 [M + 1]− = 1692 — Calcd. for C80H85Cl2FN10O26•1.7HCl•9.1H2O C: 50.09%, H: 5.51%, N: 7.30%, Cl: 6.84%, F: 0.99% Found: C: 50.07%, H: 5.27%, N: 7.31%, Cl: 6.89%, F: 1.05% |
| 2-Cl pyridin-3-yl | bond | CONH | bond | 1,3-phenylene | CH2 | [M + 3]+ = 1694 [M + 1]− = 1692 — Calcd. for C79H84Cl3N11O25•1.6HCl•11.0H2O C: 48.65%, H: 5.56%, N: 7.90%, Cl: 8.36% Found: C: 48.61%, H: 5.53%, N: 8.07%, Cl: 8.39% |
| 5-CO2Me pyridin-2-yl | bond | CONH | bond | 1,3-phenylene | CH2 | [M + 1]− = 1717 — Calcd. for C81H87Cl2N11O27•1.1HCl•1.2H2O C: 49.65%, H: 5.68%, N: 7.86%, Cl: 5.61% Found: C: 49.64%, H: 5.50%, N: 7.98%, Cl: 5.66% |

TABLE 29

| Structure | | | | | | |
|---|---|---|---|---|---|---|
| 2,6-dimethoxypyridin-3-yl | bond | CONH | bond | 1,3-phenylene | CH2 | [M + 1]− = 1719 — Calcd. for C81H89Cl2N11O27•1.3HCl•10.6H2O C: 49.69%, H: 5.74%, N: 7.87%, Cl: 5.98% Found: C: 49.62%, H: 5.50%, N: 8.10%, Cl: 5.89% |

TABLE 29-continued

| Structure | | | | | MS | Analysis |
|---|---|---|---|---|---|---|
| 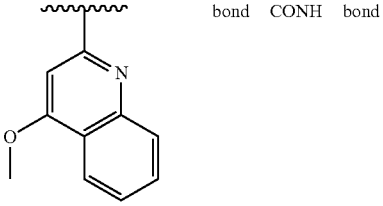 | bond | CONH | bond | 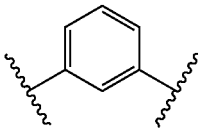 [SMILES: *c1cccc(*)c1] CH2 | [M + 3]+ = 1740<br>[M + 1]− = 1738 | Calcd. for<br>C84H89Cl2N11O26•2.3HCl•10.5H2O<br>C: 50.13%, H: 5.62%, N: 7.66%,<br>Cl: 7.57%<br>Found: C: 50.13%, H: 5.49%, N: 7.70%,<br>Cl: 7.57% |
| 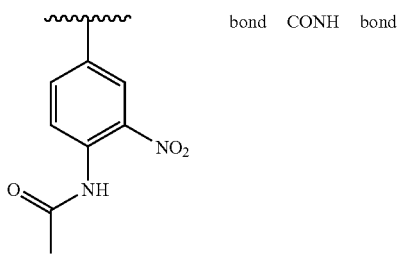 | bond | CONH | bond | 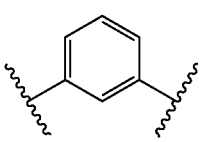 [SMILES: *c1cccc(*)c1] CH2 | [M + 1]− = 1760 | Calcd. for<br>C82H88Cl2N12O28•1.4HCl•11.1H2O<br>C: 48.96%, H: 5.59%, N: 8.36%,<br>Cl: 5.99%<br>Found: C: 48.91%, H: 5.46%, N: 8.48%,<br>Cl: 6.02% |
| 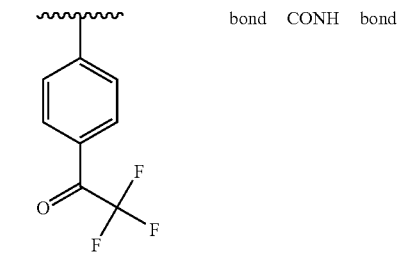 | bond | CONH | bond | 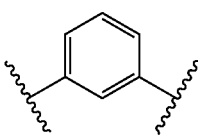 [SMILES: *c1cccc(*)c1] CH2 | [M + 1]− = 1754 | Calcd. for<br>C82H85Cl2F3N10O26•1.3HCl•10.8H2O<br>C: 49.33%, H: 5.45%, N: 7.02%,<br>Cl: 5.86%, F: 2.85%<br>Found: C: 49.27%, H: 5.50%, N: 7.20%,<br>Cl: 5.94%, F: 2.71% |
| 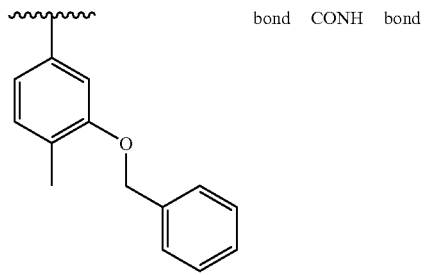 | bond | CONH | bond | 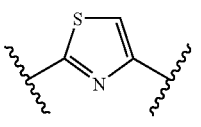 [SMILES: *c1csc(*)n1] CH2 | [M + 3]+ = 1787<br>[M + 1]− = 1785 | Calcd. for<br>C85H91Cl2N11O26S•1.8HCl•9.3H2O<br>C: 50.57%, H: 5.56%, N: 7.63%,<br>Cl: 6.67%, S: 1.59%<br>Found: C: 50.65%, H: 5.51%, N: 7.29%,<br>Cl: 6.65%, S: 1.61% |
| 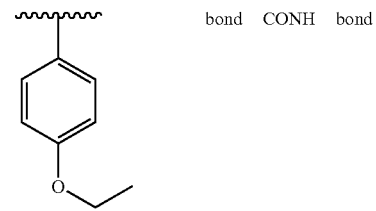 | bond | CONH | bond | 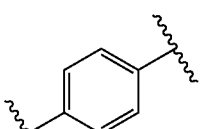 CH2 | [M + 1]− = 1702 | Calcd. for<br>C82H90Cl2N10O26•1.5HCl•9.9H2O<br>C: 50.88%, H: 5.80%, N: 7.24%,<br>Cl: 6.41%<br>Found: C: 50.86%, H: 5.80%,<br>N: 7.46%, Cl: 6.48% |
| 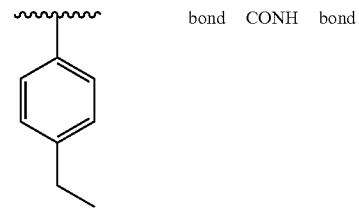 | bond | CONH | bond | 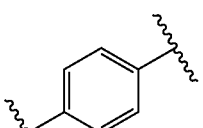 CH2 | [M + 3]+ = 1687<br>[M + 1]− = 1685 | Calcd. for<br>C82H90Cl2N10O25•1.9HCl•10.5H2O<br>C: 50.64%, H: 5.85%,<br>N: 7.20%, Cl: 7.11%<br>Found: C: 50.61%, H: 5.85%, N: 7.40%,<br>Cl: 7.11% |

TABLE 29-continued

| Structure | | | | Structure | | Data |
|---|---|---|---|---|---|---|
| 3,4-diClPh | bond | CONH | bond | 1,4-Ph | CH2 | [M + 1]- = 1725 Calcd. for C80H84Cl4N10O25•1.8HCl•10.2H2O<br>C: 48.61%, H: 5.42%, N: 7.09%, Cl: 10.40%<br>Found: C: 48.61%, H: 5.31%, N: 7.19%, Cl: 10.32% |

TABLE 30

| Structure | | | | Structure | | Data |
|---|---|---|---|---|---|---|
| 3,5-diMePh | bond | CONH | bond | 1,4-Ph | CH2 | [M + 1]- = 1686 Calcd. for C82H90Cl2N10O25•2.0HCl•11.1H2O<br>C: 50.26%, H: 5.87%, N: 7.15%, Cl: 7.24%<br>Found: C: 50.20%, H: 5.67%, N: 7.33%, Cl: 7.18% |
| 4-iPrPh | bond | CONH | bond | 1,4-Ph | CH2 | [M + 1]- = 1699 Calcd. for C83H92Cl2N10O25•1.9HCl•10.7H2O<br>C: 50.79%, H: 5.92%, N: 7.14%, Cl: 7.05%<br>Found: C: 50.74%, H: 5.72%, N: 7.36%, Cl: 6.97% |
| 3-F-4-MePh | bond | CONH | bond | 1,4-Ph | CH2 | [M + 1]- = 1689 Calcd. for C81H87Cl2FN10O25•1.8HCl•9.6H2O<br>C: 50.43%, H: 5.64%, N: 7.26%, Cl: 6.98%, F: 0.98%<br>Found: C: 50.37%, H: 5.47%, N: 7.47%, Cl: 7.01%, F: 0.97% |
| 3-BrPh | bond | CONH | bond | 1,4-Ph | CH2 | [M + 1]- = 1735 Calcd. for C80H85BrCl2N10O25•1.8HCl•17.2H2O<br>C: 45.48%, H: 5.78%, N: 6.63%, Br: 3.78%, Cl: 6.38%<br>Found: C: 45.45%, H: 5.59%, N: 6.77%, Br: 3.90%, Cl: 6.37% |
| 2-Naphthyl | bond | CONH | bond | 1,4-Ph | CH2 | [M + 1]- = 1707 Calcd. for C84H88Cl2N10O25•1.5HCl•10.1H2O<br>C: 51.87%, H: 5.68%, N: 7.20%, Cl: 6.38%<br>Found: C: 51.84%, H: 5.41%, N: 7.30%, Cl: 6.44% |
| 4-CF3Ph | bond | CONH | bond | 1,4-Ph | CH2 | [M + 1]- = 1726 Calcd. for C81H85Cl2F3N10O25•1.9HCl•12.1H2O<br>C: 48.31%, H: 5.56%, N: 6.96%, Cl: 6.87%, F: 2.83%<br>Found: C: 48.22%, H: 5.30%, N: 7.25%, Cl: 6.81%, F: 2.71% |

TABLE 30-continued

| R1 | L1 | L2 | L3 | R2 | L4 | MS | Analysis |
|---|---|---|---|---|---|---|---|
| 3-fluorophenyl | bond | CONH | bond | 1,4-phenylene | CH2 | [M + 1]− = 1675 | Calcd. for C80H85Cl2FN10O25•1.7HCl•10.9H2O<br>C: 49.66%, H: 5.65%, N: 7.24%, Cl: 6.78%, F: 0.98%<br>Found: C: 49.72%, H: 5.57%, N: 6.97%, Cl: 6.77%, F: 0.83% |
| 2-phenoxypyridin-3-yl | bond | CONH | bond | 1,3-phenylene | CH2 | [M + 1]− = 1750 | Calcd. for C85H89Cl2N11O26•1.7HCl•10.7H2O<br>C: 50.88%, H: 5.63%, N: 7.68%, Cl: 6.54%<br>Found: C: 50.80%, H: 5.48%, N: 7.82%, Cl: 6.55% |

TABLE 31

| R1 | L1 | L2 | L3 | R2 | L4 | MS | Analysis |
|---|---|---|---|---|---|---|---|
| 3-(benzo[d][1,3]dioxol-5-yl)phenyl | bond | CONH | bond | 1,3-phenylene | CH2 | [M + 1]− = 1778 | Calcd. for C87H90Cl2N10O27•1.7HCl•10.7H2O<br>C: 51.39%, H: 5.61%, N: 6.89%, Cl: 6.45%<br>Found: C: 51.40%, H: 5.54%, N: 6.81%, Cl: 6.38% |
| 3-bromo-4-methoxyphenyl | bond | CONH | bond | 1,3-phenylene | CH2 | [M + 3]+ = 1767<br>[M + 1]− = 1765 | Calcd. for C81H87BrCl2N10O26•1.7HCl•10.8H2O<br>C: 48.07%, H: 5.49%, N: 6.92%, Br: 3.95%, Cl: 6.48%<br>Found: C: 48.02%, H: 5.34%, N: 7.15%, Br: 4.17%, Cl: 6.46% |
| 2,4,5-trimethoxyphenyl | bond | CONH | bond | 1,3-phenylene | CH2 | [M + 1]− = 1748 | Calcd. for C83H92Cl2N10O28•1.8HCl•10.2H2O<br>C: 49.90%, H: 5.76%, N: 7.01%, Cl: 6.74%<br>Found: C: 49.87%, H: 5.67%, N: 7.15%, Cl: 6.79% |
| 4-((4-ethylphenoxy)methyl)phenyl | bond | CONH | bond | 1,3-phenylene | CH2 | [M + 3]+ = 1794<br>[M + 1]− = 1792 | Calcd. for C89H96Cl2N10O26•1.4HCl•11.2H2O<br>C: 52.26%, H: 5.90%, N: 6.85%, Cl: 5.89%<br>Found: C: 52.24%, H: 5.83%, N: 7.01%, Cl: 5.80% |
| 2,3,4-trimethoxyphenyl | bond | CONH | bond | 1,3-phenylene | CH2 | [M + 1]− = 1748 | Calcd. for C83H92Cl2N10O28•2.0HCl•9.2H2O<br>C: 50.16%, H: 5.70%, N: 7.05%, Cl: 7.14%<br>Found: C: 50.14%, H: 5.67%, N: 7.23%, Cl: 7.13% |

TABLE 31-continued
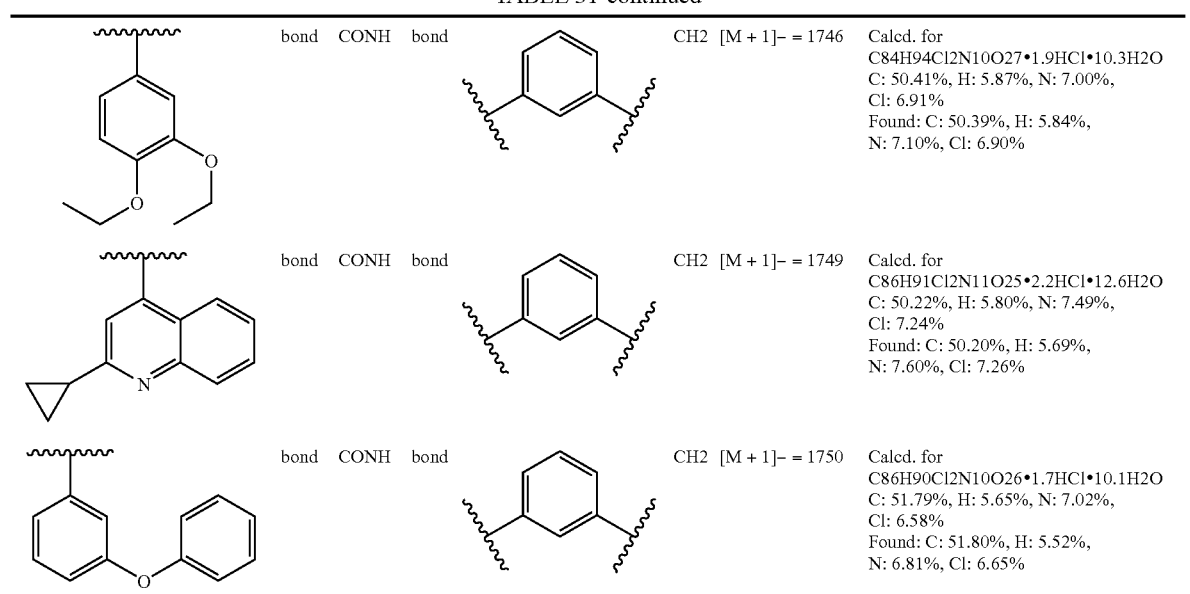
TABLE 32
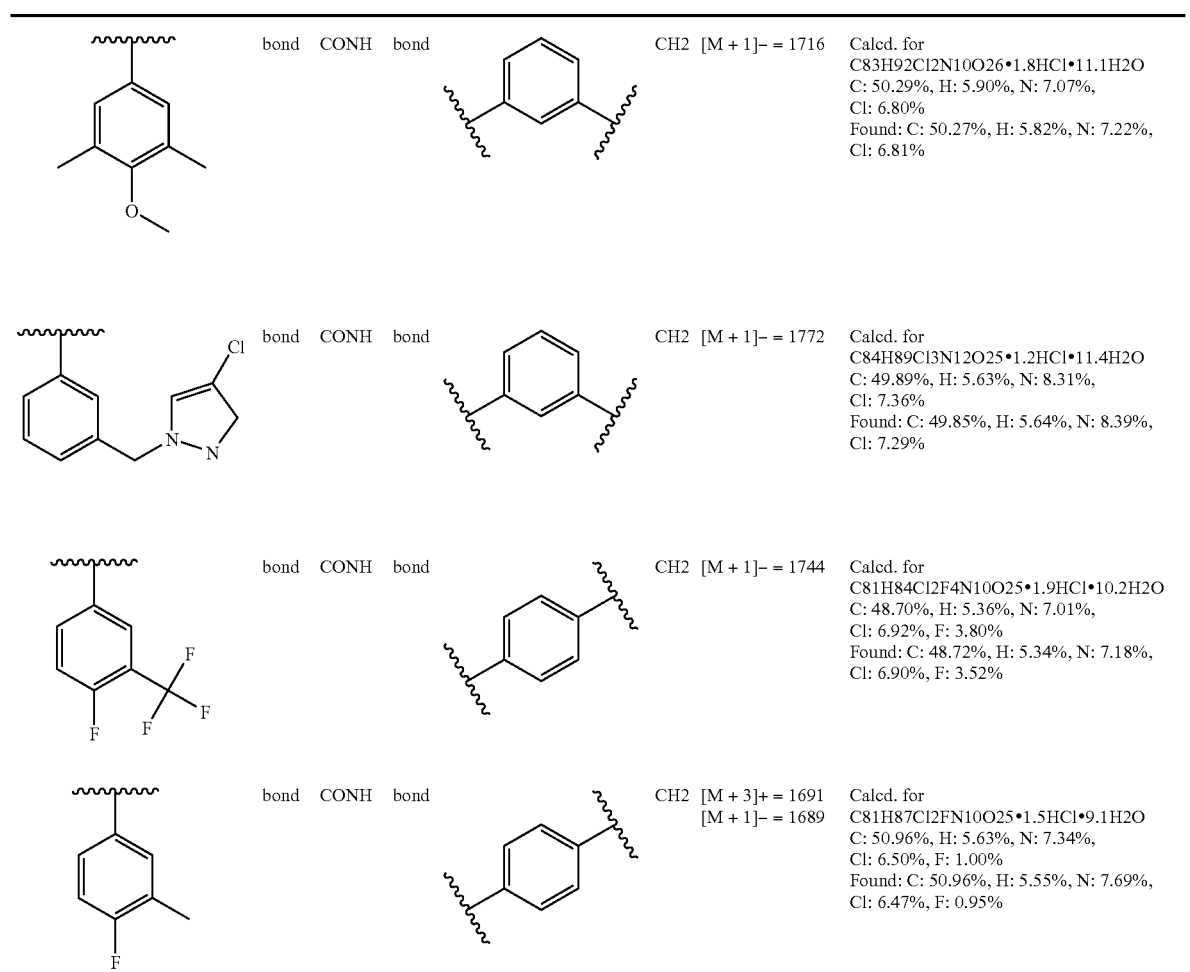

TABLE 32-continued

| Ar2 | X3 | Y | X2 | Ar1 | X1 | Mass | Elemetal Analysis |
|---|---|---|---|---|---|---|---|
| 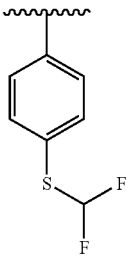 [SMILES: *c1ccc(SC(F)F)cc1] | bond | CONH | bond | 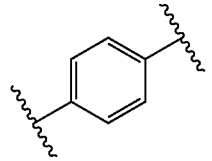 [SMILES: *c1ccc(*)cc1] | CH2 | [M + 1]− = 1739 | Calcd. for C81H86Cl2F2N10O25S•1.7HCl•9.9H2O<br>C: 49.11%, H: 5.47%, N: 7.07%,<br>Cl: 6.62%, F: 1.92%, S; 1.62%<br>Found: C: 49.11%, H: 5.35%,<br>N: 6.87%, Cl: 6.69%, F: 1.75%, S; 1.64% |
| 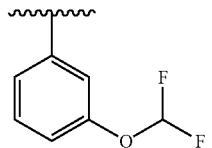 [SMILES: *c1cccc(OC(F)F)c1] | bond | CONH | bond | 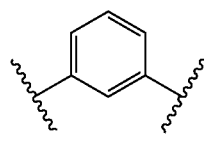 [SMILES: *c1cccc(*)c1] | CH2 | [M + 1]− = 1724 | Calcd. for C81H86Cl2F2N10O26•1.8HCl•9.4H2O<br>C: 49.65%, H: 5.48%, N: 7.15%,<br>Cl: 6.88%, F: 1.94%<br>Found: C: 49.66%, H: 5.54%, N: 7.01%,<br>Cl: 6.91%, F: 1.80% |

TABLE 33

| R$^A$ | R$^B$ | R$^C$ | R$^D$ |
|---|---|---|---|
| 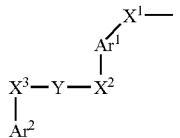 | OH | H | H |

| R$^A$ | | | | | | | |
|---|---|---|---|---|---|---|---|
| Ar2 | X3 | Y | X2 | Ar1 | X1 | Mass | Elemetal Analysis |
| 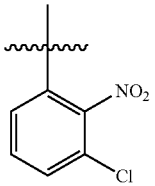 [SMILES: *c1cccc(Cl)c1[N+](=O)[O-]] | bond | CONH | bond | 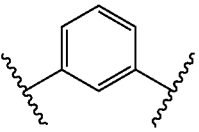 [SMILES: *c1cccc(*)c1] | CH2 | [M + 3]$^+$ = 1738<br>[M + 1]$^-$ = 1736 | Calcd. for C80H84Cl3N11O27•1.1HCl•10.1H2O<br>C: 49.02%, H: 5.42%, Cl: 7.42%, N: 7.86%<br>Found: C: 48.94%, H: 5.40%, Cl: 7.54%, N: 8.03% |
| 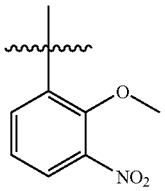 [SMILES: *c1cccc([N+](=O)[O-])c1OC] | bond | CONH | bond | 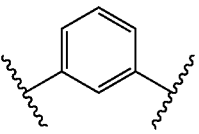 | CH2 | [M + 1]$^-$ = 1733 | Calcd. for C81H87Cl2N11O28•1.6HCl•9.9H2O<br>C: 49.38%, H: 5.55%, Cl: 6.48%, N: 7.82%<br>Found: C: 49.31%, H: 5.55%, Cl: 6.41%, N: 8.11% |
| 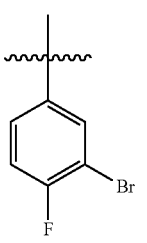 [SMILES: *c1ccc(F)c(Br)c1] | bond | CONH | bond | 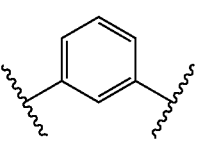 [SMILES: *c1cccc(*)c1] | CH2 | [M + 3]$^+$ = 1755<br>[M + 1]$^-$ = 1753 | Calcd. for C80H84BrCl2FN10O25•2.0HCl•9.1H2O<br>C: 48.23%, H: 5.27%, Br: 4.01%, Cl: 7.12%,<br>F: 0.95%, N: 7.03%<br>Found: C: 48.19%, H: 5.04%, Br: 3.82%,<br>Cl: 7.09%,<br>F: 1.10%, N: 7.05% |

TABLE 34

| R1 | | | | R2 | | M | Analysis |
|---|---|---|---|---|---|---|---|
| 2,6-dimethoxy-3-chlorophenyl | bond | CONH | bond | 1,3-phenylene | CH2 | [M + 3]⁺ = 1753<br>[M + 1]⁻ = 1751 | Calcd. for<br>C82H89Cl3N10O27•1.2HCl•9.2H2O<br>C: 50.19%, H: 5.58%, Cl: 7.59%, N: 7.14%<br>Found: C: 50.18%, H: 5.48%, Cl: 7.60%,<br>N: 7.19% |
| 2-chloro-3-methoxy-6-methylphenyl | bond | CONH | bond | 1,3-phenylene | CH2 | [M + 3]⁺ = 1737<br>[M + 1]⁻ = 1735 | Calcd. for<br>C82H89Cl3N10O26•1.2HCl•8.9H2O<br>C: 50.74%, H: 5.61%, Cl: 7.67%, N: 7.22%<br>Found: C: 50.74%, H: 5.58%, Cl: 7.73%,<br>N: 7.46% |
| 2,6-dichloro-3-methoxyphenyl | bond | CONH | bond | 1,3-phenylene | CH2 | [M + 3]⁺ = 1757<br>[M + 1]⁻ = 1755 | Calcd. for<br>C81H86Cl4N10O26•1.1HCl•8.5H2O<br>C: 49.87%, H: 5.38%, Cl: 9.27%, N: 7.18%<br>Found: C:49.65%, H: 5.43%, Cl: 9.48%,<br>N: 7.48% |
| 2-bromo-4,5-dimethoxyphenyl | bond | CONH | bond | 1,3-phenylene | CH2 | [M + 3]⁺ = 1797<br>[M + 1]⁻ = 1795 | Calcd. for<br>C82H89BrCl2N10O27•1.1HCl•8.2H2O<br>C: 49.61%, H: 5.41%, Br: 4.02%,<br>Cl: 5.54%, N: 7.06%<br>Found: C: 49.58%, H: 5.33%, Br: 3.72%,<br>Cl: 5.61%, N: 7.30% |
| 2-chloro-6-methylphenyl | bond | CONH | bond | 1,3-phenylene | CH2 | [M + 3]⁺ = 1707<br>[M + 1]⁻ = 1705 | Calcd. for<br>C81H87Cl3N10O25•1.1HCl•9.8H2O<br>C: 50.57%, H: 5.64%, Cl: 7.56%, N: 7.28%<br>Found: C: 50.55%, H: 5.55%, Cl: 7.62%,<br>N: 7.48% |

TABLE 35

| R1 | | | | R2 | | M | Analysis |
|---|---|---|---|---|---|---|---|
| 4-(1H-imidazol-1-yl)phenyl | bond | CONH | bond | 1,3-phenylene | CH2 | [M + 3]⁺ = 1726<br>[M + 1]⁻ = 1724 | Calcd. for<br>C83H88Cl2N12O25•2.2HCl•10.8H2O<br>C: 49.86%, H: 5.64%, Cl: 7.45%, N: 8.41%<br>Found: C: 49.82%, H: 5.48%, Cl: 7.50%,<br>N: 8.58% |

TABLE 35-continued

| R1 | L1 | L2 | L3 | R2 | L4 | MS | Analysis |
|---|---|---|---|---|---|---|---|
| 2,5-dimethyl-3-hydroxyphenyl | bond | CONH | bond | 1,3-phenylene | CH2 | $[M+3]^+ = 1689$<br>$[M+1]^- = 1687$ | Calcd. for<br>C81H88Cl2N10O26•1.3HCl•10.5H2O<br>C: 50.54%, H: 5.78%, Cl: 6.08%, N: 7.28%<br>Found: C: 50.47%, H: 5.73%, Cl: 6.14%, N: 7.57% |
| 3-hydroxyphenyl | bond | CONH | bond | 1,3-phenylene | CH2 | $[M+3]^+ = 1675$<br>$[M+1]^- = 1673$ | Calcd. for<br>C80H86Cl2N10O26•1.1HCl•9.9H2O<br>C: 50.76%, H: 5.69%, Cl: 5.81%, N: 7.40%<br>Found: C: 50.82%, H: 5.60%, Cl: 5.81%, N: 7.18% |
| 1H-indol-5-yl | bond | CONH | bond | 1,3-phenylene | CH2 | $[M+3]^+ = 1698$<br>$[M+1]^- = 1696$ | Calcd. for<br>C82H87Cl2N11O25•1.4HCl•10.3H2O<br>C: 50.92%, H: 5.68%, Cl: 6.23%, N: 7.97%<br>Found: C: 50.92%, H: 5.53%, Cl: 6.22%, N: 8.31% |
| 4-(tert-butoxycarbonylamino)phenyl | bond | CONH | bond | 1,3-phenylene | CH2 | $[M+3]^+ = 1775$<br>$[M+1]^- = 1773$ | Calcd. for<br>C85H95Cl2N11O27•1.3HCl•11.8H2O<br>C: 50.20%, H: 5.94%, Cl: 5.75%, N: 7.58%<br>Found: C: 50.21%, H: 5.79%, Cl: 5.69%, N: 7.63% |

TABLE 36

| R1 | L1 | L2 | L3 | R2 | L4 | MS | Analysis |
|---|---|---|---|---|---|---|---|
| 4-chloro-3-(1H-tetrazol-1-yl)phenyl | bond | CONH | bond | 1,3-phenylene | CH2 | $[M+3]^+ = 1761$<br>$[M+1]^- = 1759$ | Calcd. for<br>C81H85Cl3N14O25•1.5HCl•9.6H2O<br>C: 48.92%, H: 5.36%, Cl: 8.02%, N: 9.86%<br>Found: C: 48.88%, H: 5.25%, Cl: 7.93%, N: 9.98% |
| 4-nitropyridin-2-yl | bond | CONH | bond | 1,3-phenylene | CH2 | $[M+3]^+ = 1705$<br>$[M+1]^- = 1703$ | Calcd. for<br>C79H84Cl2N12O27•1.8HCl•10.3H2O<br>C: 48.52%, H: 5.48%, Cl: 6.89%, N: 8.59%<br>Found: C: 48.52%, H: 5.33%, Cl: 6.83%, N: 8.46% |

TABLE 36-continued

| R1 | | | R2 | | MS | Analysis |
|---|---|---|---|---|---|---|
| 2,6-difluoro-3-methoxyphenyl | bond | CONH | bond 1,3-phenylene | CH2 | [M + 3]+ = 1725<br>[M + 1]− = 1723 | Calcd. for C81H86Cl2F2N10O26•1.7HCl•10.4H2O<br>C: 49.29%, H: 5.54%, Cl: 6.65%,<br>F: 1.93%, N: 7.10%<br>Found: C: 49.26%, H: 5.41%, Cl: 6.71%, F: 1.82%, N: 7.25% |
| 4-methoxy-3-nitrophenyl | bond | CONH | bond 1,3-phenylene | CH2 | [M + 3]+ = 1735<br>[M + 1]− = 1732 | Calcd. for C81H87Cl2N11O28•1.0HCl•9.3H2O<br>C: 50.21%, H: 5.55%, Cl: 5.49%,<br>N: 7.95%<br>Found: C: 50.17%, H: 5.44%, Cl: 5.49%, N: 8.05% |
| 2-(Boc-aminomethyl)pyridin-4-yl | bond | CONH | bond 1,3-phenylene | CH2 | [M + 3]+ = 1786<br>[M + 1]− = 1787 | Calcd. for C85H96Cl2N12O272•1HCl•11.1H2O<br>C: 49.43%, H: 5.87%, Cl: 7.04%,<br>N: 8.14%<br>Found: C: 49.43%, H: 5.66%, Cl: 6.90%, N: 7.98% |

TABLE 37

| R1 | | | R2 | | MS | Analysis |
|---|---|---|---|---|---|---|
| 2-(tert-butoxycarbonyl)phenyl | bond | CONH | bond 1,3-phenylene | CH2 | [M + 3]+ = 1759<br>[M + 1]− = 1757 | Calcd. for C85H94Cl2N10O27•1.8HCl•11.3H2O<br>C: 50.35%, H: 5.89%, Cl: 6.64%,<br>N: 6.91%<br>Found: C: 50.33%, H: 5.76%, Cl: 6.58%, N: 7.00% |
| 2,5-dimethoxy-3-nitrophenyl | bond | CONH | bond 1,3-phenylene | CH2 | [M + 3]+ = 1764<br>[M + 1]− = 1762 | Calcd. for C82H89Cl2N11O29•1.9HCl•10.8H2O<br>C: 48.58%, H: 5.59%, Cl: 6.82%,<br>N: 7.60%<br>Found: C: 48.50%, H: 5.49%, Cl: 6.90%, N: 7.75% |
| 4-chloro-3-nitrophenyl | bond | CONH | bond 1,3-phenylene | CH2 | [M + 3]+ = 1738<br>[M + 1]− = 1736 | Calcd. for C80H84Cl3N11O27•1.6HCl•11.1H2O<br>C: 48.13%, H: 5.44%, Cl: 8.17%,<br>N: 7.72%<br>Found: C: 48.12%, H: 5.40%, Cl: 8.21%, N: 7.66% |
| 6-chloropyridin-3-yl | bond | CONH | bond 1,3-phenylene | CH2 | [M + 1]− = 1693 | Calcd. for C79H84Cl3N11O25•1.6HCl•10.7H2O<br>C: 48.78%, H: 5.54%, Cl: 8.38%,<br>N: 7.92%<br>Found: C: 48.71%, H: 5.41%, Cl: 8.54%, N: 8.08% |

TABLE 37-continued

| Structure 1 | | | Structure 2 | | MS | Analysis |
|---|---|---|---|---|---|---|
| anthraquinone | bond | CONH | bond | m-phenylene | CH2 [M + 3]⁺ = 1789 | Calcd. for C88H88Cl2N10O27•1.6HCl•11.8H2O<br>C: 51.32%, H: 5.54%, Cl: 6.20%, N: 6.80%<br>Found: C: 51.27%, H: 5.40%, Cl: 6.33%, N: 6.95% |

TABLE 38

| Structure 1 | | | Structure 2 | | MS | Analysis |
|---|---|---|---|---|---|---|
| 4-acetamidophenyl | bond | CONH | bond | m-phenylene | CH2 [M + 1]⁻ = 1714 | Calcd. for C82H89Cl2N11O26•1.8HCl•10.7H2O<br>C: 49.89%, H: 5.73%, Cl: 6.82%, N: 7.81%<br>Found: C: 49.87%, H: 5.61%, Cl: 6.83%, N: 7.95% |
| 3-fluoro-4-methoxyphenyl | bond | CONH | bond | m-phenylene | CH2 [M + 3]⁺ = 1707<br>[M + 1]⁻ = 1705 | Calcd. for C81H87Cl2FN10O26•1.2HCl•9.9H2O<br>C: 50.44%, H: 5.64%, Cl: 5.88%, F: 0.99%, N: 7.26%<br>Found: C: 50.44%, H: 5.56%, Cl: 5.95%, F: 0.98%, N: 7.30% |
| 6-methylpyridin-3-yl | bond | CONH | bond | m-phenylene | CH2 [M + 1]⁻ = 1672 | Calcd. for C80H87Cl2N11O25•1.3HCl•10.6H2O<br>C: 50.26%, H: 5.77%, Cl: 6.12%, N: 8.06%<br>Found: C: 50.17%, H: 5.76%, Cl: 6.24%, N: 8.24% |
| thioxanthone-S,S-dioxide | bond | CONH | bond | m-phenylene | CH2 [M + 1]⁻ = 1823 | Calcd. for C87H88Cl2N10O28S•1.7HCl•9.9H2O<br>C: 50.60%, H: 5.34%, Cl: 6.35%, N: 6.78%, S: 1.55%<br>Found: C: 50.67%, H: 5.26%, Cl: 6.19%, N: 6.59%, S: 1.55% |

TABLE 38-continued

| R1 | | | | R2 | | MS | Elemental Analysis |
|---|---|---|---|---|---|---|---|
| 2-methyl-6-(trifluoromethyl)pyridin-3-yl | bond | CONH | bond | 1,3-phenylene | CH2 | [M + 3]⁺ = 1742 | Calcd. for C81H86Cl2F3N11O25•1.7HCl•10.0H2O<br>C: 49.04%, H: 5.47%, Cl: 6.61%, F: 2.87%, N: 7.77%<br>Found: C: 48.99%, H: 5.34%, Cl: 6.51%, F: 2.78%, N: 7.89% |

TABLE 39

| R1 | | | | R2 | | MS | Elemental Analysis |
|---|---|---|---|---|---|---|---|
| 2,3-dihydrobenzofuran-5-yl | bond | CONH | bond | 1,3-phenylene | CH2 | [M + 3]⁺ = 1701<br>[M + 1]⁻ = 1699 | Calcd. for C82H88Cl2N10O26•1.5HCl•10.2H2O<br>C: 50.79%, H: 5.71%, Cl: 6.40%, N: 7.22%<br>Found: C: 50.73%, H: 5.61%, Cl: 6.45%, N: 7.49% |
| 3-chloro-2,4-difluorophenyl | bond | CONH | bond | 1,3-phenylene | CH2 | [M + 3]⁺ = 1729<br>[M + 1]⁻ = 1727 | Calcd. for C80H83Cl3F2N10O25•1.5HCl•9.5H2O<br>C: 49.15%, H: 5.34%, Cl: 8.16%, F: 1.94%, N: 7.17%<br>Found: C: 49.05%, H: 5.27%, Cl: 8.28%, F: 1.81%, N: 7.36% |
| 3-chloro-2-fluoro-5-(trifluoromethyl)phenyl | bond | CONH | bond | 1,3-phenylene | CH2 | [M + 1]⁻ = 1777 | Calcd. for C81H83Cl3F4N10O25•1.7HCl•10.6H2O<br>C: 47.88%, H: 5.25%, Cl: 8.20%, F: 3.74%, N: 6.89%<br>Found: C: 47.92%, H: 5.17%, Cl: 8.13%, F: 3.35%, N: 6.86% |
| 4-methoxy-3-(trifluoromethyl)phenyl | bond | CONH | bond | 1,3-phenylene | CH2 | [M + 3]⁺ = 1757 | Calcd. for C82H87Cl2F3N10O26•1.7HCl•8.4H2O<br>C: 50.00%, H: 5.40%, Cl: 6.66%, F: 2.89%, N: 7.11%<br>Found: C: 49.91%, H: 5.34%, Cl: 6.84%, F: 2.75%, N: 7.36% |
| 4-chloro-2-fluorophenyl | bond | CONH | bond | 1,3-phenylene | CH2 | [M + 1]⁻ = 1710 | Calcd. for C80H84Cl3FN10O25•1.4HCl•9.9H2O<br>C: 49.52%, H: 5.46%, Cl: 8.04%, F: 0.98%, N: 7.22%<br>Found: C: 49.34%, H: 5.38%, Cl: 8.04%, F: 0.96%, N: 7.52% |

TABLE 40

| | | | | | | | |
|---|---|---|---|---|---|---|---|
| 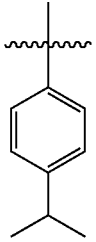 | bond | CONH | bond | 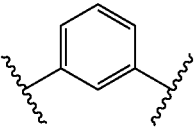 [SMILES: *c1cccc(*)c1] | CH2 | [M + 3]⁺ = 1701<br>[M + 1]⁻ = 1699 | Calcd. for<br>C83H92Cl2N10O25•1.8HCl•9.8H2O<br>C: 51.31%, H: 5.88%, Cl: 6.93%, N: 7.21%<br>Found: C: 51.24%, H: 5.77%, Cl: 6.88%,<br>N: 7.39% |
| 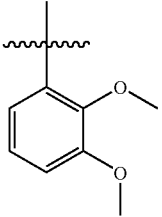 [SMILES: *c1cccc(OC)c1OC] | bond | CONH | bond | 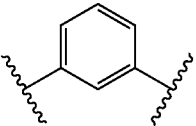 [SMILES: *c1cccc(*)c1] | CH2 | [M + 3]⁺ = 1719<br>[M + 1]⁻ = 1717 | Calcd. for<br>C82H90Cl2N10O27•1.6HCl•10.0H2O<br>C: 50.32%, H: 5.75%, Cl: 6.52%, N: 7.16%<br>Found: C: 50.32%, H: 5.73%, Cl: 6.52%,<br>N: 7.20% |
| 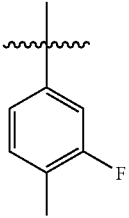 | bond | CONH | bond | 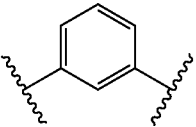 [SMILES: *c1cccc(*)c1] | CH2 | [M + 3]⁺ = 1691 | Calcd. for<br>C81H87Cl2FN10O25•1.9HCl•9.9H2O<br>C: 50.20%, H: 5.65%, Cl: 7.13%, F: 0.98%,<br>N: 7.23%<br>Found: C: 50.17%, H: 5.55%, Cl: 7.13%,<br>F: 0.90%, N: 7.48% |
| 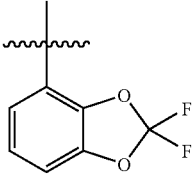 [SMILES: *c1cccc2c1OC(F)(F)O2] | bond | CONH | bond | 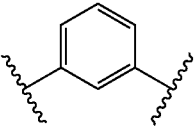 | CH2 | [M + 3]⁺ = 1739<br>[M + 1]⁻ = 1737 | Calcd. for<br>C81H84Cl2F2N10O27•1.6HCl•9.5H2O<br>C: 49.44%, H: 5.36%, Cl: 6.49%, F: 1.93%,<br>N: 7.12%<br>Found: C: 49.37%, H: 5.33%, Cl: 6.53%,<br>F: 1.88%, N: 7.32% |
| 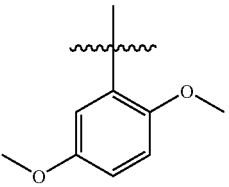 | bond | CONH | bond | 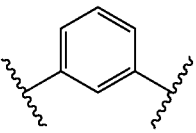 [SMILES: *c1cccc(*)c1] | CH2 | [M + 3]⁺ = 1719<br>[M + 1]⁻ = 1717 | Calcd. for<br>C82H90Cl2N10O27•1.6HCl•9.5H2O<br>C: 50.56%, H: 5.72%, Cl: 6.55%, N: 7.19%<br>Found: C: 50.52%, H: 5.60%, Cl: 6.59%,<br>N: 7.27% |

TABLE 41

| | | | | | | | |
|---|---|---|---|---|---|---|---|
| 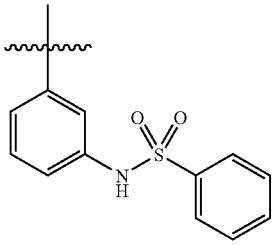 [SMILES: *c1cccc(NS(=O)(=O)c2ccccc2)c1] | bond | CONH | bond | 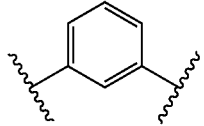 [SMILES: *c1cccc(*)c1] | CH2 | [M + 1]⁻ = 1813 | Calcd. for<br>C86H91Cl2N11O27S•1.8HCl•9.0H2O<br>C: 50.60%, H: 5.47%, Cl: 6.60%,<br>N: 7.55%, S: 1.57%<br>Found: C: 50.57%, H: 5.33%,<br>Cl: 6.63%, N: 7.51%, S: 1.40% |

TABLE 41-continued

| Structure | | | | | | |
|---|---|---|---|---|---|---|
| 3-biphenyl | bond | CONH | bond | m-phenylene | CH2 | [M + 3]+ = 1735<br>[M + 1]− = 1733 | Calcd. for<br>C86H90Cl2N10O25•1.9HCl•8.3H2O<br>C: 52.88%, H: 5.60%, Cl: 7.08%,<br>N: 7.17%<br>Found: C: 52.83%, H: 5.47%,<br>Cl: 7.11%, N: 7.39% |
| 4-isopropoxyphenyl | bond | CONH | bond | m-phenylene | CH2 | [M + 1]− = 1716 | Calcd. for<br>C83H92Cl2N10O26•1.8HCl•9.1H2O<br>C: 51.22%, H: 5.80%, Cl: 6.92%,<br>N: 7.20%<br>Found: C: 51.18%, H: 5.72%,<br>Cl: 6.83%, N: 7.47% |
| 1H-pyrazol-3-yl | bond | CONH | bond | m-phenylene | CH2 | [M + 3]+ = 1649<br>[M + 1]− = 1647 | Calcd. for<br>C77H84Cl2N12O25•1.8HCl•9.6H2O<br>C: 49.01%, H: 5.61%, Cl: 7.14%,<br>N: 8.91%<br>Found: C: 49.00%, H: 5.52%,<br>Cl: 7.13%, N: 9.00% |
| 6,7-dichloroquinolin-8-yl | bond | CONH | bond | m-phenylene | CH2 | [M + 3]+ = 1778<br>[M + 1]− = 1776 | Calcd. for<br>C83H85Cl4N11O25•2.1HCl•10.2H2O<br>C: 48.90%, H: 5.31%, Cl: 10.61%,<br>N: 7.56%<br>Found: C: 48.92%, H: 5.26%,<br>Cl: 10.60%, N: 7.68% |

TABLE 42

| Structure | | | | | | |
|---|---|---|---|---|---|---|
| 6-hydroxypyridin-2-yl | bond | CONH | bond | m-phenylene | CH2 | [M + 1]− = 1674 | Calcd. for<br>C79H85Cl2N11O26•2.5HCl•10.0H2O<br>C: 48.74%, H: 5.57%, Cl: 8.19%,<br>N: 7.91%<br>Found: C: 48.73%, H: 5.55%,<br>Cl: 8.16%, N: 8.04% |
| 2,5-dioxo-2,3,4,5-tetrahydro-1H-benzo[e][1,4]diazepin-7-yl | bond | CONH | bond | m-phenylene | CH2 | [M + 1]− = 1755 | Calcd. for<br>C83H88Cl2N12O27•2.0HCl•10.3H2O<br>C: 49.47%, H: 5.53%, Cl: 7.04%,<br>N: 8.34%<br>Found: C: 49.40%, H: 5.50%,<br>Cl: 7.02%, N: 8.61% |

TABLE 42-continued

| R1 | | | R2 | | MS | Elemental Analysis |
|---|---|---|---|---|---|---|
| 4-(furan-2-yl)quinolin-2-yl | bond | CONH | bond | m-phenylene | CH2 | [M + 1]⁻ = 1774 | Calcd. for C87H89Cl2N11O26•2.6HCl•10.4H2O<br>C: 50.78%, H: 5.51%, Cl: 7.93%, N: 7.49%<br>Found: C: 50.76%, H: 5.59%, Cl: 7.87%, N: 7.70% |
| 3-sulfamoyl-4-methylphenyl | bond | CONH | bond | m-phenylene | CH2 | [M + 1]⁻ = 1750 | Calcd. for C81H89Cl2N11O27S•2.0HCl•9.4H2O<br>C: 48.79%, H: 5.55%, Cl: 7.11%, N: 7.73%, S: 1.16%<br>Found: C: 48.72%, H: 5.50%, Cl: 7.22%, N: 7.95%, S: 1.77% |
| 4-fluoro-3-(piperidin-1-ylsulfonyl)phenyl | bond | CONH | bond | m-phenylene | CH2 | [M + 1]⁻ = 1822 | Calcd. for C85H94Cl2FN11O27S•1.9HCl•10.1H2O<br>C: 49.20%, H: 5.64%, Cl: 6.66%, F: 0.92%, N: 7.43%, S: 1.55%<br>Found: C: 49.16%, H: 5.57%, Cl: 6.58%, F: 0.84%, N: 7.59%, S: 1.62% |

TABLE 43

| R1 | | | R2 | | MS | Elemental Analysis |
|---|---|---|---|---|---|---|
| 3-pivalamidophenyl | bond | CONH | bond | m-phenylene | CH2 | [M + 3]⁺ = 1758<br>[M + 1]⁻ = 1756 | Calcd. for C85H95Cl2N11O28•1.7HCl•8.7H2O<br>C: 51.66%, H: 5.82%, Cl: 6.64%, N: 7.80%<br>Found: C: 51.64%, H: 5.83%, Cl: 6.63%, N: 7.88% |
| 4-methyl-3-(piperidin-1-ylsulfonyl)phenyl | bond | CONH | bond | m-phenylene | CH2 | [M + 1]⁻ = 1819 | Calcd. for C86H97Cl2N11O27S•2.0HCl•8.5H2O<br>C: 50.49%, H: 5.72%, Cl: 6.93%, N: 7.53%, S: 1.57%<br>Found: C: 50.45%, H: 5.69%, Cl: 6.91%, N: 7.75%, S: 1.56% |
| 2-(trifluoromethyl)-5,6,7,8-tetrahydro-1,6-naphthyridin-4-yl | bond | CONH | bond | m-phenylene | CH2 | [M + 1]⁻ = 1781 | Calcd. for C83H89Cl2F3N12O25•2.4HCl•10.3H2O<br>C: 48.50%, H: 5.49%, Cl: 7.59%, F: 2.77%, N: 8.18%<br>Found: C: 48.48%, H: 5.36%, Cl: 7.53%, F: 2.51%, N: 8.37% |

TABLE 44

| $R^A$ | $R^B$ | $R^C$ | $R^D$ |
|---|---|---|---|
| (structure with Ar1-X1, Ar2-X3-Y-X2) | OH | H | H |

$R^A$

| Ar2 | X3 | Y | X2 | Ar1 | X1 | Mass | Elemental Analysis |
|---|---|---|---|---|---|---|---|
| 3-methyl-2-nitrophenyl with O-CH2-(2-pyridyl) | bond | CONH | bond | 1,3-phenylene | CH2 | 1823 [M + H]+ | Calcd. for C87H92Cl2N12O28 3.2(HCl) 14(H2O) C: 47.64% H: 5.66% Cl: 8.40% N: 7.66% O: 30.63% Found: H (%) 5.23 C (%) 47.59 N (%) 7.74 Cl (%) 8.40 |
| 3-methyl-2-nitrophenyl with O-CH2-(3-pyridyl) | bond | CONH | bond | 1,3-phenylene | CH2 | 1823 [M + H]+ | Calcd. For C87H92Cl2N12O28 2.9(HCl) 8(H2O) C: 50.37% H: 5.39% Cl: 8.37% N: 8.10% O: 27.76% Found: H (%) 5.24 C (%) 50.23 N (%) 8.22 Cl (%) 8.12 |
| 3-methyl-2-nitrophenyl with O-CH2-(tetrahydropyran-4-yl) | bond | CONH | bond | 1,3-phenylene | CH2 | 1830 [M + H]+ | Calcd. For C87H97Cl2N11O29 2(HCl) 11(H2O) C: 49.69% H: 5.80% Cl: 6.74% N: 7.33% O: 30.44% Found: Cl (%) 6.85 H (%) 5.62 C (%) 49.57 N (%) 7.34 |

TABLE 45

| Ar2 | X3 | Y | X2 | Ar1 | X1 | Mass | Elemental Analysis |
|---|---|---|---|---|---|---|---|
| 3-methyl-2-nitrophenyl with O-CH2-(1,3-dioxolan-2-yl) | bond | CONH | bond | 1,3-phenylene | CH2 | 1818 [M + H]+ | Calcd. For C85H93Cl2N11O30 2(HCl) 10(H2O) C: 49.26% H: 5.59% Cl: 6.84% N: 7.43% O: 30.88% Found: Cl (%) 6.81 H (%) 5.14 C (%) 49.06 N (%) 7.57 |
| 3-methyl-2-nitrophenyl with O-CH2-cyclopropyl | bond | CONH | bond | 1,3-phenylene | CH2 | 1786 [M + H]+ | Calcd. For C85H93Cl2N11O28 2(HCl) 11(H2O) C: 49.59% H: 5.73% Cl: 6.89% N: 7.48% O: 30.31% Found: Cl (%) 7.06 H (%) 5.26 C (%) 49.60 N (%) 7.68 |
| 3-methyl-2-nitrophenyl with O-CH2-cyclohexyl | bond | CONH | bond | 1,3-phenylene | CH2 | 1828 [M + H]+ | Calcd. For C88H99Cl2N11O28 2(HCl) 11(H2O) C: 50.31% H: 5.90% Cl: 6.75% N: 7.33% O: 29.70% Found: Cl (%) 6.67 H (%) 5.67 C (%) 50.13 N (%) 7.24 |

TABLE 45-continued

| R^A | | | | | | | |
|---|---|---|---|---|---|---|---|
| 2-NO2, 3-OMe phenyl | bond | CONH | bond | 1,3-phenylene | CH2 | 1732 [M + H]+ | Calcd. For C81H87Cl2N11O28 2(HCl) 11(H2O) C: 48.53% H: 5.58% Cl: 7.07% N: 7.69% O: 31.13% Found: Cl (%) 7.28 H (%) 5.31 C (%) 48.31 N (%) 7.72 |
| 2-OBn, 3-NO2 phenyl | bond | CONH | bond | 1,3-phenylene | CH2 | 1808 [M + H]+ | Calcd. For C87H91Cl2N11O28 2(HCl) 15(H2O) C: 48.54% H: 5.76% Cl: 6.59% N: 7.16% O: 31.96% Found: Cl (%) 6.63 H (%) 5.08 C (%) 48.62 N (%) 7.28 |
| 2-NO2, 3-OBn, 4-Me phenyl | bond | CONH | bond | 1,2-phenylene | CH2 | 1822 [M + H]+ | Calcd. For C88H93Cl2N11O28 2(HCl) 15(H2O) C: 48.78% H: 5.81% Cl: 6.54% N: 7.11% O: 31.75% Found: Cl (%) 6.49 H (%) 5.38 C (%) 48.22 N (%) 7.84 |

TABLE 46

| R^A | | | | | | | |
|---|---|---|---|---|---|---|---|
| 2-NO2, 3-O-CH2-cyclopentyl, 4-Me phenyl | bond | CONH | bond | 1,3-phenylene | CH2 | 1814 [M + H]+ | Calcd. For C87H97Cl2N11O28 1.2(HCl) 12(H2O) C: 50.34% H: 5.93% Cl: 5.47% N: 7.42% O: 30.83% Found: Cl (%) 5.76 H (%) 5.71 C (%) 50.43 N (%) 7.57 |

TABLE 47

[Structure: Ar1—(3-CH2-phenyl)—NH—C(O)—(3,5-dichlorophenyl)—Ar2, with Y linker; (X2 = X3 = bond)]

| R^A | R^B | R^C | R^D |
|---|---|---|---|
| [Ar1/Ar2 structure shown] | OH or NRR' | H or CH2—NRR' | H |

| R^B | R^C | R^D | Mass | Elemental Analysis |
|---|---|---|---|---|
| —NH—(CH2)3—N(Me)Me | H | H | [M + 1]− = 1810 | Calcd. for C85H96Cl4N12O24·3.0HCl·12.4H2O C: 47.61%, H: 5.82%, N: 7.84%, Cl: 11.57% Found: C: 47.58%, H: 5.62%, N: 7.97%, Cl: 11.5% |

TABLE 47-continued

| Structure | | | MS | Analysis |
|---|---|---|---|---|
| ~N(H)-CH2-COOH (glycine) | H | H | [M + 3]+ = 1784<br>[M + 1]− = 1782 | Calcd. for C82H87Cl4N11O26•2.0HCl•10.8H2O<br>C: 48.00%, H: 5.43%, N: 7.51%, Cl: 10.37%<br>Found: C: 48.00%, H: 5.24%, N: 7.47%, Cl: 10.30% |
| ~N(H)-CH2CH2-COOH (β-alanine) | H | H | [M + 3]+ = 1797<br>[M + 1]− = 1799 | Calcd. for C83H89Cl4N11O26•2.0HCl•10.2H2O<br>C: 48.51%, H: 5.46%, N: 7.50%, Cl: 10.35%<br>Found: C: 48.47%, H: 5.33%, N: 7.44%, Cl: 10.41% |
| ~NH-sugar (aminosugar) | H | H | [M + 1]− = 1888 | Calcd. for C86H95Cl4N11O29•1.8HCl•12.3H2O<br>C: 47.47%, H: 5.62%, N: 7.08%, Cl: 9.45%<br>Found: C: 47.46%, H: 5.44%, N: 7.06%, Cl: 9.52% |

TABLE 48

| Structure 1 | Structure 2 | | MS | Analysis |
|---|---|---|---|---|
| ~N(Me)-CH2-[CH(OH)]4-CH2OH | H | H | [M + 1]− = 1903 | Calcd. for C87H99Cl4N11O29•2.1HCl•10.2H2O<br>C: 48.27%, H: 5.66%, N: 7.12%, Cl: 9.99%<br>Found: C: 48.26%, H: 5.63%, N: 7.25%, Cl: 9.99% |
| ~NH-CH2-C(O)-NH-C≡N | H | H | [M + 3]+ = 1809<br>[M + 1]− = 1807 | Calcd. for C83H87Cl4N13O25•2.7HCl•12.5H2O<br>C: 46.76%, H: 5.42%, N: 8.54%, Cl: 11.14%<br>Found: C: 46.78%, H: 5.19%, N: 8.56%, Cl: 11.10% |
| OH | ~CH2-N(CH2CH2OH)2 | H | [M + 1]− = 1842 | Calcd. for C85H95Cl4N11O27•2.6HCl•11.2H2O<br>C: 47.68%, H: 5.85%, N: 7.20%, Cl: 10.93%<br>Found: C: 47.64%, H: 5.45%, N: 7.41%, Cl: 10.97% |
| OH | ~CH2-N(Me)-CH2-[CH(OH)]3-CH2OH | H | [M + 1]− = 1933 | Calcd. for C88H101Cl4N11O30•2.8HCl•10.9H2O<br>C: 47.33%, H: 5.67%, N: 6.90%, Cl: 10.80%<br>Found: C: 47.29%, H: 5.53%, N: 7.00%, Cl: 10.83% |
| OH | ~CH2CH2-NH-CH2-C(O)-N−-N+(Me)3 | H | [M + 1]− = 1869 | Calcd. for C86H97Cl4N13O26•3.7HCl•11.2H2O<br>C: 46.80%, H: 5.62%, N: 8.25%, Cl: 12.37%<br>Found: C: 46.75%, H: 5.61%, N: 8.42%, Cl: 12.38% |
| OH | ~C(Me)2-NH-CH2-P(O)(OH)2 | H | [M + 1]− = 1849 | Calcd. for C82H90Cl4N11O28P•2.0HCl•11.0H2O<br>C: 46.42%, H: 5.42%, N: 7.26%, Cl: 10.03%, P: 1.46%<br>Found: C: 46.42%, H: 5.42%, N: 7.21%, Cl: 10.03%, P: 1.82% |
| OH | ~CH2-Asn | H | [M + 3]+ = 1872<br>[M + 1]− = 1870 | Calcd. for C85H92Cl4N12O28•2.8HCl•11.2H2O<br>C: 46.93%, H: 5.43%, N: 7.73%, Cl: 11.08%<br>Found: C: 46.89%, H: 5.39%, N: 7.77%, Cl: 11.15% |

TABLE 48-continued

| R | R' | R'' | MS | Analysis |
|---|---|---|---|---|
| OH | [aminoethyl-tetrahydropyran-triol group] | H | [M + 3]⁺ = 1919<br>[M + 1]⁻ = 1917 | Calcd. for C87H97Cl4N11O30.3•2HCl•12.1H2O<br>C: 46.37%, H: 5.56%, N: 6.84%, Cl: 11.33%<br>Found: C: 46.36% H: 5.34%, N: 7.00%, Cl: 11.29% |

TABLE 49

| R | R' | R'' | MS | Analysis |
|---|---|---|---|---|
| OH | [histamine group] | H | [M + 1]⁻ = 1849 | Calcd. for C86H93Cl4N13O25•3.7HCl•12.2H2O<br>C: 46.84%, H: 5.54%, N: 8.26%, Cl: 12.38%<br>Found: C: 46.83%, H: 5.52%, N: 8.34%, Cl: 12.41% |
| OH | [arginine group] | H | [M + 1]⁻ = 1912 | Calcd. for C87H98Cl4N14O27•2.8HCl•12.4H2O<br>C: 46.67%, H: 5.65%, N: 8.76%, Cl: 10.77%<br>Found: C: 46.69%, H: 5.60%, N: 8.75%, Cl: 10.72% |
| OH | [histidine group] | H | [M + 1]⁻ = 1893 | Calcd. for C87H93Cl4N13O27•3.6HCl•12.5H2O<br>C: 46.42%, H: 5.44%, N: 8.09%, Cl: 11.97%<br>Found: C: 46.39%, H: 5.27%, N: 8.11%, Cl: 11.95% |
| OH | [ethylenediamine group] | H | [M + 1]⁻ = 1798 | Calcd. for C83H92Cl4N12O25•3.4HCl•13.2H2O<br>C: 46.13%, H: 5.68%, N: 7.78%, Cl: 12.14%<br>Found: C: 46.11%, H: 5.50%, N: 7.94%, Cl: 12.17% |
| [bis(2-hydroxyethyl)amino group] | H | H | [M + 3]⁺ = 1814<br>[M + 1]⁻ = 1812 | Calcd. for C84H93Cl4N11O26•1.6HCl•9.4H2O<br>C: 49.40%, H: 5.60%, Cl: 9.72%, N: 7.54%<br>Found: C: 49.41%, H: 5.76%, Cl: 9.78%, N: 7.30% |
| [trimethylammonioethylamino group] | H | H | [M + 3]⁺ = 1812<br>[M + 1]⁻ = 1810 | Calcd. for C85H97Cl5N12O24•1.2HCl•10.4H2O<br>C: 49.10%, H: 5.77%, Cl: 10.57%, N: 8.08%<br>Found: C: 49.18%, H: 5.76%, Cl: 10.62%, N: 7.53% |
| [glycine trimethylammonium amide group] | H | H | [M + 3]⁺ = 1841<br>[M + 1]⁻ = 1839 | Calcd. for C85H95Cl4N13O25•2.3HCl•9.6H2O<br>C: 48.68%, H: 5.60%, Cl: 10.65%, N: 8.68%<br>Found: C: 48.83%, H: 5.63%, Cl: 10.60%, N: 8.23% |
| OH | [β-alanine group] | H | [M + 3]⁺ = 1829<br>[M + 1]⁻ = 1827 | Calcd. for C84H81Cl4N11O27•1.4HCl•8.7H2O<br>C: 49.55%, H: 5.44%, Cl: 9.40%, N: 7.57%<br>Found: C: 49.60%, H: 5.51%, Cl: 9.34%, N: 7.57% |

TABLE 50

| R | R' | R'' | MS | Analysis |
|---|---|---|---|---|
| OH | [taurine group, NH-CH2-CH2-SO3H] | H | [M + 3]⁺ = 1864<br>[M + 1]⁻ = 1862 | Calcd. for C83H91Cl4N11O28S•1.5HCl•11.2H2O<br>C: 47.00%, H: 5.46%, Cl: 9.19%, N: 7.26%, S: 1.51%<br>Found: C: 47.10%, H: 5.30%, Cl: 9.11%, N: 6.99%, S: 1.42% |

TABLE 50-continued

| | | | | |
|---|---|---|---|---|
| OH | 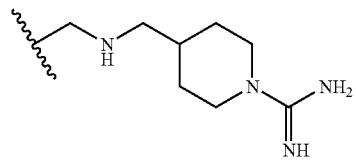 [SMILES: *CNCC1CCN(C(=N)N)CC1] | H | [M + 3]⁺ = 1896<br>[M + 1]⁻ = 1894 | Calcd. for C88H100Cl4N14O25•2.9HCl•10.2H2O<br>C: 48.37%, H: 5.69%, Cl: 11.20%, N: 8.97%<br>Found: C: 48.39%, H: 5.72%, Cl: 11.15%, N: 8.95% |
| 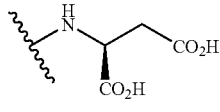 | | H | H [M + 3]⁺ = 1842<br>[M + 1]⁻ = 1840 | Calcd. for C84H89Cl4N11O28•1.1HCl•7.6H2O<br>C: 49.96%, H: 5.26%, Cl: 8.95%, N: 7.63%<br>Found: C: 50.09%, H: 5.25%, Cl: 8.90%, N: 6.89% |
| 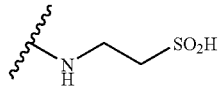 | | H | H [M + 3]⁺ = 1834<br>[M + 1]⁻ = 1832 | Calcd. for C82H89Cl4N11O27S•0.6HCl•5.7H2O<br>C: 50.27%, H: 5.20%, Cl: 8.32%, N: 7.86%, S: 1.64%<br>Found: C: 50.46%, H: 5.36%, Cl: 8.25%, N: 6.91%, S: 1.47% |
| 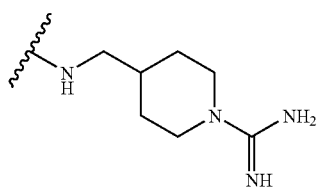 [SMILES: *NCC1CCN(C(=N)N)CC1] | | H | H [M + 3]⁺ = 1866<br>[M + 1]⁻ = 1864 | Calcd. for C87H98Cl4N14O24•2.1HCl•8.6H2O<br>C: 49.83%, H: 5.64%, Cl: 10.31%, N: 9.35%<br>Found: C: 50.09%, H: 5.64%, Cl: 10.24%, N: 8.33% |
| 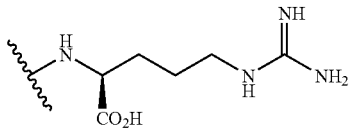 [SMILES: *N[C@@H](CCCNC(=N)N)C(=O)O] | | H | H [M + 3]⁺ = 1883<br>[M + 1]⁻ = 1881 | Calcd. for C86H96Cl4N14O26•2.5HCl•9.2H2O<br>C: 48.26%, H: 5.50%, Cl: 10.77%, N: 9.16%<br>Found: C: 48.41%, H: 5.46%, Cl: 10.68%, N: 8.60% |
| 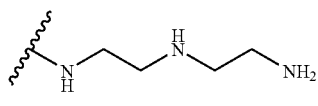 [SMILES: *NCCNCCN] | | H | H [M + 3]⁺ = 1812<br>[M + 1]⁻ = 1810 | Calcd. for C84H95Cl4N13O24•3.2HCl•9.7H2O<br>C: 47.95%, H: 5.63%, Cl: 12.13%, N: 8.65%<br>Found: C: 48.03%, H: 5.56%, Cl: 11.91%, N: 8.39% |
| 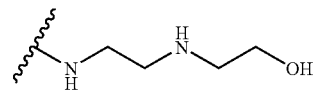 [SMILES: *NCCNCCO] | | H | H [M + 3]⁺ = 1813<br>[M + 1]⁻ = 1811 | Calcd. for C84H94Cl4N12O25•2.6HCl•9.5H2O<br>C: 48.52%, H: 5.60%, Cl: 11.25%, N: 8.08%<br>Found: C: 48.48%, H: 5.52%, Cl: 11.27%, N: 8.00% |

TABLE 51

| | | | | |
|---|---|---|---|---|
| OH | 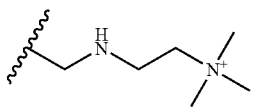 [SMILES: *CNCC[N+](C)(C)C] | H | [M + 3]⁺ = 1842<br>[M + 1]⁻ = 1840 | Calcd. for C86H99Cl4N12O25•4HCl•10H2O<br>C: 56.06%, H: 5.42%, N: 9.12%, Cl: 7.70%<br>Found: C: 46.85%, H: 5.58%, N: 7.84%, Cl: 12.74% |
| OH | 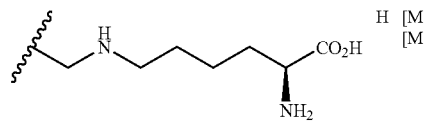 | H | [M + 3]⁺ = 1885<br>[M + 1]⁻ = 1883 | Calcd. for C87H98Cl4N12O27•4HCl•10H2O<br>C: 55.42%, H: 5.24%, N: 8.91%, Cl: 7.52%<br>Found: C: 47.10%, H: 5.51%, N: 7.75%, Cl: 12.81% |
| OH | 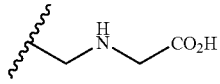 [SMILES: *CNCC(=O)O] | H | [M + 3]⁺ = 1814<br>[M + 1]⁻ = 1812 | Calcd. for C83H89Cl4N11O27•3HCl•12H2O<br>C: 54.94%, H: 4.94%, N: 8.49%, Cl: 7.82%<br>Found: C: 46.74%, H: 5.30%, N: 7.42%, Cl: 11.41% |

TABLE 52

| | $R^A$ | $R^B$ | $R^C$ | $R^D$ |
|---|---|---|---|---|
| | Ar₁ = 3-methylbenzyl; Ar₂ = 3,5-dichlorophenyl (X₂ = X₃ = bond) | OH or NRR' | H or CH₂—NRR' | H |

| $R^B$ | $R^C$ | $R^D$ | Mass | Elemetal Analysis |
|---|---|---|---|---|
| —N[(CH₂)₂OH]₂ | H | H | [M + 3]⁺ = 1858<br>[M + 1]⁻ = 1856 | Calcd. for C87H99Cl2F3N12O26•3.7HCl•11.4H2O<br>C: 47.56%, H: 5.76%, N: 7.65%, Cl: 9.20%, F: 2.59%<br>Found: C: 47.72%, H: 5.59%, N: 7.88%, Cl: 9.25%, F: 2.29% |
| —NH(CH₂)₃NMe₂ | H | H | [M + 3]⁺ = 1855<br>[M + 1]⁻ = 1853 | Calcd. for C88H102Cl2F3N13O24•3.6HCl•10.5H2O<br>C: 48.61%, H: 5.87%, N: 8.38%, Cl: 9.13%, F: 2.62%<br>Found: C: 48.55%, H: 5.75%, N: 8.52%, Cl: 9.16%, F: 2.47% |
| —NH(CH₂)₂N⁺Me₃ | H | H | [M + 3]⁺ = 1855<br>[M + 1]⁻ = 1853 | Calcd. for C88H103Cl3F3N13O24•2.7HCl•12.3H2O<br>C: 47.82%, H: 5.94%, N: 8.24%, Cl: 9.14%, F: 2.58%<br>Found: C: 47.82%, H: 5.85%, N: 8.34%, Cl: 9.11%, F: 2.47% |
| —NHCH₂CO₂H | H | H | [M + 1]⁻ = 1825 | Calcd. for C85H93Cl2F3N12O26•2.6HCl•11.7H2O<br>C: 47.88%, H: 5.63%, N: 7.88%, Cl: 7.65%, F: 2.67%<br>Found: C: 47.91%, H: 5.64%, N: 7.97%, Cl: 7.69%, F: 2.52% |
| —NH(CH₂)₂CO₂H | H | H | [M + 3]⁺ = 1842<br>[M + 1]⁻ = 1840 | Calcd. for C86H95Cl2F3N12O26•2.0HCl•8.9H2O<br>C: 49.81%, H: 5.58%, N: 8.10%, Cl: 6.84%, F: 2.75%<br>Found: C: 49.78%, H: 5.58%, N: 8.29%, Cl: 6.90%, F: 2.57% |

TABLE 53

| $R^B$ | $R^C$ | $R^D$ | Mass | Elemetal Analysis |
|---|---|---|---|---|
| —NH—CH₂—C(O)—N⁺(CH₃)₃ (glycine betaine-linked) | H | H | [M + 3]⁺ = 1884<br>[M + 1]⁻ = 1882 | Calcd. for C88H101Cl2F3N14O25•3.6HCl•11.1H2O<br>C: 47.74%, H: 5.77%, N: 8.86%, Cl: 8.97%, F: 2.57%<br>Found: C: 47.70%, H: 5.73%, N: 8.99%, Cl: 8.93%, F: 2.45% |
| glucosamine-linked (NH-pyranose with 3 OH, CH₂OH) | H | H | [M + 1]⁻ = 1929 | Calcd. for C89H101Cl2F3N12O29•2.5HCl•10.7H2O<br>C: 48.27%, H: 5.68%, N: 7.59%, Cl: 7.20%, F: 2.57%<br>Found: C: 48.21%, H: 5.63%, N: 7.74%, Cl: 7.21%, F: 2.46% |
| N-methyl-glucamine-linked (N(CH₃)CH₂(CHOH)₄CH₂OH) | H | H | [M + 1]⁻ = 1945 | Calcd. for C90H105Cl2F3N12O29•2.9HC.10.9H2O<br>C: 48.14%, H: 5.80%, N: 7.49%, Cl: 7.74%, F: 2.54%<br>Found: C: 48.03%, H: 5.79%, N: 7.83%, Cl: 7.68%, F: 2.32% |
| aspartate-linked (—NH—CH(CO₂H)—CH₂—CO₂H) | H | H | [M + 1]⁻ = 1884 | Calcd. for C87H95Cl2F3N12O28•2.8HCl•10.8H2O<br>C: 47.90%, H: 5.52%, N: 7.71%, Cl: 7.80%, F: 2.61%<br>Found: C: 47.87%, H: 5.39%, N: 7.77%, Cl: 7.82%, F: 2.50% |
| lysine-linked (—NH—(CH₂)₄—CH(NH₂)—CO₂H) | H | H | [M + 3]⁺ = 1899<br>[M + 1]⁻ = 1897 | Calcd. for C89H102Cl2F3N13O26•3.5HCl•12.1H2O<br>C: 47.65%, H: 5.83%, N: 8.12%, Cl: 8.69%, F: 2.54%<br>Found: C: 47.62%, H: 5.67%, N: 8.24%, Cl: 8.61%, F: 2.34% |

TABLE 53-continued

| R group | | | | Mass data | Elemental analysis |
|---|---|---|---|---|---|
| OH | -CH2CH2-NH-CH2CH2-CO2H | | H | [M + 3]$^+$ = 1871<br>[M + 1]$^-$ = 1869 | Calcd. for<br>C87H97Cl2F3N12O27•3.5HCl•12.5H2O<br>C: 55.86%, H: 5.23%, N: 8.99%,<br>Cl: 3.79%, F: 3.05%<br>Found: C: 46.95%, H: 5.53%, N: 7.70%,<br>Cl: 8.71%, F: 2.34% |
| OH | -CH2CH2-N(CH2CH2OH)2 | | H | [M + 1]$^-$ = 1885 | Calcd. for<br>C88H101Cl2F3N12O27•13HCl•3H2O<br>C: 56.02%, H: 5.40%, N: 8.91%,<br>Cl: 3.76%, F: 3.02%<br>Found: C: 47.50%, H: 5.72%, N: 7.74%,<br>Cl: 8.10%, F: 2.38% |
| OH | -CH2CH2-NH-CH2CH2-SO3H | | H | [M + 3]$^+$ = 1907<br>[M + 1]$^-$ = 1905 | Calcd. for<br>C86H97Cl2F3N12O28S•2HCl•11H2O<br>C: 54.17%, H: 5.13%, N: 8.82%,<br>Cl: 3.72%, F: 2.99%, S: 1.69%<br>Found: C: 47.61%, H: 5.52%, N: 7.82%,<br>Cl: 6.47%, F: 2.52%, S: 1.26% |
| OH | -CH2CH2-NH-CH2-PO(OH)2 | | H | [M + 3]$^+$ = 1893<br>[M + 1]$^-$ = 1891 | Calcd. for<br>C85H96Cl2F3N12O28P•2.5HCl•11H2O<br>C: 53.94%, H: 5.11%, N: 8.88%,<br>Cl: 3.75%, F: 3.01%<br>Found: C: 46.84%, H: 5.54%, N: 7.73%,<br>Cl: 7.24%, F: 2.48% |

TABLE 54

| R group | | | | Mass data | Elemental analysis |
|---|---|---|---|---|---|
| OH | -CH2CH2-NH-C(O)-CH2-N(-)-N$^+$(CH3)3 | | H | [M + 3]$^+$ = 1913<br>[M + 1]$^-$ = 1911 | Calcd. for<br>C89H103Cl2F3N14O26•3HCl•12H2O<br>C: 55.89%, H: 5.43%, N: 10.25%,<br>Cl: 3.71%, F: 2.98%<br>Found: C: 47.52%, H: 5.81%,<br>N: 9.21%, Cl: 8.16%, F: 2.29% |
| OH | -CH2CH2-NH-CH2-(4-piperidinyl-N-C(=NH)NH2) | | H | [M + 3]$^+$ = 1938<br>[M + 1]$^-$ = 1936 | Calcd. for<br>C91H106Cl2F3N15O25•3.5HCl•11H2O<br>C: 56.40%, H: 5.51%, N: 10.84%,<br>Cl: 3.66%, F: 2.94%<br>Found: C: 48.07%, H: 5.93%,<br>N: 9.67%, Cl: 8.48%, F: 2.27% |
| OH | -CH2CH2-N(CH3)-CH2-[CH(OH)]4-CH2OH | | H | [M + 3]$^+$ = 1977<br>[M + 1]$^-$ = 1975 | Calcd. for<br>C91H107Cl2F3N12O30•3HCl•12H2O<br>C: 55.29%, H: 5.46%, N: 8.50%,<br>Cl: 3.59%, F: 2.88%<br>Found: C: 47.42%, H: 5.89%,<br>N: 7.42%, Cl: 7.42%, F: 2.36% |
| OH | -CH2CH2-NH-CH(CO2H)-CH2-C(O)NH2 | | H | [M + 3]$^+$ = 1914<br>[M + 1]$^-$ = 1912 | Calcd. for<br>C88H98Cl2F3N13O28•3HCl•13H2O<br>C: 55.23%, H: 5.16%, N: 9.51%,<br>Cl: 3.71%, F: 2.98%<br>Found: C: 46.77%, H: 5.47%,<br>N: 8.16%, Cl: 7.95%, F: 2.43% |
| -NH-CH2CH2-SO3H | | | H | [M + 3]$^+$ = 1877<br>[M + 1]$^-$ = 1875 | Calcd. for<br>C85H95Cl2F3N12O27S•2HCl•10H2O<br>C: 54.40%, H: 5.10%, N: 8.96%,<br>Cl: 3.78%, F: 3.04%, S: 1.71%<br>Found: C: 48.06%, H: 5.37%,<br>N: 8.11%, Cl: 6.77%, F: 2.58%,<br>S: 1.35% |

Example 12

The following compounds were prepared in a similar manner as described above.

TABLE 55

| R$^A$ | R$^B$ | R$^C$ | R$^D$ |
|---|---|---|---|
| (structure: X$_1$–Ar$_1$–X$_2$–Y–X$_3$–Ar$_2$) | OH | H | H |

Y = CO—NR
    NR—CO

R$^A$

| Ar2 | X3 | Y | X2 | Ar1 | X1 | Mass | Elemental Analysis |
|---|---|---|---|---|---|---|---|
| 2-Me, 5-attach phenyl with 3-OCH$_2$-benzotriazol-1-yl | bond | CONH | bond | pyridine-2,4-diyl | CH2 | [M + 3]$^+$ = 1820<br>[M + 1]$^-$ = 1818 | calcd. for C88H93Cl2N13O26•1.8HCl•10.6H2O<br>C: 50.91%, H: 5.63%, N: 8.77%, Cl: 6.49%<br>found: C: 50.91%, H: 5.55%, N: 8.77%, Cl: 6.50% |
| 2-Me, 5-attach phenyl with 3-OCH$_2$-furan-2-yl | bond | CONH | bond | 1,3-phenylene | CH2 | [M + 1]$^-$ = 1797 | calcd. for C87H94Cl2N10O26S•1.7HCl•9.8H2O<br>C: 51.29%, H: 5.70%, N: 6.88%, Cl: 6.44%, S: 1.57%<br>found: C: 51.26%, H: 5.67%, N: 6.93%, Cl: 6.39%, S: 1.38% |
| 3-OCF$_3$-phenyl | bond | CONH | bond | (3R)-pyrrolidine-1,3-diyl | CH2CH2 | [M + 3]$^+$ = 1750 | calcd. for C80H90Cl2F3N11O26•1.9HCl•11.2H2O<br>C: 47.55%, H: 5.70%, N: 7.63%, Cl: 6.84%, F: 2.82<br>found: C: 47.46%, H: 5.60%, N: 7.80%, Cl: 6.84%, F: 2.45 |

TABLE 56

| Ar2 | X3 | Y | X2 | Ar1 | X1 | Mass | Elemental Analysis |
|---|---|---|---|---|---|---|---|
| 3-OCF$_3$-phenyl | bond | CONH | bond | 2-oxo-pyrimidine-1,4-diyl | CH2CH2 | [M + 1]$^-$ = 1773 | calcd. for C80H85Cl2F3N12O27•2.1HCl•13.5H2O<br>C: 45.88%, H: 5.49%, N: 8.03%, Cl: 6.94%, F: 2.72<br>found: C: 45.85%, H: 5.30%, N: 8.03%, Cl: 6.92%, F: 2.96 |
| 4-OCF$_3$-phenyl | bond | CONH | bond | 2-oxo-pyrimidine-1,4-diyl | CH2CH2 | [M + 1]$^-$ = 1773 | calcd. for C80H85Cl2F3N12O27•2.1HCl•4.3H2O<br>C: 45.57%, H: 5.53%, N: 7.97%, Cl: 6.89%, F: 2.70<br>found: C: 45.52%, H: 5.28%, N: 7.98%, Cl: 6.85%, F: 2.56 |
| 3,5-dichlorophenyl | bond | CONH | bond | 2-oxo-pyrimidine-1,4-diyl | CH2CH2 | [M + 1]$^-$ = 1759 | calcd. for C79H84Cl4N12O26•2.1HCl•14.2H2O<br>C: 45.36%, H: 5.52%, N: 8.04%, Cl: 10.34%<br>found: C: 45.23%, H: 5.46%, N: 8.34%, Cl: 10.29% |

TABLE 56-continued

| Structure | | | | | | | |
|---|---|---|---|---|---|---|---|
| 3-(Me₂N)(CF₃)-phenyl | bond | CONH | bond | pyrimidinone (N-linked) | CH2CH2 | [M + 3]⁺ = 1803 | calcd. for C82H90Cl2F3N13O26•3.0HCl•12.0H2O C: 46.30%, H: 5.54%, N: 8.56%, Cl: 8.33%, F: 2.68 found: C: 46.25%, H: 5.54%, N: 8.71%, Cl: 8.25%, F: 2.89 |
| 4-(SCF₃)-phenyl | bond | CONH | bond | pyrimidinone | CH2CH2 | [M + 3]⁺ = 1792 | calcd. for C80H85Cl2F3N12O26S•1.4HCl•12.6H2O C: 46.45%, H: 5.44%, N: 8.13%, Cl: 5.83%, S: 1.55%, F: 2.76% found: C: 46.44%, H: 5.36%, N: 8.16%, Cl: 5.81%, S: 1.58%, F: 2.88% |
| 4-(O-butyl)-phenyl | bond | CONH | bond | pyrimidinone | CH2CH2 | [M + 3]⁺ = 1764 | calcd. for C83H94Cl2N12O27•1.2HCl•11.8H2O C: 49.38%, H: 5.93%, N: 8.33%, Cl: 5.62% found: C: 49.35%, H: 5.85%, N: 8.47%, Cl: 5.58% |

TABLE 57

| Structure | | | | | | | |
|---|---|---|---|---|---|---|---|
| 3-(OCF₂CHF₂)-phenyl | bond | CONH | bond | pyrimidinone | CH2CH2 | [M + 3]⁺ = 1808 | calcd. for C81H86Cl2F4N12O27•1.7HCl•11.2H2O C: 46.99, H: 5.36%, N: 8.12%, Cl: 6.34%, F: 3.67 found: C: 46.97%, H: 5.30%, N: 8.23%, Cl: 6.36%, F: 3.70 |
| 3,5-diMe-phenyl | bond | CONH | bond | pyrimidinone | CH2CH2 | [M + 3]⁺ = 1720 | calcd. for C81H90Cl2N12O26•1.1HCl•11.0H2O C: 49.72, H: 5.83%, N: 8.59%, Cl: 5.62% found: C: 49.69%, H: 5.72%, N: 8.65%, Cl: 5.61% |
| 3-(OCF₃)-phenyl | bond | CONH | bond | 5-F-pyrimidinone | CH2CH2 | [M + 1]⁻ = 1793 | calcd. for C80H84Cl2F4N12O27•2.0HCl•13.8H2O C: 45.45, H: 5.42%, N: 7.95%, Cl: 6.71%, F: 3.59 found: C: 45.46%, H: 5.39%, N: 8.10%, Cl: 6.75%, F: 3.06 |
| 3-(OCF₃)-phenyl | bond | CONH | bond | 5-Me-pyrimidinone | CH2CH2 | [M + 3]⁺ = 1790 | calcd. for C81H87Cl2F3N12O27•2.1HCl•11.0H2O C: 47.15, H: 5.43%, N: 8.15%, Cl: 7.05%, F: 2.76 found: C: 47.14%, H: 5.44%, N: 8.27%, Cl: 7.09%, F: 2.75 |
| 3-(OCF₃)-phenyl | bond | CONH | bond | tetrahydropyrimidinone | CH2CH2CH2 | [M + 3]⁺ = 1794 | calcd. for C81H91Cl2F3N12O27•1.8HCl•14.3H2O C: 45.98, H: 5.78%, N: 7.94%, Cl: 6.37%, F: 2.69 found: C: 45.97%, H: 5.88%, N: 7.81%, Cl: 6.45%, F: 2.35 |

TABLE 57-continued

| Ar2 | X3 | Y | X2 | Ar1 | X1 | Mass | Elemental Analysis |
|---|---|---|---|---|---|---|---|
| 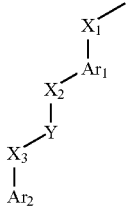 (3-OCF3 phenyl) | bond | CONH | bond | 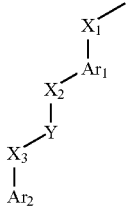 | CH2CH2CH2 | [M + 3]+ = 1790 | calcd. for C81H87Cl2F3N12O27•2.2HCl•13.4H2O C: 46.10, H: 5.54%, N: 7.97%, Cl: 7.06%, F: 2.70 found: C: 46.07%, H: 5.50%, N: 7.99%, Cl: 7.13%, F: 2.54 |

TABLE 58

| Ar2 | X3 | Y | X2 | Ar1 | X1 | Mass | Elemental Analysis |
|---|---|---|---|---|---|---|---|
| 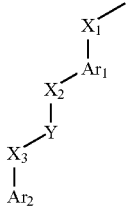 (3,4-diCl phenyl) | CH2 | CONH | bond | 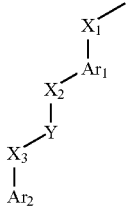 | CH2CH2 | [M + 3]+ = 1774 | calcd. for C80H86Cl4N12O26•1.5HCl•11.7H2O C: 47.13, H: 5.48%, N: 8.24%, Cl: 9.56% found: C: 47.12%, H: 5.39%, N: 8.39%, Cl: 9.51% |
| 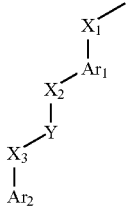 (4-OCF3 phenyl) | CH2 | CONH | bond | 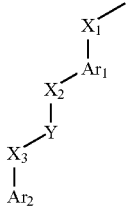 | CH2CH2 | [M + 3]+ = 1790 | calcd. for C81H87Cl2F3N12O27•1.8HCl•11.0H2O C: 47.40, H: 5.44%, N: 8.19%, Cl: 6.56%, F: 2.78 found: C: 47.32%, H: 5.34%, N: 8.40%, Cl: 6.54%, F: 2.79 |

TABLE 59

| R$^A$ | R$^B$ | R$^C$ | R$^D$ |
|---|---|---|---|
| 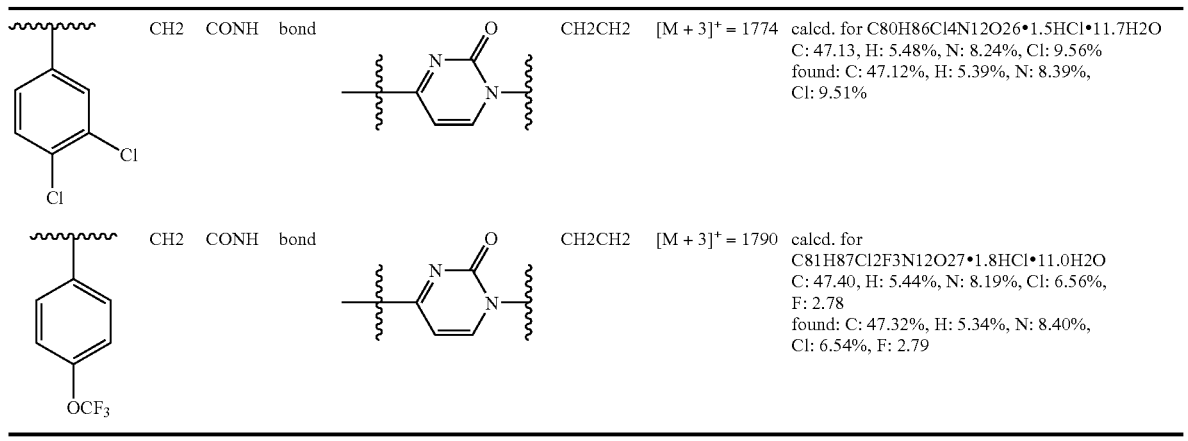 Y = CO—NR / NR—CO | OH | H | H |

R$^A$

| Ar2 | X3 | Y | X2 | Ar1 | X1 | Mass | Elemental Analysis |
|---|---|---|---|---|---|---|---|
| 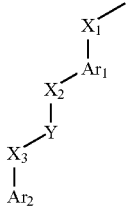 | bond | CONH | bond | 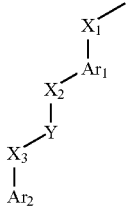 | CH2 | [M + 3]+ = 1789 [M + 1]− = 1787 | calcd. for C87H100Cl2N10O27•1.7HCl•13.2H2O C: 50.03%, H: 6.18%, N: 6.71%, Cl: 6.28% found: C: 49.98%, H: 6.06%, N: 6.80%, Cl: 6.21% |

TABLE 59-continued

| Structure 1 | L1 | L2 | L3 | Structure 2 | L4 | MS | Analysis |
|---|---|---|---|---|---|---|---|
| 4-cyanobenzyloxy-methylphenyl | bond | CONH | bond | 1,3-phenylene | CH2 | [M + 1]⁻ = 1802 | calcd. for C89H93Cl2N11O26•1.9HCl•13.0H2O<br>C: 50.73%, H: 5.78%, N: 7.31%, Cl: 6.56%<br>found: C: 50.67%, H: 5.55%, N: 7.38%, Cl: 6.52% |

TABLE 60

| Structure 1 | L1 | L2 | L3 | Structure 2 | L4 | MS | Analysis |
|---|---|---|---|---|---|---|---|
| 3-(dimethylamino)-5-trifluoromethylphenyl | bond | NHCO | NH | 1,3-phenylene | CH2 | [M + 1]⁻ = 1784 | calcd. for C83H91Cl2F3N12O25•2.3HCl•16.4H2O<br>C: 46.07%, H: 5.87%, N: 7.77%, Cl: 7.05%, F: 2.63%<br>found: C: 46.02%, H: 5.73%, N: 7.79%, Cl: 7.13%, F: 2.60% |
| 4-trifluoromethoxyphenyl | bond | NHCO | NH | 1,3-phenylene | CH2 | [M + 1]⁻ = 1757 | calcd. for C81H86Cl2F3N11O26•1.8HCl•11.5H2O<br>C: 47.92%, H: 5.50%, N: 7.59%, Cl: 6.64%, F: 2.81%<br>found: C: 47.92%, H: 5.58%, N: 7.64%, Cl: 6.57%, F: 2.80% |
| 3-trifluoromethoxyphenyl | bond | NHCO | NH | 1,3-phenylene | CH2 | [M + 1]⁻ = 1757 | calcd. for C81H86Cl2F3N11O26•2.0HCl•13.5H2O<br>C: 46.92%, H: 5.59%, N: 7.43%, Cl: 6.84%, F: 2.75%<br>found: C: 46.94%, H: 5.64%, N: 7.43%, Cl: 6.87%, F: 2.76% |
| 3-trifluoromethoxyphenyl | bond | CONH | bond | tetrahydropyrimidin-2-one-4,1-diyl | CH2CH2 | [M + 1]⁻ = 1777 | calcd. for C80H89Cl2F3N12O27•1.4HCl•11.9H2O<br>C: 47.01%, H: 5.63%, N: 8.22%, Cl: 5.90%, F: 2.79%<br>found: C: 47.17%, H: 5.59%, N: 7.64%, Cl: 5.93%, F: 2.66% |

TABLE 61

| Structure 1 | L1 | L2 | L3 | Structure 2 | L4 | MS | Analysis |
|---|---|---|---|---|---|---|---|
| 3,5-dimethyl-4-methoxyphenyl | bond | CONH | bond | pyrimidin-2-one-4,1-diyl | CH2CH2 | [M + 1]⁻ = 1747 | calcd. for C82H92Cl2N12O27•1.9HCl•15.0H2O<br>C: 47.17%, H: 5.98%, N: 8.05%, Cl: 6.62%<br>found: C: 47.18%, H: 5.82%, N: 8.16%, Cl: 6.54% |

TABLE 61-continued

| Ar | | | | | Linker | MS | Analysis |
|---|---|---|---|---|---|---|---|
| 3-CF₃-4-F-phenyl | bond | CONH | bond | pyrimidinone (N,C) | CH2CH2 | [M + 1]⁻ = 1776 | calcd. for C80H84Cl2F4N12O26•1.3HCl•14.6H2O<br>C: 46.04%, H: 5.53%, N: 8.05%, Cl: 5.61%, F: 3.64%<br>found: C: 45.98%, H: 5.33%, N: 8.04%, Cl: 5.62%, F: 3.53% |
| 3-Cl-4-F-phenyl | bond | CONH | bond | pyrimidinone | CH2CH2 | [M + 1]⁻ = 1742 | calcd. for C79H84Cl3FN12O26•1.5HCl•13.9H2O<br>C: 46.33%, H: 5.58%, N: 8.21%, Cl: 7.79%, F: 0.93%<br>found: C: 46.32%, H: 5.54%, N: 8.27%, Cl: 7.75%, F: 0.95% |
| 3-F-4-Cl-phenyl | bond | CONH | bond | pyrimidinone | CH2CH2 | [M + 1]⁻ = 1742 | calcd. for C79H84Cl3FN12O26•1.2HCl•14.7H2O<br>C: 46.25%, H: 5.63%, N: 8.19%, Cl: 7.26%, F: 0.93%<br>found: C: 46.21%, H: 5.49%, N: 8.28%, Cl: 7.26%, F: 1.03% |

TABLE 62

| Ar | | | | | Linker | MS | Analysis |
|---|---|---|---|---|---|---|---|
| 3-Me-4-F-phenyl | bond | CONH | bond | pyrimidinone | CH2CH2 | [M + 1]⁻ = 1722 | calcd. for C80H87Cl2FN12O26•1.9HCl•13.8H2O<br>C: 47.09%, H: 5.75%, N: 8.24%, Cl: 6.78%, F: 0.93%<br>found: C: 47.07%, H: 5.65%, N: 8.38%, Cl: 6.79%, F: 1.11% |
| 3,4-diCl-phenyl | bond | CONH | bond | pyrimidinone | CH2CH2 | [M + 1]⁻ = 1757 | calcd. for C79H84Cl4N12O26•1.8HCl•13.0H2O<br>C: 46.08%, H: 5.47%, N: 8.16%, Cl: 9.99%<br>found: C: 46.03%, H: 5.31%, N: 8.27%, Cl: 9.94% |
| 4-(OCH2CF3)-phenyl | bond | CONH | bond | pyrimidinone | CH2CH2 | [M + 1]⁻ = 1787 | calcd. for C81H87Cl2F3N12O27•1.7HCl•13.9H2O<br>C: 46.31%, H: 5.59%, N: 8.00%, Cl: 6.24%, F: 2.71%<br>found: C: 46.26%, H: 5.57%, N: 8.15%, Cl: 6.27%, F: 2.78% |
| 3-CF₃-5-F-phenyl | bond | CONH | bond | pyrimidinone | CH2CH2 | [M + 1]⁻ = 1775 | calcd. for C80H84Cl2F4N12O26•1.9HCl•12.2H2O<br>C: 46.52%, H: 5.38%, N: 8.14%, Cl: 6.69%, F: 3.68%<br>found: C: 46.54%, H: 5.29%, N: 8.30%, Cl: 6.68%, F: 3.61% |

TABLE 63

| R^A | R^B | R^C | R^D | X1 | Mass | Elemental Analysis |
|---|---|---|---|---|---|---|
| 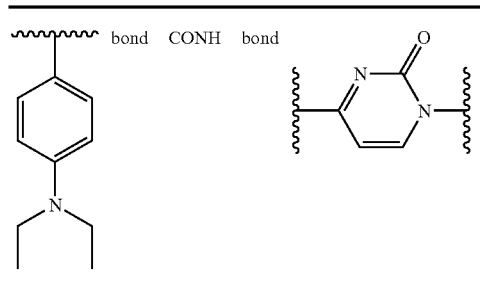 | | | | CH2CH2 | [M + 1]⁻ = 1760 | calcd. for C83H95Cl2N13O26•1.8HCl•12.2H2O<br>C: 48.70%, H: 5.97%, N: 8.90%, Cl: 6.58%<br>found: C: 48.68%, H: 5.89%, N: 9.05%, Cl: 6.49% |

TABLE 64

| R^A | R^B | R^C | R^D |
|---|---|---|---|
| 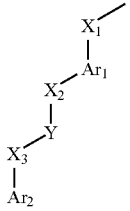 $Y = \begin{array}{c} CO-NR \\ NR-CO \end{array}$ | OH | H | H |

R^A

| Ar2 | X3 | Y | X2 | Ar1 | X1 | Mass | Elemental Analysis |
|---|---|---|---|---|---|---|---|
| 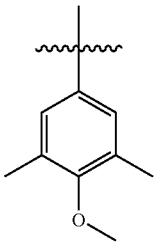 | bond | CONH | bond | 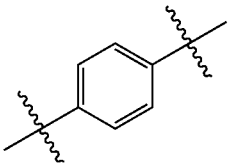 [SMILES: *c1ccc(*)cc1] | CH2 | [M + 3]⁺ = 1718 | calcd. for C83H92Cl2N10O26•1.0HCl•12.4H2O<br>C: 50.25%, H: 5.96%, N: 7.06%, Cl: 6.08%<br>found: C: 50.26%, H: 5.86%, N: 7.17%, Cl: 6.15% |
| 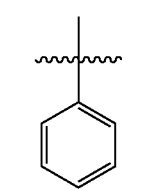 | bond | CONH | bond | 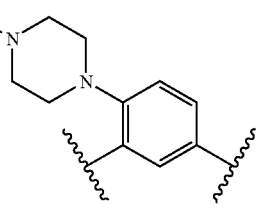 | CH2 | [M + 1]⁻ = 1756 | calcd. for C85H96Cl2N12O25•2.4HCl•13.2H2O<br>C: 49.04%, H: 6.04%, N: 8.07%, Cl: 7.49%<br>found: C: 49.02%, H: 5.86%, N: 8.10%, Cl: 7.50% |
| 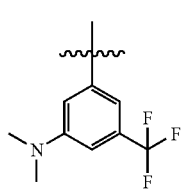 [SMILES: *c1cc(N(C)C)cc(C(F)(F)F)c1] | bond | CONH | bond | 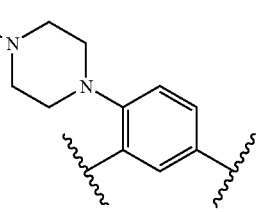 | CH2 | [M + 1]⁻ = 1867 | calcd. for C88H100Cl2F3N13O25•3.1HCl•11.8H2O<br>C: 48.19%, H: 5.82%, N: 8.30%, Cl: 8.24%, F: 2.60%<br>found: C: 48.20%, H: 5.78%, N: 8.30%, Cl: 8.29%, F: 2.46% |

TABLE 65

| | | | | | | | |
|---|---|---|---|---|---|---|---|
| 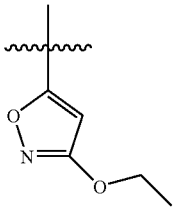 [SMILES: *c1cc(OCC)no1] | bond | CONH | bond | 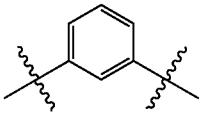 [SMILES: *c1cccc(*)c1] | CH2 | [M + 1]⁻ = 1692 | calcd. for C79H87Cl2N11O27•1.9HCl•11.2H2O C: 48.30%, H: 5.71%, N: 7.84%, Cl: 7.04% found: C: 48.29%, H: 5.58%, N: 7.81%, Cl: 6.96% |
| 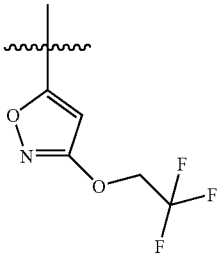 [SMILES: *c1cc(OCC(F)(F)F)no1] | bond | CONH | bond | 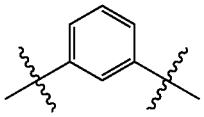 | CH2 | [M + 1]⁻ = 1746 | calcd. for C79H84Cl2F3N11O27•1.6HCl•9.9H2O C: 47.82%, H: 5.35%, N: 7.77%, Cl: 6.43%, F: 2.87% found: C: 47.79%, H: 5.18%, N: 7.79%, Cl: 6.51%, F: 2.76% |
| 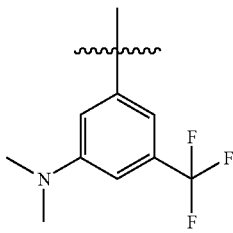 [SMILES: *c1cc(N(C)C)cc(C(F)(F)F)c1] | bond | CONH | bond | 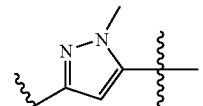 | CH2 | [M + 3]⁺ = 1774 [M + 1]⁻ = 1772 | calcd. for C81H90Cl2F3N13O25•2.7HCl•10.7H2O C: 47.12%, H: 5.57%, N: 8.82%, Cl: 8.07%, F: 2.76% found: C: 47.13%, H: 5.40%, N: 8.83%, Cl: 8.02%, F: 2.65% |
| 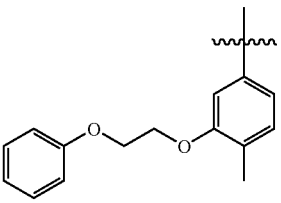 [SMILES: *c1ccc(C)c(OCCOc2ccccc2)c1] | bond | CONH | bond | 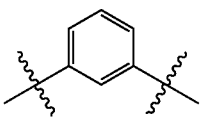 [SMILES: *c1cccc(*)c1] | CH2 | [M + 1]⁻ = 1808 | calcd. for C89H96Cl2N10O27•1.5HCl•11H2O C: 51.85%, H: 5.84%, N: 6.79%, Cl: 6.02% found: C: 51.89%, H: 5.59%, N: 6.77%, Cl: 5.99% |
| 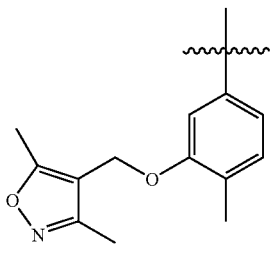 [SMILES: *c1ccc(C)c(OCc2c(C)noc2C)c1] | bond | CONH | bond | 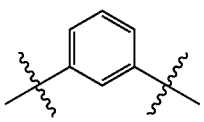 [SMILES: *c1cccc(*)c1] | CH2 | [M + 1]⁻ = 1797 | calcd. for C87H95Cl2N11O27•1.7HCl•11.2H2O C: 50.69%, H: 5.82%, N: 7.47%, Cl: 6.36% found: C: 50.72%, H: 5.78%, N: 7.46%, Cl: 6.33% |

TABLE 66

| | | | | | | | |
|---|---|---|---|---|---|---|---|
| 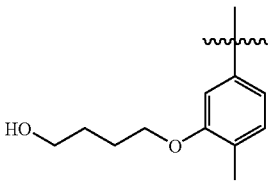 [SMILES: *c1ccc(C)c(OCCCCO)c1] | bond | CONH | bond | 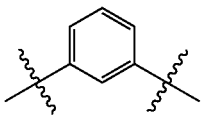 [SMILES: *c1cccc(*)c1] | CH2 | [M + 1]⁻ = 1759 | calcd. for C82H87Cl2F3N10O26•1.9HCl•11.1H2O C: 51.07%, H: 5.94%, N: 7.01%, Cl: 6.21% found: C: 51.07%, H: 5.75%, N: 7.12%, Cl: 6.17% |

TABLE 66-continued

| Structure | | | | | | |
|---|---|---|---|---|---|---|
| (3-methoxy-3-methylbutoxy-methylphenyl) | bond | CONH | bond | (phenyl) | CH2 | [M + 1]⁻ = 1787    calcd. for C87H100Cl2N10O27•2HCl•10.2H2O<br>C: 51.09%, H: 6.03%, N: 6.85%, Cl: 6.93%<br>found: C: 51.06%, H: 5.98%, N: 6.95%, Cl: 6.87% |
| (2-ethylbutoxy-methylphenyl) | bond | CONH | bond | (phenyl) | CH2 | [M + 1]⁻ = 1771    calcd. for C87H100Cl2N10O26•1.6HCl•9.7H2O<br>C: 52.10%, H: 6.08%, N: 6.98%, Cl: 6.36%<br>found: C: 52.09%, H: 6.07%, N: 7.11%, Cl: 6.33% |
| (N-ethyl-N-phenylaminoethoxy-methylphenyl) | bond | CONH | bond | (phenyl) | CH2 | [M + 1]⁻ = 1835    calcd. for C91H101Cl2N11O26•2.8HCl•10.6H2O<br>C: 51.34%, H: 5.92%, N: 7.24%, Cl: 7.99%<br>found: C: 51.28%, H: 5.84%, N: 7.47%, Cl: 7.91% |
| (phenyl) | bond | CONH | bond | (pyridyl) | CH2 | [M + 3]⁺ = 1658<br>[M + 1]⁻ = 1660    calcd for C82H87Cl2F3N10O26•1.9HCl•11.1H2O<br>C: 48.83%, H: 5.73%, N: 7.93%, Cl: 7.30%<br>found: C: 48.85%, H: 5.66%, N: 7.85%, Cl: 7.31% |

TABLE 67

| Structure | | | | | | |
|---|---|---|---|---|---|---|
| (isothiazolyl-O-CH2CF3) | bond | CONH | bond | (phenyl) | CH2 | [M + 1]⁻ = 1762    calcd. for C79H84Cl2F3N11O26S•1.4HCl•11.1H2O<br>C: 47.10%, H: 5.38%, N: 7.65%, Cl: 5.98%, F: 2.83%, S: 1.59%<br>found: C: 47.09%, H: 5.37%, N: 7.60%, Cl: 5.92%, F: 2.74%, S: 1.50% |
| (4-(2,2,2-trifluoroethoxy)phenyl) | bond | CONH | bond | (phenyl) | CH2 | [M + 1]⁻ = 1755    calcd. for C82H87Cl2F3N10O26•1.9HCl•11.1H2O<br>C: 48.36%, H: 5.62%, N: 6.88%, Cl: 6.09%, F: 2.80%<br>found: C: 48.32%, H: 5.53%, N: 6.96%, Cl: 6.06%, F: 2.78% |

TABLE 67-continued

| Structure 1 | | | | Structure 2 | | | | Analysis |
|---|---|---|---|---|---|---|---|---|
| 3-OCF₃-phenyl | bond | CONH | bond | pyridine (2,4-diyl) | CH2 | | [M + 1]⁻ = 1743 | calcd. for C82H87Cl2F3N10O26•1.9HCl•11.1H2O<br>C: 48.22%, H: 5.46%, N: 7.73%, Cl: 5.69%, F: 2.86%<br>found: C: 48.19%, H: 5.36%, N: 7.78%, Cl: 5.76%, F: 2.74% |
| 3-OCF₃-phenyl | bond | NHCO | bond | thiophene (2,5-diyl) | CH2 | | [M + 1]⁻ = 1748 | calcd. for C82H87Cl2F3N10O26•1.9HCl•11.1H2O<br>C: 46.08%, H: 5.45%, N: 6.80%, Cl: 6.89%, F: 2.77%, S: 1.56<br>found: C: 46.04%, H: 5.35%, N: 6.96%, Cl: 6.94%, F: 2.65%, S: 1.30 |
| 3-OCF₃-phenyl | bond | NHCO | bond | furan (2,5-diyl) | CH2 | | [M + 1]⁻ = 1732 | calcd. for C79H83Cl2F3N10O27•1.9HCl•12.5H2O<br>C: 46.81%, H: 5.47%, N: 6.91%, Cl: 6.82%, F: 2.81%<br>found: C: 46.77%, H: 5.39%, N: 7.01%, Cl: 6.75%, F: 2.67% |

TABLE 68

| Structure 1 | | | | Structure 2 | | | | Analysis |
|---|---|---|---|---|---|---|---|---|
| 3-OCF₃-phenyl | bond | CONH | bond | pyridine (2,5-diyl) | CH2 | | [M + 1]⁻ = 1742 | calcd. for C80H84Cl2F3N11O26•1.9HCl•12.5H2O<br>C: 47.15%, H: 5.48%, N: 7.56%, Cl: 6.78%, F: 2.80%<br>found: C: 47.14%, H: 5.43%, N: 7.67%, Cl: 6.78%, F: 2.70% |
| 3-OCF₃-phenyl | bond | CONH | bond | 5-Br-1,3-phenylene | CH2 | | [M + 1]⁻ = 1820 | calcd. for C81H84Cl2F3BrN10O26•2HCl•14.3H2O<br>C: 45.21%, H: 5.37%, N: 6.51%, Cl: 6.59%, F: 2.65%, Br: 3.71%<br>found: C: 45.18%, H: 5.14%, H: 6.71%, Cl: 6.64%, F: 2.57%, Br: 3.49% |
| 3-OCF₃-phenyl | bond | CONH | bond | 5-(4-pyridyl)-1,3-phenylene | CH2 | | [M + 1]⁻ = 1819 | calcd. for C86H88Cl2F3N11O26•1.5HCl•15.4H2O<br>C: 48.00%, H: 5.64%, N: 7.16%, Cl: 5.77%, F: 2.65%<br>found: C: 47.96%, H: 5.64%, N: 7.24%, Cl: 5.78%, F: 2.60% |
| 3-OCF₃-phenyl | bond | CONH | bond | 5-(hydroxymethyl)-1,3-phenylene | CH2 | | [M + 1]⁻ = 1772 | calcd. for C82H87Cl2F3N10O27•1.3HCl•13.5H2O<br>C: 47.65%, H: 5.61%, N: 6.78%, Cl: 6.00%, F: 2.76%<br>found C: 47.65%, H: 5.59%, N: 6.91%, Cl: 5.99%, F: 2.73% |

TABLE 68-continued

| | | | | | | |
|---|---|---|---|---|---|---|
| 3-OCF3-phenyl | bond | CONH | bond | 2-HO, 5-linked phenyl (with another link at 1-position) | CH2 | [M + 1]⁻ = 1758 calcd. for C81H85Cl2F3H10O27•1.7HCl•13.2H2O C: 47.27%, H: 5.54%, N: 6.81%, Cl: 6.37%, F: 2.77% found: C: 47.25%, H: 5.35%, N: 6.95%, Cl: 6.30%, F: 2.72% |

TABLE 69

| | | | | | | |
|---|---|---|---|---|---|---|
| 3-OCF3-phenyl | bond | CONH | bond | 2-(4-methoxybenzyloxy)phenyl | CH2 | [M + 1]⁻ = 1878 calcd. for C89H93Cl2F3N10O28•1.8HCl•13.5H2O C: 48.87%, H: 5.61%, N: 6.40%, Cl: 6.16%, F: 2.6% found: C: 48.85%, H: 5.42%, N: 647.%, Cl: 6.07%, F: 2.58% |
| 3-OCF3-phenyl | bond | CONH | bond | 2-(2-morpholinoethoxy)phenyl | CH2 | [M + 1]⁻ = 1771 calcd. for C87H96Cl2F3N11O28•2.5HCl•14.6H2O C: 46.95%, H: 5.78%, N: 6.92%, Cl: 7.17%, F: 2.56% found: C: 46.92%, H: 5.70%, N: 6.99%, Cl: 7.17%, F: 2.51% |
| 3-OCF3-phenyl | bond | CONH | bond | 3,5-bis-linked-benzyl-NH-Et | CH2 | [M + 1]⁻ = 1799 calcd. for C84H92Cl2F3N11O26•2.2HCl•16.4H2O C: 46.61%, H: 5.76%, N: 7.12%, Cl: 8.02%, F: 2.63% found: C: 46.60%, H: 5.67%, N: 7.28%, Cl: 7.97%, F: 2.53% |
| 3-OCF3-phenyl | bond | CONH | bond | 4-OH-phenyl (3,5-bis-linked) | CH2 | [M + 1]⁻ = 1758 calcd. for C81H85Cl2F3N10O27•2.0HCl•12.0H2O C: 46.87%, H: 5.79%, N: 6.91%, Cl: 7.16%, F: 2.56% found: C: 46.85%, H: 5.65%, N: 6.96%, Cl: 7.21%, F: 2.53% |
| 3-OCF3-phenyl | bond | CONH | bond | 3,5-bis-linked-benzyl-morpholine | CH2 | [M + 1]⁻ = 1841 calcd. for C86H94Cl2F3N11O27•2.4HCl•15.5H2O C: 46.77%, H: 5.81%, N: 6.98%, Cl: 7.06%, F: 2.58% found: C: 46.76%, H: 5.63%, N: 7.10%, Cl: 7.06%, F: 2.68% |

TABLE 70

| Ar1 | L1 | L2 | L3 | Ar2 | L4 | MS | Elemental analysis |
|---|---|---|---|---|---|---|---|
| 3-OCF₃-phenyl | bond | CONH | bond | 2-(morpholinoethoxy)-phenyl (1,4-disub) | CH2 | [M + 3]⁺ = 1872 | calcd. for C87H96Cl2F3N11O28•2.5HCl•14.8H2O C: 48.62%, H: 5.53%, N: 6.91%, Cl: 6.83%, F: 2.81% found: C: 48.63%, H: 5.40%, N: 6.96%, Cl: 6.88%, F: 2.67% |
| 3-OCF₃-phenyl | bond | CONH | bond | 5-carboxy-1,3-phenylene | CH2 | [M + 1]⁻ = 1786 | calcd. for C82H85Cl2F3N10O28•2.1HCl•14.4H2O C: 46.40%, H: 5.50%, N: 6.60%, Cl: 6.85%, F: 2.69% found: C: 46.39%, H: 5.43%, N: 6.78%, Cl: 6.64%, F: 2.62% |
| 3-OCF₃-phenyl | bond | CONH | bond | 5-(2-carboxyvinyl)-1,3-phenylene | CH2 | [M + 1]⁻ = 1812 | calcd. for C84H87Cl2F3N10O28•2.0HCl•13.3H2O C: 47.48%, H: 5.48%, N: 6.59%, Cl: 6.67%, F: 2.68% found: C: 47.45%, H: 5.37%, N: 6.71%, Cl: 6.73%, F: 2.79% |
| 3-OCF₃-phenyl | bond | CONH | bond | 5-(3-morpholino-3-oxoprop-1-enyl)-1,3-phenylene | CH2 | [M + 1]⁻ = 1881 | calcd. for C88H94Cl2F3N11O28•2.0HCl•13.0H2O C: 48.29%, H: 5.62%, N: 7.04%, Cl: 6.48%, F: 2.60% found: C: 48.46%, H: 5.55%, N: 7.12%, Cl: 6.55%, F: 2.73% |
| 3-OCF₃-phenyl | bond | NHCO | bond | thiazole-2,4-diyl | CH2 | [M + 1]⁻ = 1748 | calcd. for C78H82Cl2F3N11O26S1•2.0HCl•13.0H2O C: 45.55%, H: 5.39%, N: 7.49%, Cl: 6.90%, F: 2.77%, S: 1.56% found: C: 45.55%, H: 5.40%, N: 7.49%, Cl: 6.82%, F: 2.93%, S: 1.75% |

TABLE 71

| Ar1 | L1 | L2 | L3 | Ar2 | L4 | MS | Elemental analysis |
|---|---|---|---|---|---|---|---|
| 3-OCF₃-phenyl | bond | CONH | bond | 5-(furan-2-yl)-1,3-phenylene | CH2 | [M + 1]⁻ = 1807 | calcd. for C85H87Cl2F3N10O27•2.0HCl•12.8H2O C: 48.34%, H: 5.47%, N: 6.63%, Cl: 6.71%, F: 2.70% found C: 48.32%, H: 5.50%, N: 6.68%, Cl: 6.72%, F: 2.85% |

TABLE 71-continued

| Ar1 | L1 | L2 | L3 | Ar2 | R | MS | Analysis |
|---|---|---|---|---|---|---|---|
| 3-OCF₃-phenyl | bond | CONH | bond | pyridine-3,5-diyl | CH2 | [M + 1]⁻ = 1743 | calcd. for C80H84Cl2F3N11O26•1.3HCl•14.5H2O<br>C: 46.82%, H: 5.61%, N: 7.51%, Cl: 5.70%, F: 2.78%<br>found: C: 46.77%, H: 5.38%, N: 7.57%, Cl: 5.76%, F: 2.75% |
| 3-OCF₃-phenyl | bond | CONH | bond | 5-(acetylamino)-1,3-phenylene | CH2 | [M + 1]⁻ = 1799 | calcd. for C83H88Cl2F3N11O27•1.9HCl•15.9H2O<br>C: 46.25%, H: 5.69%, N: 7.15%, Cl: 6.42%, F: 2.64%<br>found: C: 46.26%, H: 5.67%, N: 7.24%, Cl: 6.48%, F: 2.59% |
| 3-OCF₃-phenyl | bond | CONH | bond | 5-(methanesulfonylamino)-1,3-phenylene | CH2 | [M + 1]⁻ = 1835 | calcd. for C82H88Cl2F3N11O28S1•1.9HCl•13.9H2O<br>C: 45.70%, H: 5.50%, N: 7.15%, Cl: 6.42%, F: 2.64%, S: 1.49%<br>found: C: 45.69%, H: 5.43%, N: 7.18%, Cl: 6.45%, F: 2.56%, S: 1.37% |
| 3-OCF₃-phenyl | bond | CONH | bond | 5-nitro-1,3-phenylene | CH2 | [M + 1]⁻ = 1787 | calcd. for C81H84Cl2F3N11O28•1.9HCl•14.0H2O<br>C: 46.13%, H: 5.44%, N: 7.31%, Cl: 6.56%, F: 2.70%<br>found: C: 46.11%, H: 5.37%, N: 7.31%, Cl: 6.53%, F: 2.63% |

TABLE 72

| Ar1 | L1 | L2 | L3 | Ar2 | R | MS | Analysis |
|---|---|---|---|---|---|---|---|
| 3-OCF₃-phenyl | bond | CONH | bond | 5-cyano-1,3-phenylene | CH2 | [M + 1]⁻ = 1767 | calcd. for C82H84Cl2F3N11O26•2.0HCl•13.8H2O<br>C: 47.15%, H: 5.48%, N: 7.38%, Cl: 6.79%, F: 2.73%<br>found: C: 47.12%, H: 5.43%, N: 7.47%, Cl: 6.80%, F: 2.72% |
| 3-OCF₃-phenyl | bond | CONH | bond | 2,3-dihydro-1,4-benzodioxine-5,7-diyl | CH2 | [M + 1]⁻ = 1799 | calcd. for C83H87Cl2F3N10O28•1.7HCl•13.6H2O<br>C: 47.30%, H: 5.54%, N: 6.65%, Cl: 6.22%, F: 2.70%<br>found: C: 47.28%, H: 5.48%, N: 6.71%, Cl: 6.18%, F: 2.69% |

TABLE 72-continued

| Ar1 | bond | CONH | bond | Ar2 | CH2 | [M+1]− | Analysis |
|---|---|---|---|---|---|---|---|
| 3-OCF3-phenyl | bond | CONH | bond | 3,5-disubst phenyl with CH2N(CH3)2 | CH2 | 1799 | calcd. for C84H92Cl2F3N11O26•2.9HCl•14.9H2O C: 46.41%, H: 5.78%, N: 7.09%, Cl: 7.99%, F: 2.62 found: C: 46.36%, H: 5.71%, N: 7.28%, Cl: 8.02%, F: 2.49% |
| 3-OCF3-phenyl | bond | CONH | bond | 3,5-disubst phenyl with CH2-pyrrolidinyl | CH2 | 1825 | calcd. for C86H94Cl2F3N11O26•2.8HCl•13.5H2O C: 47.58%, H: 5.75%, N: 7.10%, Cl: 7.84%, F: 2.63% found: C: 47.53%, H: 5.65%, N: 7.29%, Cl: 7.88%, F: 2.63% |
| 3-OCF3-phenyl | bond | CONH | bond | 3,5-disubst phenyl with CH2NH-iPr | CH2 | 1813 | calcd. for C85H94Cl2F3N11O26•2.8HCl•13.1H2O C: 47.45%, H: 5.76%, N: 7.16%, Cl: 7.91%, F: 2.65% found: C: 47.40%, H: 5.68%, N: 7.35%, Cl: 7.98%, F: 2.66% |

TABLE 73

| Ar1 | bond | CONH | bond | Ar2 | CH2 | [M+1]− | Analysis |
|---|---|---|---|---|---|---|---|
| 3-OCF3-phenyl | bond | CONH | bond | 3,5-disubst phenyl with CH2-imidazolyl | CH2 | 1822 | calcd. for C85H89Cl2F3N12O26•2.8HCl•13.7H2O C: 47.01%, H: 5.53%, N: 7.74%, Cl: 7.84%, F: 2.62% found: C: 46.98%, H: 5.50%, N: 7.90%, Cl: 7.90%, F: 2.58% |
| 3-OCF3-phenyl | bond | CONH | bond | 2,4-disubst phenyl with 4-methylpiperazinyl | CH2 | 1840 | calcd. for C86H95Cl2F3N12O26•2.5HCl•15.3H2O C: 46.79%, H: 5.85%, N: 7.61%, Cl: 7.23%, F: 2.58% found: C: 46.78%, H: 5.90%, N: 7.74%, Cl: 7.21%, F: 2.49% |
| 3-OCF3-phenyl | bond | CONH | bond | 3,5-disubst pyridinyl | CH2 | 1743 | calcd. for C80H84Cl2F3N11O26•1.6HCl•13.4H2O C: 47.03%, H: 5.54%, N: 7.54%, Cl: 6.25%, F: 2.79% found: C: 46.99%, H: 5.36%, N: 7.65%, Cl: 6.22%, F: 2.85% |

TABLE 73-continued

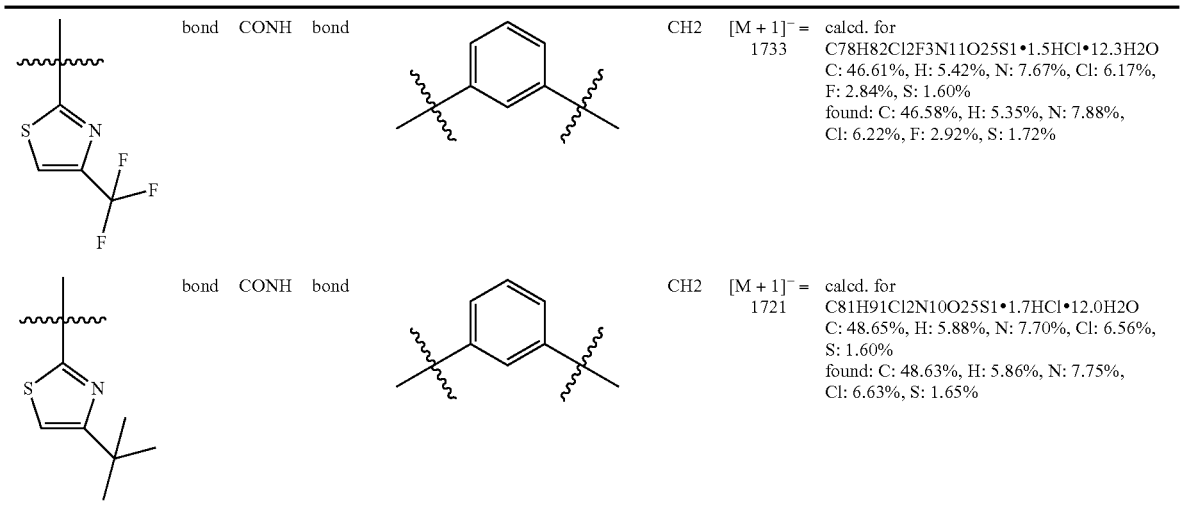

| | bond | CONH | bond | | CH2 | [M + 1]⁻ = 1733 | calcd. for C78H82Cl2F3N11O25S1•1.5HCl•12.3H2O C: 46.61%, H: 5.42%, N: 7.67%, Cl: 6.17%, F: 2.84%, S: 1.60% found: C: 46.58%, H: 5.35%, N: 7.88%, Cl: 6.22%, F: 2.92%, S: 1.72% |
| | bond | CONH | bond | | CH2 | [M + 1]⁻ = 1721 | calcd. for C81H91Cl2N10O25S1•1.7HCl•12.0H2O C: 48.65%, H: 5.88%, N: 7.70%, Cl: 6.56%, S: 1.60% found: C: 48.63%, H: 5.86%, N: 7.75%, Cl: 6.63%, S: 1.65% |

TABLE 74

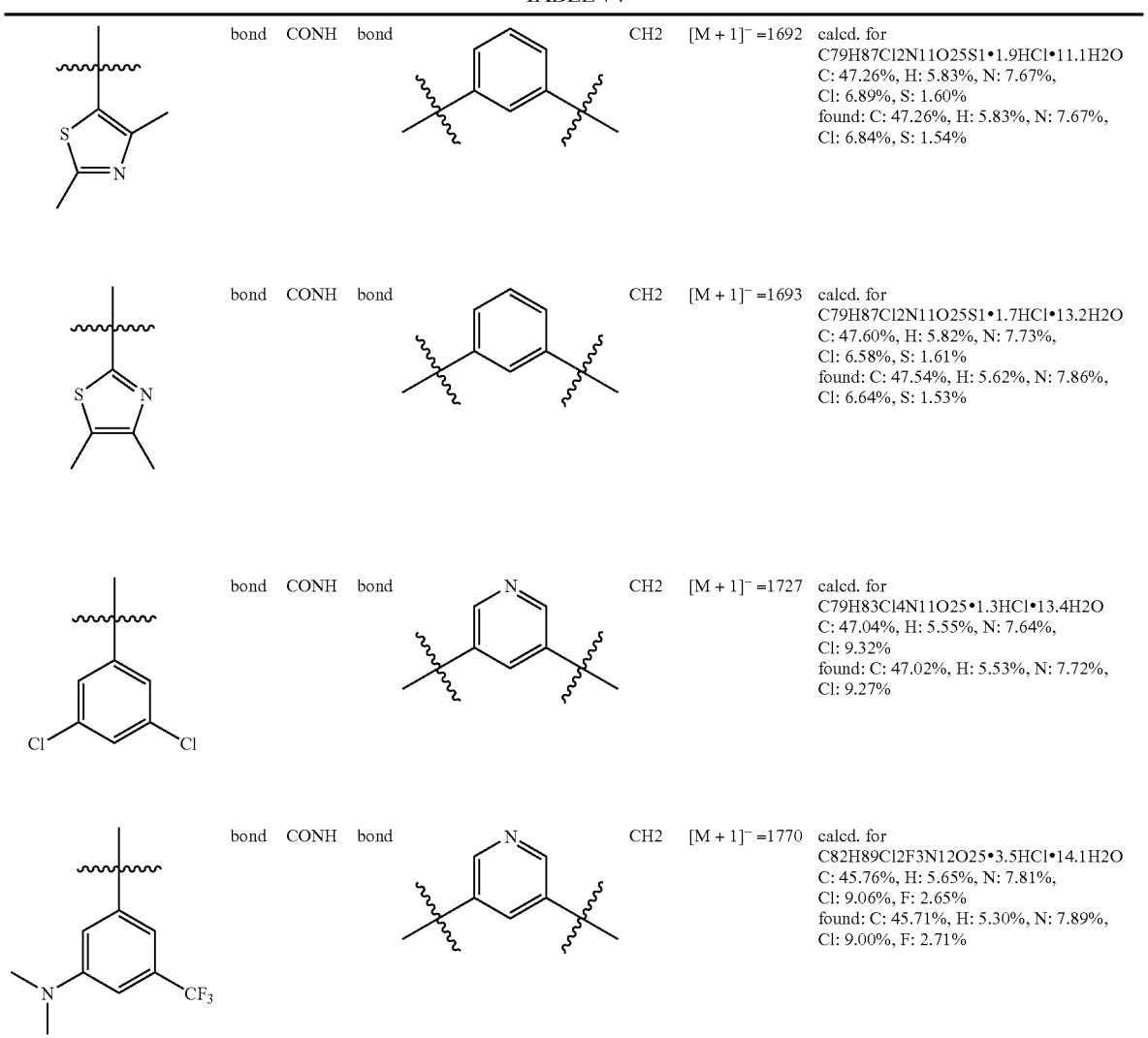

| | bond | CONH | bond | | CH2 | [M + 1]⁻ =1692 | calcd. for C79H87Cl2N11O25S1•1.9HCl•11.1H2O C: 47.26%, H: 5.83%, N: 7.67%, Cl: 6.89%, S: 1.60% found: C: 47.26%, H: 5.83%, N: 7.67%, Cl: 6.84%, S: 1.54% |
| | bond | CONH | bond | | CH2 | [M + 1]⁻ =1693 | calcd. for C79H87Cl2N11O25S1•1.7HCl•13.2H2O C: 47.60%, H: 5.82%, N: 7.73%, Cl: 6.58%, S: 1.61% found: C: 47.54%, H: 5.62%, N: 7.86%, Cl: 6.64%, S: 1.53% |
| | bond | CONH | bond | | CH2 | [M + 1]⁻ =1727 | calcd. for C79H83Cl4N11O25•1.3HCl•13.4H2O C: 47.04%, H: 5.55%, N: 7.64%, Cl: 9.32% found: C: 47.02%, H: 5.53%, N: 7.72%, Cl: 9.27% |
| | bond | CONH | bond | | CH2 | [M + 1]⁻ =1770 | calcd. for C82H89Cl2F3N12O25•3.5HCl•14.1H2O C: 45.76%, H: 5.65%, N: 7.81%, Cl: 9.06%, F: 2.65% found: C: 45.71%, H: 5.30%, N: 7.89%, Cl: 9.00%, F: 2.71% |

TABLE 74-continued
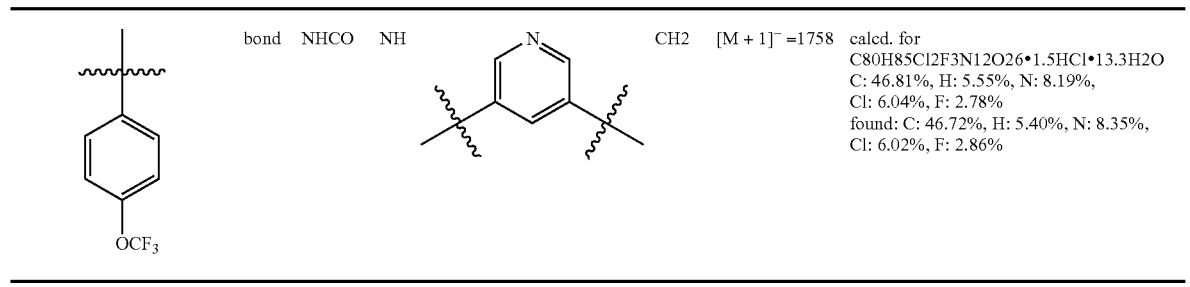
TABLE 75
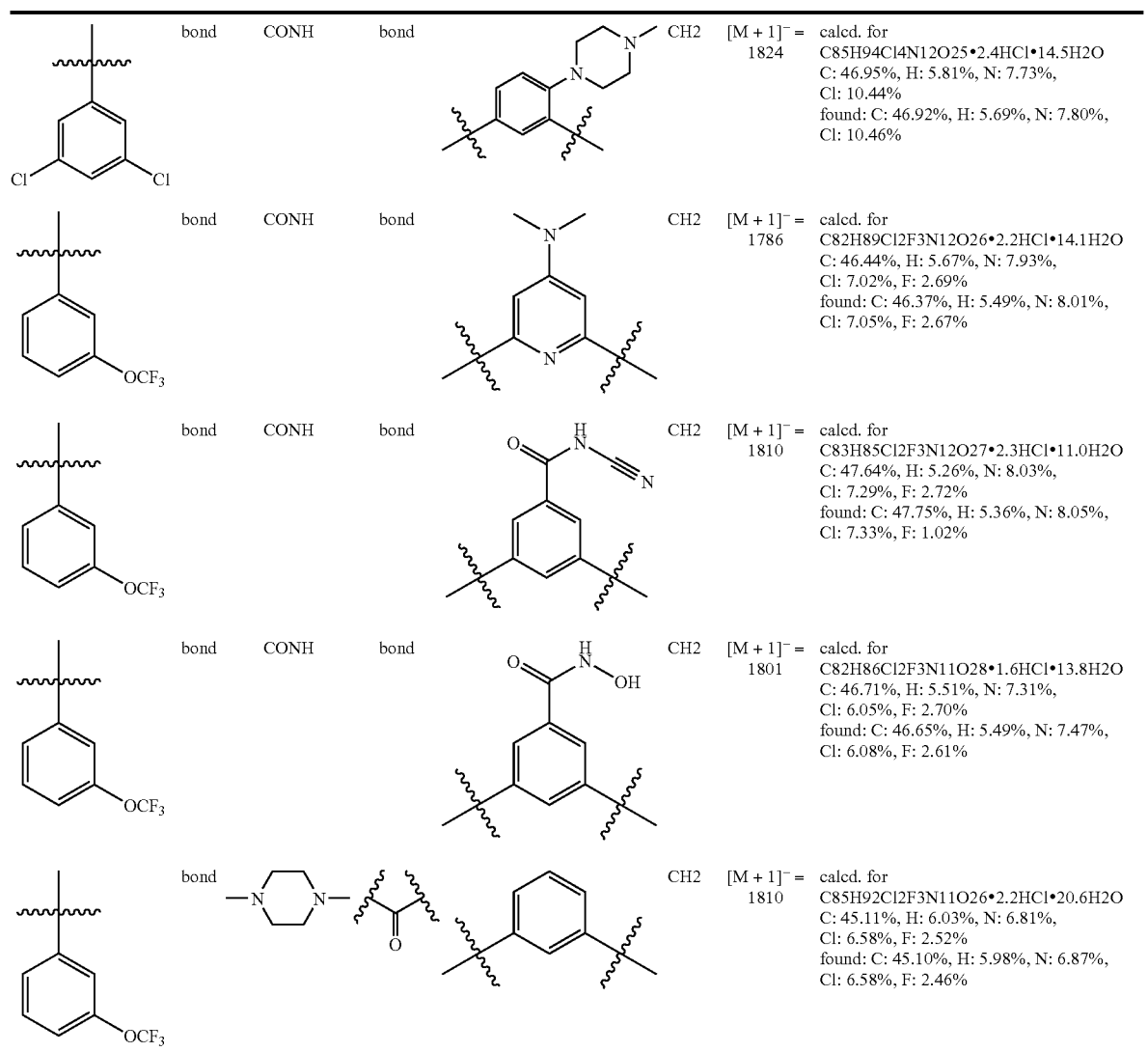
TABLE 76
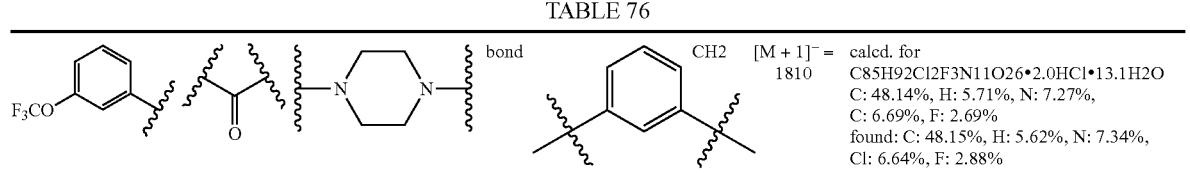

TABLE 77

| $R^A$ | $R^B$ | $R^C$ | $R^D$ |
|---|---|---|---|
| X₁–Ar₁–X₂–Y–X₃–Ar₂ | OH | H | H |

Y = CO—NR
    NR—CO

| $R^A$ | | | | | | | |
|---|---|---|---|---|---|---|---|
| Ar2 | X3 | Y | X2 | Ar1 | X1 | Mass | Elemental Analysis |
| 4-(piperidin-1-yl)-3-(dimethylamino)phenyl | bond | CONH | bond | 1,3-phenylene | CH2 | [M + 1]⁻ =1783 | calcd. for C87H100Cl2N12O25•3HCl•13H2O<br>C: 58.55%, H: 5.65%, N: 9.42%, Cl: 3.97%<br>found: C: 49.28%, H: 6.01%, N: 8.06%, Cl: 7.96% |
| 4-(piperidin-1-yl)-3-(acetylamino)phenyl | bond | CONH | bond | 1,3-phenylene | CH2 | [M + 3]⁺ =1799<br>[M + 1]⁻ =1797 | calcd. for C87H98Cl2N12O26•2HCl•11.5H2O<br>C: 58.09%, H: 5.49%, N: 9.34%, Cl: 3.94%<br>found: C: 50.06%, H: 5.92%, N: 8.13%, Cl: 7.12% |

TABLE 78

| | | | | | |
|---|---|---|---|---|---|
|  | bond | CONH | bond | 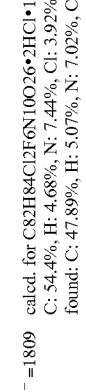 | CH2 | [M + 3]⁺ =1867<br>[M + 1]⁻ =1865 | calcd. for C88H97Cl2F3N12O26•3HCl•14H2O<br>C: 56.62%, H: 5.24%, N: 9.00%, Cl: 3.8%, F: 3.05%<br>found: C: 47.63%, H: 5.62%, N: 7.63%, Cl: 7.63%, F: 2.43% |
| | bond | CONH | bond | | CH2 | [M + 1]⁻ =1809 | calcd. for C82H84Cl2F6N10O26•2HCl•10H2O<br>C: 54.4%, H: 4.68%, N: 7.44%, Cl: 3.92%, F: 6.3%<br>found: C: 47.89%, H: 5.07%, N: 7.02%, Cl: 6.68%, F: 5.40% |
|  | bond | CONH | bond | | CH2 | [M + 1]⁻ =1880 | calcd. for C88H98Cl2F3N13O26•3HCl•17H2O<br>C: 56.17%, H: 5.25%, N: 9.68%, Cl: 3.77%, F: 3.03%<br>found: C: 46.04%, H: 5.69%, N: 7.99%, Cl: 7.98%, F: 2.38% |
| | bond | CONH | bond |  | CH2 | [M + 1]⁻ =1839 | calcd. for C86H95Cl2F3N12O26•3HCl•13H2O<br>C: 56.12%, H: 5.2%, N: 9.13%, Cl: 3.85%, F: 3.10%<br>found: C: 47.39%, H: 5.43%, N: 7.75%, Cl: 7.91%, F: 2.56% |

TABLE 79

| R1 | L1 | L2 | L3 | R2 | L4 | MS | Analysis |
|---|---|---|---|---|---|---|---|
| 3-(N-(dimethylaminoacetyl)amino)-5-(trifluoromethyl)phenyl | bond | CONH | bond | 1,3-phenylene | CH2 | [M + 1]⁻ = 1825 | calcd. for C85H93Cl2F3N12O26•2.5HCl•13.5H2O<br>C: 55.89%, H: 5.13%, N: 9.20%, Cl: 3.88%, F: 3.12%<br>found: C: 47.03%, H: 5.52%, N: 7.74%, Cl: 7.67%, F: 2.55% |
| 3-(trifluoromethoxy)phenyl | bond | CONH | bond | 2-(morpholinomethyl)-1,4-phenylene | CH2 | [M + 3]⁺ = 1842<br>[M + 1]⁻ = 1840 | calcd. for C86H94Cl2F3N11O27•2.5HCl•14.5H2O<br>C: 56.09%, H: 5.14%, N: 8.37%, Cl: 3.85%, F: 3.09%<br>found: C: 46.96%, H: 5.673%, N: 7.15%, Cl: 7.65%, F: 2.60% |
| 3-(trifluoromethoxy)phenyl | bond | CONH | bond | 5-(methoxycarbonyl)-1,3-phenylene | CH2 | [M + 3]⁺ = 1801<br>[M + 1]⁻ = 1799 | calcd. for C83H87Cl2F3N10O28•2HCl•11H2O<br>C: 55.37%, H: 4.87%, N: 7.78%, Cl: 3.94%, F: 3.17%<br>found: C: 48.01%, H: 5.42%, N: 6.82%, Cl: 6.77%, F: 2.75% |
| 3-(trifluoromethoxy)phenyl | bond | CONH | bond | 5-(4-methylpiperazine-1-carbonyl)-1,3-phenylene | CH2 | [M + 3]⁺ = 1869<br>[M + 1]⁻ = 1867 | calcd. for C87H95Cl2F3N12O27•2.5HCl•15.5H2O<br>C: 55.92%, H: 5.12%, N: 8.99%, Cl: 3.79%, F: 3.05%<br>found: C: 46.48%, H: 5.95%, N: 7.53%, Cl: 7.33%, F: 2.50% |

TABLE 80

| R1 | L1 | L2 | L3 | R2 | L4 | MS | Analysis |
|---|---|---|---|---|---|---|---|
| 3-(trifluoromethoxy)phenyl | bond | CONH | bond | 5-(morpholine-4-carbonyl)-1,3-phenylene | CH2 | [M + 1]⁻ = 1854 | calcd. for C86H92Cl2F3N11O28•2.5HCl•13.5H2O<br>C: 55.66%, H: 5.00%, N: 8.30%, Cl: 3.82%, F: 3.07%<br>found: C: 47.73%, H: 5.78%, N: 6.82%, Cl: 6.21%, F: 2.65% |
| 3-(trifluoromethoxy)phenyl | bond | CONH | bond | 5-carbamoyl-1,3-phenylene | CH2 | [M + 1]⁻ = 1784 | calcd. for C82H86Cl2F3N11O27•2HCl•14H2O<br>C: 55.16%, H: 4.85%, N: 8.63%, Cl: 3.97%, F: 3.19%<br>found: C: 46.7%, H: 5.53%, N: 7.45%, Cl: 6.64%, F: 2.67% |

TABLE 80-continued

| Structure 1 | | | Structure 2 | | | Data |
|---|---|---|---|---|---|---|
| 3-(trifluoromethoxy)phenyl-bond | CONH | bond | N-methylpiperazinyl-CH2-phenyl(2,4-disubstituted) | CH2 | [M + 3]⁺ = 1855 | calcd. for C87H97Cl2F3N12O26•2.5HCl•5H2O<br>C: 56.34%, H: 5.27%, N: 9.06%, Cl: 3.82%, F: 3.07%<br>found: C: 47.13%, H: 5.72%, N: 7.65%, Cl: 7.33%, F: 2.55% |
| 3-(dimethylamino)-4-morpholinophenyl-bond | CONH | bond | 1,3-phenylene | CH2 | [M + 1]⁻ = 1785 | calcd. for C86H98Cl2N12O26•2HCl•14H2O<br>C: 57.81%, H: 5.53%, N: 9.41%, Cl: 3.97%<br>found: C: 48.77, H: 5.98%, N: 7.97%, Cl: 6.86% |

TABLE 81

| Structure 1 | | | Structure 2 | | | Data |
|---|---|---|---|---|---|---|
| 3,4-bis(dimethylamino)phenyl-bond | CONH | bond | 1,3-phenylene | CH2 | [M + 1]⁻ = 1743 | calcd. for C84H96Cl2N12O25•2.5HCl•15H2O<br>C: 57.83%, H: 5.55%, N: 9.63%, Cl: 4.06%<br>found: C: 47.92, H: 6.13%, N: 7.95%, Cl: 7.59% |
| 3-(trifluoromethyl)-4-morpholinophenyl-bond | NHCO | bond | 1,4-phenylene | CH2 | [M + 1]⁻ = 1810 | calcd. for C85H92Cl2F3N11O26•2HCl•13H2O<br>C: 56.35%, H: 5.12%, N: 8.50%, Cl: 3.91%, F: 3.15<br>found: C: 48.20, H: 5.63%, N: 7.19%, Cl: 6.76%, F: 2.73 |
| 4-(dimethylamino)-3-(trifluoromethyl)phenyl-bond | NHCO | bond | 1,4-phenylene | CH2 | [M + 1]⁻ = 1768 | calcd. for C83H90Cl2F3N11O25•2HCl•16H2O<br>C: 56.35%, H: 5.12%, N: 8.50%, Cl: 3.91%, F: 3.22%<br>found: C: 48.20, H: 5.63%, N: 7.19%, Cl: 6.76%, F: 2.83% |

TABLE 81-continued
| | | | | | | |
|---|---|---|---|---|---|---|
| 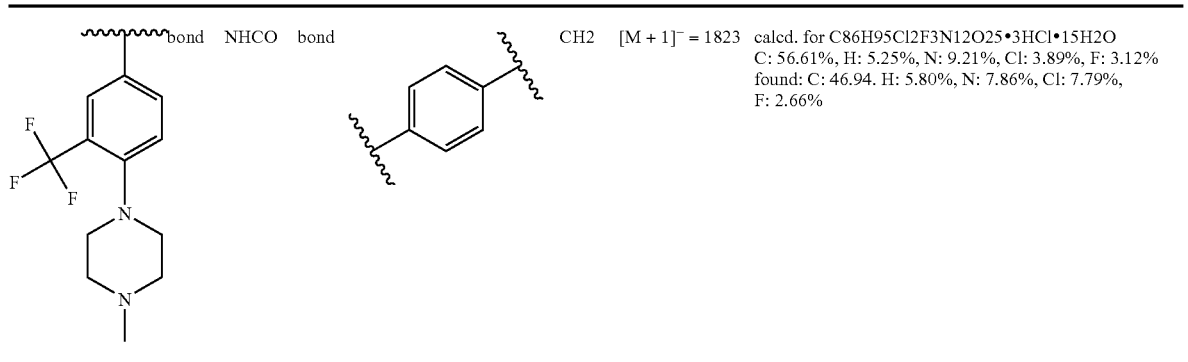 | bond | NHCO | bond | 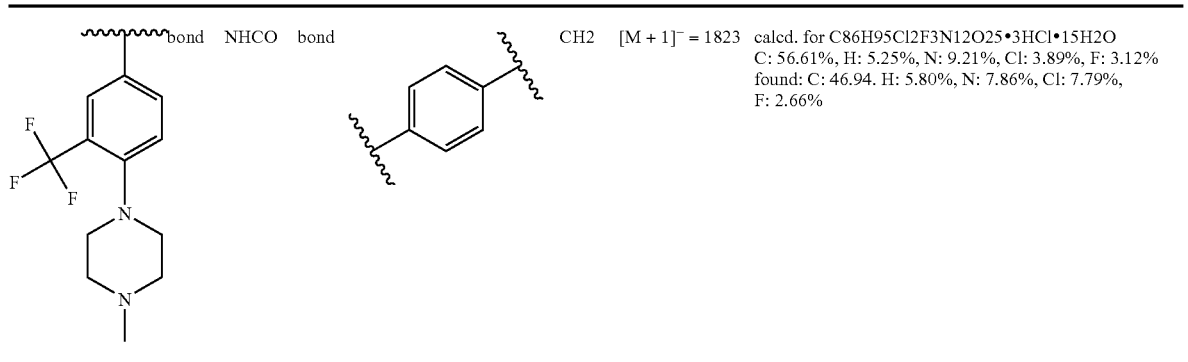 | CH2 | [M + 1]⁻ = 1823 calcd. for C86H95Cl2F3N12O25•3HCl•15H2O<br>C: 56.61%, H: 5.25%, N: 9.21%, Cl: 3.89%, F: 3.12%<br>found: C: 46.94. H: 5.80%, N: 7.86%, Cl: 7.79%, F: 2.66% |
TABLE 82
| | | | | | | |
|---|---|---|---|---|---|---|
| 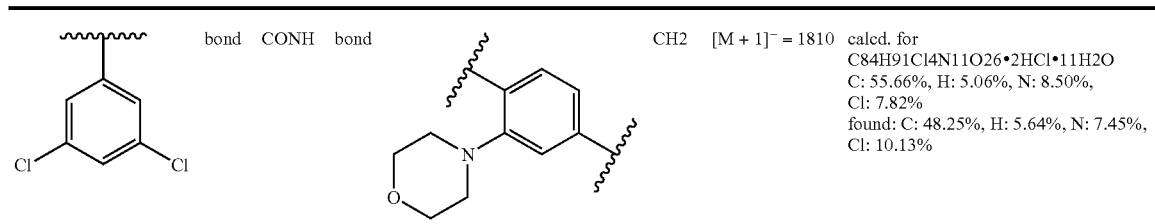 | bond | CONH | bond | 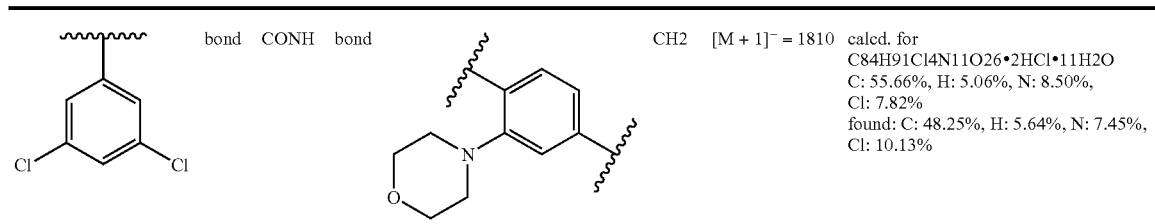 | CH2 | [M + 1]⁻ = 1810 calcd. for C84H91Cl4N11O26•2HCl•11H2O<br>C: 55.66%, H: 5.06%, N: 8.50%, Cl: 7.82%<br>found: C: 48.25%, H: 5.64%, N: 7.45%, Cl: 10.13% |
| 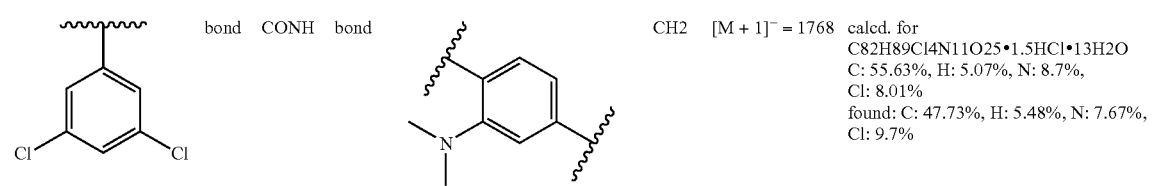 | bond | CONH | bond | 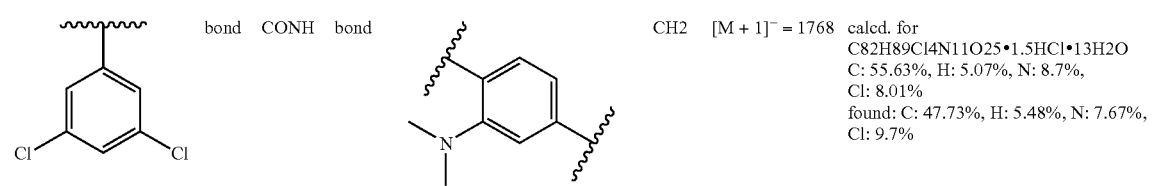 | CH2 | [M + 1]⁻ = 1768 calcd. for C82H89Cl4N11O25•1.5HCl•13H2O<br>C: 55.63%, H: 5.07%, N: 8.7%, Cl: 8.01%<br>found: C: 47.73%, H: 5.48%, N: 7.67%, Cl: 9.7% |
| 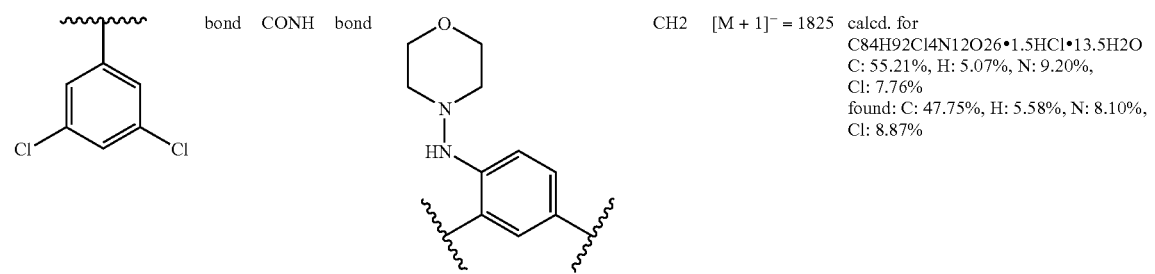 | bond | CONH | bond | 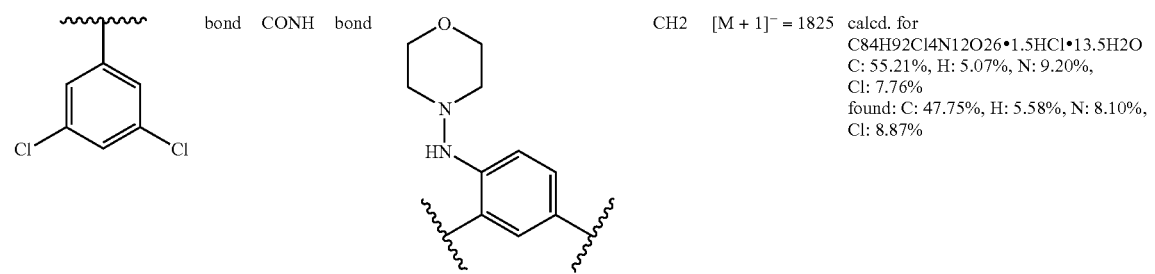 | CH2 | [M + 1]⁻ = 1825 calcd. for C84H92Cl4N12O26•1.5HCl•13.5H2O<br>C: 55.21%, H: 5.07%, N: 9.20%, Cl: 7.76%<br>found: C: 47.75%, H: 5.58%, N: 8.10%, Cl: 8.87% |

TABLE 83

| R^A | R^B | R^C | R^D |
|---|---|---|---|
| (structure with X1, Ar1, X2, Y, X3, Ar2) | OH | H | H |

Y = CO—NR
    NR—CO

R^A

| Ar2 | X3 | Y | X2 | Ar1 | X1 | Mass | Elemental Analysis |
|---|---|---|---|---|---|---|---|
| 2-methylallyloxy-methylphenyl | bond | CONH | bond | 1,3-phenylene | CH2 | [M + 1]⁻ = 1742 | calcd. for C85H94Cl2N10O26•2.0HCl•15.8H2O C: 48.61%, H: 6.12%, N: 6.67%, Cl: 6.75% found: C: 48.55%, H: 6.05%, N: 6.76%, Cl: 6.80% |
| MOM-oxy-methylphenyl | bond | CONH | bond | 1,3-phenylene | CH2 | [M + 1]⁻ = 1732 | calcd. for C83H92Cl2N10O27•1.5HCl•12.4H2O C: 49.58%, H: 5.93%, N: 6.97%, Cl: 6.17% found: C: 49.56%, H: 5.86%, N: 6.96%, Cl: 6.18% |
| cyanopropoxy-methylphenyl | bond | CONH | bond | 1,3-phenylene | CH2 | [M + 1]⁻ = 1755 | calcd. for C85H93Cl2N11O26•1.5HCl•11.3H2O C: 50.69%, H: 5.86%, N: 7.65%, Cl: 6.16% found: C: 50.67%, H: 5.79%, N: 7.72%, Cl: 6.24% |
| 3-(trifluoromethoxy)phenyl | bond | CONH | bond | thiazole-2,4-diyl | CH2 | [M + 1]⁻ = 1748 | calcd. for C78H82Cl2F3N11O26S•1.8HCl•11.8H2O C: 46.20%, H: 5.34%, N: 7.60%, Cl: 6.64%, F: 2.81%, S: 1.58% found: C: 46.19%, H: 5.37%, N: 7.71%, Cl: 6.59%, F: 2.86%, S: 1.69% |

TABLE 84

| Ar2 | X3 | Y | X2 | Ar1 | X1 | Mass | Elemental Analysis |
|---|---|---|---|---|---|---|---|
| 3-(trifluoromethoxy)phenyl | bond | CONH | bond | morpholino-NH-phenylene | CH2 | [M + 3]⁺ = 1844 [M + 1]⁻ = 1842 | calcd. for C85H93Cl2F3N12O27•1.7HCl•15.2H2O C: 46.86%, H: 5.79%, N: 7.72%, Cl: 6.02% found: C: 46.86%, H: 5.75%, N: 7.77%, Cl: 5.98% |
| 3-(trifluoromethoxy)phenyl | bond | CONH | bond | bis(2-methoxyethyl)amino-phenylene | CH2 | [M + 1]⁻ = 1873 | calcd. for C87H98Cl2F3N11O28•2.2HCl•13.4H2O C: 47.60%, H: 5.83%, N: 7.02%, Cl: 6.78%, F: 2.60% found: C: 47.36%, H: 5.89%, N: 7.00%, Cl: 6.71%, F: 2.90% |

TABLE 84-continued

| | | | | | | |
|---|---|---|---|---|---|---|
| 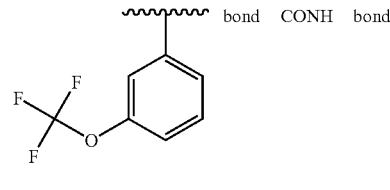 | bond | CONH | bond 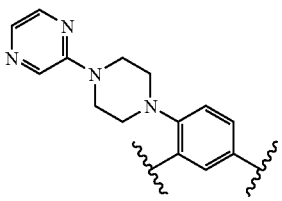 [SMILES: *c1ccc(N2CCN(c3cnccn3)CC2)c(*)c1] | CH2 | [M + 1]⁻ = 1904 | calcd. for C89H95Cl2F3N14O26•2.5HCl•17.0H2O C: 46.43%, H: 5.76%, N: 8.52%, Cl: 6.93%, F: 2.48% found: C: 46.38%, H: 5.67%, N: 8.64%, Cl: 6.92%, F: 2.72% |
| 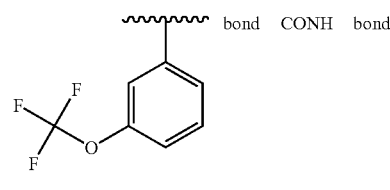 | bond | CONH | bond 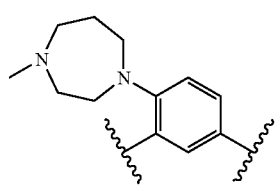 [SMILES: *c1ccc(N2CCCN(C)CC2)c(*)c1] | CH2 | [M + 1]⁻ = 1854 | calcd. for C87H97Cl2F3N12O26•2.7HCl•14.4H2O C: 47.23%, H: 5.85%, N: 7.60%, Cl: 7.53%, F: 2.58% found: C: 47.25%, H: 5.79%, N: 7.69%, Cl: 7.53%, F: 2.57% |
| 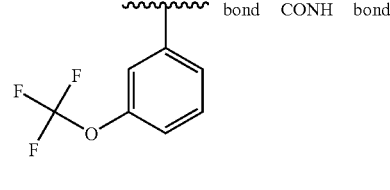 | bond | CONH | bond 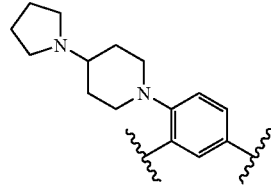 [SMILES: *c1ccc(N2CCC(N3CCCC3)CC2)c(*)c1] | CH2 | [M + 1]⁻ = 1894 | calcd. for C90H101Cl2F3N12O26•2.6HCl•15.1H2O C: 47.80%, H: 5.96%, N: 7.43%, Cl: 7.21%, F: 2.52% found: C: 47.80%, H: 5.89%, N: 7.44%, Cl: 7.24%, F: 2.62% |
| 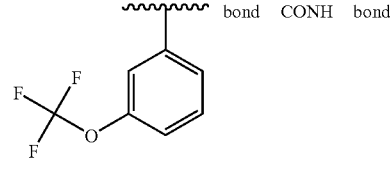 | bond | CONH | bond 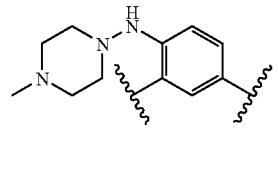 [SMILES: *c1ccc(NN2CCN(C)CC2)c(*)c1] | CH2 | [M + 3]⁺ = 1857 [M + 1]⁻ = 1855 | calcd. for C86H96Cl2F3N13O26•3.0HCl•13.6H2O C: 46.74%, H: 5.76%, N: 8.24%, Cl: 8.02%, F: 2.58% found: C: 46.76%, H: 5.76%, N: 8.28%, Cl: 7.96%, F: 2.60% |

TABLE 85

| | | | | | | |
|---|---|---|---|---|---|---|
| 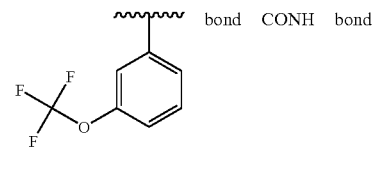 | bond | CONH | bond 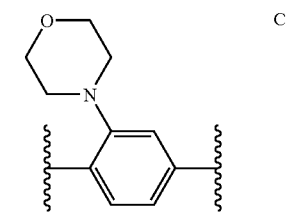 | CH2 | [M + 1]⁻ = 1827 | calcd. for C85H92Cl2F3N11O27•1.7HCl•13.5H2O C: 47.87%, H: 5.70%, N: 7.22%, Cl: 6.15%, F: 2.67% found: C: 47.85%, H: 5.68%, N: 7.28%, Cl: 6.17%, F: 2.82% |
| 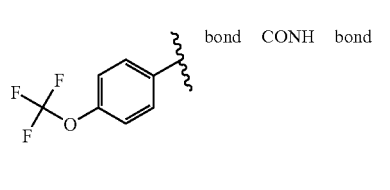 | bond | CONH | bond 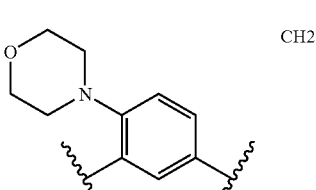 | CH2 | [M + 1]⁻ = 1827 | calcd. for C85H92Cl2F3N11O27•1.9HCl•11.1H2O C: 48.69%, H: 5.58%, N: 7.35%, Cl: 6.59%, F: 2.72% found: C: 48.68%, H: 5.54%, N: 7.43%, Cl: 6.67%, F: 2.66% |
| 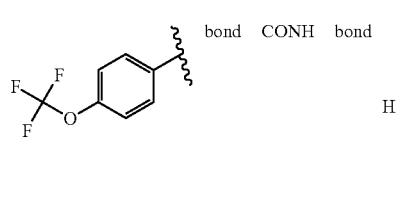 | bond | CONH | bond 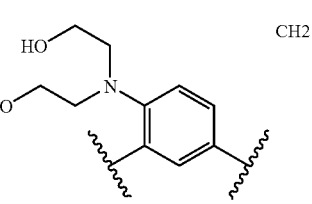 | CH2 | [M + 1]⁻ = 1845 | calcd. for C85H94Cl2F3N11O28•2.2HCl•11.5H2O C: 47.86%, H: 5.63%, N: 7.22%, Cl: 6.98%, F: 2.67% found: C: 47.84%, H: 5.68%, N: 7.29%, Cl: 7.06%, F: 2.56% |

TABLE 85-continued

| Ar1 | L1 | L2 | L3 | Ar2 | L4 | MS | Analysis |
|---|---|---|---|---|---|---|---|
| 3,5-dichlorophenyl | bond | CONH | bond | morpholine-ethyl-NH-phenyl | CH2 | [M + 1]⁻ = 1854 | calcd. for C86H96Cl4N12O26•3.2HCl•11.7H2O<br>C: 47.32%, H: 5.66%, N: 7.70%, Cl: 11.69%<br>found: C: 47.31%, H: 5.74%, N: 7.78%, Cl: 11.65% |
| 3,5-dichlorophenyl | bond | CONH | bond | ethoxyethyl-piperazine-phenyl | CH2 | [M + 1]⁻ = 1882 | calcd. for C88H100Cl4N12O26•2.8HCl•12.1H2O<br>C: 47.96%, H: 5.81%, N: 7.63%, Cl: 10.94%<br>found: C: 47.94%, H: 5.77%, N: 7.83%, Cl: 11.00% |
| 3,5-dichlorophenyl | bond | CONH | bond | ethyl-piperazine-phenyl | CH2 | [M + 1]⁻ = 1838 | calcd. for C86H96Cl4N12O25•3.0HCl•13.8H2O<br>C: 47.00%, H: 5.81%, N: 7.65%, Cl: 11.29%<br>found: C: 46.99%, H: 5.64%, N: 7.79%, Cl: 11.21% |

TABLE 86

| Ar1 | L1 | L2 | L3 | Ar2 | L4 | MS | Analysis |
|---|---|---|---|---|---|---|---|
| 4-(trifluoromethoxy)phenyl | bond | NHCO | NH | morpholino-NH-phenyl | CH2 | [M + 3]⁺ = 1859<br>[M + 1]⁻ = 1857 | calcd. for C85H94Cl2F3N13O27•2.4HCl•12.7H2O<br>C: 46.96%, H: 5.65%, N: 8.38%, Cl: 7.18%, F: 2.62%<br>found: C: 46.89%, H: 5.57%, N: 8.55%, Cl: 7.21%, F: 2.59% |
| 4-(trifluoromethoxy)phenyl | bond | CONH | bond | morpholino-NH-phenyl | CH2 | [M + 1]⁻ = 1842 | calcd. for C85H93Cl2F3N12O27•1.5HCl•13.9H2O<br>C: 47.53%, H: 5.74%, N: 7.83%, Cl: 5.78%, F: 2.65%<br>found: C: 47.50%, H: 5.54%, N: 7.84%, Cl: 5.80%, F: 2.64% |
| 4-(trifluoromethoxy)phenyl | bond | NHCO | NH | morpholino-NH-phenyl | CH2 | [M + 1]⁻ = 1857 | calcd. for C85H94Cl2F3N13O27•1.8HCl•11.6H2O<br>C: 47.88%, H: 5.63%, N: 8.54%, Cl: 6.32%, F: 2.67%<br>found: C: 47.88%, H: 5.56%, N: 8.51%, Cl: 6.36%, F: 2.61% |
| 4-(trifluoromethoxy)phenyl | bond | CONH | bond | morpholino-NH-phenyl | CH2 | [M + 1]⁻ = 1842 | calcd. for C85H93Cl3F3N12O27•1.3HCl•13.8H2O<br>C: 47.74%, H: 5.75%, N: 7.86%, Cl: 5.47%, F: 2.67%<br>found: C: 47.72%, H: 5.67%, N: 7.94%, Cl: 5.42%, F: 2.64% |
| 4-(trifluoromethoxy)phenyl | bond | CONH | bond | dimethylamino-NH-phenyl | CH2 | [M + 3]⁺ = 1802<br>[M + 1]⁻ = 1800 | calcd. for C83H91Cl2F3N12O26•1.6HCl•13.7H2O<br>C: 47.34%, H: 5.74%, N: 7.98%, Cl: 6.06%, F: 2.71%<br>found: C: 47.29%, H: 5.73%, N: 8.10%, Cl: 6.12%, F: 2.84% |
| 4-butoxyphenyl | bond | CONH | bond | morpholino-NH-phenyl | CH2 | [M + 3]⁺ = 1832<br>[M + 1]⁻ = 1830 | calcd. for C88H102Cl2N12O27•1.6HCl•11.4H2O<br>C: 50.46%, H: 6.08%, N: 8.03%, Cl: 6.09%<br>found: C: 50.46%, H: 5.95%, N: 8.11%, Cl: 6.06% |

TABLE 87

| Ar2 | X3 | Y | X2 | Ar1 | X1 | Mass | Elemental Analysis |
|---|---|---|---|---|---|---|---|
| 4-(OCF3)-phenyl | bond | CONH | bond | morpholin-N-yl-NH-phenyl | CH2 | [M + 3]+ = 1844<br>[M + 1]− = 1842 | calcd. for C85H93Cl2F3N12O27•1.9HCl•11.6H2O<br>C: 48.14%, H: 5.61%, N: 7.93%, Cl: 6.52%, F: 2.69%<br>found: C: 48.11%, H: 5.60%, N: 8.03%, Cl: 6.44%, F: 2.84% |
| 3-(SCHF2)-phenyl | bond | CONH | bond | morpholin-N-yl-NH-phenyl | CH2 | [M + 3]+ = 1842<br>[M + 1]− = 1840 | calcd. for C85H94Cl2F2N12O26S•2.0HCl•9.8H2O<br>C: 48.84%, H: 5.57%, N: 8.04%, Cl: 6.78%, F: 1.82%, S: 1.53%<br>found: C: 48.83%, H: 5.47%, N: 8.10%, Cl: 6.79%, F: 1.96%, S: 1.53% |
| 4-(OCF3)-phenyl | bond | NHCO | NH | N,N-dimethyl-hydrazino-phenyl | CH2 | [M + 3]+ = 1816<br>[M + 1]− = 1814 | calcd. for C83H92Cl2F3N13O26•1.9HCl•10.8H2O<br>C: 47.94%, H: 5.60%, N: 8.76%, Cl: 6.65%, F: 2.74%<br>found: C: 47.93%, H: 5.61%, N: 8.80%, Cl: 6.72%, F: 2.53% |

TABLE 88

| RA | RB | RC | RD |
|---|---|---|---|
| X1–Ar1–X2–Y–X3–Ar2 structure<br>Y = CO—NR or NR—CO | OH | H | H |

RA

| Ar2 | X3 | Y | X2 | Ar1 | X1 | Mass | Elemental Analysis |
|---|---|---|---|---|---|---|---|
| 3-(SCHF2)-phenyl | bond | CONH | bond | 1,4-phenyl | CH2 | [M + 1]− = 1739 | calcd. for C81H86Cl2F2N10O25S•1.3HCl•8.3H2O<br>C: 50.21%, H: 5.41%, N: 7.23%, Cl: 6.04%, F: 1.96%, S: 1.65%<br>found: C: 50.35%, H: 5.50%, N: 6.75%, Cl: 6.05%, F: 1.72%, S: 1.39% |
| 3-(OCF3)-phenyl | bond | CONH | bond | 4-methylpiperazin-N-yl-phenyl | CH2 | [M + 3]+ = 1841<br>[M + 1]− = 1839 | calcd. for C86H95Cl2F3N12O26•2.4HCl•10.3H2O<br>C: 48.87%, H: 5.63%, N: 7.95%, Cl: 7.38%, F: 2.70%<br>found: C: 48.99%, H: 5.67%, N: 7.45%, Cl: 7.43%, F: 2.18% |
| 3-(OCF3)-phenyl | bond | CONH | bond | morpholin-N-yl-phenyl | CH2 | [M + 3]+ = 1828<br>[M + 1]− = 1826 | calcd. for C85H92Cl2F3N11O27•1.9HCl•11.8H2O<br>C: 48.40%, H: 5.61%, N: 7.30%, Cl: 6.55%, F: 2.70%<br>found: C: 48.38%, H: 5.54%, N: 7.41%, Cl: 6.56%, F: 2.55% |

TABLE 88-continued
| | bond | CONH | bond | | | CH2 | [M + 1]⁻ = 1841 | calcd. for C86H97Cl2F3N12O26•0.8HCl•16.2H2O C: 47.74%, H: 6.07%, N: 7.77%, Cl: 4.59%, F: 2.63% found: C: 47.78%, H: 5.78%, N: 7.98%, Cl: 4.76%, F: 1.73% |
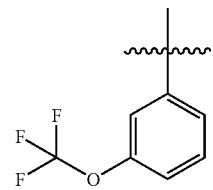 [SMILES: *c1cccc(OC(F)(F)F)c1]
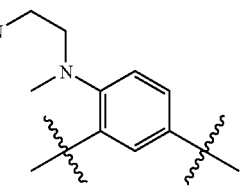

TABLE 89
| | | | | | |
|---|---|---|---|---|---|
| 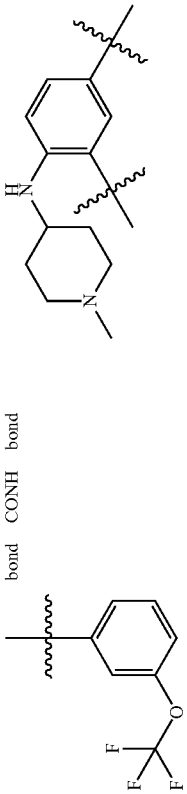 | bond | CONH | bond | 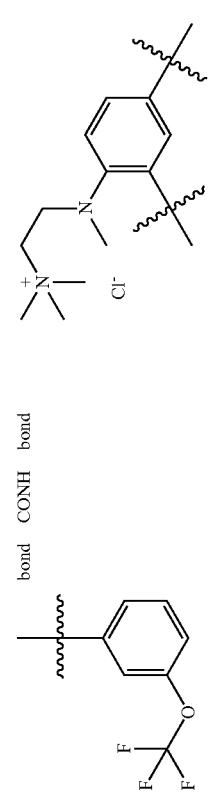 | CH2 [M + 3]+ =1855<br>[M + 1]− =1853 | calcd. for C87H97Cl2F3N12O26•2.7HCl•12.7H2O<br>C: 47.89%, H: 5.78%, N: 7.70%, Cl: 7.64%, F: 2.61%<br>found C: 48.82%, H: 5.81%, N: 6.72%, Cl: 7.78%, F: 2.07% |
| 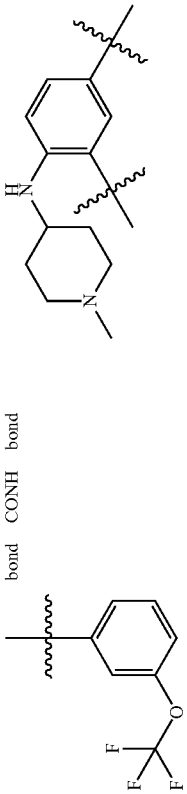 | bond | CONH | bond | 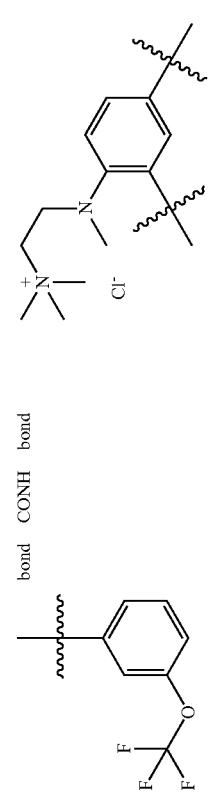 | CH2 [M + 1]− =1857 | calcd. for C87H100Cl3F3N12O26•1.1HCl•10.6H2O<br>C: 49.19%, H: 5.80%, N: 7.91%, Cl: 6.84%, F: 2.68%<br>found C: 49.39%, H: 5.84%, N: 7.37%, Cl: 6.82%, F: 2.45% |
| 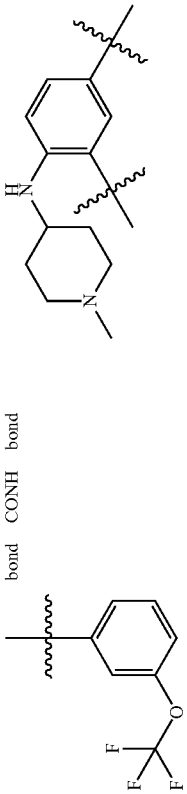 | bond | CONH | bond | 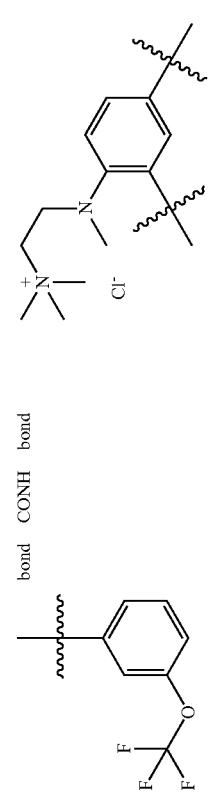 | CH2 [M + 1]− =1938 | calcd. for C91H104Cl2F3N13O27•3.7HCl•14.8H2O<br>C: 46.68%, H: 5.91%, N: 7.78%, Cl: 8.63%, F: 2.43%<br>found C: 46.75%, H: 5.91%, N: 7.64%, Cl: 8.59%, F: 2.19% |

TABLE 90

| $R^A$ | $R^B$ | $R^C$ | $R^D$ |
|---|---|---|---|
| (structure with X1-Ar1, X2-Y, X3-Ar2) | OH | H | H |

Y = CO—NR
    NR—CO $R^A$

| Ar2 | X3 | Y | X2 | Ar1 | X1 | Mass | Elemental Analysis |
|---|---|---|---|---|---|---|---|
| 4-(OCF2F)phenyl | bond | CONH | bond | 1-methyl-pyrazole-3,5-diyl | CH2 | [M + 1]⁻ = 1745 | calcd. for C79H85Cl2F3N12O26•1.9HCl•12.5H2O C: 46.49%, H: 5.53%, Cl: 6.77, F: 2.79, N: 8.24% found: C: 46.46%, H: 5.47%, Cl: 6.75, F: 2.69, N: 8.33% |
| 4-(OCF2F)phenyl | bond | CONH | bond | 1-propyl-pyrazole-3,5-diyl | CH2 | [M + 1]⁻ = 1773 | calcd. for C81H89Cl2F3N12O26•2.0HCl•14.9H2O C: 45.98%, H: 5.75%, Cl: 6.70, F: 2.69, N: 7.94% found: C: 45.95%, H: 5.73%, Cl: 6.90, F: 2.66, N: 7.97% |
| 4-(OCF2F)phenyl | bond | CONH | bond | 1-(2-dimethylaminoethyl)-pyrazole-3,5-diyl | CH2 | [M + 1]⁻ = 1802 | calcd. for C82H92Cl2F3N13O26•2.8HCl•16.0H2O C: 44.89%, H: 5.83%, Cl: 7.76, F: 2.60, N: 8.30% found: C: 44.93%, H: 5.81%, Cl: 7.76, F: 2.67, N: 8.26% |

TABLE 91

| | | | | | | | |
|---|---|---|---|---|---|---|---|
| 4-(OCF2F)phenyl | bond | CONH | bond | 1-(2-methoxyethyl)-pyrazole-3,5-diyl | CH2 | [M + 1]⁺ = 1789 | calcd. for C81H89Cl2F3N12O27•1.8HCl•14.5H2O C: 45.95%, H: 5.70%, Cl: 6.36, F: 2.69, N: 7.94% found: C: 45.89%, H: 5.54%, Cl: 6.45, F: 2.88, N: 7.91% |

TABLE 91-continued

| | | | | | | |
|---|---|---|---|---|---|---|
| [4-(trifluoromethoxy)phenyl] | bond | NHCO | bond | [piperidine] | CH2CH2 | [M + 1]⁺ = 1762 calcd. for C81H92Cl2F3N11O26•1.2HCl•16.9H2O<br>C: 46.07%, H: 6.06%, Cl: 5.37, F: 2.70, N: 7.30%<br>found: C: 46.08%, H: 5.91%, Cl: 5.29, F: 2.24, N: 7.34% |
| [3,5-dichlorophenyl] | bond | CONH | bond | [1-methylpyrazole] | CH2 | [M + 1]⁺ = 1729 calcd. for C78H84Cl4N12O25•1.7HCl•13.0H2O<br>C: 46.20%, H: 5.55%, Cl: 9.97, N: 8.29%<br>found: C: 46.06%, H: 5.29%, Cl: 9.98, N: 8.21% |
| [3,5-dichlorophenyl] | bond | CONH | bond | [1-(2-dimethylaminoethyl)pyrazole] | CH2 | [M + 1]⁺ = 1786 calcd. for C81H91Cl4N13O25•2.4HCl•12.5H2O<br>C: 46.30%, H: 5.68%, Cl: 10.80, N: 8.67%<br>found: C: 46.21%, H: 5.63%, Cl: 10.85, N: 8.69% |
| [3,5-dichlorophenyl] | bond | CONH | bond | [piperazine] | CH2CH2 | [M + 1]⁺ = 1747 calcd. for C79H90Cl4N12O25•2.4HCl•15.0H2O<br>C: 45.03%, H: 5.85%, Cl: 10.77, N: 7.98%<br>found: C: 45.14%, H: 5.73%, Cl: 10.75, N: 7.81% |

TABLE 92

| | | | | | | |
|---|---|---|---|---|---|---|
| [3,5-dichlorophenyl] | bond | NHCO | NH | [piperazine] | CH2CH2 | [M + 1]⁺ = 1762 calcd. for C79H91Cl4N13O25•2.0HCl•14.0H2O<br>C: 45.41%, H: 5.84%, Cl: 10.18, N: 8.71%<br>found: C: 45.46%, H: 5.80%, Cl: 10.01, N: 8.12% |
| [3,5-dimethyl-4-methoxyphenyl] | bond | CONH | bond | [1-methylpyrazole] | CH2 | [M + 1]⁺ = 1719 calcd. for C81H92Cl2N12O26•1.8HCl•16.5H2O<br>C: 46.69%, H: 6.13%, Cl: 6.47, N: 8.07%<br>found: C: 46.84%, H: 5.98%, Cl: 6.52, N: 8.09% |

TABLE 92-continued

| | | | | | | | |
|---|---|---|---|---|---|---|---|
| 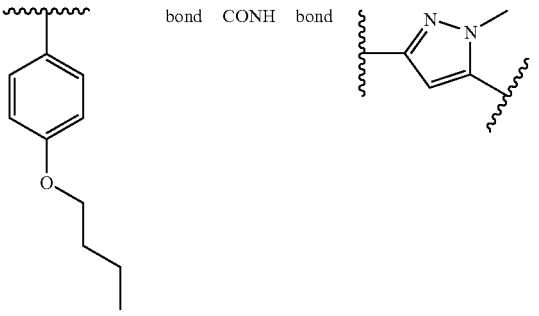 | bond | CONH | bond | 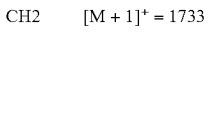 | CH2 | $[M + 1]^+ = 1733$ | calcd. for C82H94Cl2N12O26•1.7HCl•13.5H2O<br>C: 48.28%, H: 6.06%, Cl: 6.43, N: 8.24%<br>found: C: 48.25%, H: 5.90%, Cl: 6.52, N: 8.08% |
| 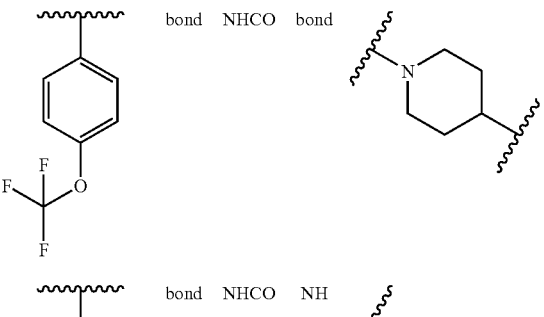 | bond | NHCO | bond | 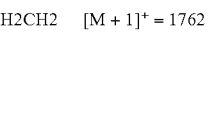 | CH2CH2 | $[M + 1]^+ = 1762$ | calcd. for C81H92Cl2F3N11O26•1.7HCl•13.0H2O<br>C: 47.23%, H: 5.86%, Cl: 6.37, F: 2.77, N: 7.48%<br>found: C: 47.06%, H: 5.79%, Cl: 6.38, F: 2.78, N: 7.39% |
| 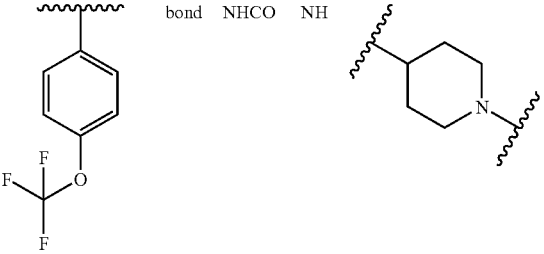 | bond | NHCO | NH | 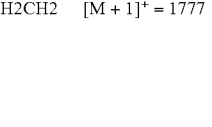 | CH2CH2 | $[M + 1]^+ = 1777$ | calcd. for C81H93Cl2F3N12O26•2.5HCl•12.5H2O<br>C: 46.44%, H: 5.80%, Cl: 7.62, F: 2.72, N: 8.02%<br>found: C: 46.30%, H: 5.82%, Cl: 7.63, F: 2.64, N: 7.81% |

TABLE 93

| $R^A$ | $R^B$ | $R^C$ | $R^D$ |
|---|---|---|---|
| 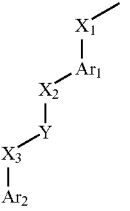<br>Y = CO—NR<br>NR—CO | OH | H | H |

| $R^A$ | | | | | | | |
|---|---|---|---|---|---|---|---|
| Ar2 | X3 | Y | X2 | Ar1 | X1 | Mass | Elemental Analysis |
| 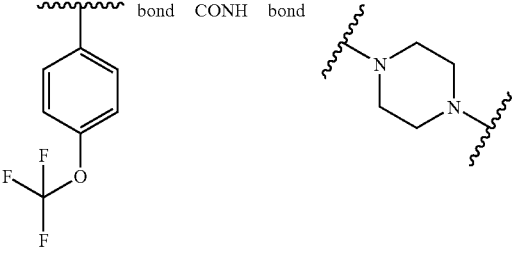 | bond | CONH | bond | 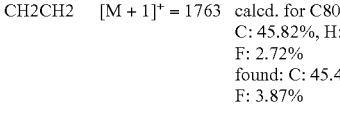 | CH2CH2 | $[M + 1]^+ = 1763$ | calcd. for C80H91Cl2F3N12O26•2.4HCl•13.6H2O<br>C: 45.82%, H: 5.80%, N: 8.02%, Cl: 7.44%, F: 2.72%<br>found: C: 45.47%, H: 5.68%, N: 8.42%, Cl: 7.51%, F: 3.87% |

TABLE 93-continued

| Ar1 | L1 | L2 | L3 | Ar2 | L4 | MS | Analysis |
|---|---|---|---|---|---|---|---|
| 4-(OCF2F)-C6H4- | bond | NHCO | bond | piperazine | CH2CH2 | [M + 1]+ = 1763 | calcd. for C80H91Cl2F3N12O26•2.7HCl•14.1H2O<br>C: 45.39%, H: 5.80%, N: 7.94%, Cl: 7.87%, F: 2.69%<br>found: C: 45.11%, H: 5.82%, N: 8.00%, Cl: 7.88% F: 2.44% |
| 4-(OCF2F)-C6H4- | bond | NHCO | NH | piperazine | CH2CH2 | [M + 1]+ = 1778 | calcd. for C80H92Cl2F3N13O26•2.5HCl•15.3H2O<br>C: 44.77%, H: 5.87%, N: 8.48%, Cl: 7.43%, F: 2.66%<br>found: C: 44.56%, H: 5.82%, N: 8.43%, Cl: 7.46%, F: 2.75% |

TABLE 94

| Ar1 | L1 | L2 | L3 | Ar2 | L4 | MS | Analysis |
|---|---|---|---|---|---|---|---|
| 3-(OCF3)-C6H4- | bond | NHCO | bond | pyridine-2,6-diyl | CH2 | [M + 1]− = 1743 | calcd. for C80H84Cl2F3N11O26•1.8HCl•13.5H2O<br>C: 46.82%, H: 5.54%, N: 7.51%, Cl: 6.56%, F: 2.78%<br>found: C: 46.80%, H: 5.39%, N: 7.63%, Cl: 6.58% F: 2.71% |
| 3-(OCF3)-C6H4- | bond | CONH | bond | pyridine-2,4-diyl | CH2 | [M + 1]− = 1742<br>[M − Cl]− = 1780 | calcd. for C80H84Cl2F3N11O26•2.6HCl•14.5H2O<br>C: 45.77%, H: 5.55%, N: 7.34%, Cl: 7.77% F: 2.71%<br>found: C: 45.77%, H: 5.61%, N: 7.37%, Cl: 7.86%, F: 2.84% |
| 3-(OCF3)-C6H4- | bond | NHCO | NH | piperazine | CH2CH2 | [M + H]+ = 1778 | calcd. for C80H92Cl2F3N13O26•0.4HCl•18.3H2O<br>C: 45.24%, H: 6.12%, N: 8.57%, Cl: 4.01% F: 2.68%<br>found: C: 44.88%, H: 5.74%, N: 8.38%, Cl: 3.98% F: 2.72% |
| 3,5-dimethyl-4-methoxy-C6H2- | bond | NHCO | NH | piperazine | CH2CH2 | [M + H]+ = 1752 | calcd. for C82H99Cl2N13O26•2.7HCl•13H2O<br>C: 47.21%, H: 6.17%, N: 8.73%, Cl: 7.99%<br>found: C: 47.09%, H: 6.12%, N: 8.53%, Cl: 8.01% |

TABLE 94-continued

| | | | | | | | |
|---|---|---|---|---|---|---|---|
| 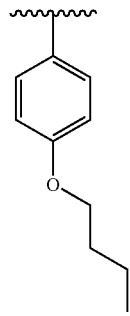 | bond | NHCO | NH | 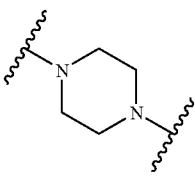 | CH2CH2 | $[M + H]^+ = 1766$ | calcd. for C83H101Cl2N13O26•2.6HCl•13.5H2O<br>C: 47.34%, H: 6.25%, N: 8.65%, Cl: 7.74%<br>found: C: 47.32%, H: 6.11%, N: 8.67%, Cl: 7.69% |

TABLE 95

| | | | | | | | |
|---|---|---|---|---|---|---|---|
| 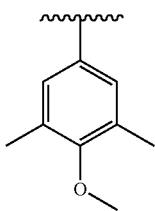 | bond | CONH | bond | 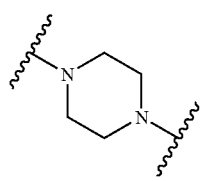 [SMILES: *N1CCN(*)CC1] | CH2CH2 | $[M + H]^+ = 1737$ | calcd. for C82H98Cl2N12O26•2.4HCl•16H2O<br>C: 46.58%, H: 6.31%, N: 7.95%, Cl: 7.38%<br>found: C: 46.69%, H: 6.04%, N: 7.90%, Cl: 7.53% |
| 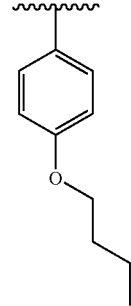 | bond | CONH | bond | 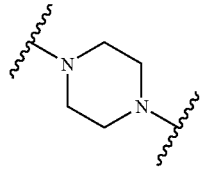 [SMILES: *N1CCN(*)CC1] | CH2CH2 | $[M + H]^+ = 1751$ | calcd. for C83H100Cl2N12O26•2.4HCl•17H2O<br>C: 46.44%, H: 6.41%, N: 7.83%, Cl: 7.27%<br>found: C: 46.38%, H: 6.12%, N: 7.85%, Cl: 7.33% |
| 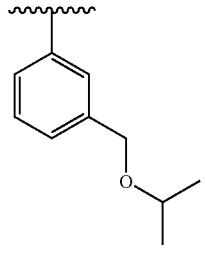 [SMILES: *c1cccc(COC(C)C)c1] | bond | CONH | bond | 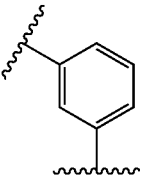 [SMILES: *c1cccc(*)c1] | CH2 | $[M + 1]^- = 1729$ | calcd. for C84H94Cl2N10O26•1.9HCl•10.8H2O<br>C: 50.59%, H: 5.94%, N: 7.02%, Cl: 6.93%<br>found: C: 50.43%, H: 5.64%, N: 7.15%, Cl: 6.97% |

TABLE 96

| R^A | R^B | R^C | R^D |
|---|---|---|---|
| (structure with X1-Ar1-X2-Y-X3-Ar2; Y = CO—NR or NR—CO) | OH | H | H |

| Ar2 | X3 | Y | X2 | Ar1 | X1 | Mass | Elemental Analysis |
|---|---|---|---|---|---|---|---|
| 3-(trifluoromethoxy)phenyl | bond | CONH | bond | (1-methylimidazole-2,5-diyl) | CH2 | [M + 1]$^+$ = 1745 | calcd. for C79H85Cl2F3N12O26•2.0HCl•13.0H2O C: 46.20%, H: 5.55%, Cl: 6.91, F: 2.78, N: 8.18% found: C: 46.25%, H: 5.50%, Cl: 6.46, F: 2.77, N: 8.24% |
| 3-(trifluoromethoxy)phenyl | bond | CONH | bond | (1,3,4-thiadiazole-2,5-diyl) | CH2 | [M + 1]$^+$ = 1749 | calcd. for C77H81Cl2F3N12O26S•2.0HCl•14.0H2O C: 44.60%, H: 5.40%, Cl: 6.84, F: 2.75, N: 8.10, S: 1.55% found: C: 44.51%, H: 5.24%, Cl: 7.02, F: 2.42, N: 8.06, S: 1.55% |

TABLE 97

| R^A | R^B | R^C | R^D |
|---|---|---|---|
| (structure with X1-Ar1-X2-Y-X3-Ar2; Y = CO—NR or NR—CO) | OH | H | H |

| Ar2 | X3 | Y | X2 | Ar1 | X1 | Mass | Elemental Analysis |
|---|---|---|---|---|---|---|---|
| 3-(difluoromethoxy)phenyl (F2HCF2CO-) | bond | CONH | bond | 1,3-phenylene | CH2 | [M + 3]$^+$ = 1775  [M − 1]$^+$ = 1773 | calcd. for C82H86Cl2N10O26•2HCl•11H2O C: 48.14%, H: 5.32%, N: 6.84, Cl: 6.89% found: C: 47.97%, H: 5.09%, N: 6.78%, Cl: 6.68% |
| 2,2-difluorobenzo[d][1,3]dioxol-5-yl | bond | CONH | bond | 1,3-phenylene | CH2 | [M + 3]$^+$ = 1738  [M − 1]$^+$ = 1736 | calcd. for C81H84Cl2F2N10O27•2HCl•12H2O C: 47.97%, H: 5.36%, N: 6.93, Cl: 6.99% found: C: 47.87%, H: 4.68%, N: 6.87%, Cl: 6.81% |

TABLE 97-continued

| R | | | | Ar | | Data |
|---|---|---|---|---|---|---|
| (F3CO, NMe2 phenyl) | bond | CONH | bond | (m-phenylene) | CH2 | [M + 3]+ = 1786<br>[M − 1]+ = 1784 | calcd. for<br>C83H90Cl2F3N11O26•2HCl•12H2O<br>C: 48.06%, H: 5.54%, N: 7.42%,<br>Cl: 6.83%<br>found: C: 47.98%, H: 5.24%, N: 7.44%,<br>Cl: 7.46% |
| (F3CS phenyl) | bond | CONH | bond | (m-phenylene) | CH2 | [M + 3]+ = 1759<br>[M − 1]+ = 1757 | calcd. for<br>C81H85Cl2F3N10O25•2HCl11H2O<br>C: 4792%, H: 5.32%, N: 6.90%, Cl: 6.98%<br>found: C: 47.93%, H: 5.17%, N: 6.90%,<br>Cl: 6.86% |

TABLE 98

| R | | | | Ar | | Data |
|---|---|---|---|---|---|---|
| (3-isopropoxyphenyl) | bond | CONH | bond | (m-phenylene) | CH2 | [M + 3]+ = 1718<br>[M + 1]− = 1716 | calcd. for<br>C83H92Cl2N10O26•2HCl•12H2O<br>C: 49.70%, H: 5.82%, N: 6.98%,<br>Cl: 7.07%<br>found: C: 49.37%, H: 5.47%, N: 7.00%,<br>Cl: 6.57% |
| (4-butoxyphenyl) | bond | CONH | bond | (m-phenylene) | CH2 | [M + 3]+ = 1731<br>[M + 1]− = 1729 | calcd. for<br>C84H94Cl2N10O26•2HCl•14H2O<br>C:49.07%, H: 5.98%, N: 6.81%,<br>Cl: 6.89%<br>found: C: 49.24%, H: 5.91%, N: 6.89%,<br>Cl: 6.59% |
| (3-butoxyphenyl) | bond | CONH | bond | (m-phenylene) | CH2 | [M + 3]+ = 1731<br>[M + 1]− = 1729 | calcd. for<br>C84H94Cl2N10O26•2HCl•10H2O<br>C: 50.85%, H: 5.79%, N: 7.06,<br>Cl: 7.14%<br>found: C: 50.97%, H: 5.86%, N: 7.07%,<br>Cl: 6.79% |
| (3,4,5-trimethoxyphenyl) | bond | CONH | bond | (m-phenylene) | CH2 | [M + 3]+ = 1749<br>[M + 1]− = 1747 | calcd. for<br>C83H92Cl2N10O28•2HCl•14H2O<br>C: 48.05%, H: 5.79%, N: 6.75%,<br>Cl: 6.83%<br>found: C: 47.70%, H: 5.73%, N: 6.79%,<br>Cl: 6.95% |
| (3-(2-ethoxyethoxymethyl)phenyl) | bond | CONH | bond | (m-phenylene) | CH2 | [M + 3]+ = 1761<br>[M + 1]− = 1759 | calcd. for<br>C85H96Cl2N10O27•2HCl•12H2O<br>C: 49.80%, H: 5.90%, N: 6.83%,<br>Cl: 6.91%<br>found: C: 49.82%, H: 5.31%, N: 6.90%,<br>Cl: 7.24% |
| (3-(propoxymethyl)phenyl) | bond | CONH | bond | (m-phenylene) | CH2 | [M + 3]+ = 1731<br>[M + 1]− = 1729 | calcd. for<br>C84H94Cl2N10O26•2HCl•11H2O<br>C: 50.39%, H: 5.84%, N: 6.99,<br>Cl: 7.08%<br>found: C: 50.28%, H: 5.96%, N: 7.17%,<br>Cl: 6.97% |

TABLE 98-continued

| $R^A$ | $R^B$ | $R^C$ | $R^D$ | Mass | Elemental Analysis |
|---|---|---|---|---|---|
| (3-(2-ethoxyethoxy)phenyl with CH2 linker) | bond | CONH | bond (1,3-phenylene with CH2) | [M + 3]⁺ = 1747<br>[M + 1]⁻ = 1745 | calcd. for C84H94Cl2N10O27•2HCl•16H2O<br>C: 48.60%, H: 6.12%, N: 6.74%, Cl: 6.83%<br>found: C: 48.57%, H: 5.82%, N: 7.05%, Cl: 7.05% |

TABLE 99

| $R^A$ | $R^B$ | $R^C$ | $R^D$ |
|---|---|---|---|
| (Ar1 = 3-methylphenyl with CH2; NH–C(=O)–Ar2 where Ar2 = 3,5-dichlorophenyl; X2 = X3 = bond) Y | OH or NH—R | H or CH2—NH—R | H |

| $R^B$ | $R^C$ | $R^D$ | Mass | Elemental Analysis |
|---|---|---|---|---|
| (H2N-CH2CH2-N⁺(piperazinium)-CH2CH2-NH–, 2 Cl⁻) | H | H | [M + 1]⁻ = 1907 | calcd. for C90H106Cl6N14O24•1.2HCl•9.6H2O<br>C: 49.20%, H: 5.80%, N: 8.92%, Cl: 11.62%<br>found: C: 49.43%, H: 5.75%, N: 7.39%, Cl: 11.62% |
| OH | (neopentyl-NH-CH3) | H | [M + 1]⁻ = 1768 | calcd. for C82H89Cl4N11O25.2•1HCl•8.5H2O<br>C: 49.24%, H: 5.45%, N: 7.70%, Cl: 10.81%<br>found: C: 49.31%, H: 5.54%, N: 7.01%, Cl: 10.77% |
| OH | (gluconamide-type: CH2–NH–CH(COOH)–CH(OH)–CH(OH)–CH(OH)–CH2OH) | H | [M + 1]⁻ = 1933 | calcd. for C87H97Cl4N11O31•2.2HCl•10.1H2O<br>C: 47.57%, H: 5.48%, N: 7.01%, Cl: 10.01%<br>found: C: 47.65%, H: 5.50%, N: 6.38%, Cl: 10.07% |
| OH | (–CH2–NH–CH2CH2–N⁺(piperazinium)–CH2CH2–NH2, 2 Cl⁻) | H | [M + 1]⁻ = 1937 | calcd. for C91H108Cl6N14O25•2.7HCl•14.8H2O<br>C: 46.01%, H: 5.95%, N: 8.25%, Cl: 12.98%<br>found: C: 46.10%, H: 5.87%, N: 7.98%, Cl: 12.90% |

TABLE 100

| $R^B$ | $R^C$ | $R^D$ | Mass | Elemental Analysis |
|---|---|---|---|---|
| OH | (–CH2–NH–CH2CH2–(1H-tetrazol-5-yl)) | H | [M + 1]⁻ = 1850 | calcd. for C84H91Cl4N15O25•2.0HCl•11.0H2O<br>C: 47.51%, H: 5.46%, N: 9.89%, Cl: 10.02%<br>found: C: 47.59%, H: 5.43%, N: 9.27%, Cl: 10.09% |

TABLE 100-continued

| Structure 1 | Col2 | Structure 3 | Col4 | MS | Analysis |
|---|---|---|---|---|---|
| (lysine-like: NH-CH2CH2CH2CH2-CH(NH2)-CO2H) | H | H | | [M + 1]⁻ = 1853 | calcd. for C86H96Cl4N12O26•2.7HCl•7.4H2O<br>C: 48.17%, H: 5.34%, N: 7.84%, Cl: 11.08%<br>found: C: 48.14%, H: 5.55%, N: 7.88%, Cl: 11.11% |
| (N-methyl glutamate-like) | H | H | | [M + 1]⁻ = 1854 | calcd. for C85H91Cl4N11O28•2.0HCl•8.9H2O<br>C: 48.85%, H: 5.34%, N: 7.37%, Cl: 10.18%<br>found: C: 48.91%, H: 5.24%, N: 7.00%, Cl: 10.25% |
| OH | | (N-methyl glutamate-like) | H | [M + 1]⁻ = 1884 | calcd. for C86H93Cl4N11O29•1.7HCl•10.6H2O<br>C: 48.28%, H: 5.46%, N: 7.20%, Cl: 9.45%<br>found: C: 48.28%, H: 5.40%, N: 7.16%, Cl: 9.41% |
| OH | | (N-carboxymethyl-N-methyl-aminopolyol) | H | [M + 1]⁻ = 1976 | calcd. for C89H101Cl4N11O32•2.9HCl•11.8H2O<br>C: 46.54%, H: 5.59%, N: 6.71%, Cl: 10.65%<br>found: C: 46.47%, H: 5.17%, N: 6.76%, Cl: 10.59% |
| (MeNH-CH2CH2-N⁺(Me)2-CH2CH2-N⁺Me3) | | H | H | [M + 3]⁺⁺ = 948 | calcd. for C89H107Cl6N13O24•2.0HCl•12.7H2O<br>C: 47.36%, H: 6.00%, N: 8.07%, Cl: 12.56%<br>found: C: 47.25%, H: 5.63%, N: 8.24%, Cl: 12.51% |
| OH | | (MeNH-CH2CH2-N⁺(Me)2-CH2CH2-N⁺Me3) | H | [M + 3]⁺⁺ = 958 | calcd. for C90H109Cl6N13O25•2.8HCl•14.8H2O<br>C: 45.91%, H: 5.95%, N: 7.73%, Cl: 13.25%<br>found: C: 45.79%, H: 5.52%, N: 8.01%, Cl: 13.20% |

TABLE 101

| Col1 | Structure 2 | Col3 | MS | Analysis |
|---|---|---|---|---|
| OH | (NH-CH(CO2H)-CH2-CO2H, aspartate-like) | H | [M + 3]⁺ = 1872<br>[M + 1]⁻ = 1870 | calcd. for C85H91Cl4N11O29•2.5HCl•12H2O<br>C: 54.52%, H: 4.9%, N: 8.23%, Cl: 7.57%<br>found: C: 46.85%, H: 5.32%, N: 7.08%, Cl: 10.85% |
| (NH-CH2CH2-N⁺(Me)2-CH2-CO2Me) | | H | H | [M + 1]⁻ = 1868 | calcd. for C87H99Cl4N12O26•3HCl•11H2O<br>C: 55.86%, H: 5.33%, N: 8.99%, Cl: 7.58%<br>found: C: 48.11%, H: 5.62%, N: 7.88%, Cl: 11.09% |
| (NH-CH2CH2-N⁺(Me)2-CH2-CO2H) | | H | H | [M + 3]⁺ = 1856 | calcd. for C85H91Cl4N11O29•3HCl•13H2O<br>C: 55.64%, H: 5.27%, N: 9.05%, Cl: 7.64%<br>found: C: 47.21%, H: 5.54%, N: 7.71%, Cl: 11.02% |
| (NH-CH2-(3-hydroxyisoxazol-5-yl)) | | H | H | [M + 1]⁻ = 1821 | calcd. for C85H91Cl4N11O29•2HCl•14H2O<br>C: 55.33%, H: 4.86%, N: 9.22%, Cl: 7.78%<br>found: C: 47.17%, H: 5.41%, N: 7.91%, Cl: 9.64% |

TABLE 101-continued

| $R^A$ | | $R^C$ | $R^D$ | Mass | Elemental Analysis |
|---|---|---|---|---|---|
| OH | ![structure]  ~NH-CH2CH2-N(Me)Me | H | | $[M+3]^+ = 1827$ | calcd. for C85H96Cl4N12O25•4.5HCl•14.7H2O<br>C: 45.24%, H: 5.80%, N: 7.45%, Cl: 13.36%<br>found: C: 45.15%, H: 5.79%, N: 7.81%, Cl: 13.41% |
| OH | ~NH-CH2CH2-N(morpholine) | H | | $[M+3]^+ = 1870$<br>$[M+1]^- = 1868$ | calcd. for C87H98Cl4N12O26•3.4HCl•14.4H2O<br>C: 46.38%, H: 5.82%, N: 7.46%, Cl: 11.64%<br>found: C: 46.31%, H: 5.56%, N: 7.54%, Cl: 11.68% |
| ~NH-CH2CH2-N(morpholine) | | H | H | $[M+3]^+ = 1839$ | calcd. for C86H96Cl4N12O25•2.9HCl•14.1H2O<br>C: 46.97%, H: 5.82%, N: 7.64%, Cl: 11.12%<br>found: C: 46.94%, H: 5.70%, N: 7.62%, Cl: 11.10% |

TABLE 102

| $R^A$ | $R^C$ | $R^D$ | Mass | Elemental Analysis |
|---|---|---|---|---|
| ~NH-CH2CH2-N(Me)Me | H | H | $[M+1]^- = 1795$ | calcd. for C84H94Cl4N12O24 2•7HCl•13.4H2O<br>C: 47.20%, H: 5.82%, N: 7.86%, Cl: 11.11%<br>found: C: 46.17%, H: 5.66%, N: 7.91%, Cl: 11.07% |
| ~NH-CH2CH2CH2-N+(Me)3 | H | H | $[M+1]^- = 1823$ | calcd. for C86H99Cl4N12O24•2.6HCl•13.1H2O<br>C: 47.88%, H: 5.97%, N: 7.79%, Cl: 10.85%<br>found: C: 46.87%, H: 5.84%, N: 7.60%, Cl: 10.86% |

TABLE 103

| $R^A$ | $R^B$ | $R^C$ | $R^D$ |
|---|---|---|---|
| ![Ar1-CH2-NH-C(O)-Ar2(OCF3)]<br>$X_2 = X_3 = $ bond | OH or NH—R | H or CH2—NH—R | H |

| $R^B$ | $R^C$ | $R^D$ | Mass | Elemental Analysis |
|---|---|---|---|---|
| —NH(CH2)2SO3H | H | H | $[M+3]^+ = 1850$<br>$[M+1]^- = 1848$ | calcd for C83H90Cl2F3N11O28S•1.2HCl•10.7H2O<br>C: 47.79%, H: 5.44%, N: 7.39%, Cl: 5.44%, F: 2.73%, S: 1.54%<br>found: C: 47.78%, H: 5.23%, N: 7.32%, Cl: 5.37%, F: 2.88%, S: 1.25% |
| ~NH-CH(CO2H)-CH2-CO2H | H | H | $[M+1]^- = 1857$ | calcd. for C85H90Cl2F3N11O29•1.8HCl•12.1H2O<br>C: 47.68%, H: 5.46%, N: 7.20%, Cl: 6.29%, F: 2.66%<br>found: C: 47.67%, H: 5.43%, N: 7.31%, Cl: 6.29%, F: 2.66% |
| —NH(CH2)2NHSO2NH2 | H | H | $[M+1]^- = 1863$ | calcd. for C83H92Cl2F3N13O27S•2.0HCl•11.0H2O<br>C: 46.70%, H: 5.48%, N: 8.53%, Cl: 6.64%, F: 2.67%, S: 1.50%<br>found: C: 46.76%, H: 5.46%, N: 8.42%, Cl: 6.57%, F: 2.61%, S: 1.33% |
| —NH(CH2)2O(CH2)2OH | H | H | $[M+3]^+ = 1831$<br>$[M+1]^- = 1829$ | calcd. for C85H94Cl2F3N11O27•1.9HCl•10.9H2O<br>C: 48.72%, H: 5.66%, N: 7.35%, Cl: 6.60%, F: 2.72%<br>found: C: 48.66%, H: 5.43%, N: 7.41%, Cl: 6.56%, F: 2.66% |

TABLE 104

| Structure 1 | Col2 | Structure 3 | Col4 | MS | Analysis |
|---|---|---|---|---|---|
| ~N(H)-CH(CO2H)-CH2-CONH2 | H | | H | [M + 1]⁻ = 1855 | calcd. for C85H91Cl2F3N12O28•2.0HCl•12.3H2O<br>C: 47.46%, H: 5.51%, N: 7.81%, Cl: 6.59%, F: 2.65%<br>found: C: 47.44%, H: 5.29%, N: 7.75%, Cl: 6.51%, F: 2.62% |
| ~N(H)-CH2CH2-N⁺(CH3)2-N(H)-C(O)CH3 | H | | H | [M + 1]⁻ = 1869 | calcd. for C87H98Cl2F3N13O26•2.9HCl•13.0H2O<br>C: 47.68%, H: 5.74%, N: 8.31%, Cl: 7.93%, F: 2.60%<br>found: C: 47.57%, H: 5.53%, N: 8.57%, Cl: 7.94%, F: 2.54% |
| OH | | ~CH2-N(H)-CH(CO2H)-CH2-CONH2 | H | [M + 1]⁻ = 1885 | calcd. for C86H93Cl2F3N12O29•1.7HCl•11.5H2O<br>C: 47.91%, H: 5.50%, N: 7.80%, Cl: 6.08%, F: 2.64%<br>found: C: 47.96%, H: 5.36%, N: 7.83%, Cl: 6.00%, F: 2.55% |
| OH | | ~CH2-N(H)-CH2CH2-CO2H | H | [M + 3]⁺ = 1844<br>[M + 1]⁻ = 1842 | calcd. for C85H92Cl2F3N11O28•2.1HCl•11.1H2O<br>C: 48.15%, H: 5.53%, N: 7.27%, Cl: 6.86%, F: 2.69%<br>found: C: 48.10%, H: 5.36%, N: 7.42%, Cl: 6.86%, F: 2.57% |
| OH | | ~CH2-N(H)-CH2CH2-SO3H | H | [M + 1]⁻ = 1878 | calcd. for C84H92Cl2F3N11O29S•1.2HCl•12.0H2O<br>C: 47.15%, H: 5.52%, N: 7.20%, Cl: 5.30%,<br>F: 2.66%,<br>S: 1.50%<br>found: C: 47.14%, H: 5.29%, N: 7.24%, Cl: 5.42%, F: 2.60%, S: 1.37% |
| OH | | ~CH2-N(H)-CH2-PO3H | H | [M + 1]⁻ = 1865 | calcd. for C83H91Cl2F3N11O29P•1.6HCl•12.4H2O<br>C: 46.43%, H: 5.51%, N: 7.18%, Cl: 5.94%,<br>F: 2.65%,<br>P: 1.44%<br>found: C: 46.42%, H: 5.34%, N: 7.16%, Cl: 6.00%, F: 2.58%, P: 1.60% |

TABLE 105

| Col1 | Col2 | Col3 | Col4 | Col5 |
|---|---|---|---|---|
| OH | ~N(H)-...-NHSO₂NH₂ | H | [M+1]⁻ = 1892 | calcd. for C84H94Cl2F3N13O28S•2.0HCl•12.6H2O C: 45.99%, H: 5.57%, N: 8.30%, Cl: 6.46% F: 2.60%, S: 1.46% found: C: 45.75%, H: 5.49%, N: 8.60%, Cl: 6.53%, F: 2.57%, S: 1.68% |
| OH | ~N(H)-...-N(H)C(O)CH(NH₂)(CH₂)₄-CO₂H | H | [M+3]⁺ = 2030 | calcd. for C94H111Cl2F3N14O29•3.0HCl•12.9H2O•0.2CF3COOH C: 47.37%, H: 5.90%, N: 8.19%, Cl: 7.41% F: 2.86% found: C: 47.40%, H: 5.91%, N: 8.15%, Cl: 7.50%, F: 2.96% |
| OH | ~N(H)-...-N(H)C(O)CH(NH₂)(CH₂)₃NHC(=NH)NH₂ with CO₂H | H | [M+3]⁺ = 2058 | calcd. for C94H111Cl2F3N16O29•2.7HCl•12.8H2O•0.07CF3COOH C: 46.47%, H: 5.72%, N: 9.09%, Cl: 6.76% F: 3.93% found: C: 46.49%, H: 5.71%, N: 9.06%, Cl: 6.75%, F: 3.95% |
| OH | ~N(H)-...-O-CH2CH2OH | H | [M+1]⁻ = 1858 | calcd. for C86H96Cl2F3N11O28•2.3HCl•11.9H2O C: 47.87%, H: 5.70%, N: 7.14%, Cl: 7.06% F: 2.64% found: C: 47.82%, H: 5.60%, N: 7.21%, Cl: 7.03%, F: 2.55% |
| OH | H | H | [M+1]⁻ = 1813 | calcd. for C84H90Cl2F3N11O27•1.8HCl•10.4H2O C: 48.82%, H: 5.49%, N: 7.46%, Cl: 6.52% F: 2.76% found: C: 48.77%, H: 4.53%, N: 7.14%, Cl: 6.59%, F: 2.61% |
| ~N(H)-CH2CH2-COOH | H | H | [M+3]⁺ = 1827 [M+1]⁻ = 1825 | calcd. for C86H97Cl2F3N12O25S•2.9HCl•12.4H2O C: 47.91%, H: 5.83%, N: 7.80%, Cl: 8.06% F: 2.64% found: C: 47.89%, H: 5.60%, N: 8.01%, Cl: 8.01%, F: 2.72% |
| ~N(H)-(CH2)3-N(CH3)2 | | | | |

TABLE 106

| Structure | | | MS | Analysis |
|---|---|---|---|---|
| (ethyl trimethyl ammonium chloride amine) | H | H | $[M+3]^+ = 1827$<br>$[M+1]^- = 1825$ | calcd. for C86H98Cl3F3N12O25•1.9HCl•13.3H2O<br>C: 47.56%, H: 5.87%, N: 7.74%, Cl: 8.00% F: 2.62%<br>found: C: 47.54%, H: 5.69%, N: 7.87%, Cl: 8.06% F: 2.55% |
| (histidine methyl ester amine) | H | H | $[M+1]^- = 1892$ | calcd. for C88H94Cl2F3N13O27•3.0HCl•14.1H2O<br>C: 46.83%, H: 5.59%, N: 8.01%, Cl: 7.85% F: 2.53%<br>found: C: 46.78%, H: 5.51%, N: 8.13%, Cl: 7:18% F: 2.51% |
| (ethylthio-tetrazolyl-ethyl trimethyl ammonium amine) | H | H | $[M+1]^- = 1955$ | calcd. for C89H103Cl2F3N16O25S•1.9HCl•14.5H2O<br>C: 46.02%, H: 5.81%, N: 9.65%, Cl: 7.48% F: 2.45%, S: 1.38%<br>found: C: 45.97%, H: 5.66%, N: 9.77%, Cl: 7.49% F: 2.48%, S: 1.35% |
| (bis(2-hydroxyethyl)amine) | H | H | $[M+1]^- = 1828$ | calcd. for C85H94Cl2F3N11O27•2.1HCl•11.9H2O<br>C: 48.14%, H: 5.70%, N: 7.27%, Cl: 6.85% F: 2.69%<br>found: C: 47.13%, H: 5.66%, N: 7.25%, Cl: 6.81% F: 2.72% |
| (histidine amine) | H | H | $[M+1]^- = 1878$ | calcd. for C87H92Cl2F3N13O27•2.8HCl•14.4H2O<br>C: 46.62%, H: 5.56%, N: 8.12%, Cl: 7.59% F: 2.54%<br>found: C: 46.65%, H: 5.48%, N: 7.96%, Cl: 7.58% F: 2.49% |
| (morpholinoethyl amine) | H | H | $[M+1]^- = 1853$ | calcd. for C87H97Cl2F3N12O26•2.8HCl•15.0H2O<br>C: 46.92%, H: 5.87%, N: 7.55%, Cl: 7.64% F: 2.56%<br>found: C: 46.89%, H: 5.65%, N: 7.55%, Cl: 7.64% F: 2.46% |

TABLE 107

| Structure | | | MS | Analysis |
|---|---|---|---|---|
| (2-(2-hydroxyethylamino)ethoxy) | H | H | $[M+3]^+ = 1830$<br>$[M+1]^- = 1828$ | calcd. for C85H94Cl2F3N11O27•2.9HCl•11.8H2O<br>C: 47.53%, H: 5.65%, N: 7.17%, Cl: 8.09% F: 2.65%<br>found: C: 47.46%, H: 5.49%, N: 7.21%, Cl: 8.13% F: 2.64% |

TABLE 108

| R$^A$ | R$^B$ | R$^C$ | R$^D$ |
|---|---|---|---|
| (structure: Ar$_1$ = 1-ethyl-2-oxo-pyrimidin-4-yl linked via CH$_2$CH$_2$ to N; benzamide NH—Y; Ar$_2$ = 3,5-dichlorophenyl; X$_2$ = X$_3$ = bond) | OH or NH—R | H or CH2—NH—R | H |

| R$^B$ | R$^C$ | R$^D$ | Mass | Elemental Analysis |
|---|---|---|---|---|
| —NH(CH$_2$)$_2$O(CH$_2$)$_2$OH | H | H | [M + 3]$^+$ = 1847 | calcd. for C83H93Cl4N13O27•2.3HCl•13.5H2O<br>C: 45.86%, H: 5.67%, N: 8.38%, Cl: 10.28%<br>found: C: 45.80%, H: 5.45%, N: 8.50%, Cl: 10.26% |
| —NH(CH$_2$)$_2$NHSO$_2$NH$_2$ | H | H | [M + 3]$^+$ = 1881 | calcd. for C81H91Cl4N15O27S•2.1HCl•11.1H2O<br>C: 45.10%, H: 5.39%, N: 9.74%, Cl: 10.03%, S: 1.49%<br>found: C: 45.16%, H: 5.36%, N: 9.54%, Cl: 9.98%, S: 1.28% |
| —NHCH$_2$CONHCN | H | H | [M + 3]$^+$ = 1841 | calcd. for C82H87Cl4N15O26•2.5HCl•12.9H2O<br>C: 45.51%, H: 5.37%, N: 9.71%, Cl: 10.65%<br>found: C: 45.50%, H: 5.36%, N: 9.73%, Cl: 10.67% |
| —NH(CH$_2$)$_2$OMe | H | H | [M + 3]$^+$ = 1817 | calcd. for C82H91Cl4N13O26•1.8HCl•11.8H2O<br>C: 47.02%, H: 5.60%, N: 8.69%, Cl: 9.82%<br>found: C: 47.04%, H: 5.54%, N: 8.64%, Cl: 9.85% |
| —NHCH$_2$CONH2 | H | H | [M + 3]$^+$ = 1816 | calcd. for C81H88Cl4N14O26•2.0HCl•11.9H2O<br>C: 46.27%, H: 5.45%, N: 9.33%, Cl: 10.12%<br>found: C: 46.27%, H: 5.34%, N: 9.38%, Cl: 10.16% |

TABLE 109

| R$^A$ | R$^B$ | R$^C$ | R$^D$ |
|---|---|---|---|
| (structure: Ar$_1$ = 5-methylpyridin-2-yl linked via CH$_2$ to N; benzamide NH—Y; Ar$_2$ = 3-trifluoromethoxyphenyl; X$_2$ = X$_3$ = bond) | OH or NH—R | H or CH2—NH—R | H |

| R$^B$ | R$^C$ | R$^D$ | Mass | Elemental Analysis |
|---|---|---|---|---|
| —NH—CH$_2$CH$_2$—NHSO$_2$NH$_2$ | H | H | [M + 1]$^-$ = 1864 | calcd. for C82H91Cl2F3N14O27S•2.2HCl•14.3H2O<br>C: 44.72%, H: 5.57%, N: 8.90%, Cl: 6.76%, F: 2.59%, S: 1.46%<br>found: C: 44.67%, H: 5.38%, N: 8.99%, Cl: 6.79%, F: 2.70%, S: 1.51% |

TABLE 110

| $R^A$ | $R^B$ | $R^C$ | N-terminal |
|---|---|---|---|
|  | OH or NH—R | H or CH2—NH—R | (N-methyl leucine structure) |

| $R^B$ | $R^C$ | N-terminal | Mass | Elemental Analysis |
|---|---|---|---|---|
| OH | H | (alanyl, NH2) | $[M+3]^+ = 1687$ <br> $[M+1]^- = 1685$ | calcd. for C77H77Cl2F3N10O26•1.8HCl•13.6H2O <br> C: 46.31%, H: 5.33%, N: 7.01%, Cl: 6.75%, F: 2.85% <br> found: C: 46.34%, H: 5.42%, N: 6.95%, Cl: 6.79%, F: 2.66% |
| OH | H | (prolyl) | $[M+1]^- = 1711$ | calcd. for C79H79Cl2F3N10O26•1.4HCl•14.4H2O <br> C: 46.91%, H: 5.44%, N: 6.92%, Cl: 5.96%, F: 2.82% <br> found: C: 46.86%, H: 5.32%, N: 6.84%, Cl: 5.99%, F: 2.93% |

TABLE 111

| $R^B$ | $R^C$ | N-terminal | Mass | Elemental Analysis |
|---|---|---|---|---|
| OH | H | (lysyl) | $[M+1]^- = 1743$ | calcd. for C80H84Cl2F3N11O26•2.6HCl•15.2H2O <br> C: 45.49%, H: 5.58%, N: 7.29%, Cl: 7.72%, F: 2.70% <br> found: C: 45.53%, H: 5.52%, N: 7.07%, Cl: 7.77%, F: 2.56% |
| OH | H | (histidyl) | $[M+1]^- = 1751$ | calcd. for C80H79Cl2F3N12O26•2.7HCl•15.7H2O <br> C: 45.03%, H: 5.34%, N: 7.88%, Cl: 7.81%, F: 2.67% <br> found: C: 44.99%, H: 5.17%, N: 7.99%, Cl: 7.77%, F: 2.66% |

Example 13

The following compounds were prepared in a similar manner as described above.

TABLE 112
| Structure | Mass | Elemental Analysis |
|---|---|---|
| Chiral 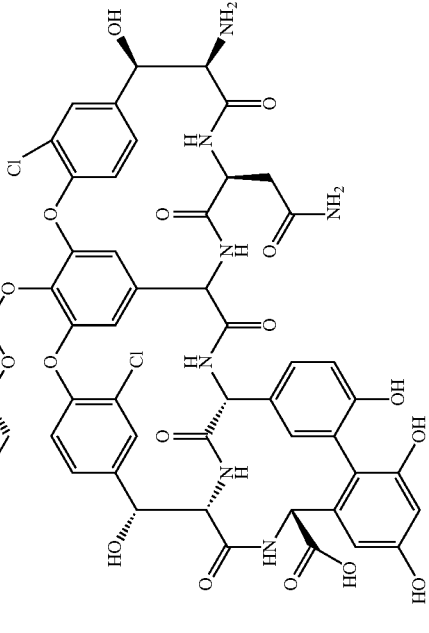 | [M + H]⁺ = 1695 | calcd. for C81H80Cl2N10O27 2.9(HCl) 15(H2O)<br>C: 46.94%, H: 5.49%, Cl: 8.38%, N: 6.76%, O: 32.42%<br>found: C: 47.04%, H: 4.92%, Cl: 8.25%, N: 6.95% |

TABLE 112-continued
| Structure | Mass | Elemental Analysis |
|---|---|---|
| Chiral 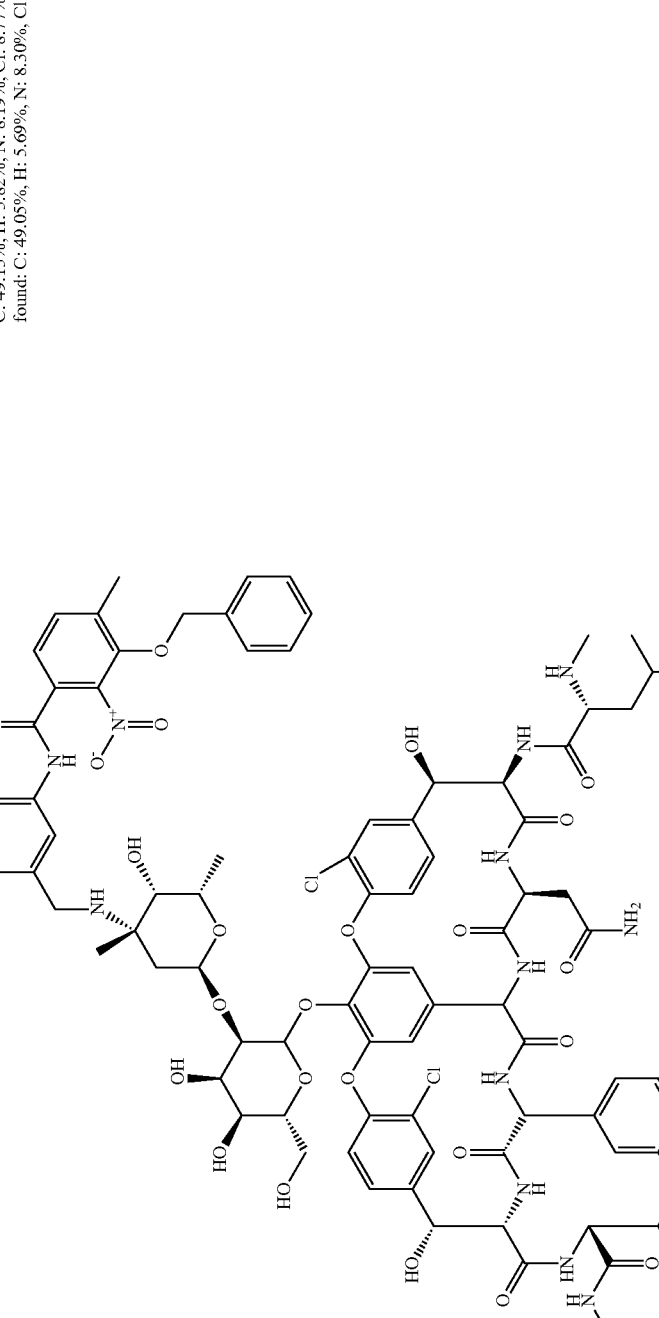 | [M + 1]$^+$ = 1878 | calcd. for C91H101Cl2N13C27•3.5HCl•12H2O C: 49.15%, H: 5.82%, N: 8.19%, Cl: 8.77%, C: 28.06%, found: C: 49.05%, H: 5.69%, N: 8.30%, Cl: 8.61% |

TABLE 112-continued
| Structure | Mass | Elemental Analysis |
|---|---|---|
| Chiral 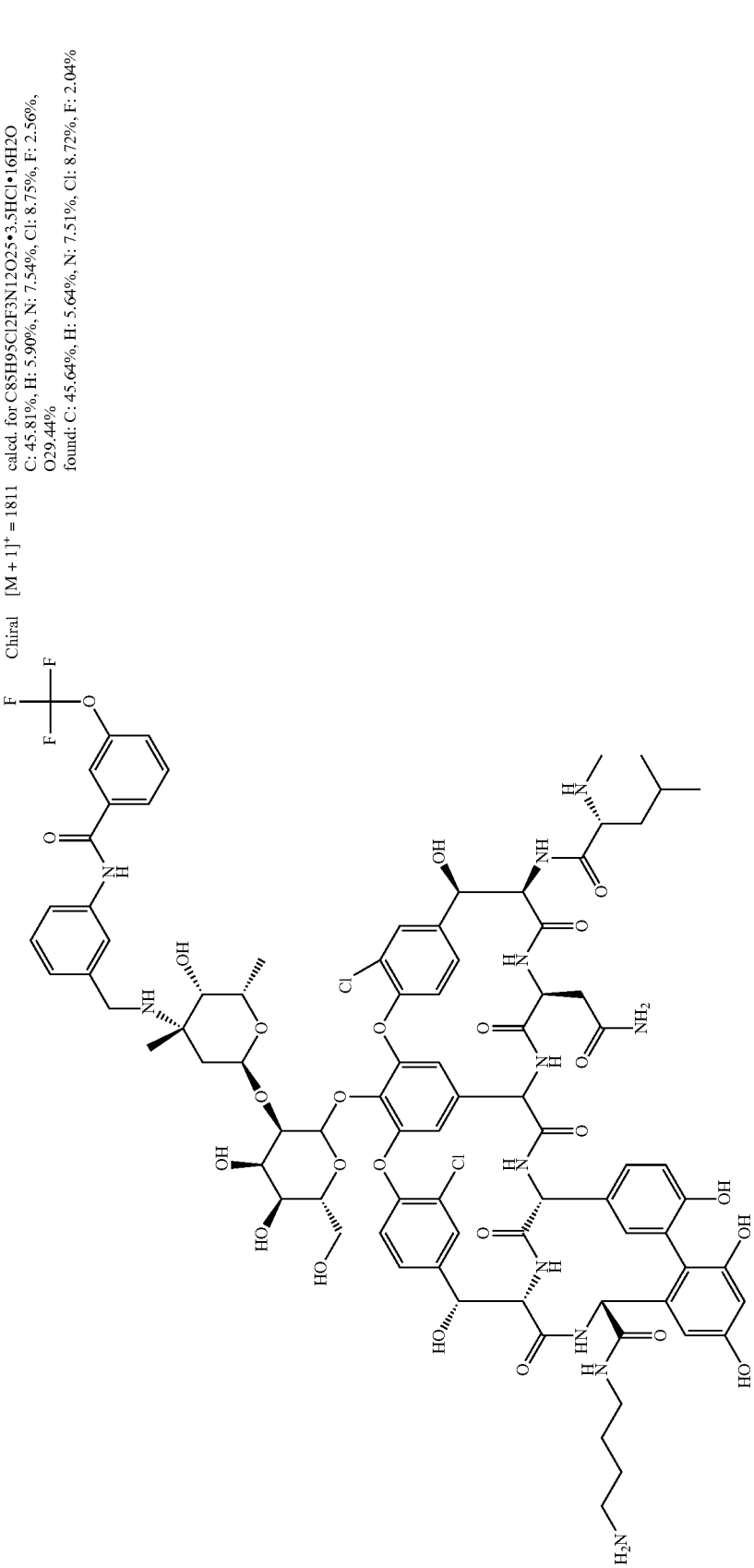 | [M + 1]+ = 1811 | calcd. for C85H95Cl2F3N12O25•3.5HCl•16H2O C: 45.81%, H: 5.90%, N: 7.54%, Cl: 8.75%, F: 2.56%, O29.44% found: C: 45.64%, H: 5.64%, N: 7.51%, Cl: 8.72%, F: 2.04% |

TABLE 113
| Structure | Mass | Elemental Analysis |
|---|---|---|
| Chiral 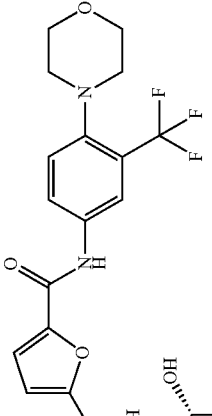 | [M + 1]<sup>+</sup> = 1800 | calcd. for C83H90Cl2F3N11O27•1.9HCl•13H2O C: 47.36%, H: 5.65%, N: 7.32%, Cl: 6.57%, F: 2.71%, O: 30.40%, found: C: 47.48%, H: 5.55%, N: 7.44%, Cl: 6.49%, F: 2.74% |

TABLE 113-continued
| Structure | Mass | Elemental Analysis |
|---|---|---|
| 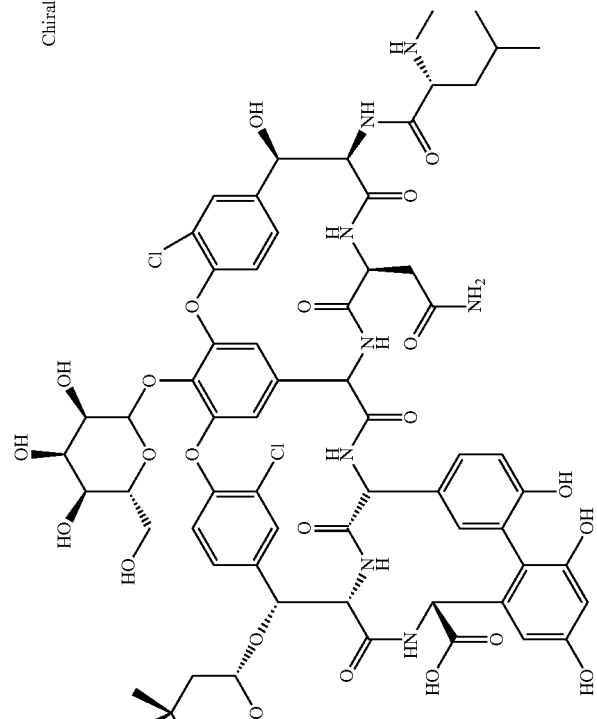 | [M + 1]⁺ = 1768 | calcd. for C83H90Cl2F3N11O25•2.1HCl•13H2O C: 47.92%, H: 5.72%, N: 7.41%, Cl: 6.99%, F 2.74%, O29.23%, found: C: 47.82%; H: 5.74%; N: 7.53%; Cl: 7.24%, F: 2.96% |

TABLE 113-continued
| Structure | Mass | Elemental Analysis |
|---|---|---|
| 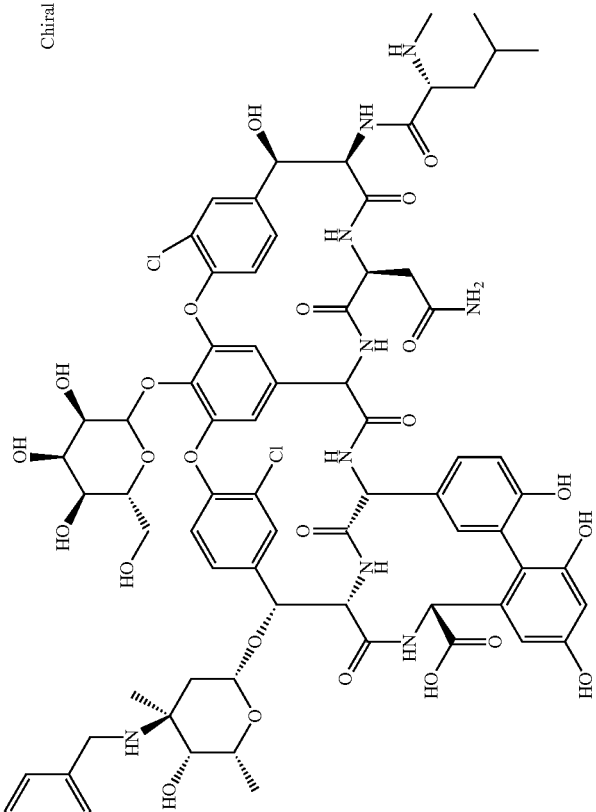 | [M + 1]⁺ = 1741 Chiral | calcd. for C81H85Cl2F3N10O26•1.5HCl•11H2O C: 48.76%, H: 5.48%, N: 7.02%, Cl: 6.22%, F: 2.86%, O: 29.67%, found: C: 48.55%, H: 5.58%, N: 7.03%, Cl: 6.20%, F: 2.91% |

TABLE 113-continued
| Structure | Mass | Elemental Analysis |
|---|---|---|
| 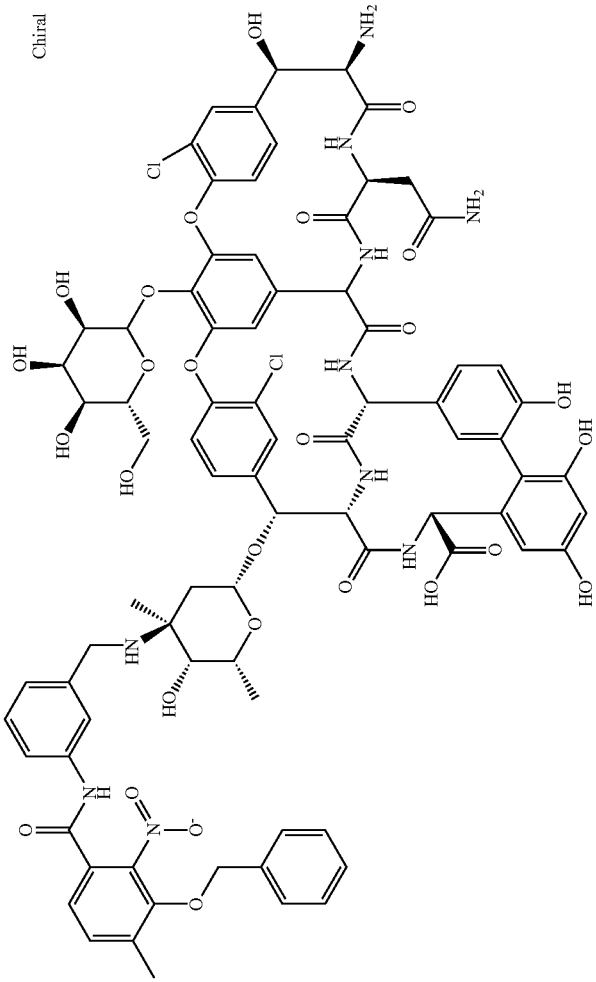 Chiral | [M + 1]+ = 1695 | calcd. for C81H80Cl2N10O27•2HCl•12H2O C: 49.0%, H: 5.38%, N: 7.05%, Cl: 7.14%, C: 31.43%, found: C: 49.16%, H: 5.24%, N: 7.18%, Cl: 7.0% |

Example 14

The following compounds were prepared in a similar manner as described above.

TABLE 114
| Structure | Mass | Elemental Analysis |
|---|---|---|
| Chiral | [M + 1]⁺ = 1921 | calcd. for C90H95Cl2F3N12O28•3.3HCl•13.8H2O<br>C: 47.21%, H: 5.54%, N: 7.34%, Cl: 8.21%, F: 2.49%<br>found: C: 47.17%, H: 5.40%, N: 7.53%, Cl: 8.18%, F: 2.65% |
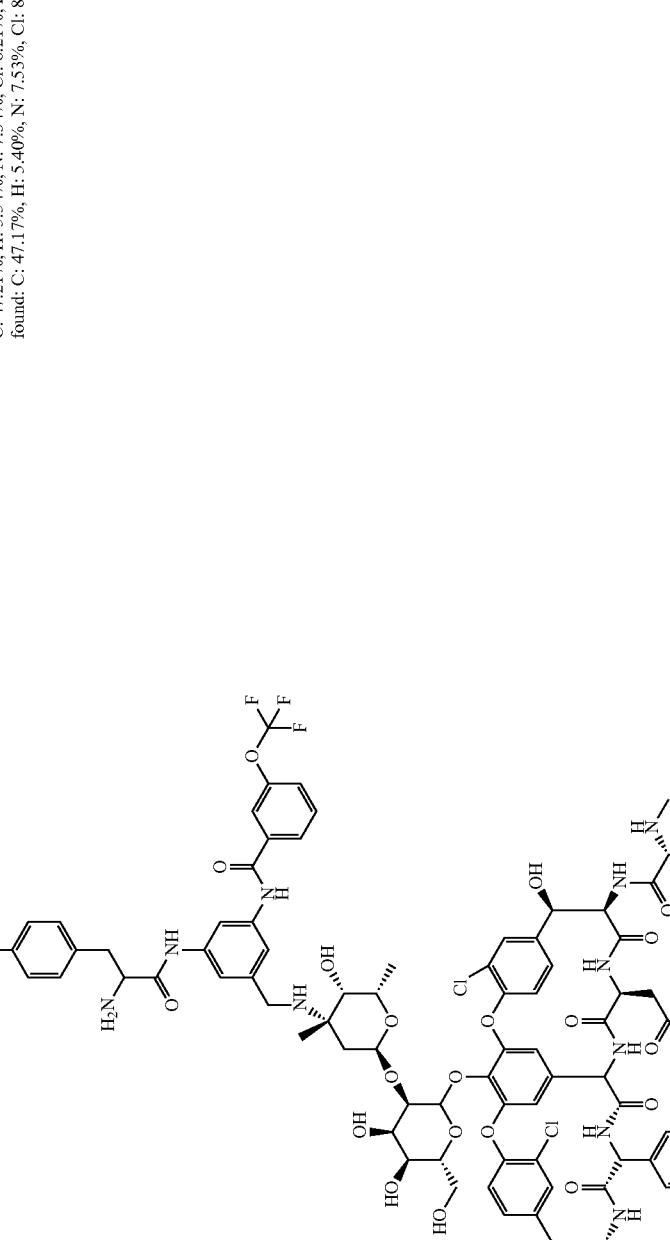

TABLE 114-continued
| Structure | Chiral | Mass | Elemental Analysis |
|---|---|---|---|
| 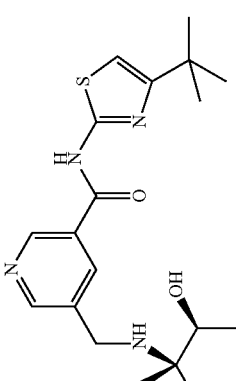 | Chiral | [M + 1]⁺ = 1723 | calcd. for C80H90Cl2N12O25S1•1.6HCl•13.2H2O<br>C: 47.60%, H: 5.89%, N: 8.33%, Cl: 6.32%, S: 1.59%<br>found: C: 47.62%, H: 5.80%, N: 8.27%, Cl: 6.29%, S: 1.64% |

TABLE 114-continued
| Structure | Mass | Elemental Analysis |
|---|---|---|
| Chiral 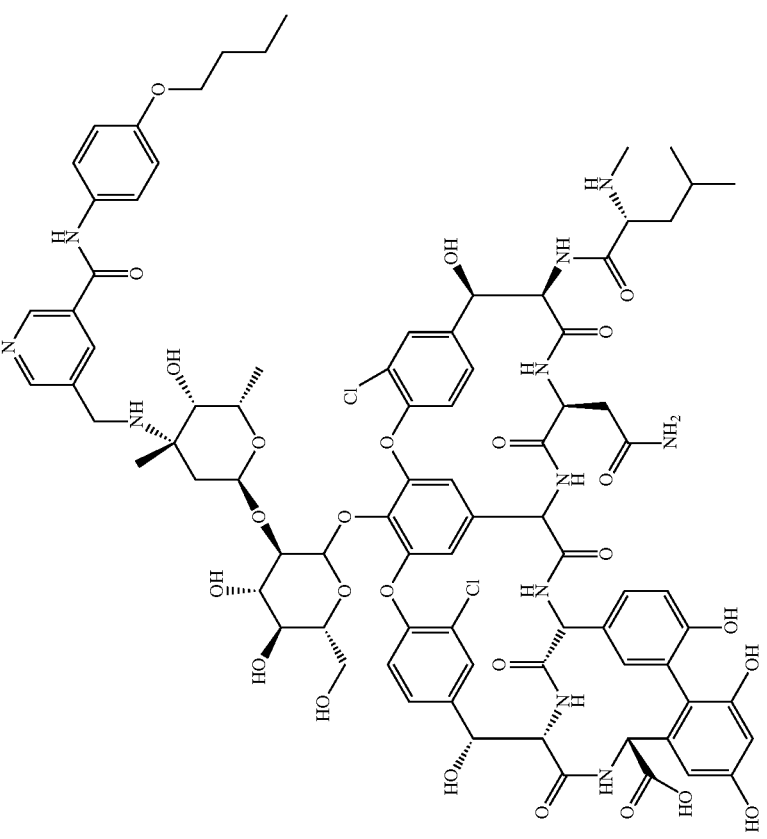 | [M + 1]⁺ = 1732 | calcd. for C83H93Cl2N11O26•1.0HCl•13.8H2O C: 49.43%, H: 6.08%, N: 7.64%, Cl: 5.27% found: C: 49.47%, H: 6.01%, N: 7.65%, Cl: 4.98% |

TABLE 115
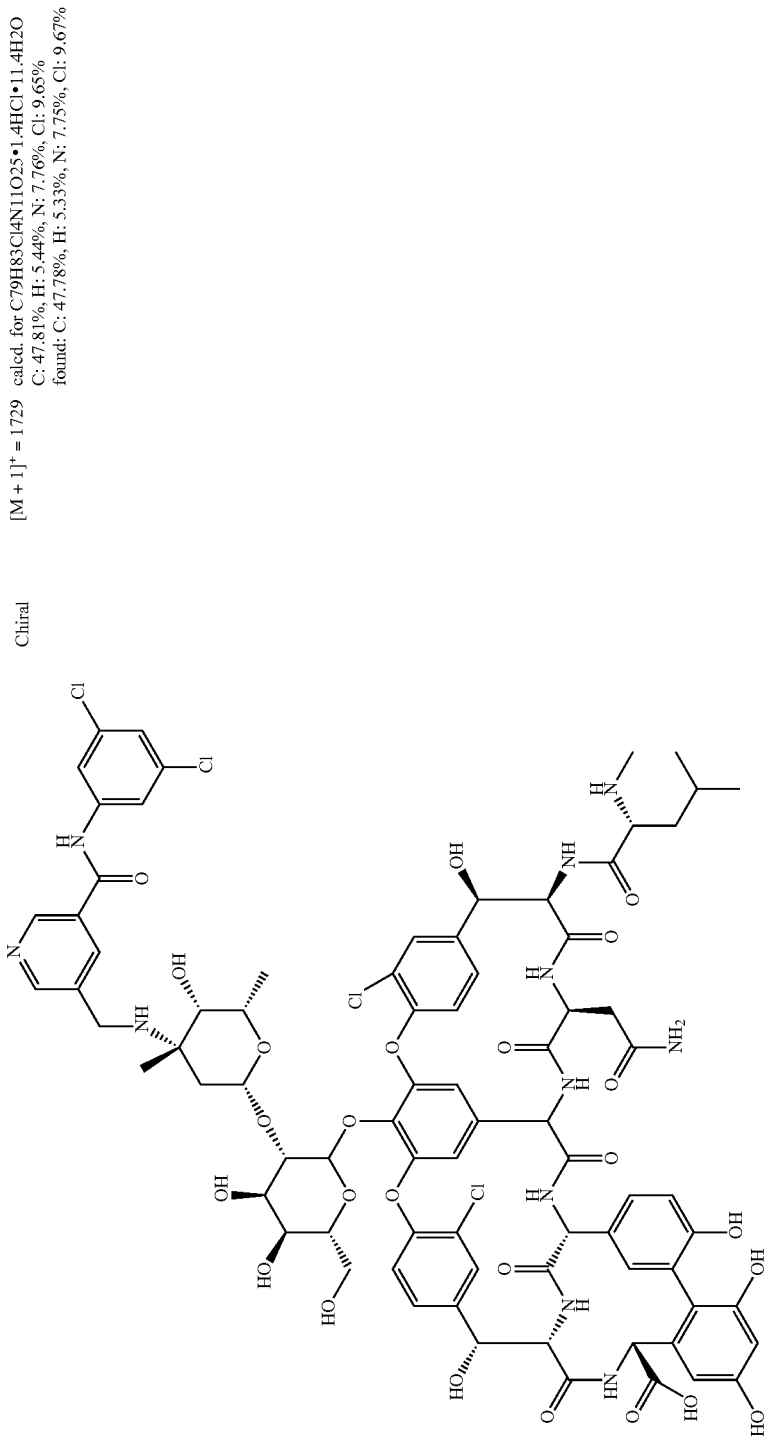
Chiral
[M + 1]⁺ = 1729  calcd. for C79H83Cl4N11O25•1.4HCl•11.4H2O
C: 47.81%, H: 5.44%, N: 7.76%, Cl: 9.65%
found: C: 47.78%, H: 5.33%, N: 7.75%, Cl: 9.67%

TABLE 115-continued
| | | |
|---|---|---|
| | Chiral | $[M+1]^+ = 1758$ calcd. for C81H86Cl2F3N11O26•1.9HCl•12.4H2O<br>C: 47.45%, H: 5.54%, N: 7.52%, Cl: 6.74%, F: 2.78<br>found: C: 47.43%, H: 5.46%, N: 7.56%, Cl: 6.75%, F: 2.83 |
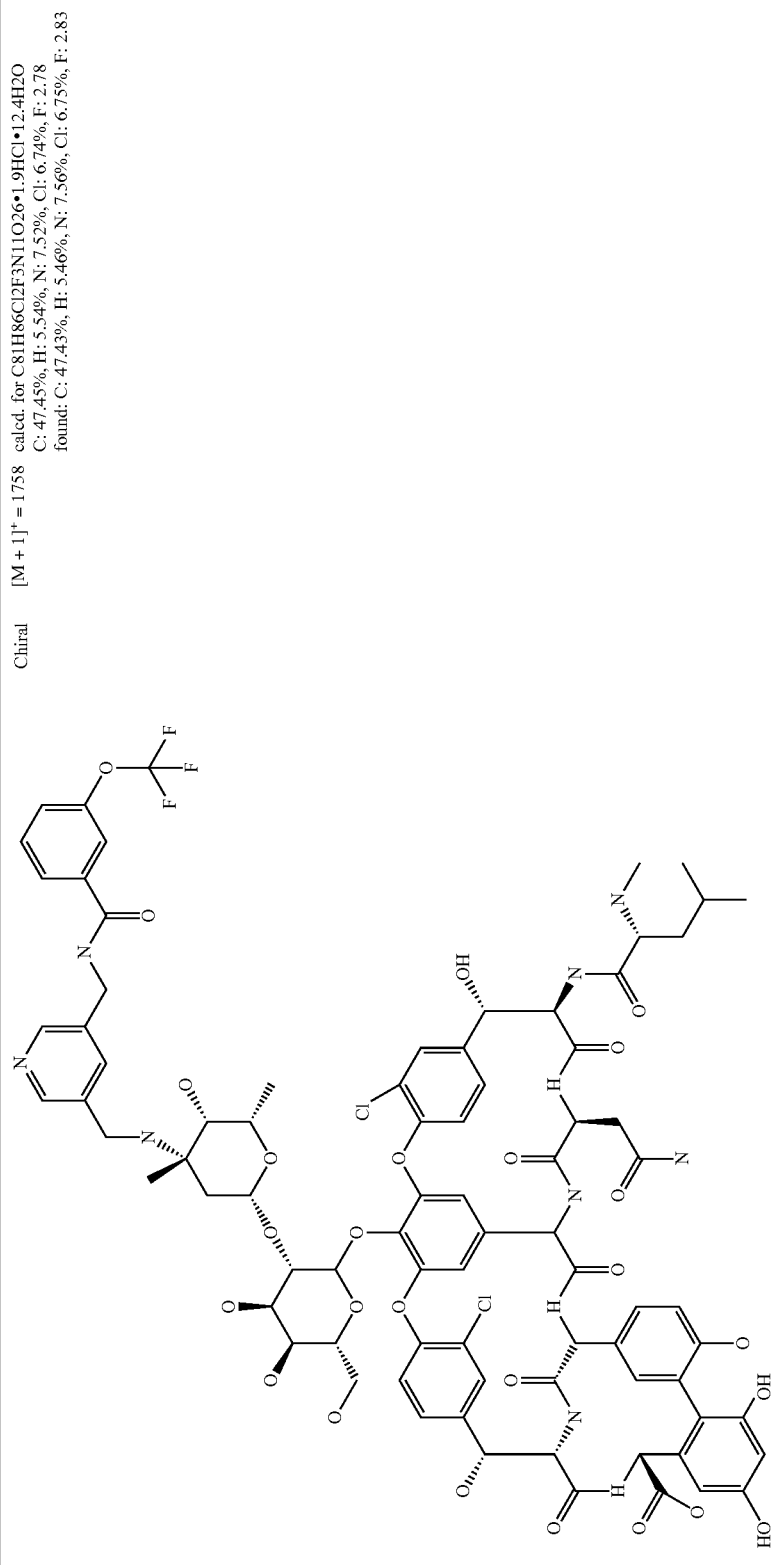

TABLE 115-continued
Chiral [M + 1]⁺ = 1785 calcd. for C87H100Cl2N12O25•2.8HCl•11.5H2O
C: 49.90%, H: 6.06%, N: 8.03%, Cl: 8.13%
found: C: 49.87%, H: 6.00%, N: 8.15%, Cl: 8.14%
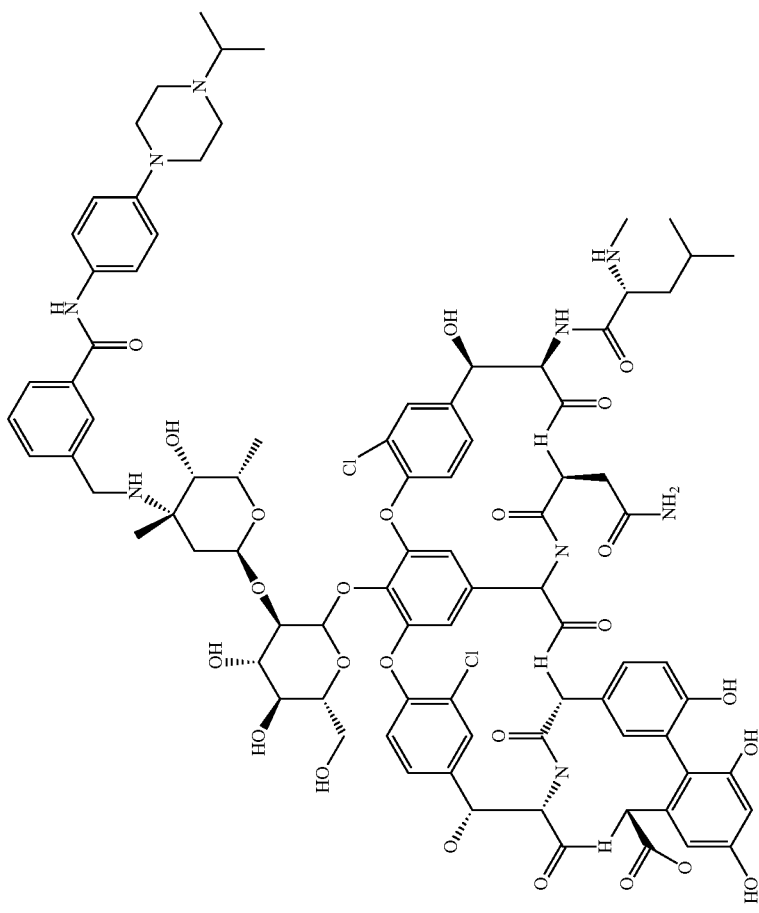

TABLE 116
[M + 1]+ = 1823  calcd. for C86H95Cl2F3N12O25•1.6HCl•11.3H2O
C: 49.50%, H: 5.76%, N: 8.06%, Cl: 6.12%, F: 2.73%
found: C: 49.47%, H: 5.74%, N: 8.13%, Cl: 6.16%, F: 2.66%
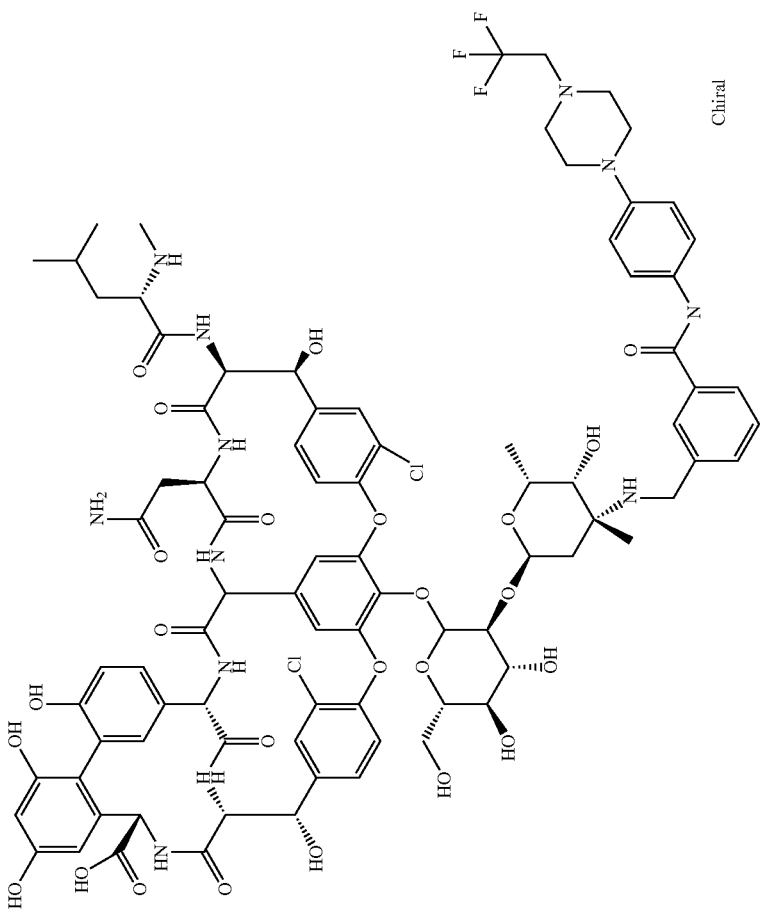

TABLE 116-continued
| Chiral | [M + 1]⁺ = 1756 calcd. for C81H86Cl2F3N11O26•2.6HCl•9.9H2O<br>C: 47.91%, H: 5.38%, N: 7.59%, Cl: 8.03%, F: 2.81%<br>found: C: 47.87%, H: 5.32%, N: 7.67%, Cl: 7.96%, F: 2.86% |
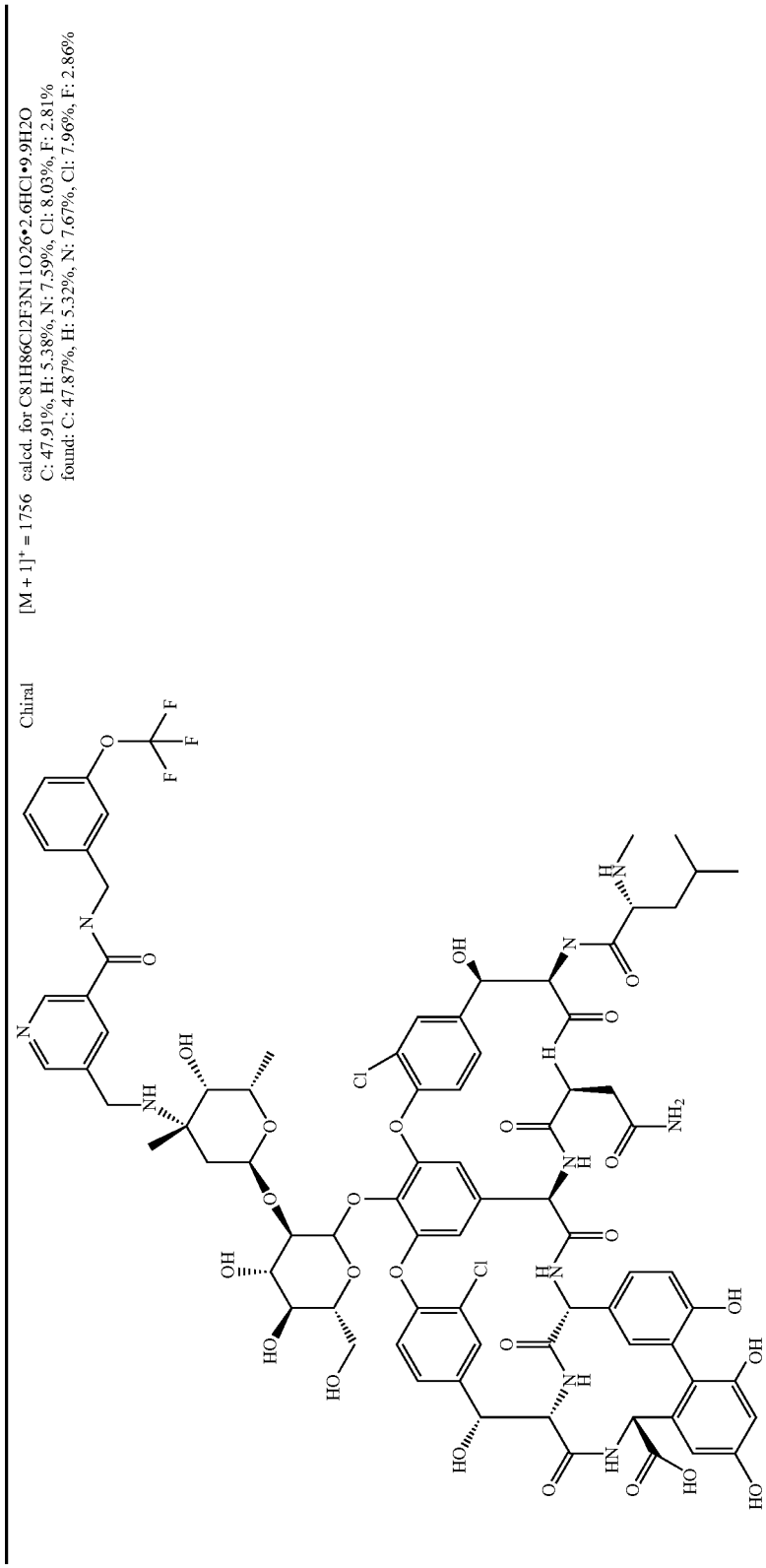

TABLE 116-continued
Chiral [M + 1]+ = 1788 calcd. for C80H86Cl2F3N13O27•2.2HCl•9.8H2O
C: 46.96%, H: 5.31%, N: 8.90%, Cl: 7.28, F: 2.79%
found: C: 46.93%, H: 5.30%, N: 9.02%, Cl: 7.33, F: 2.79%
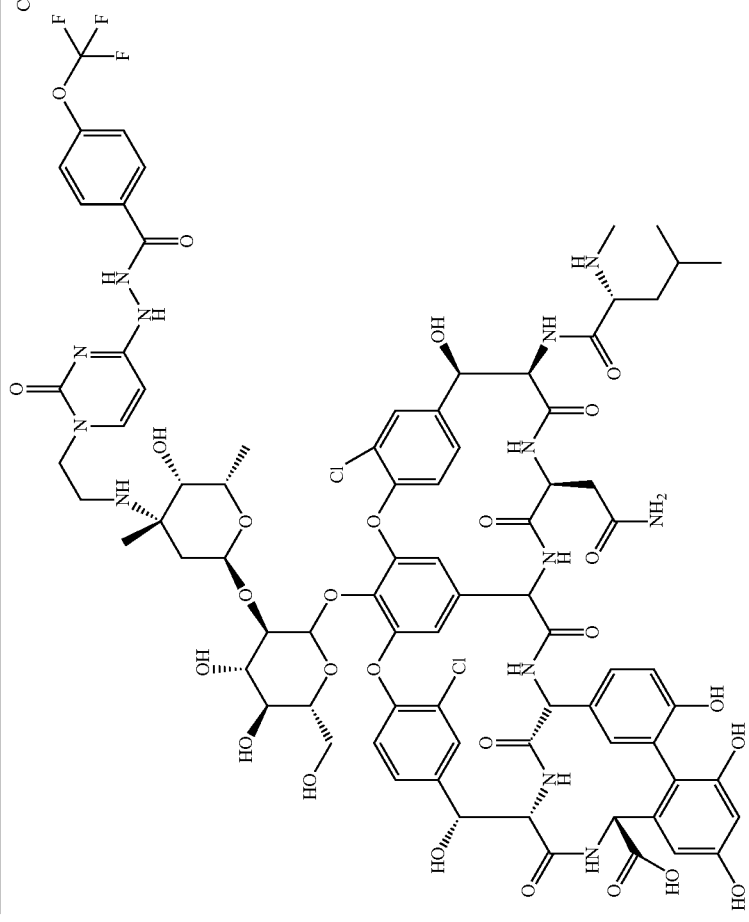

TABLE 117
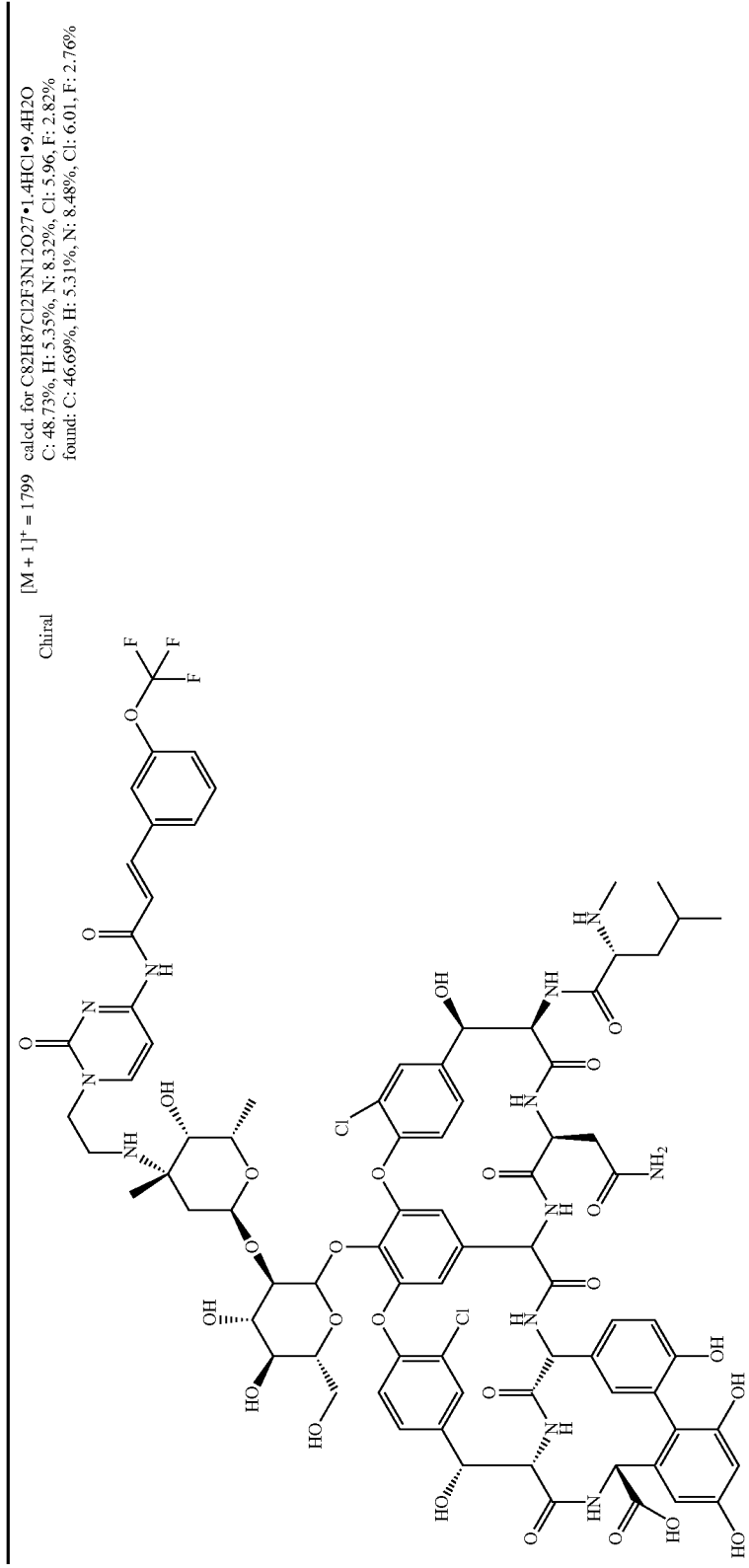
Chiral  [M + 1]⁺ = 1799  calcd. for C82H87Cl2F3N12O27•1.4HCl•9.4H2O
C: 48.73%, H: 5.35%, N: 8.32%, Cl: 5.96, F: 2.82%
found: C: 46.69%, H: 5.31%, N: 8.48%, Cl: 6.01, F: 2.76%

TABLE 117-continued
Chiral
[M + 1]+ = 1749 calcd. for C81H87Cl3N12O26•1.2HCl•11.2H2O
C: 48.73%, H: 5.58%, N: 8.42%, Cl: 7.46%
found: C: 48.68%, H: 5.49%, N: 8.50%, Cl: 7.403%
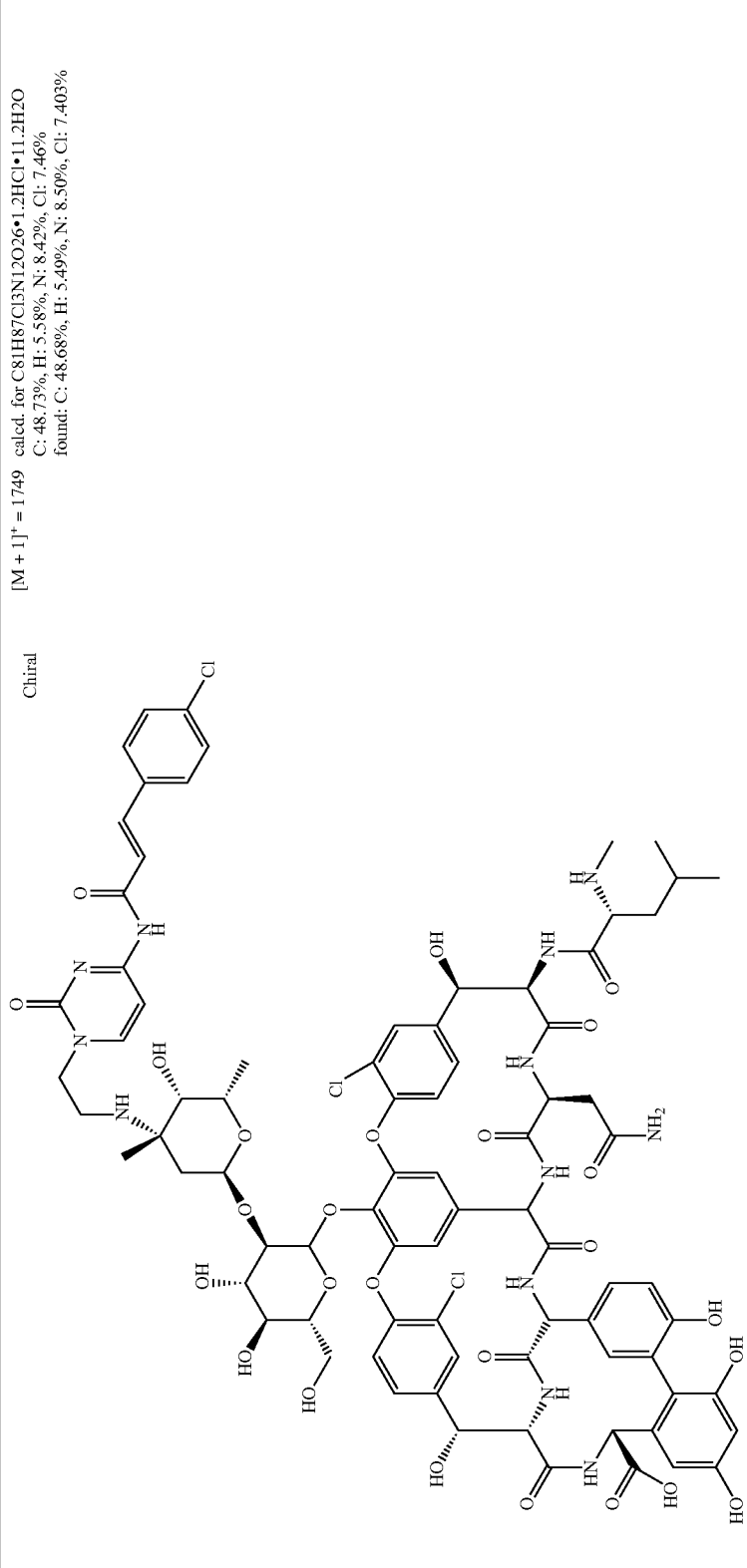

TABLE 117-continued
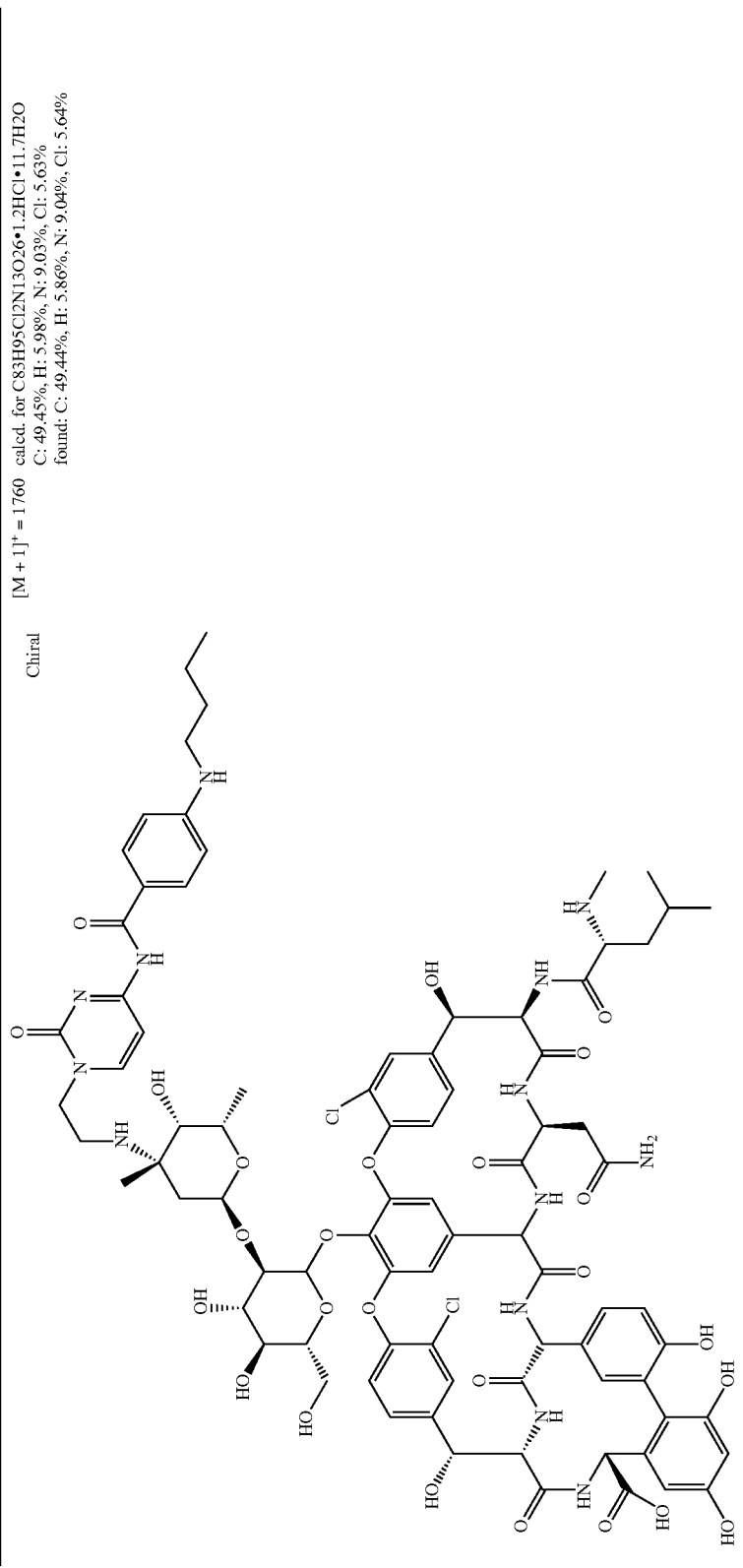
Chiral  [M + 1]⁺ = 1760  calcd. for C83H95Cl2N13O26•1.2HCl•11.7H2O
C: 49.45%, H: 5.98%, N: 9.03%, Cl: 5.63%
found: C: 49.44%, H: 5.86%, N: 9.04%, Cl: 5.64%

TABLE 118
Chiral [M + 1]⁺ = 1805  calcd. for C81H86Cl2F4N12O27•1.7HCl•10.4H2O
C: 47.32%, H: 5.32%, N: 8.18%, Cl: 6.38%, F: 3.70%
found: C: 47.33%, H: 5.36%, N: 8.30%, Cl: 6.35%, F: 3.70%
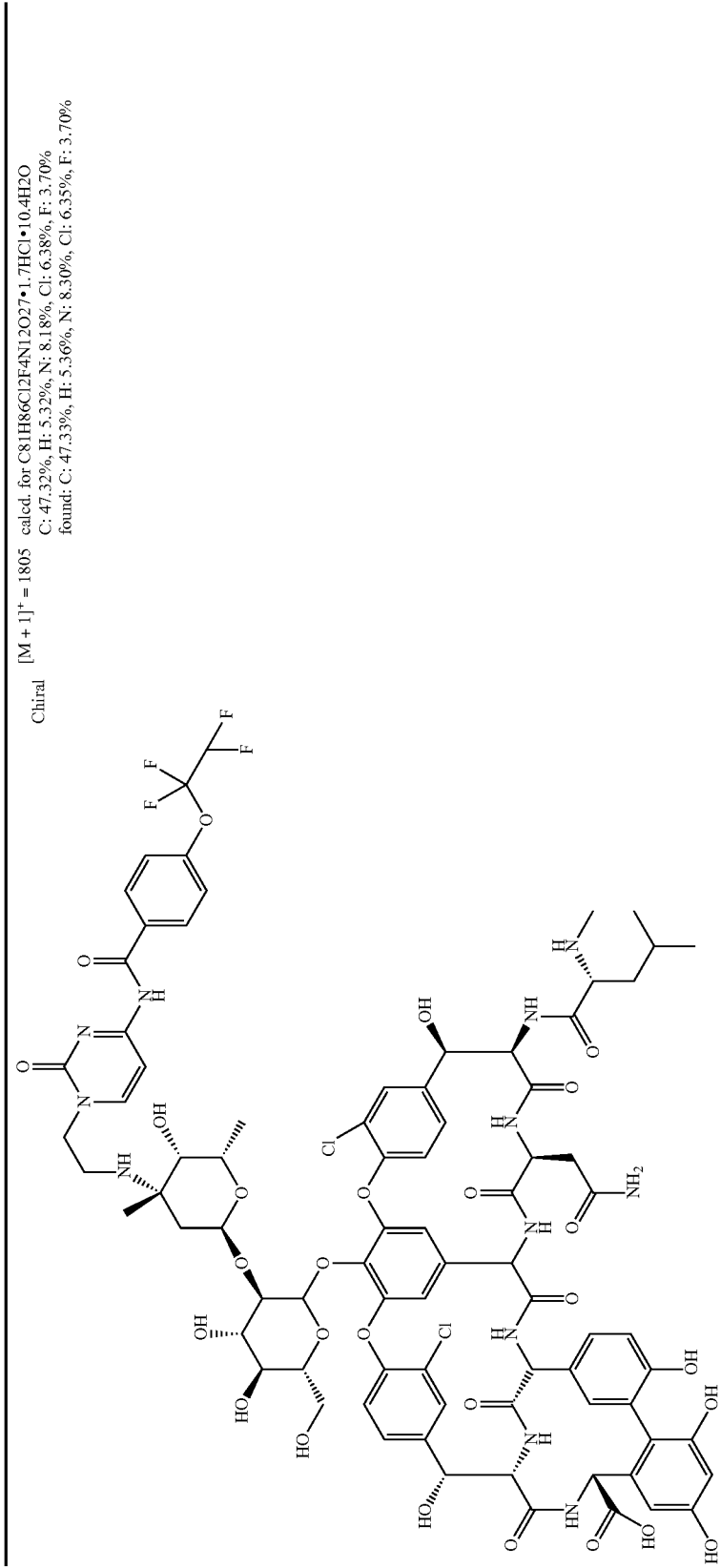

TABLE 118-continued
Chiral [M + 1]⁺ = 1789 calcd. for C80H85Cl2F3N12O26S•1.7HCl•10.3H2O
C: 47.14%, H: 5.31%, N: 8.25%, Cl: 6.44%, F: 2.80%, S: 1.57%
found: C: 47.10%, H: 5.26%, N: 8.32%, Cl: 6.48%, F: 2.88%, S: 1.53%
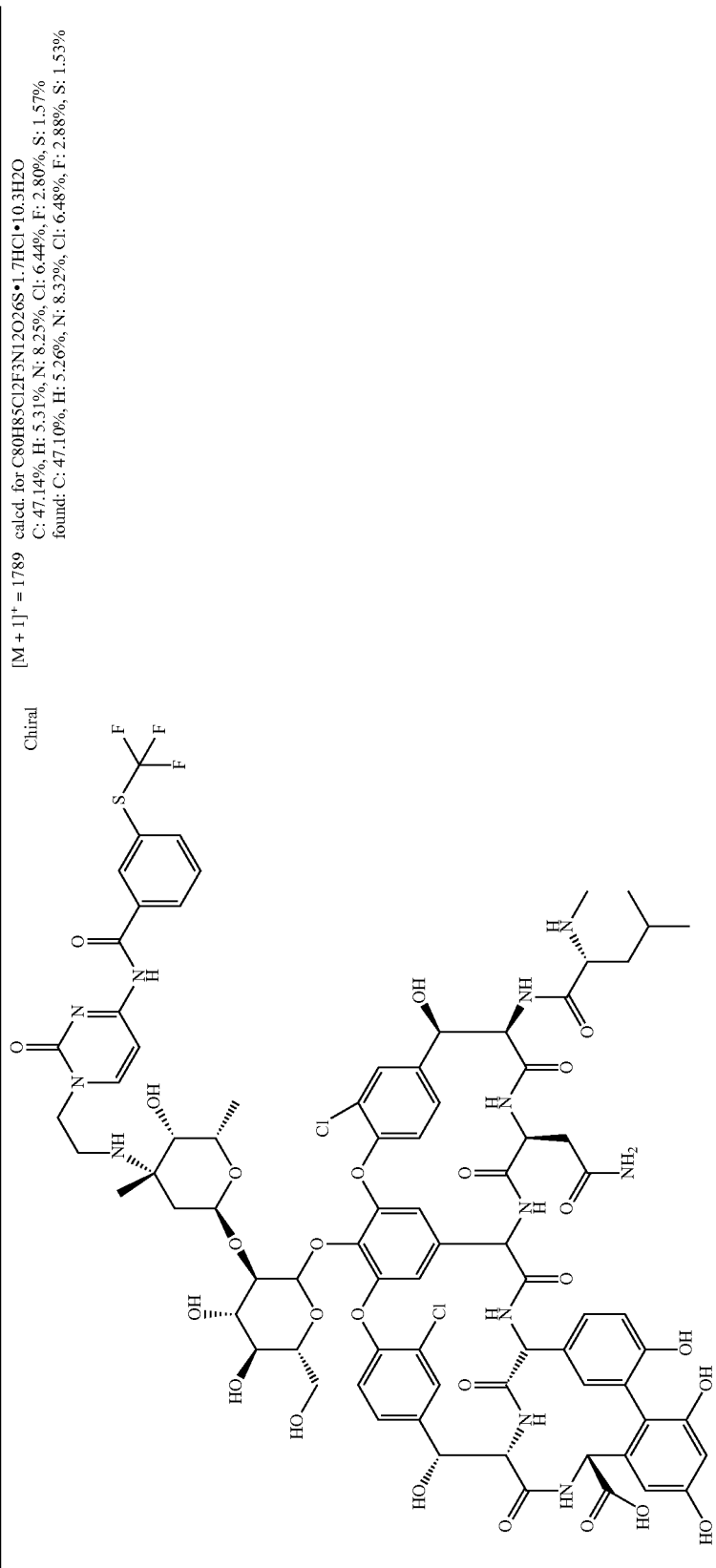

TABLE 118-continued
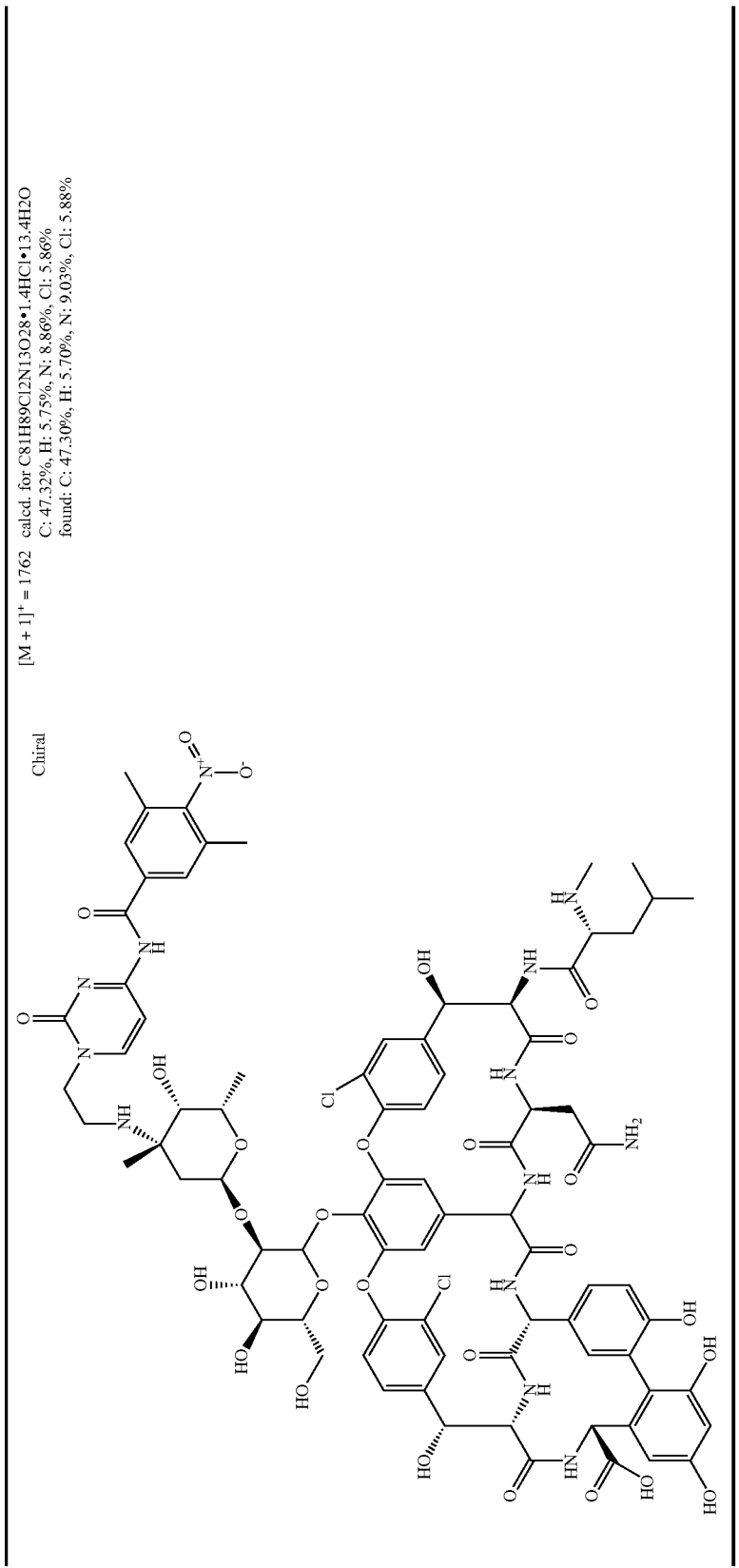
Chiral
[M + 1]⁺ = 1762   calcd. for C81H89Cl2N13O28•1.4HCl•13.4H2O
C: 47.32%, H: 5.75%, N: 8.86%, Cl: 5.86%
found: C: 47.30%, H: 5.70%, N: 9.03%, Cl: 5.88%

TABLE 119
[M + 1]+ = 1741 calcd. for C79H84Cl3FN12O26•1.4HCl•13.1H2O
C: 46.74%, H: 5.54%, N: 8.28%, Cl: 7.68%, F: 0.94%
found: C: 46.72%, H: 5.26%, N: 8.34%, Cl: 7.70%, F: 1.04%
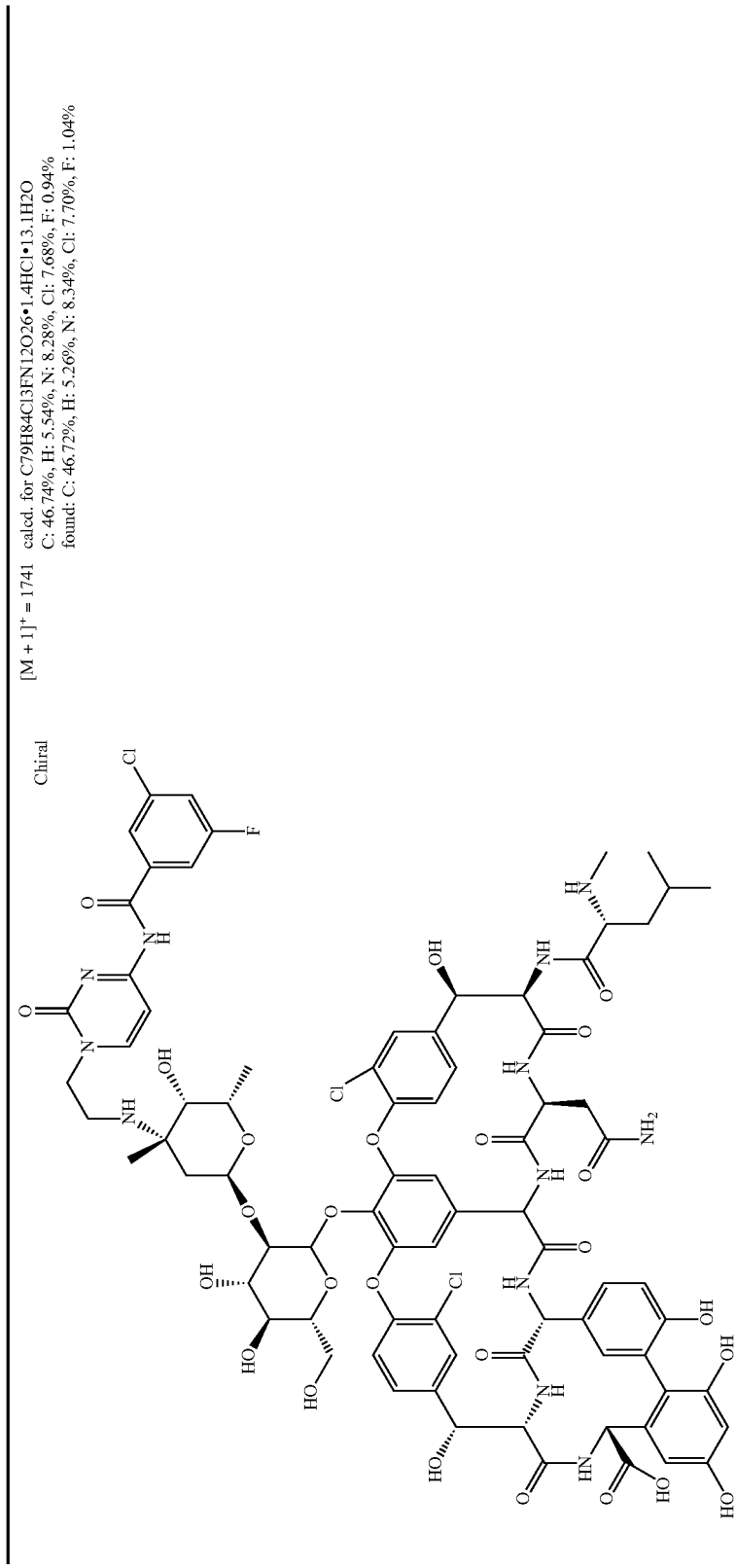

TABLE 119-continued
[M + 1]⁺ = 1771  calcd. for C80H86Cl2F2N12O26S·1.5HCl·10.9H2O
C: 47.48%, H: 5.44%, N: 8.31%, Cl: 6.13%, F: 1.88%, S: 1.58%
found: C: 47.48%, H: 5.31%, N: 8.35%, Cl: 6.19%, F: 1.96%, S: 1.59%
Chiral
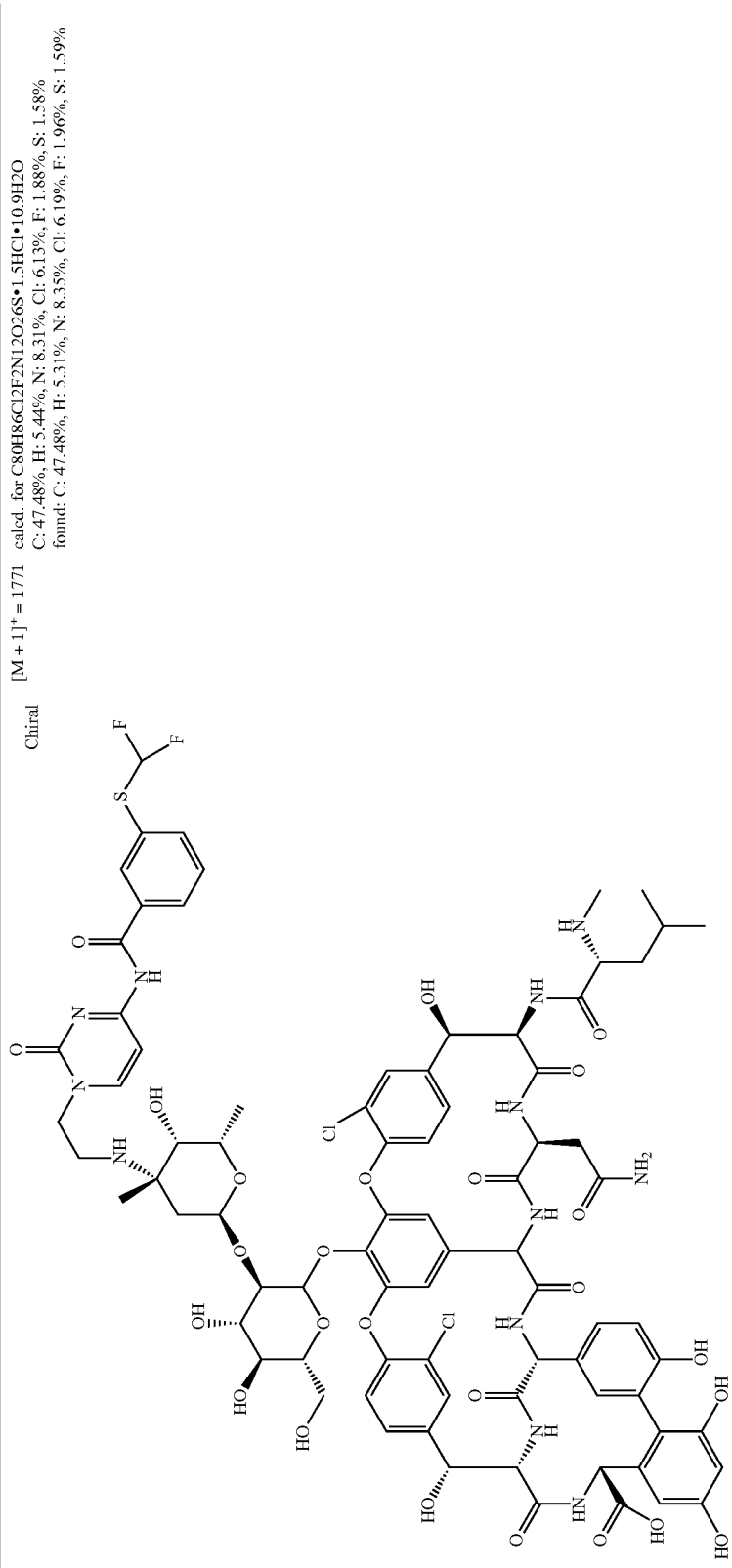

TABLE 119-continued
Chiral
[M + 1]+ = 1710  calcd. for C80H94Cl2N12O26•1.5HCl•13.0H2O
C: 48.94%, H: 6.03%, N: 8.56%, Cl: 6.32%
found: C: 48.89%, H: 5.91%, N: 8.63%, Cl: 6.33%
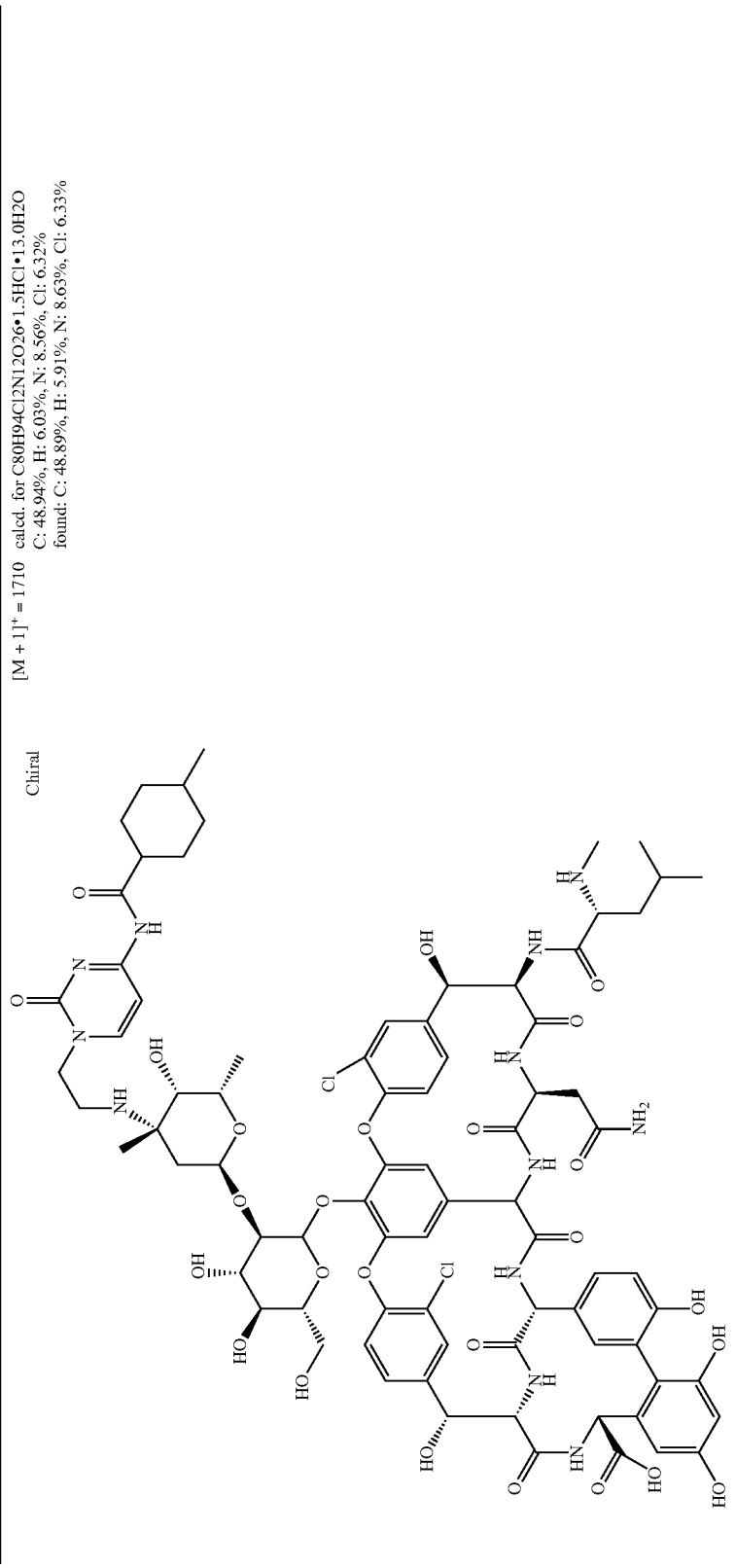

TABLE 120
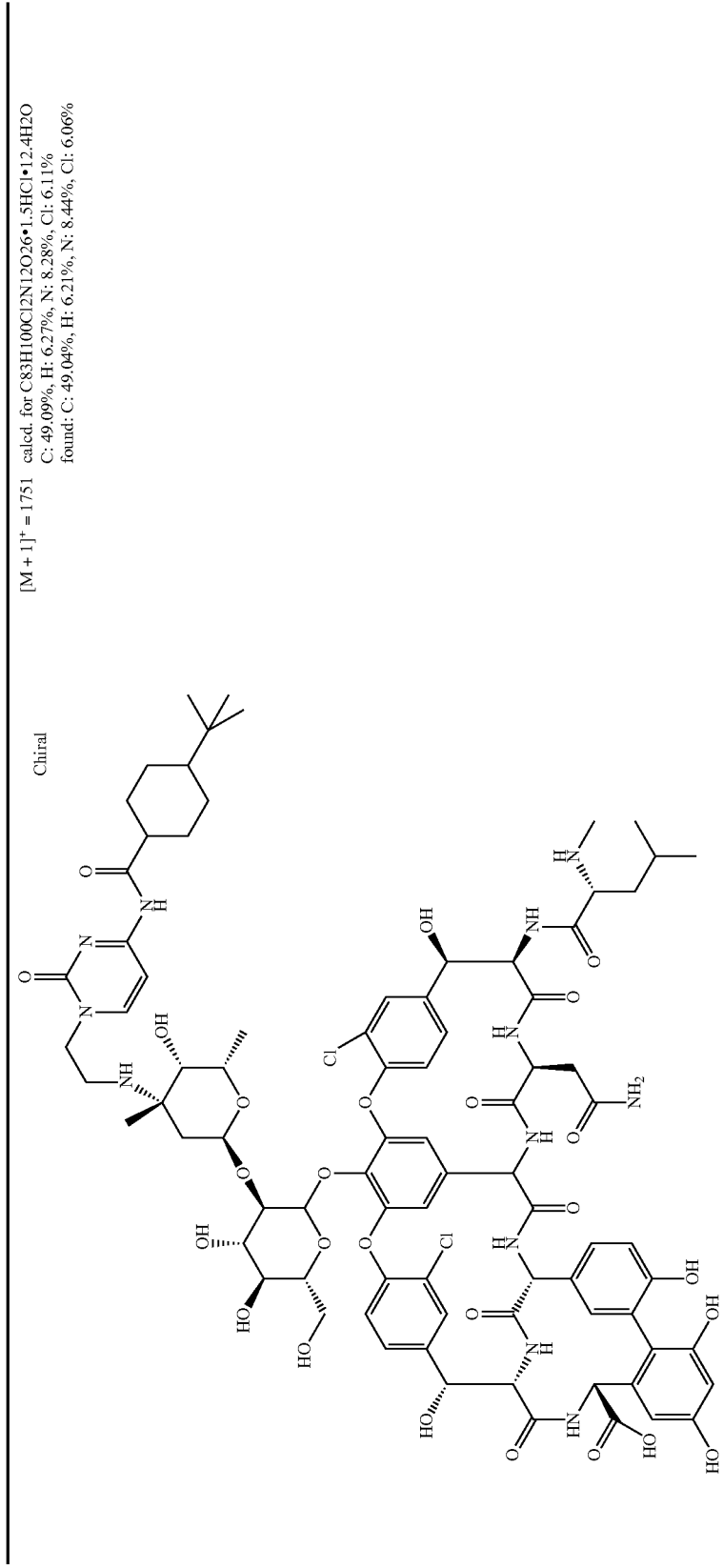
[M + 1]⁺ = 1751   calcd. for C83H100Cl2N12O26•1.5HCl•12.4H2O
C: 49.09%, H: 6.27%, N: 8.28%, Cl: 6.11%
found: C: 49.04%, H: 6.21%, N: 8.44%, Cl: 6.06%

TABLE 120-continued
Chiral  [M + 1]⁺ = 1775  calcd. for C84H96Cl2N12O27•1.5HCl•11.8H2O
C: 49.36%, H: 5.97%, N: 8.22%, Cl: 6.07%
found: C: 49.31%, H: 5.77%, N: 8.34%, Cl: 6.02%
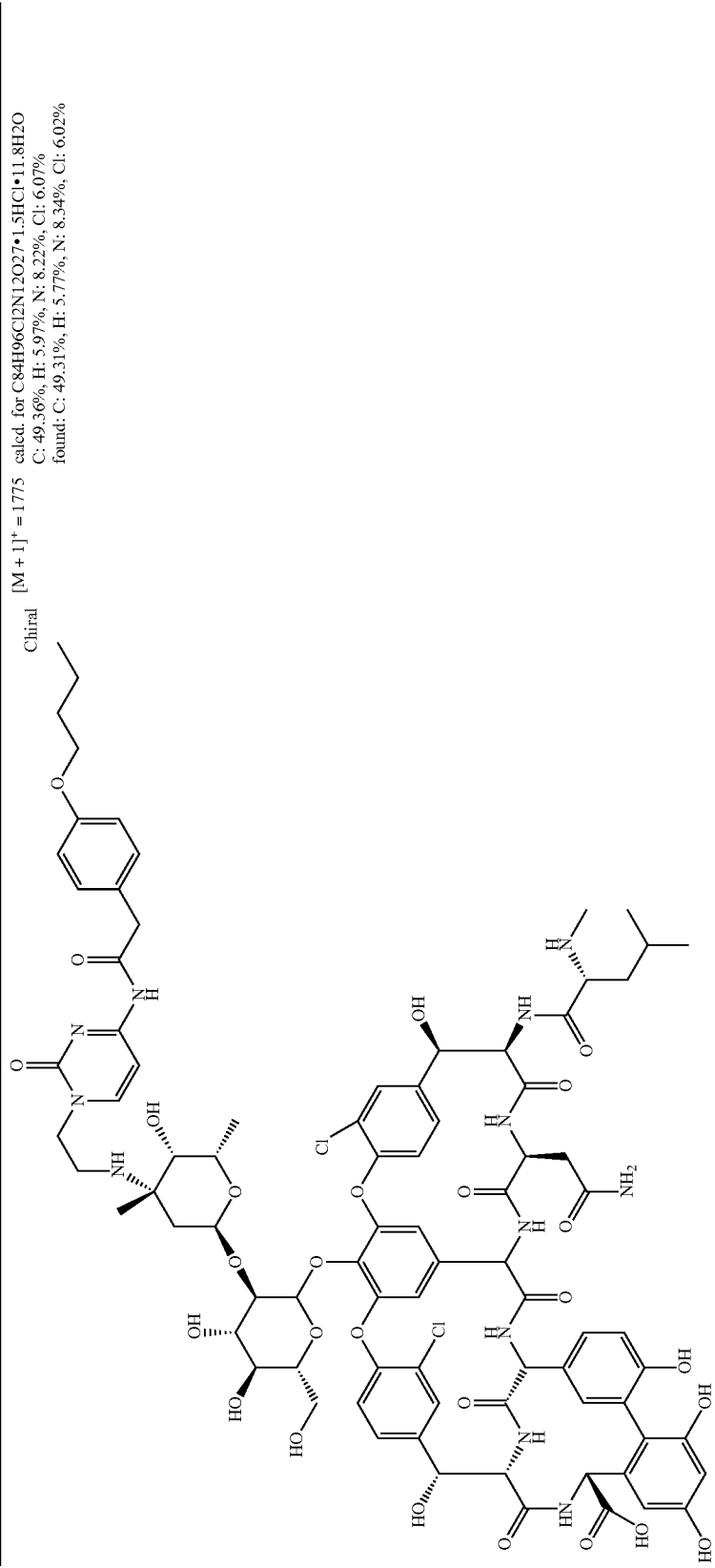

TABLE 120-continued
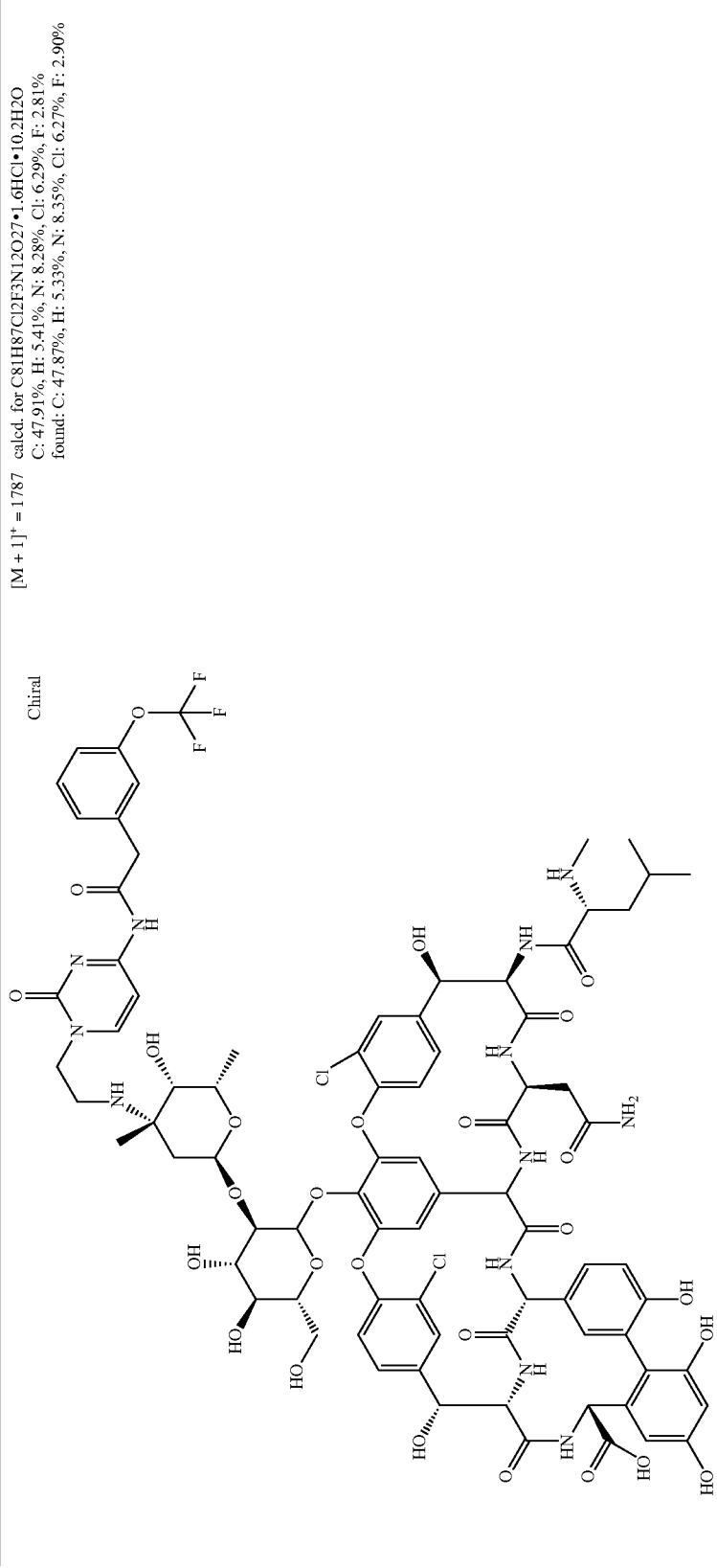
[M + 1]+ = 1787  calcd. for C81H87Cl2F3N12O27•1.6HCl•10.2H2O
C: 47.91%, H: 5.41%, N: 8.28%, Cl: 6.29%, F: 2.81%
found: C: 47.87%, H: 5.33%, N: 8.35%, Cl: 6.27%, F: 2.90%

TABLE 121
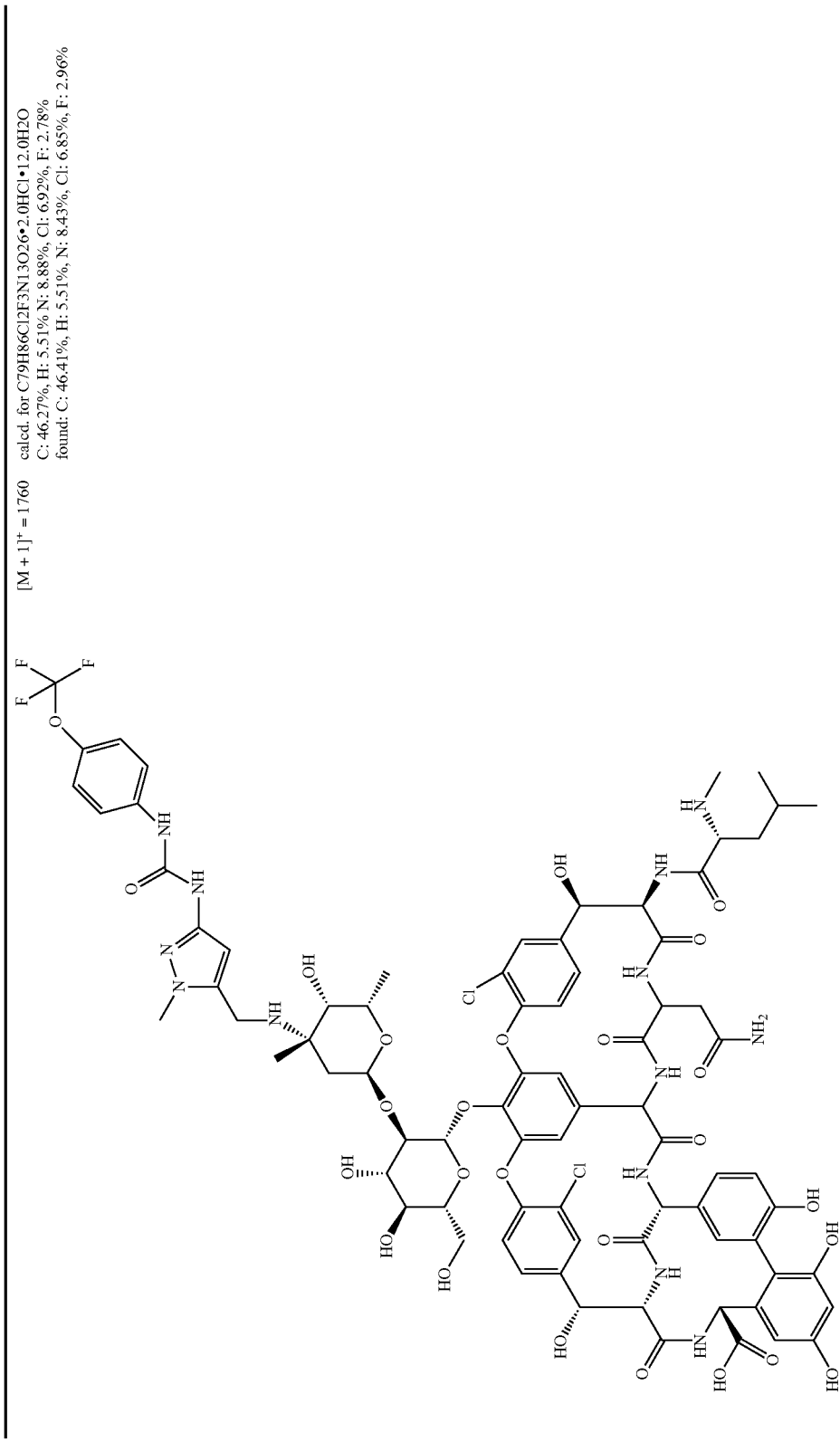
[M + 1]+ = 1760
calcd. for C79H86Cl2F3N13O26•2.0HCl•12.0H2O
C: 46.27%, H: 5.51% N: 8.88%, Cl: 6.92%, F: 2.78%
found: C: 46.41%, H: 5.51%, N: 8.43%, Cl: 6.85%, F: 2.96%

TABLE 121-continued
[M + 1]⁺ = 1760    calcd. for C81H90Cl2F3N11O26•2.0HCl•10.0H2O
C: 48.29%, H: 5.60%, N: 7.65%, Cl: 7.04%, F: 2.83%
found: C: 48.33%, H: 5.63%, N: 7.51%, Cl: 7.00%, F: 3.08%
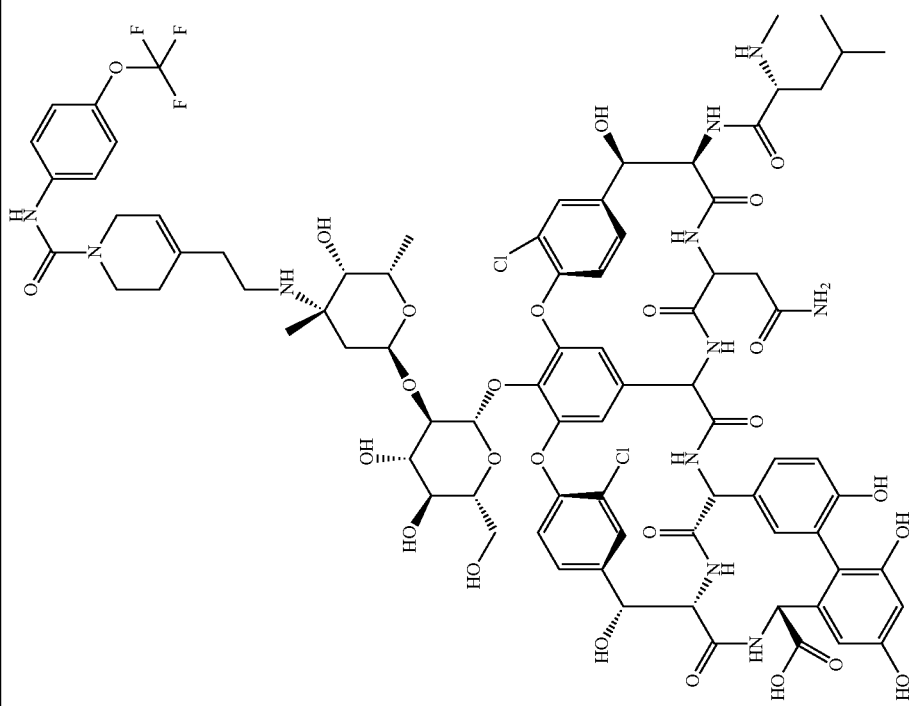

TABLE 121-continued
[M + 1]⁺ = 1778    calcd. for C81H92Cl2F3N11O27•1.9HCl•10.5H2O
C: 47.74%, H: 5.68%, N: 7.56%, Cl: 6.78%, F: 2.80%
found: C: 47.73%, H: 5.58%, N: 7.63%, Cl: 6.71%, F: 2.74%
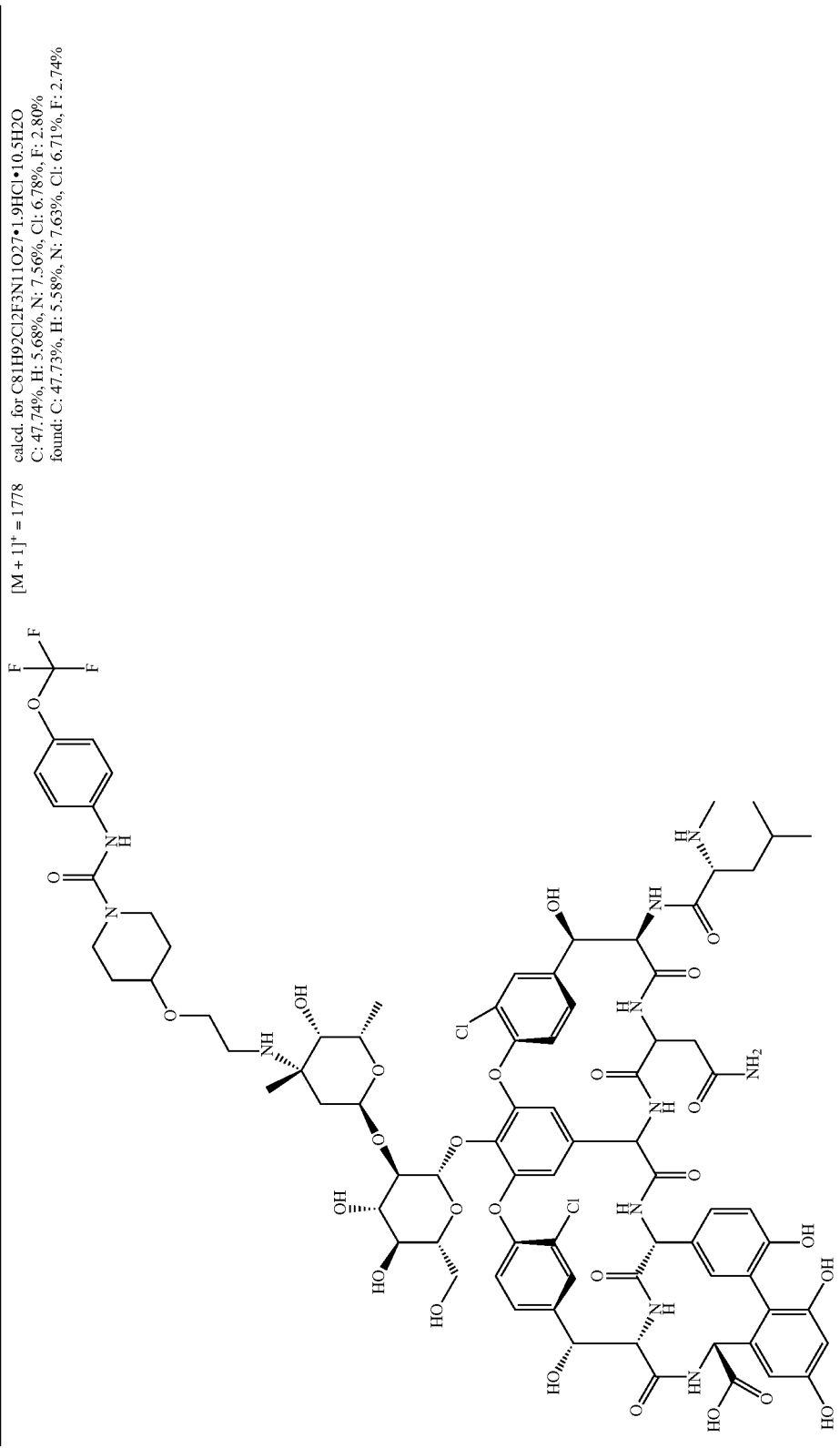

TABLE 122
| | | |
|---|---|---|
| Chiral | [M + 1]+ = 1777 | calcd. for C81H93Cl2F3N12O26·2.8HCl·11.5H2O<br>C: 46.60%, H: 5.74%, N: 8.05%, Cl: 8.15%, F: 2.73%<br>found: C: 46.61%, H: 5.59%, N: 7.80%, Cl: 8.09%, F: 2.44% |
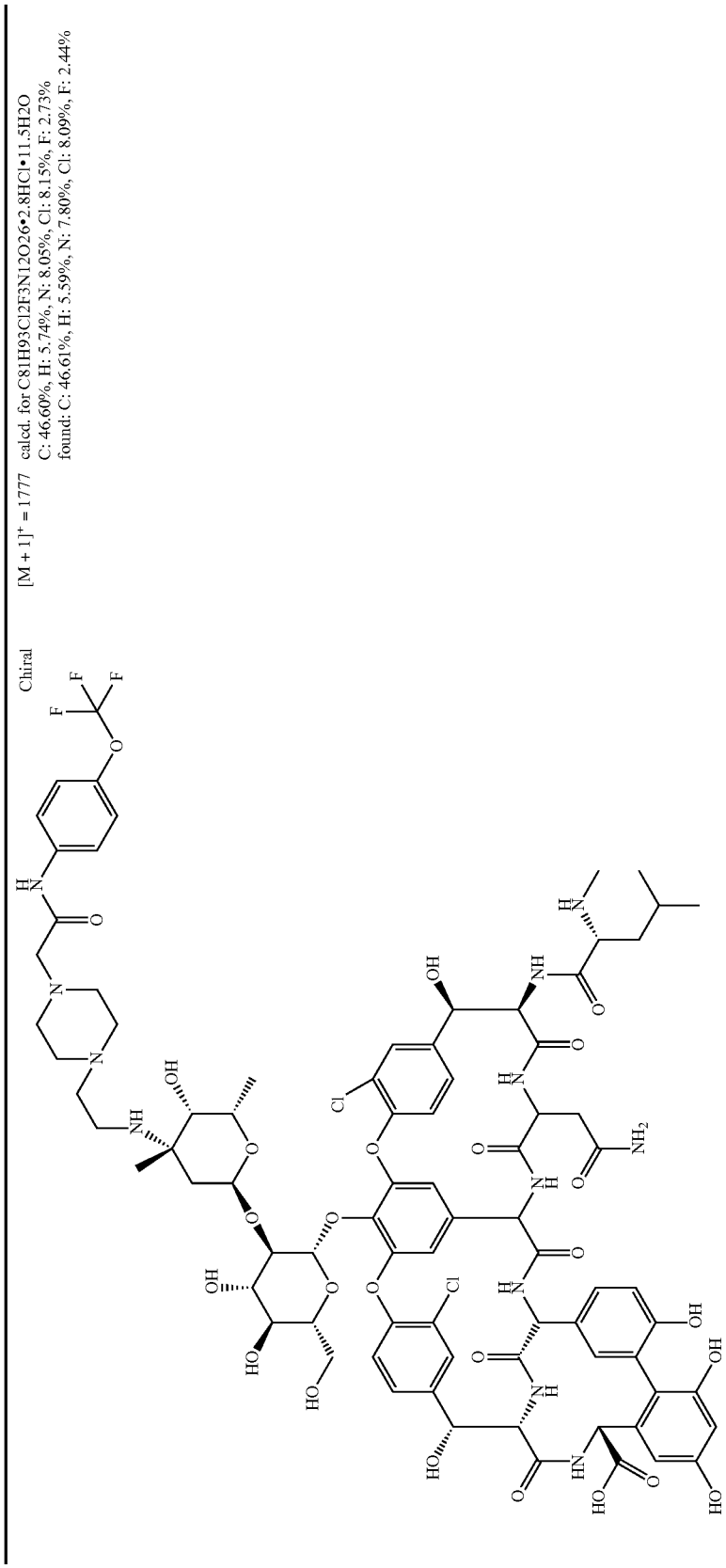

TABLE 122-continued
Chiral
$[M+H]^+ = 1750$ calcd. for C79H88Cl2F3N11O27·1.8HCl·12.2H2O
C: 46.58%, H: 5.65%, N: 7.56%, Cl: 6.61%, F: 2.80%
found: C: 46.41%, H: 5.48%, N: 7.71%, Cl: 6.65%, F: 2.77%
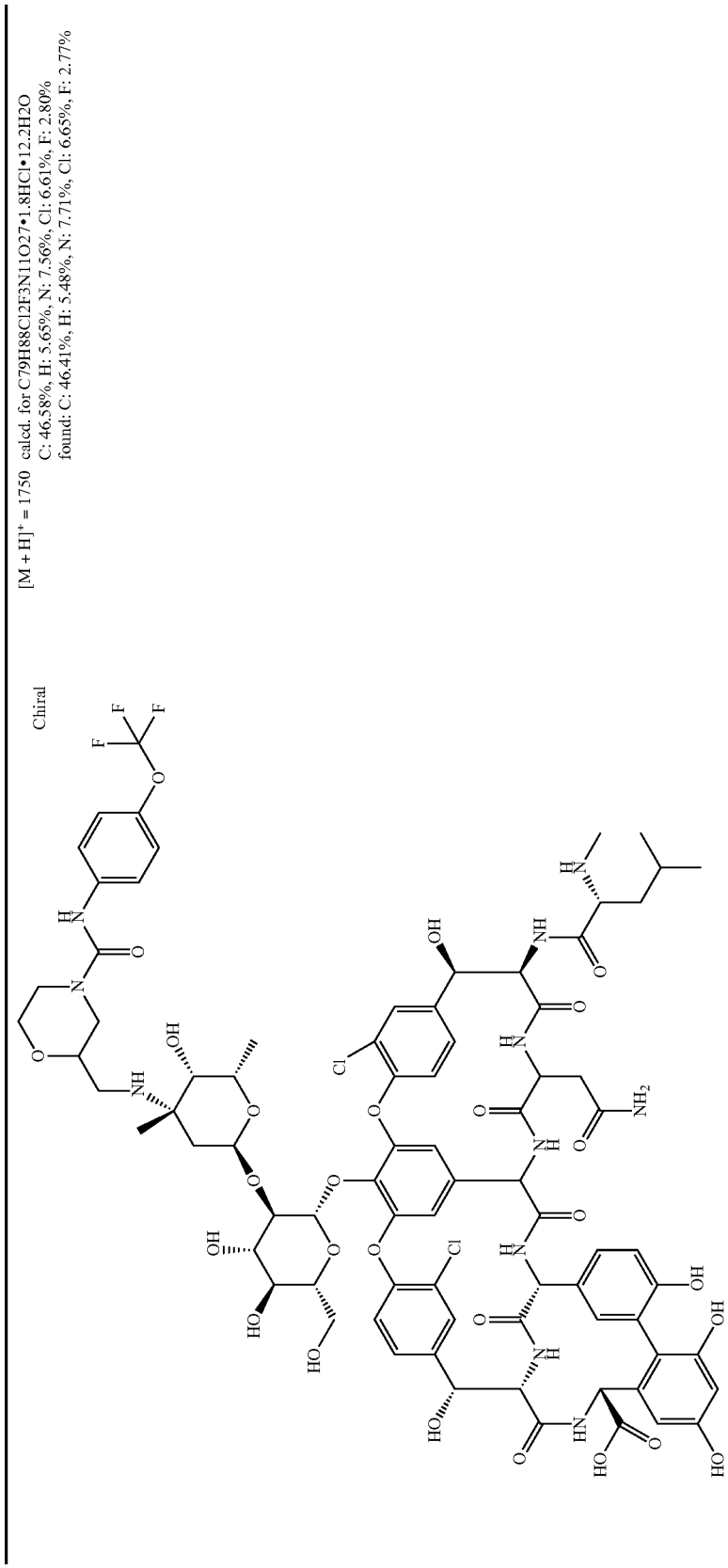

TABLE 122-continued
Chiral [M + H]⁺ = 1807 calcd. for C82H95Cl2F3N12O27·3.1HCl·11.2H2O
C: 46.38%, H: 5.72%, N: 7.92%, Cl: 8.52%, F: 2.68%
found: C: 46.24%, H: 5.66%, N: 7.95%, Cl: 8.62%, F: 2.82%
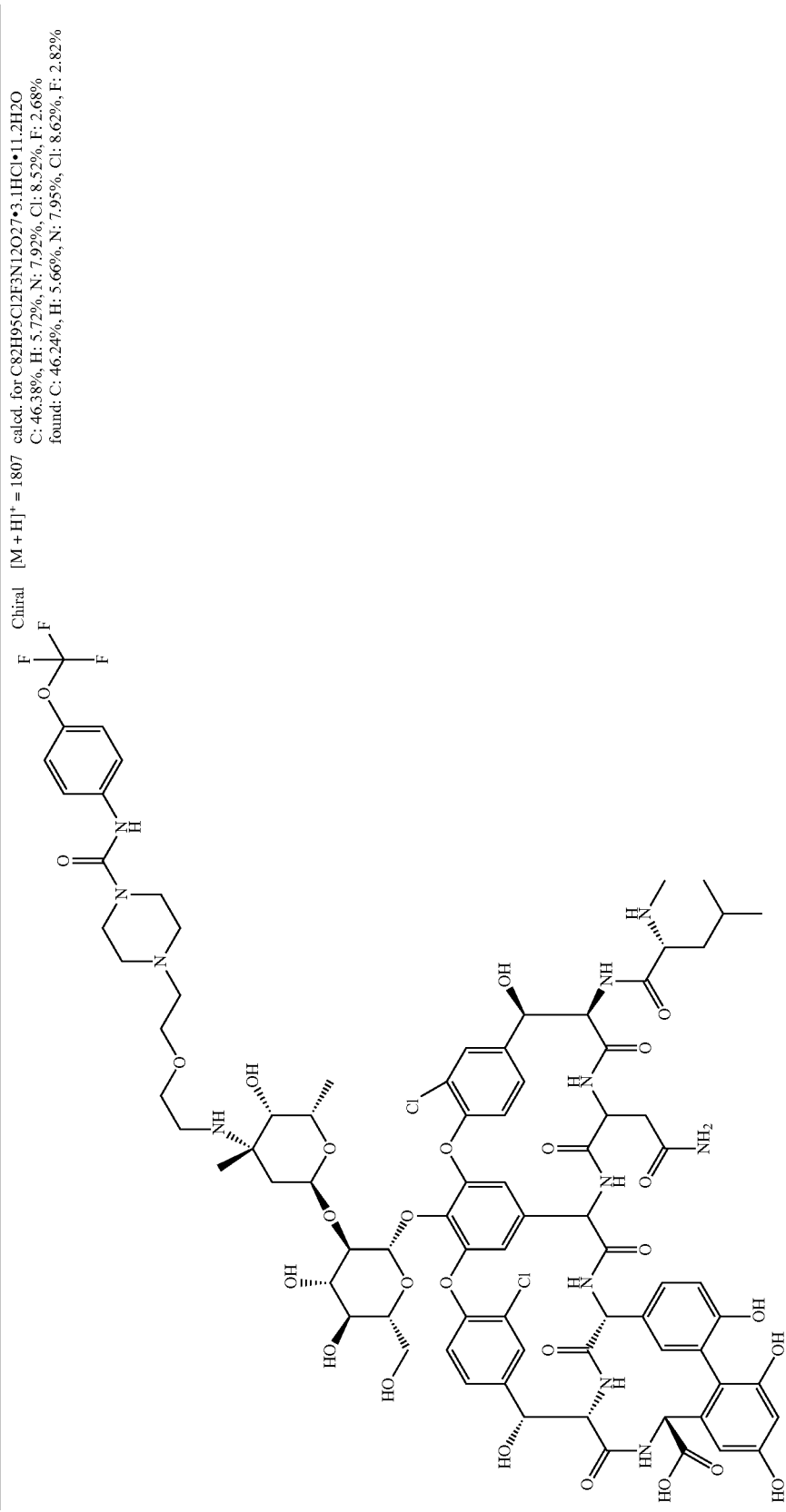

TABLE 123
[M + 1]⁺ = 1765
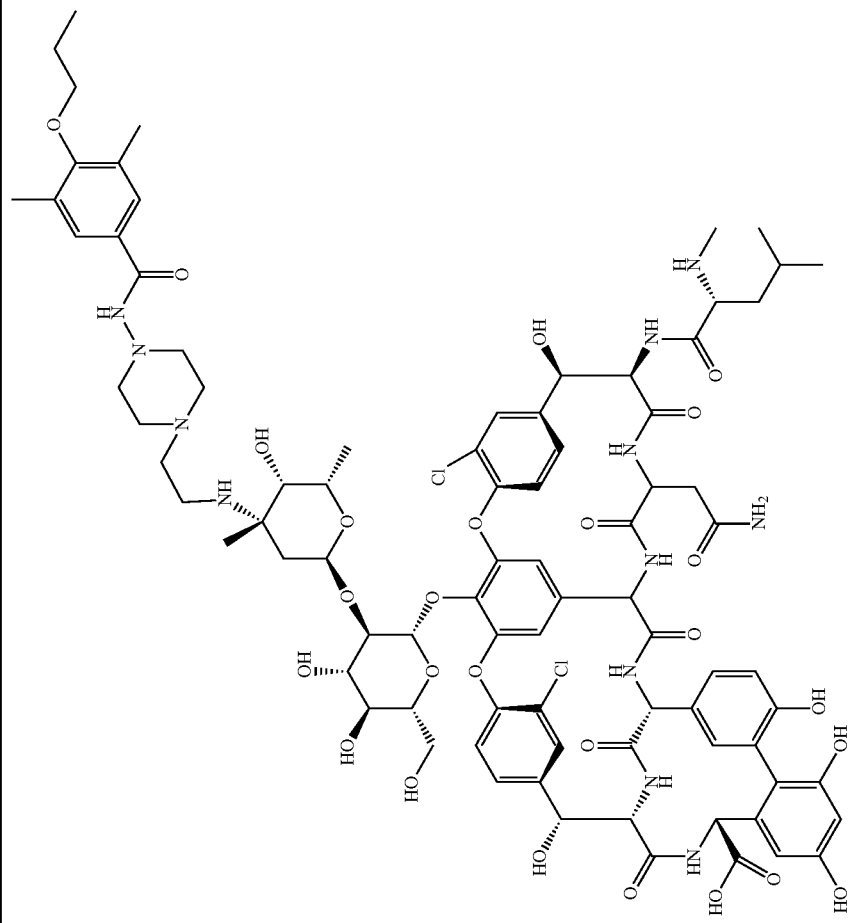

TABLE 123-continued
| [M + 1]⁻ = 1855 | calcd. for C86H95Cl2F3N12O27·1.5HCl·9.2H2O<br>C: 49.73%, H: 5.58%, N: 8.09%, Cl: 5.97%, F: 2.74%<br>found: C: 49.71%, H: 5.58%, N: 8.18%, Cl: 5.95%, F: 2.80% |
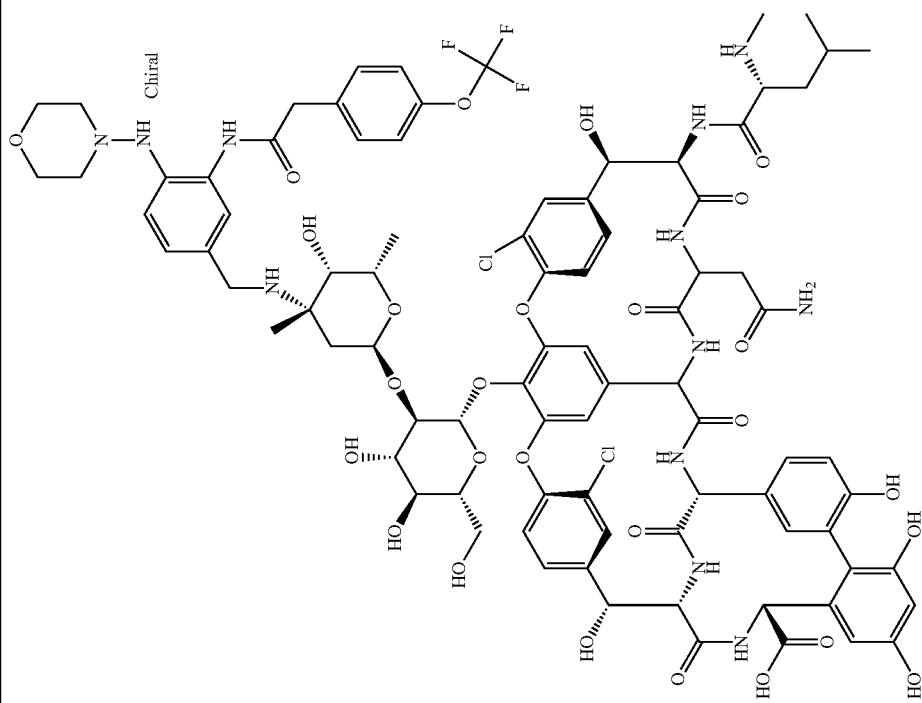

TABLE 123-continued
[M + 1]⁻ = 1839  calcd. for C85H94Cl4N12O26•1.8HCl•11.2H2O
C: 48.41%, H: 5.65%, N: 7.97%, Cl: 9.75%
found: C: 48.41%, H: 5.66%, N: 8.07%, Cl: 9.71%
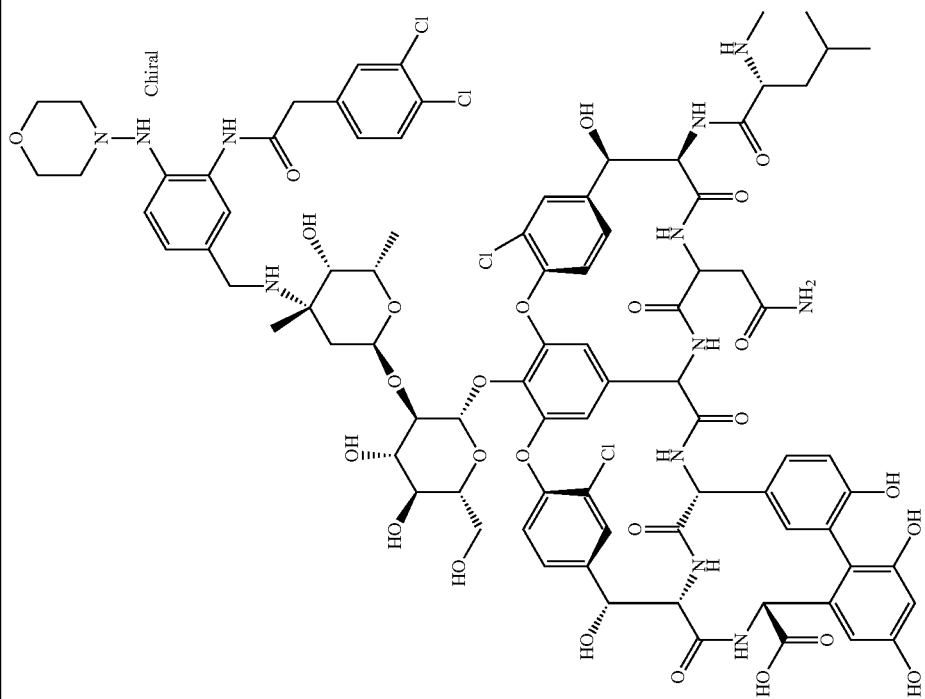

TABLE 124
| Structure | Mass | Elemental Analysis |
|---|---|---|
| Chiral 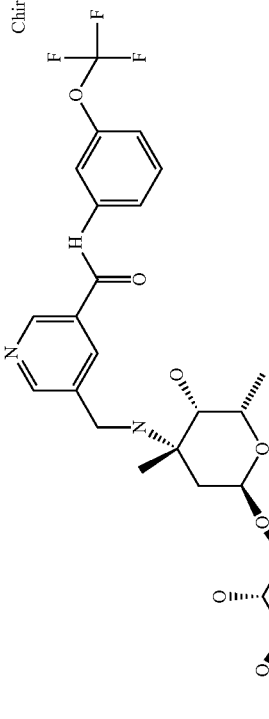 | [M + 1]⁺ = 1784 | calcd. for C82H90Cl2F3N13O25•2.4HCl•1.0H2O<br>C: 47.97%, H: 5.52%, N: 8.87%, Cl: 7.60%, F: 2.78%<br>found: C: 47.98%, H: 5.39%, N: 8.98%, Cl: 7.61%, F: 2.82% |

TABLE 124-continued
| Structure | Mass | Elemental Analysis |
|---|---|---|
| Chiral 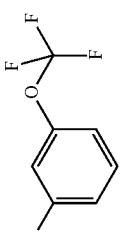 | [M + 1]⁺ = 1809 | calcd. for C83H89Cl2F3N14O25•2.3HCl•10.7H2O<br>C: 47.76%, H: 5.44%, N: 9.40%, Cl: 7.30%, F: 2.73%<br>found: C: 47.75%, H: 5.24%, N: 9.41%, Cl: 7.29%, F: 2.77% |

TABLE 124-continued
| Structure | Mass | Elemental Analysis |
|---|---|---|
| Chiral 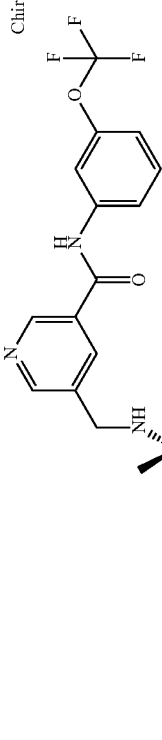 | [M + 1]⁺ = 1784 | calcd. for C82H90Cl2F3N13O25•2.3HCl•10.7H2O C: 47.84%, H: 5.53%, N: 8.85%, Cl: 7.58%, F: 2.77% found: C: 47.80%, H: 5.45%, N: 8.92%, Cl: 7.53%, F: 2.87% |

TABLE 125
Chiral
[M + 1]+ = 1800  calcd. for C82H90Cl2F3N13O26•2.3HCl•10.5H2O
C: 47.47%, H: 5.50%, N: 8.78%, Cl: 7.35%, F: 2.75%
found: C: 47.46%, H: 5.40%, N: 8.88%, Cl: 7.37%, F: 2.68%
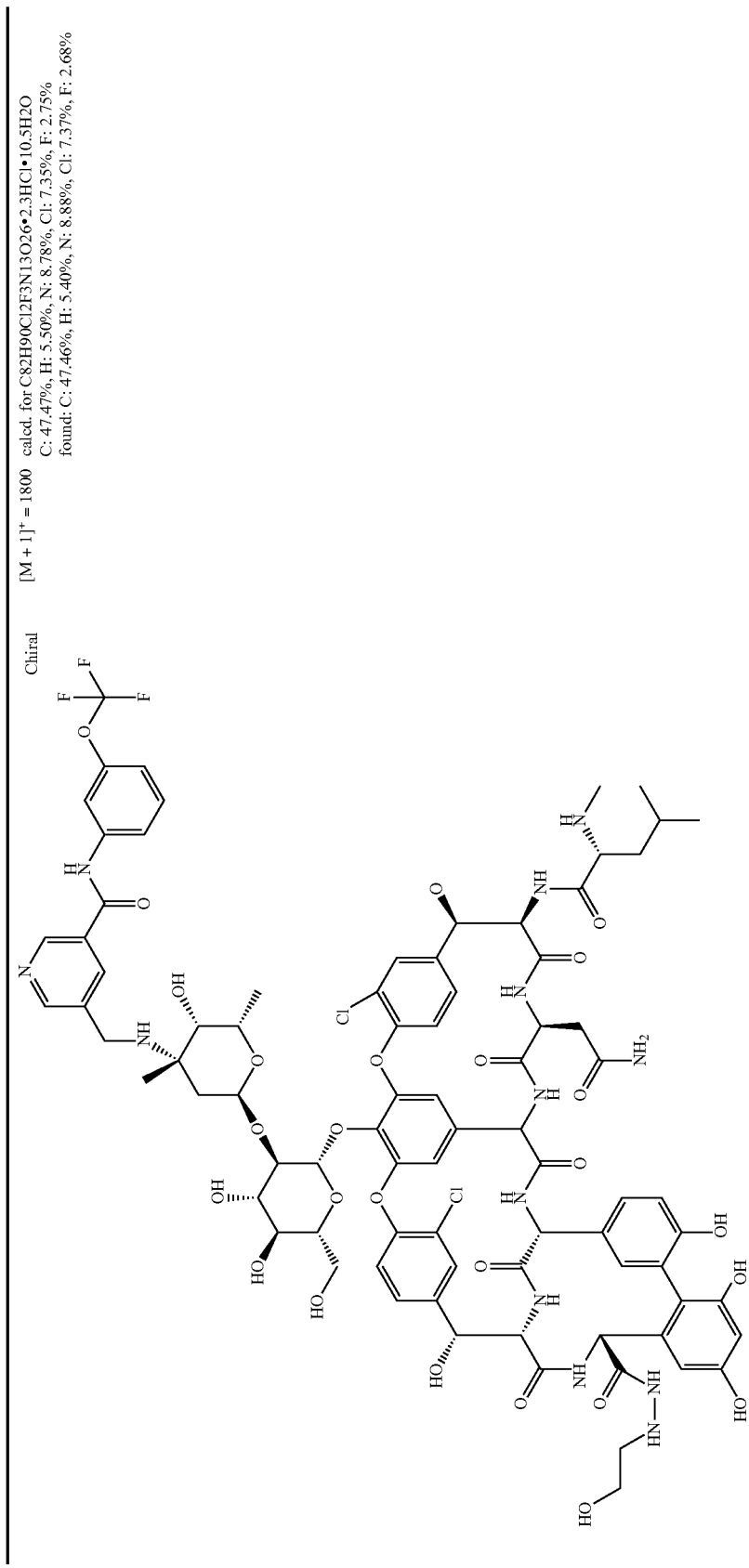

TABLE 125-continued
| Chiral | [M + 1]$^+$ = 1830 calcd. for C82H91Cl4N13O27•1.9HCl•10.3H2O<br>C: 47.18%, H: 5.48%, N: 8.72%, Cl: 10.02%<br>found: C: 47.14%, H: 5.38%, N: 8.82%, Cl: 10.06% |
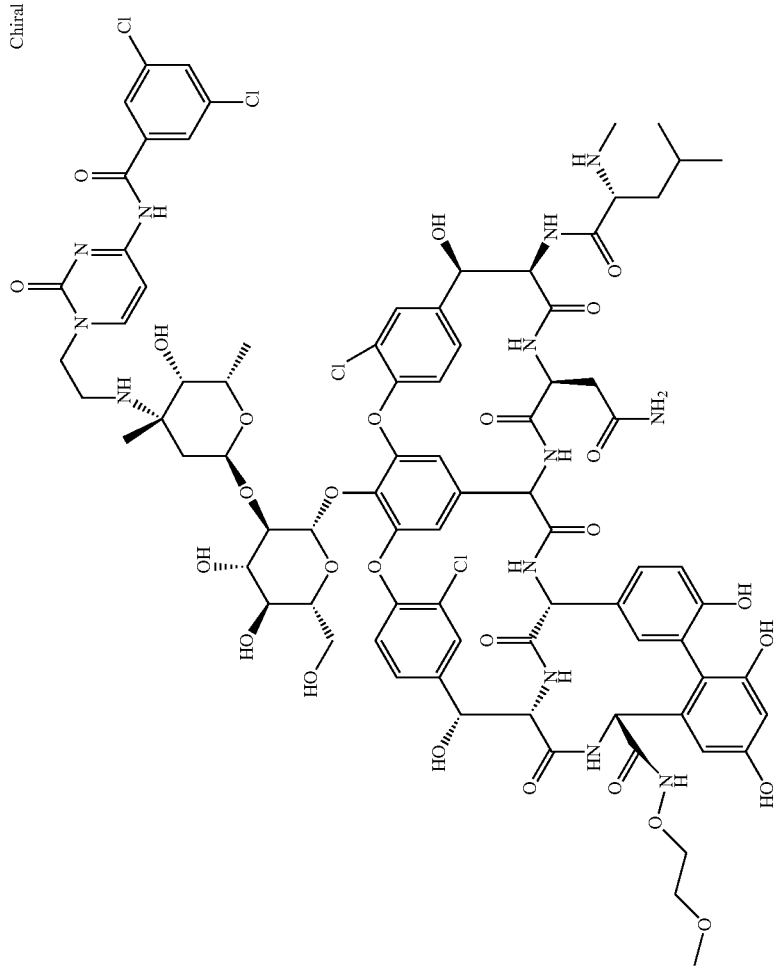

TABLE 125-continued
Chiral [M + 1]⁺ = 1844  calcd. for C82H90Cl2F3N15O27·2.2HCl·7.2H2O
C: 47.91%, H: 5.23%, N: 10.22%, Cl: 7.24, F: 2.77%
found: C: 47.94%, H: 5.25%, N: 10.05%, Cl: 7.28, F: 2.65%
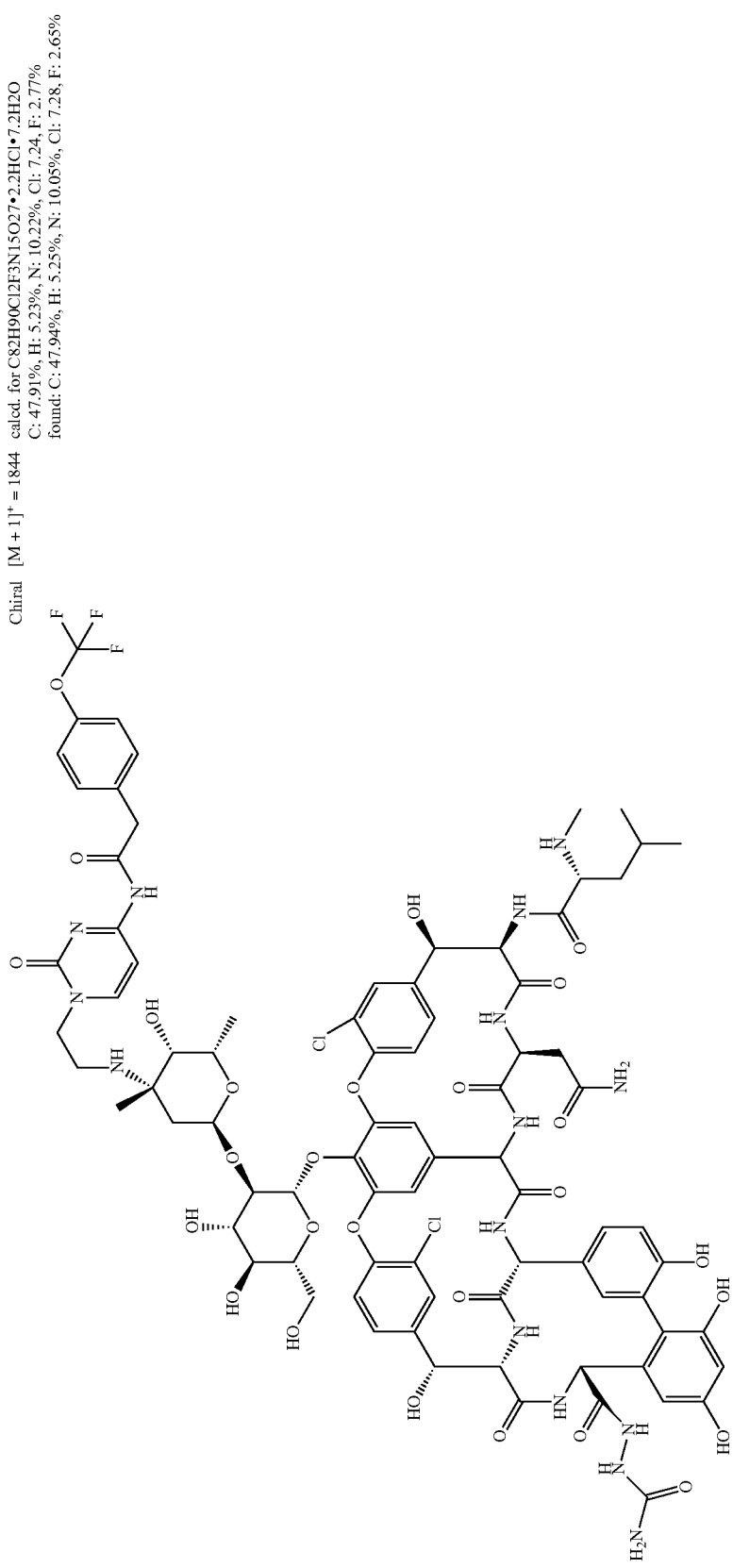

TABLE 126
| | | |
|---|---|---|
| Chiral | $[M + 1]^+ = 1843$ | calcd. for C83H91Cl2F3N14O27•2.2HCl•10.0H2O<br>C: 47.36%, H: 5.42%, N: 9.32%, Cl: 7.07, F: 2.71%<br>found: C: 47.32%, H: 5.36%, N: 9.34%, Cl: 7.11, F: 2.78% |
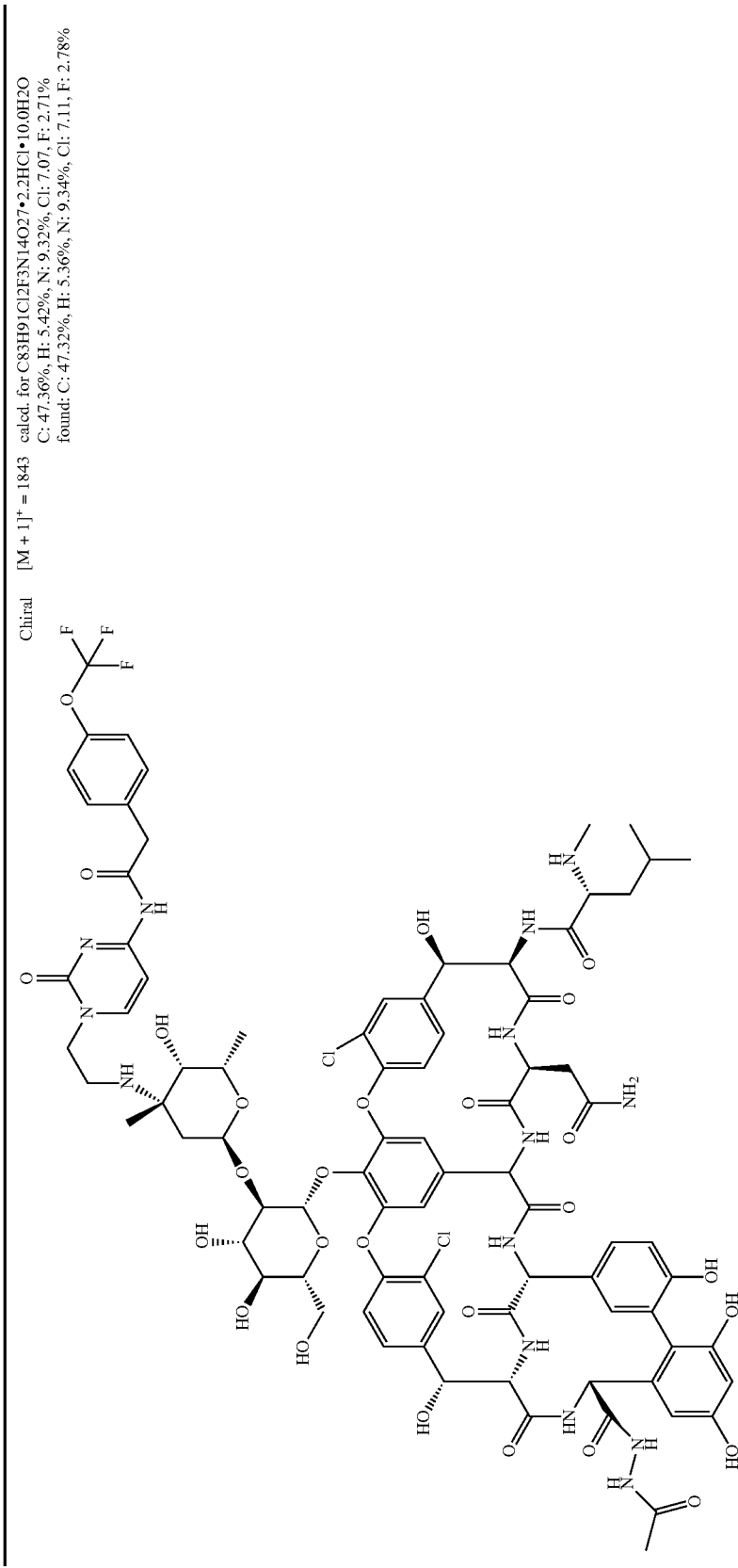

TABLE 126-continued
Chiral [M + 1]⁺ = 1885 calcd. for C85H96Cl4N14O27•2.7HCl•9.9H2O
C: 47.17%, H: 5.52%, N: 9.06%, Cl: 10.97%
found: C: 47.16%, H: 5.43%, N: 9.10%, Cl: 10.96%
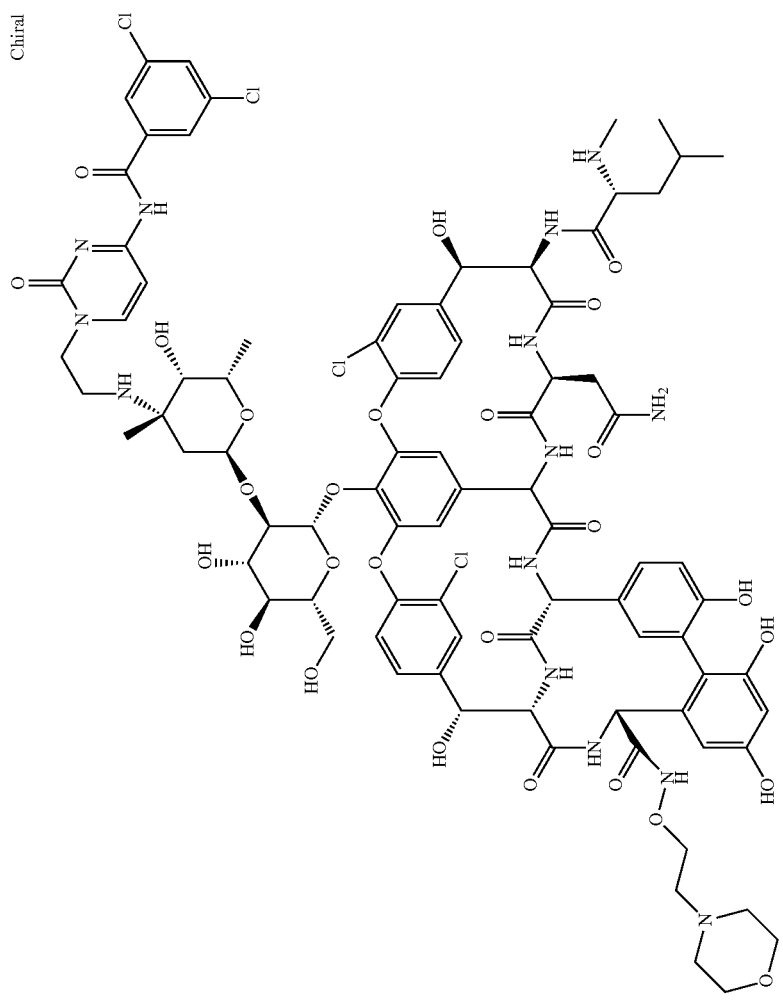

TABLE 126-continued
Chiral [M + 1]⁺ = 1844 calcd. for C83H93Cl4N13O27•1.7HCl•9.9H2O
found: C: 47.77%, H: 5.53%, N: 8.73%, Cl: 9.68%
C: 47.75%, H: 5.35%, N: 8.74%, Cl: 9.74%
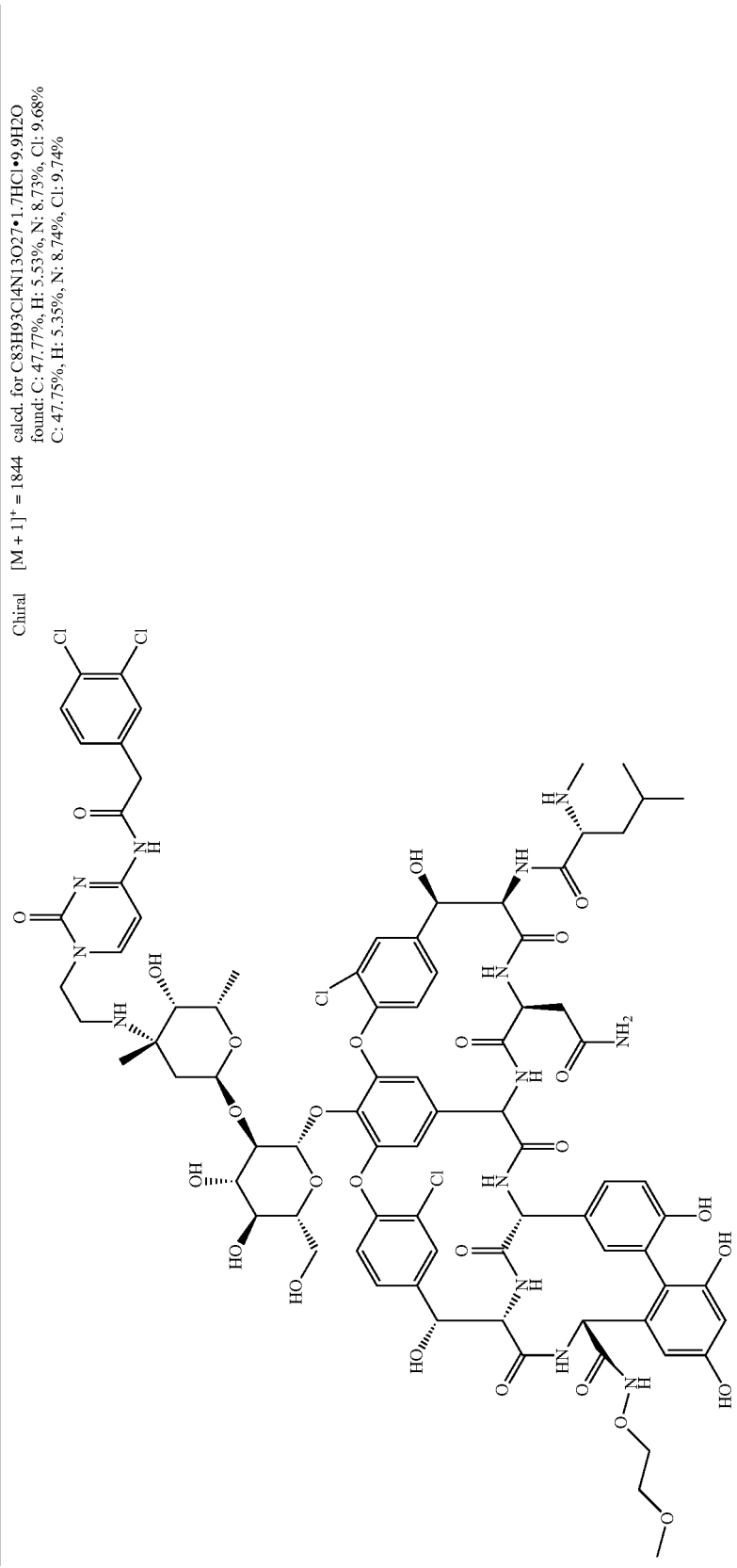

TABLE 127
| Structure | Mass | Elemental Analysis |
|---|---|---|
| 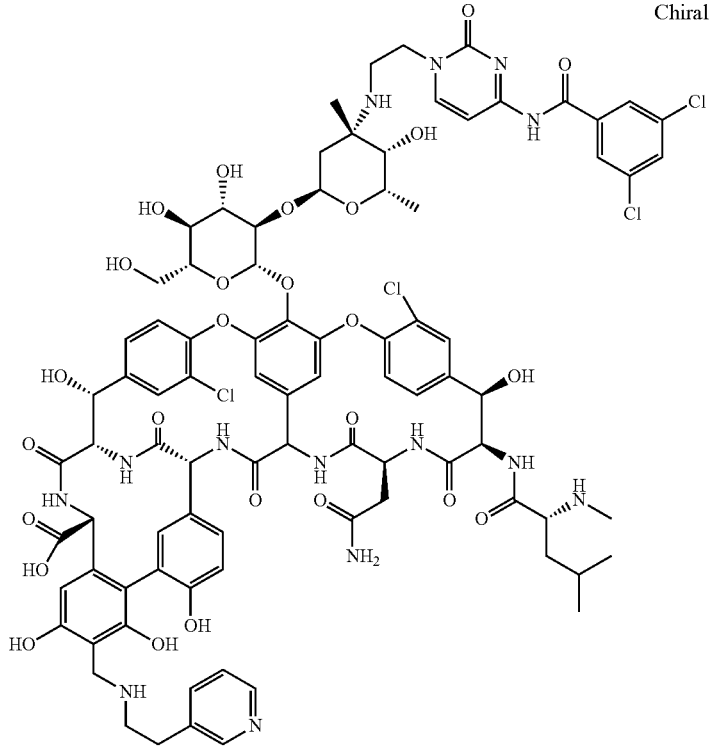 [SMILES: CN[C@H](CC(C)C)C(=O)N[C@H]1C(=O)N[C@@H](CC(N)=O)C(=O)NC2C(=O)N[C@H]3C(=O)N[C@H](C(=O)N[C@@H](C(=O)O)c4cc(O)c(CNCCc5cccnc5)c(O)c4-c4cc3ccc4O)[C@H](O)c3ccc(c(Cl)c3)Oc3cc2cc(c3O[C@@H]2O[C@H](CO)[C@@H](O)[C@H](O)[C@H]2O[C@H]2C[C@](C)(NCCn3ccc(NC(=O)c4cc(Cl)cc(Cl)c4)nc3=O)[C@H](O)[C@H](C)O2)Oc2ccc(cc2Cl)[C@H]1O] | [M + 1]⁺ = 1891 | calcd. for C87H94Cl4N14O26•4.2HCl•11.6H2O C: 46.32%, H: 5.42%, N: 8.69%, Cl: 12.89% found: C: 46.32%, H: 5.28%, N: 8.81%, Cl: 12.83% |
Reference Example 35
The following compounds were prepared in a similar manner as described above.

TABLE 128
| Structure | Mass | Elemental Analysis |
|---|---|---|
| Chiral | [M + 1]+ = 1562 | calcd. for C73H73Cl2N9O26•2HCl•10H2O<br>C: 48.27%, H: 5.27%, N: 6.94%, Cl: 7.81%, O: 31.71%<br>found: C: 48.02%, H: 5.05%, N: 7.01%, Cl: 7.81% |
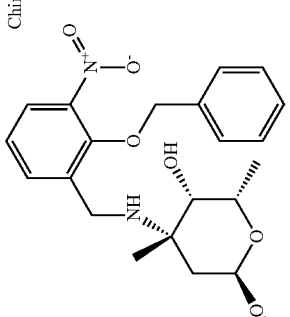

TABLE 128-continued
| Structure | Mass | Elemental Analysis |
|---|---|---|
| Chiral 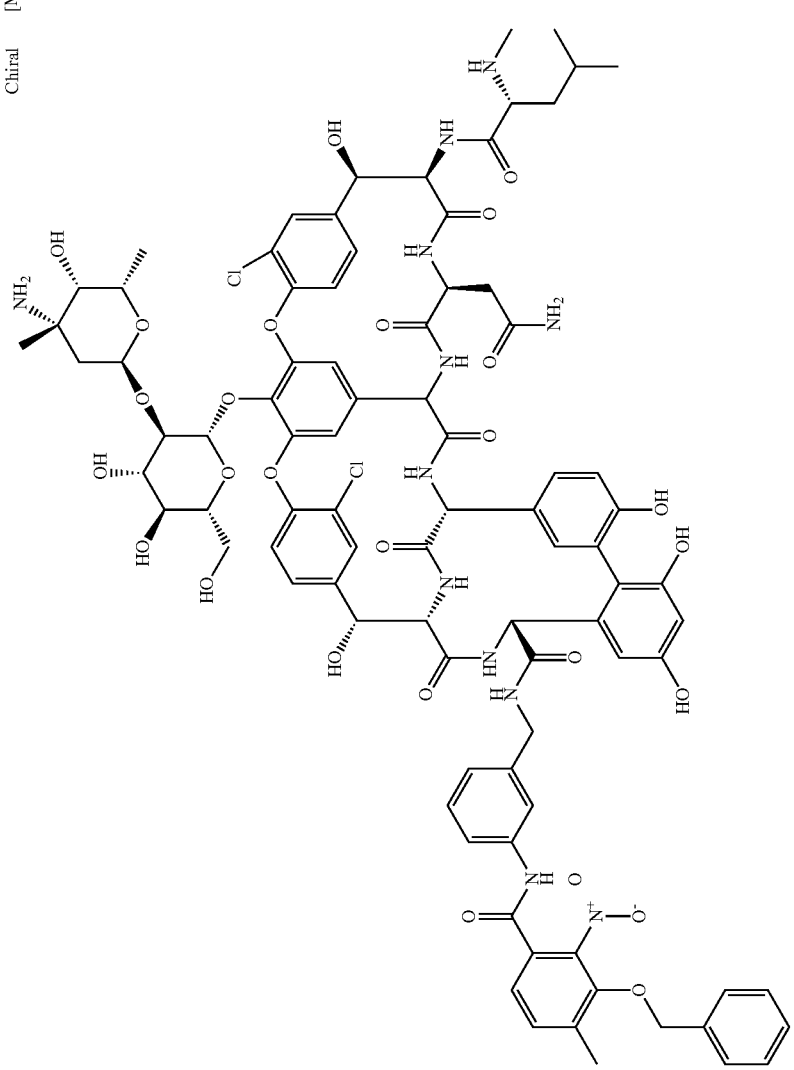 | [M + 1]+ = 1821 | calcd. for C88H94Cl2N12O27•2HCl•14H2O C: 49.21%, H: 5.82%, N: 7.83%, Cl: 6.60%, O: 30.54%, found: C: 49.21%, H: 6.03%, N: 7.90%, Cl: 6.75% |

Test Example 1

In Vitro Assay of Antimicrobial Activity

Method

For several compounds of the invention, minimal inhibitory concentration (MIC) was determined by the microdilution method using cation adjusted Mueller-Hinton broth well known in the art.

Results

The compounds of the invention showed a strong antimicrobial activity against various bacteria, including vancomycin-resistant strains. In particular, as shown in the following table, the compound of the invention, showed notability stronger antimicrobial activity against vancomycin-resistant *enterococcus* (VRE VanA) than existing drugs.

TABLE 129

| Strain No. | Compound 6 (Example 1) | Compound 10 (Example 2) | Compound 16 (Example 4) | VCM | TEIC |
|---|---|---|---|---|---|
| *E. faecalis* SR7914 (VRE: Van A) | 4 | 2 | 4 | >64 | >64 |
| *E. faecium* SR7917 (VRE: Van A) | 4 | 2 | 4 | >64 | >64 |

VCM and TEIC mean vancomycin and teicoplanin, respectively.

Formulations

It is to be noted that the following Formulations 1 to 8 are mere illustration, but not intended to limit the scope of the invention. The term "active ingredient" means the compounds of the invention, a tautomer, a prodrug, a pharmaceutically acceptable salt or a solvate thereof.

Formulation 1

Hard gelatin capsules are prepared using of the following ingredients:

|  | Dose (mg/capsule) |
|---|---|
| Active ingredient | 250 |
| Starch, dried | 200 |
| Magnesium stearate | 10 |
| Total | 460 mg |

Formulation 2

A tablet is prepared using of the following ingredients:

|  | Dose (mg/tablet) |
|---|---|
| Active ingredient | 250 |
| Cellulose, microcrystals | 400 |
| Silicon dioxide, fumed | 10 |
| Stearic acid | 5 |
| Total | 665 mg |

The components are blended and compressed to form tablets each weighing 665 mg.

Formulation 3

An aerosol solution is prepared containing the following components:

|  | Weight |
|---|---|
| Active ingredient | 0.25 |
| Ethanol | 25.75 |
| Propellant 22 (chlorodifluoromethane) | 74.00 |
| Total | 100.00 |

The active compound is mixed with ethanol and the admixture added to a portion of the propellant 22, cooled to −30° C. and transferred to filling device. The required amount is then fed to stainless steel container and diluted with the reminder of the propellant. The valve units are then fitted to the container.

Formulation 4

Table ts, each containing 60 mg of active ingredient, are made as follows.

|  |  |
|---|---|
| Active ingredient | 60 mg |
| Starch | 45 mg |
| Microcrystals cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch, and cellulose are passed through a No. 45 mesh U.S. sieve, and the mixed thoroughly. The aqueous solution containing polyvinylpyrrolidone is mixed with the resultant powder, and the admixture then is passed through a No. 14 mesh U.S. sieve. The granules so produced are dried at 50° C. and passed through a No. 18 mesh U.S. sieve. The sodium carboxymethyl starch, magnesium stearate, and talc, previously passed through No. 60 mesh U.S. sieve, are then added to the granules which, after mixing, are compressed on a tablet machine to yield tablets each weighing 150 mg.

Formulation 5

Capsules, each containing 80 mg of active ingredient, are made as follows:

|  |  |
|---|---|
| Active ingredient | 80 mg |
| Starch | 59 mg |
| Microcrystals cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

Formulation 6

Suppository, each containing 225 mg of active ingredient, are made as follows:

| Active ingredient | 225 mg |
|---|---|
| Saturated fatty acid glycerides | 2000 mg |
| Total | 2225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions, each containing 50 mg of active ingredient per 5 ml dose, are made as follows:

| Active ingredient | 50 mg |
|---|---|
| Sodium carboxymethyl cellulose | 50 mg |
| Syrup | 1.25 mL |
| Benzoic acid solution | 0.10 mL |
| Flavor | q.v. |
| Color | q.v. |
| Purified water to total | 5 mL |

The active ingredient is passed through a No. 45 U.S. sieve, and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8

An intravenous formulation may be prepared as follows:

| Active ingredient | 100 mg |
|---|---|
| Isotonic saline | 1000 mL |

The solution of the above ingredients generally is administered intravenously to a subject at a rate of 1 mL per minute.

INDUSTRIAL APPLICABILITY

The glycopeptide derivatives of the invention, pharmaceutically acceptable salts and solvates thereof are useful in the medical treatment and show a biological activity, including antimicrobial activity. Accordingly, the present invention provides a method for the treatment of infections diseases, particularly diseases caused by gram-positive microbial in animal, and the compounds of the invention is particularly useful in the treatment of infections with methicillin resistant *staphylococcus*. The compound is also useful for the treatment of infections with *enterococcus* including vancomycin-resistant *enterococcus* (VRE). Example of such disease includes severe infections with *staphylococcus* such as staphylococcal endocarditis and staphylococcal sepsis.

What is claimed is:

1. A compound represented by formula (3a):

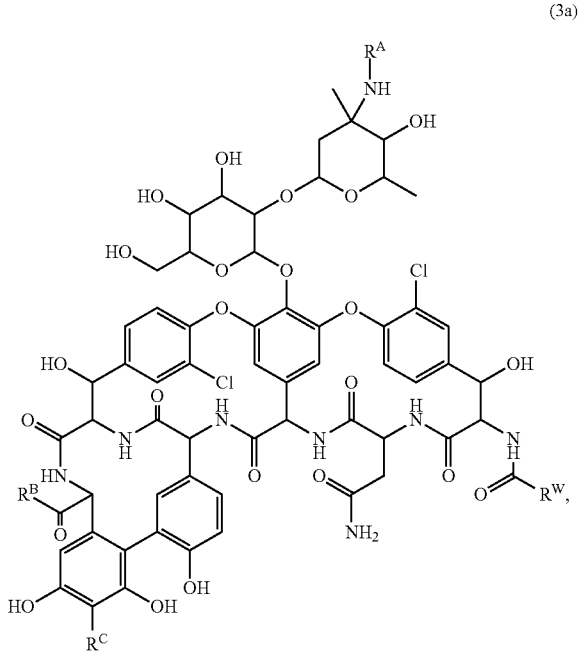

(3a)

or a pharmaceutically acceptable salt thereof,
wherein
$R^A$ is $X^1$—$Ar^1$-$X^2$—Y—$X^3$—$Ar^2$,
wherein, $X^1$, $X^2$ and $X^3$ are independently,
1) a single bond,
2) a heteroatom-containing group selected from the group consisting of —N=, =N—, —$NR^1$—, —O—, —S—, —SO— and —$SO_2$, wherein $R^1$ is hydrogen or lower alkyl, or
3) an optionally substituted alkylene or an optionally substituted alkenylene, each of which is optionally interrupted by one or more of the same or different heteroatomic group(s);
Y is —$NR^2CO$—, —$CONR^2$—,

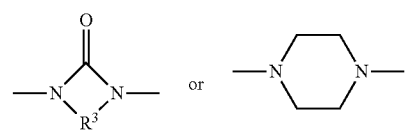

wherein $R^2$ is hydrogen or lower alkyl,
wherein $R^3$ is alkylene;
$Ar^1$ is a carbocycle or heterocycle which is optionally substituted and may have an unsaturated bond;
$Ar^2$ is a phenyl substituted with aralkyloxy and optionally one or more additional substituent(s) selected from the group consisting of lower alkyl and nitro;
$R^B$ is —OH, —$NR^5R^{5'}$, —NH—$R^Q$, —NH—$COR^Q$, —NH—$CONHR^Q$, —O—$R^Q$, or —$OR^6$,
wherein $R^5$ and $R^{5'}$ are independently hydrogen or an optionally substituted alkyl,
wherein each $R^Q$ is independently hydrogen, an optionally substituted alkyl, or an amino sugar residue, and
wherein $R^6$ is an optionally substituted alkyl that optionally includes a heteroatomic group;
$R^C$ is hydrogen or an optionally substituted alkyl that optionally includes a heteroatomic group; and $R^W$ is an optionally substituted alkyl.

2. The compound according to claim 1 represented by formula (5):

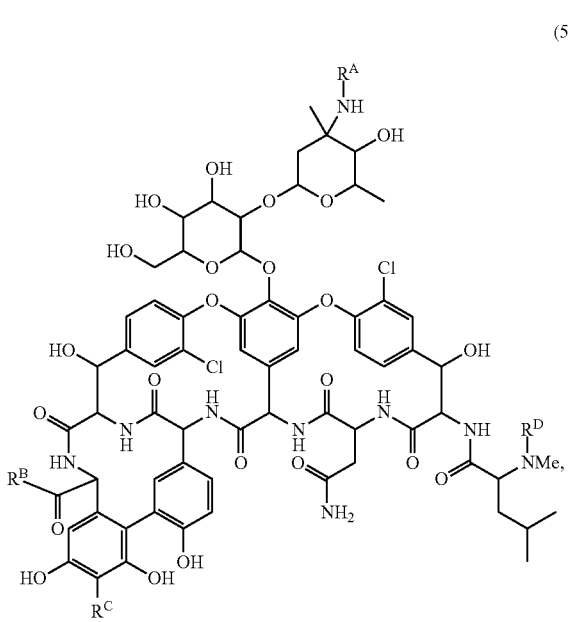

(5)

or a pharmaceutically acceptable salt thereof,
wherein
$R^A$ is —$X^1$—$Ar^1$-$X^2$—Y—$X^3$—$Ar^2$,
wherein $X^1$, $X^2$ and $X^3$ are independently
1) a single bond,
2) a heteroatom-containing group selected from the group consisting of —N=, =N—, —$NR^1$—, —O—, —S—, —SO— and —$SO_2$—, wherein $R^1$ is hydrogen or lower alkyl, or
3) an optionally substituted alkylene or an optionally substituted alkenylene, each of which is optionally interrupted by one or more of the same or different heteroatomic group(s);
Y is —$NR^2CO$—, —$CONR^2$—,

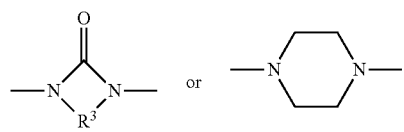

wherein $R^2$ is hydrogen or lower alkyl,
wherein $R^3$ is alkylene;
$Ar^1$ is a carbocycle or heterocycle which is optionally substituted and may have an unsaturated bond;
$Ar^2$ is a phenyl substituted with aralkyloxy and optionally one or more additional substituent(s) selected from the group consisting of lower alkyl and nitro;
$R^B$ is —OH, —$NR^5R^{5'}$, NH—$R^Q$, —NH—$COR^Q$, —NH—$CONHR^Q$, —O—$R^Q$, or —$OR^6$,
wherein $R^5$ and $R^{5'}$ are independently hydrogen or an optionally substituted alkyl,
wherein each $R^Q$ is independently hydrogen, an optionally substituted alkyl, or an amino sugar residue, and
wherein $R^6$ is an optionally substituted alkyl that optionally includes a heteroatomic group;
$R^C$ is hydrogen or an optionally substituted alkyl that optionally includes a heteroatomic group; and
$R^D$ is hydrogen or lower alkyl.

3. The compound according to claim 2 represented by formula (7):

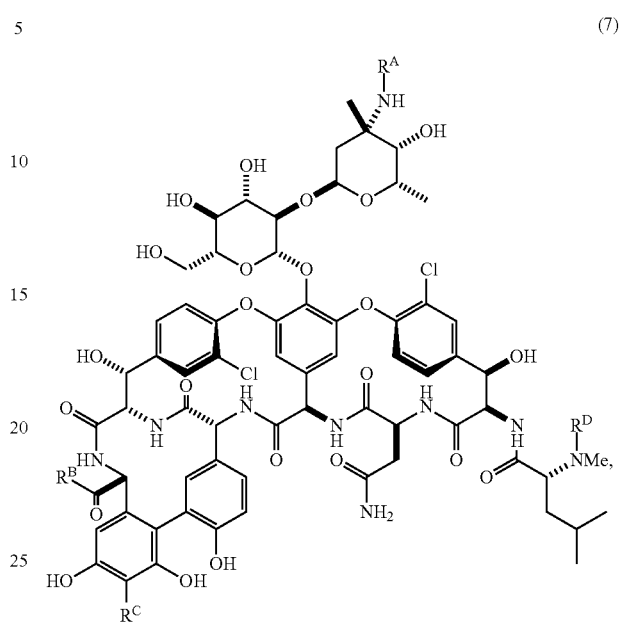

(7)

or a pharmaceutically acceptable salt thereof,
wherein
$R^A$ is —$X^1$—$Ar^1$-$X^2$—Y—$X^3$—$Ar^2$,
wherein $X^1$, $X^2$ and $X^3$ are independently
1) a single bond,
2) a heteroatom-containing group selected from the group consisting of —N=, =N—, —$NR^1$—, —O—, —S—, —SO— and —$SO_2$—, wherein $R^1$ is hydrogen or lower alkyl, or
3) an optionally substituted alkylene or an optionally substituted alkenylene, each of which is optionally interrupted by one or more of the same or different heteroatomic group(s);
Y is —$NR^2CO$—, —$CONR^2$—,

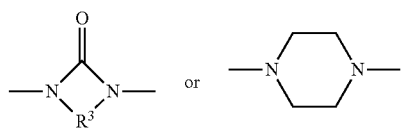

wherein $R^2$ is hydrogen or lower alkyl,
wherein $R^3$ is alkylene;
$Ar^1$ is a carbocycle or heterocycle which is optionally substituted and may have an unsaturated bond;
$Ar^2$ is a phenyl substituted with aralkyloxy and optionally one or more additional substituent(s) selected from the group consisting of lower alkyl and nitro;
$R^B$ is —OH, —$NR^5R^{5'}$, NH—$R^Q$, —NH—$COR^Q$, —NH—$CONHR^Q$, —O—$R^Q$, or —$OR^6$,
wherein $R^5$ and $R^{5'}$ are independently hydrogen or an optionally substituted alkyl,
wherein each $R^Q$ is independently hydrogen, an optionally substituted alkyl, or an amino sugar residue, and
wherein $R^6$ is an optionally substituted alkyl that optionally includes a heteroatomic group;
$R^C$ is hydrogen or an optionally substituted alkyl that optionally includes a heteroatomic group; and
$R^D$ is hydrogen or lower alkyl.

4. The compound according to claim 1, or a pharmaceutically acceptable salt thereof, wherein $Ar^1$ is optionally substituted aryl, optionally substituted heteroaryl, or optionally substituted cycloalkyl.

5. The compound according to claim 1, or a pharmaceutically acceptable salt thereof, wherein $Ar^1$ is optionally substituted aryl, and Y is —NHCO— or —CONH—.

6. The compound according to claim 1, or a pharmaceutically acceptable salt thereof, wherein $Ar^1$ is phenyl optionally substituted with an optionally substituted amino.

7. The compound according to claim 1, or a pharmaceutically acceptable salt thereof, wherein $Ar^1$ is optionally substituted heteroaryl.

8. The compound according to claim 1, or a pharmaceutically acceptable salt thereof, wherein Y is —$NR^2CO$— or —$CONR^2$— and $R^2$ is hydrogen or lower alkyl.

9. The compound according to claim 1, or a pharmaceutically acceptable salt thereof, wherein $X^1$ is lower alkylene.

10. The compound according to claim 1, or a pharmaceutically acceptable salt thereof, wherein $X^2$ is a single bond, lower alkylene, or a heteroatom-containing group selected from the group consisting of —N=, =N—, —$NR^1$—, —O—, —S—, —SO— and —$SO_2$—, wherein $R^1$ is hydrogen or lower alkyl.

11. The compound according to claim 1, or a pharmaceutically acceptable salt thereof, wherein $X^3$ is a single bond, lower alkylene, or a heteroatom-containing group selected from the group consisting of —N=, =N—, —$NR^1$—, —O—, —S—, —SO— and —$SO_2$—, wherein $R^1$ is hydrogen or lower alkyl.

12. The compound according to claim 1, or a pharmaceutically acceptable salt thereof, wherein
$X^1$ is lower alkylene;
$X^2$ is a single bond, lower alkylene, or a heteroatom-containing group selected from the group consisting of —N=, =N—, —$NR^1$—, —O—, —S—, —SO— and —$SO_2$—, wherein $R^1$ is hydrogen or lower alkyl;
$X^3$ is a single bond, lower alkylene, or a heteroatom-containing group selected from the group consisting of —N=, =N—, —$NR^1$—, —O—, —S—, —SO— and —$SO_2$—, wherein $R^1$ is hydrogen or lower alkyl;
Y is —NHCO— or —CONH—; and
$Ar^1$ is optionally substituted phenyl.

13. The compound according to claim 1, or a pharmaceutically acceptable salt thereof, wherein
$X^1$ is lower alkylene;
$X^2$ is a single bond, lower alkylene, or a heteroatom-containing group selected from the group consisting of —N=, =N—, —$NR^1$—, —O—, —S—, —SO— and —$SO_2$—, wherein $R^1$ is hydrogen or lower alkyl;
$X^3$ is a single bond, lower alkylene, or a heteroatom-containing group selected from the group consisting of —N=, =N—, —$NR^1$—, —O—, —S—, —SO— and —$SO_2$—, wherein $R^1$ is hydrogen or lower alkyl;
Y is —NHCO— or —CONH—; and
$Ar^1$ is optionally substituted heteroaryl or optionally substituted heterocycle.

14. The compound according to claim 1, or a pharmaceutically acceptable salt thereof, wherein
$X^1$ is lower alkylene;
$X^2$ is a single bond, lower alkylene, or a heteroatom-containing group selected from the group consisting of —N=, =N—, —$NR^1$—, —O—, —S—, —SO— and —$SO_2$—, wherein $R^1$ is hydrogen or lower alkyl;
$X^3$ is a single bond, lower alkylene, or a heteroatom-containing group selected from the group consisting of —N=, =N—, —$NR^1$—, —O—, —S—, —SO— and —$SO_2$—, wherein $R^1$ is hydrogen or lower alkyl;
Y is —NHCO— or —CONH—;
$Ar^1$ is optionally substituted phenyl, optionally substituted heteroaryl or optionally substituted heterocycle; and
wherein the compound meets at least one of the following requirements (1)-(3) for $R^B$, $R^C$ and $R^D$:
  (1) $R^B$ is —$NR^5R^{5'}$, NH—$R^Q$, NH—$COR^Q$, NH—$CONHR^Q$, or —O—$R^Q$; wherein $R^5$ and $R^{5'}$ are independently hydrogen or optionally substituted alkyl; and $R^Q$ is independently hydrogen or optionally substituted alkyl;
  (2) $R^C$ is optionally substituted alkyl in which the alkyl moiety may be interrupted with a heteroatom-containing group selected from the group consisting of —N=, =N—, —$NR^1$—, —O—, —S—, —SO— and —$SO_2$—, wherein $R^1$ is hydrogen or lower alkyl;
  (3) $R^D$ is lower alkyl.

15. The compound according to claim 1 represented by formula (10):

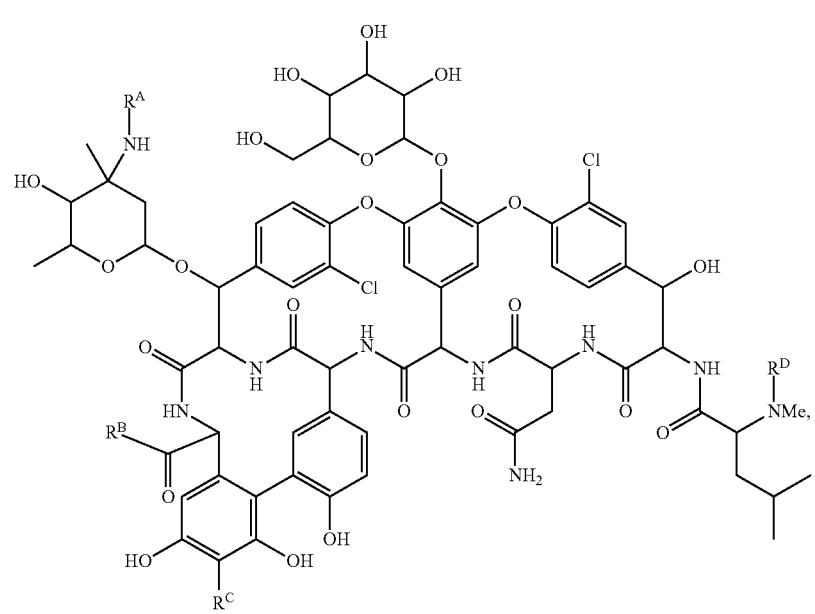

(10)

or a pharmaceutically acceptable salt thereof,
wherein
$R^A$ is —$X^1$—$Ar^1$—$X^2$—Y—$X^3$—$Ar^2$,
wherein, $X^1$, $X^2$ and $X^3$ are independently
1) a single bond;
2) a heteroatom-containing group selected from the group consisting of —N═, ═N—, —$NR^1$—, —O—, —S—, —SO— and —$SO_2$—, wherein $R^1$ is hydrogen or lower alkyl; or
3) an optionally substituted alkylene or an optionally substituted alkenylene, each of which is optionally interrupted by one or more of the same or different heteroatomic group(s);
Y is —$NR^2CO$—, —$CONR^2$ or

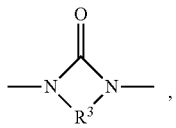

wherein $R^2$ is hydrogen or lower alkyl,
wherein $R^3$ is alkylene;
$Ar^1$ is a carbocycle or heterocycle which is optionally substituted and may have an unsaturated bond;
$Ar^2$ is a phenyl substituted with aralkyloxy and optionally one or more additional substituent(s) selected from the group consisting of lower alkyl and nitro;
$R^B$ is —OH or —$NR^5R^{5\prime}$, wherein $R^5$ and $R^{5\prime}$ are independently hydrogen or optionally substituted alkyl;
$R^C$ is hydrogen or optionally substituted alkyl that may comprise optionally includes a heteroatomic group; and
$R^D$ is hydrogen or lower alkyl.

16. The compound according to claim 15, or a pharmaceutically acceptable salt thereof, wherein
$X^1$ is lower alkylene;
$X^2$ is a single bond or lower alkylene that optionally includes a heteroatomic group;
$X^3$ is a single bond;
Y is —NHCO— or —CONH—;
$Ar^1$ is optionally substituted phenyl;
$R^B$ is OH; and
$R^C$ and $R^D$ are hydrogen.

17. The compound according to claim 1, or a pharmaceutically acceptable salt thereof, wherein
$X^1$ is lower alkylene;
$X^2$ and $X^3$ are independently a single bond, lower alkylene, or a heteroatom-containing group selected from the group consisting of —N═, ═N—, —$NR^1$—, —O—, —S—, —SO— and —$SO_2$—, wherein $R^1$ is hydrogen or lower alkyl;
Y is

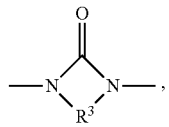

wherein $R^3$ is alkylene; and
$Ar^1$ is optionally substituted phenyl.

18. The compound according to claim 2, or a pharmaceutically acceptable salt thereof, wherein $R^B$ is —OH; $R^C$ is hydrogen; and $R^D$ is hydrogen.

19. The compound according to claim 2, or a pharmaceutically acceptable salt thereof, wherein $R^B$ is —OH; $R^C$ is optionally substituted alkyl that optionally includes a heteroatomic group in the alkyl moiety; and $R^D$ is hydrogen.

20. The compound according to claim 2, or a pharmaceutically acceptable salt thereof, wherein $R^B$ is —OH; $R^C$ is alkyl that is substituted with a hydrophilic substituent and optionally includes a heteroatomic group in the alkyl moiety; and $R^D$ is hydrogen.

21. The compound according to claim 2, or a pharmaceutically acceptable salt thereof, wherein
$R^B$ is —$NR^5R^{5\prime}$, —NH—$R^Q$, —NH—$COR^Q$, —NH—$CONHR^Q$, or —O—$R^Q$,
$R^5$ and $R^{5\prime}$ are independently hydrogen or an optionally substituted alkyl,
$R^Q$ is independently hydrogen, an optionally substituted alkyl, or an amino sugar residue;
$R^C$ is hydrogen; and
$R^D$ is hydrogen.

22. The compound according to claim 2, or a pharmaceutically acceptable salt thereof, wherein
$R^B$ is —$NR^5R^{5\prime}$, NH—$R^Q$, —NH—$COR^Q$, —NH—$CONHR^Q$, or —O—$R^Q$;
$R^5$ is hydrogen;
$R^{5\prime}$ is alkyl;
$R^Q$ is independently hydrogen or an optionally substituted alkyl;
$R^C$ is hydrogen; and
$R^D$ is hydrogen.

* * * * *